US008921281B2

(12) United States Patent
Fischer et al.

(10) Patent No.: US 8,921,281 B2
(45) Date of Patent: Dec. 30, 2014

(54) SYNTHETIC POLYPEPTIDE LIBRARIES AND METHODS FOR GENERATING NATURALLY DIVERSIFIED POLYPEPTIDE VARIANTS

(75) Inventors: Nicolas Fischer, Geneva (CH); Marie Kosco-Vilbois, Minzier (FR); Ulla Ravn, Geneva (CH); Franck Gueneau, Saint-Julien-en-Genevois (FR); Sophie Venet-Bonnot, Saint-Julien-en-Genevois (FR)

(73) Assignee: NovImmune S.A., Geneva (CH)

( * ) Notice: Subject to any disclaimer, the term of this patent is extended or adjusted under 35 U.S.C. 154(b) by 956 days.

(21) Appl. No.: 12/784,190

(22) Filed: May 20, 2010

(65) Prior Publication Data

US 2011/0065610 A1 Mar. 17, 2011

Related U.S. Application Data

(60) Provisional application No. 61/179,850, filed on May 20, 2009, provisional application No. 61/287,336, filed on Dec. 17, 2009, provisional application No. 61/314,794, filed on Mar. 17, 2010.

(51) Int. Cl.
*C40B 50/06* (2006.01)
*C12N 15/66* (2006.01)
*C07K 16/00* (2006.01)
*C40B 40/08* (2006.01)

(52) U.S. Cl.
CPC .......... *C12N 15/66* (2013.01); *C07K 2317/565* (2013.01); *C07K 16/005* (2013.01); *C40B 40/08* (2013.01); *C07K 2317/622* (2013.01); *C07K 2317/21* (2013.01); *C40B 50/06* (2013.01)
USPC ........................................................ 506/26

(58) Field of Classification Search
None
See application file for complete search history.

(56) References Cited

U.S. PATENT DOCUMENTS 4,946,778 A 8/1990 Ladner et al.
5,223,409 A 6/1993 Ladner et al.
(Continued)

FOREIGN PATENT DOCUMENTS

EP 0281604 3/1993
EP 0396612 7/1996
(Continued)

OTHER PUBLICATIONS

Al-Lazikani B et al., "Standard conformations for the canonical structures of immunoglobulins." J Mol Biol. Nov. 7, 1997;273(4):927-48.

(Continued)

*Primary Examiner* — Christian Boesen
(74) *Attorney, Agent, or Firm* — Cooley LLP; Ivor R. Elrifi

(57) ABSTRACT

The invention provides compositions and methods for generating libraries of DNA sequences encoding homologous polypeptides, and uses of the libraries to identify naturally diversified polypeptide variants. The invention also provides compositions and methods for generating collections of synthetic antibody fragments in which one or several complementary determining regions (CDR) are replaced by a collection of the corresponding CDR captured from a natural source. The invention further provides compositions and methods for diversifying a portion of a polypeptide by inserting a diversified sequence of synthetic or natural origin without the need for modification of the original polypeptide coding sequence.

38 Claims, 43 Drawing Sheets

(56) References Cited

U.S. PATENT DOCUMENTS

| | | |
|---|---|---|
| 5,225,539 A | 7/1993 | Winter |
| 5,260,203 A | 11/1993 | Ladner et al. |
| 5,403,484 A | 4/1995 | Ladner et al. |
| 5,427,908 A | 6/1995 | Dower et al. |
| 5,512,463 A | 4/1996 | Stemmer |
| 5,514,548 A | 5/1996 | Krebber et al. |
| 5,514,568 A | 5/1996 | Stemmer |
| 5,518,889 A | 5/1996 | Ladner et al. |
| 5,565,325 A | 10/1996 | Blake |
| 5,565,332 A | 10/1996 | Hoogenboom et al. |
| 5,571,698 A | 11/1996 | Ladner et al. |
| 5,576,195 A | 11/1996 | Robinson et al. |
| 5,580,717 A | 12/1996 | Dower et al. |
| 5,595,898 A | 1/1997 | Robinson et al. |
| 5,618,920 A | 4/1997 | Robinson et al. |
| 5,658,727 A | 8/1997 | Barbas et al. |
| 5,667,988 A | 9/1997 | Barbas et al. |
| 5,693,493 A | 12/1997 | Robinson et al. |
| 5,698,417 A | 12/1997 | Robinson et al. |
| 5,698,435 A | 12/1997 | Robinson et al. |
| 5,702,892 A | 12/1997 | Mulligan-Kehoe |
| 5,723,287 A | 3/1998 | Russell et al. |
| 5,733,743 A | 3/1998 | Johnson et al. |
| 5,759,817 A | 6/1998 | Barbas |
| 5,780,225 A | 7/1998 | Wigler et al. |
| 5,821,047 A | 10/1998 | Garrard et al. |
| 5,824,520 A | 10/1998 | Mulligan-Kehoe |
| 5,830,663 A | 11/1998 | Embleton et al. |
| 5,837,242 A | 11/1998 | Holliger et al. |
| 5,837,500 A | 11/1998 | Ladner et al. |
| 5,849,500 A | 12/1998 | Breitling et al. |
| 5,855,885 A | 1/1999 | Smith et al. |
| 5,858,657 A | 1/1999 | Winter et al. |
| 5,869,620 A | 2/1999 | Whitlow et al. |
| 5,871,907 A | 2/1999 | Winter et al. |
| 5,885,793 A | 3/1999 | Griffiths et al. |
| 5,922,545 A | 7/1999 | Mattheakis et al. |
| 5,955,341 A | 9/1999 | Kang et al. |
| 5,962,255 A | 10/1999 | Griffiths et al. |
| 5,969,108 A | 10/1999 | McCafferty et al. |
| 5,985,588 A | 11/1999 | Breitling et al. |
| 6,010,884 A | 1/2000 | Griffiths et al. |
| 6,017,732 A | 1/2000 | Jespers et al. |
| 6,025,165 A | 2/2000 | Whitlow et al. |
| 6,027,725 A | 2/2000 | Whitlow et al. |
| 6,096,551 A | 8/2000 | Barbas et al. |
| 6,103,889 A | 8/2000 | Whitlow et al. |
| 6,121,424 A | 9/2000 | Whitlow et al. |
| 6,127,132 A | 10/2000 | Breitling et al. |
| 6,140,471 A | 10/2000 | Johnson et al. |
| 6,172,197 B1 | 1/2001 | McCafferty et al. |
| 6,174,708 B1 | 1/2001 | Sodoyer et al. |
| 6,204,023 B1 | 3/2001 | Robinson et al. |
| 6,225,447 B1 | 5/2001 | Winter et al. |
| 6,235,469 B1 | 5/2001 | Kang et al. |
| 6,248,516 B1 | 6/2001 | Winter et al. |
| 6,291,158 B1 | 9/2001 | Winter et al. |
| 6,291,161 B1 | 9/2001 | Lerner et al. |
| 6,291,650 B1 | 9/2001 | Winter et al. |
| 6,297,004 B1 | 10/2001 | Russell et al. |
| 6,300,064 B1 | 10/2001 | Knappik et al. |
| 6,303,313 B1 | 10/2001 | Wigler et al. |
| 6,326,155 B1 | 12/2001 | Maclennan et al. |
| 6,331,415 B1 | 12/2001 | Cabilly et al. |
| 6,387,627 B1 | 5/2002 | Breitling et al. |
| 6,399,763 B1 | 6/2002 | Frenken et al. |
| 6,468,738 B1 | 10/2002 | Kang et al. |
| 6,479,243 B1 | 11/2002 | Wigler et al. |
| 6,492,160 B1 | 12/2002 | Griffiths et al. |
| 6,515,110 B1 | 2/2003 | Whitlow et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,599,697 B1 | 7/2003 | Sodoyer et al. |
| 6,610,472 B1 | 8/2003 | Zhu et al. |
| 6,635,424 B2 | 10/2003 | Wigler et al. |
| 6,696,245 B2 | 2/2004 | Winter et al. |
| 6,696,248 B1 | 2/2004 | Knappik et al. |
| 6,706,484 B1 | 3/2004 | Knappik et al. |
| 6,730,483 B2 | 5/2004 | Breitling et al. |
| 6,806,079 B1 | 10/2004 | McCafferty et al. |
| 6,828,422 B1 | 12/2004 | Achim et al. |
| 6,916,605 B1 | 7/2005 | McCafferty et al. |
| 6,955,900 B1 | 10/2005 | Barbas, III et al. |
| 6,979,538 B2 | 12/2005 | Ladner et al. |
| 6,982,321 B2 | 1/2006 | Winter |
| 6,989,250 B2 | 1/2006 | Soderlind et al. |
| 7,063,943 B1 | 6/2006 | McCafferty et al. |
| 7,067,284 B1 | 6/2006 | Barbas et al. |
| 7,118,866 B2 | 10/2006 | Kang et al. |
| 7,135,310 B2 * | 11/2006 | Bradbury et al. ............ 435/91.1 |
| 7,195,866 B2 | 3/2007 | Griffiths et al. |
| 7,196,187 B2 | 3/2007 | Frenken et al. |
| 7,208,293 B2 | 4/2007 | Ladner et al. |
| 7,264,963 B1 | 9/2007 | Knappik et al. |
| 7,635,666 B1 | 12/2009 | McCafferty et al. |
| 2003/0232333 A1 | 12/2003 | Ladner et al. |
| 2006/0134098 A1 | 6/2006 | Bebbington et al. |
| 2006/0222654 A1 | 10/2006 | Delcayre et al. |

FOREIGN PATENT DOCUMENTS

| | | |
|---|---|---|
| EP | 0550400 | 7/1996 |
| EP | 0436597 | 4/1997 |
| EP | 0349578 | 10/1998 |
| EP | 0527839 | 12/1998 |
| EP | 0597960 | 1/1999 |
| EP | 0605522 | 6/1999 |
| EP | 0585287 | 10/1999 |
| EP | 0371998 | 11/1999 |
| EP | 0425661 | 10/2000 |
| EP | 0472638 | 10/2000 |
| EP | 0731167 | 11/2000 |
| EP | 0706569 | 1/2001 |
| EP | 0547201 | 3/2001 |
| EP | 0970126 | 4/2001 |
| EP | 0617706 | 10/2001 |
| EP | 0774511 | 1/2002 |
| EP | 0859841 | 6/2002 |
| EP | 0934526 | 1/2003 |
| EP | 0779933 | 4/2003 |
| EP | 0906571 | 4/2003 |
| EP | 0580737 | 6/2004 |
| EP | 0865487 | 8/2004 |
| EP | 0616640 | 9/2004 |
| EP | 0573611 | 10/2004 |
| EP | 1471142 | 11/2004 |
| EP | 0318554 | 1/2005 |
| EP | 0866136 | 1/2005 |
| EP | 0656941 | 6/2005 |
| EP | 0589877 | 10/2005 |
| EP | 0742821 | 4/2006 |
| EP | 0844306 | 9/2006 |
| EP | 1433846 | 4/2007 |
| EP | 1279731 | 5/2007 |
| EP | 1143006 | 4/2008 |
| EP | 1479771 | 10/2008 |
| EP | 1024191 | 11/2008 |
| EP | 1495146 | 11/2008 |
| EP | 1997891 | 12/2008 |
| EP | 1144616 | 1/2009 |
| EP | 1065271 | 3/2009 |
| EP | 2058400 | 5/2009 |
| EP | 1025218 | 8/2009 |
| EP | 1820858 | 8/2009 |
| EP | 2055777 | 10/2009 |
| EP | 1452599 | 8/2010 |

OTHER PUBLICATIONS

Balint RF, Larrick JW. "Antibody engineering by parsimonious mutagenesis." Gene. Dec. 27, 1993;137(1):109-18.

(56) References Cited

OTHER PUBLICATIONS

Boder ET and Wittrup KD., "Yeast surface display for screening combinatorial polypeptide libraries," Nat Biotechnol. Jun. 1997; 15(6):553-7.
Collis A et al., "Analysis of the Antigen Combining Site: Correlations Between Length and Sequence Composition of the Hypervariable Loops and the Nature of the Antigen," J Mol Biol 2003 325; 337-354.
Daugherty PS et al., "Analysis of the Antigen Combining Site: Correlations Between Length and Sequence Composition of the Hypervariable Loops and the Nature of the Antigen" Protein Eng. Sep. 1998; 11(9):825-32.
De Bruin R et al., "Selection of high-affinity phage antibodies from phage display libraries," Nat Biotechnol Apr. 17, 1999: 397-399.
de Kruif J et al., "Selection and application of human single chain Fv antibody fragments from a semi-synthetic phage antibody display library with designed CDR3 regions," J Mol Biol. Apr. 21, 1995; 248(1):97-105.
Ewert S et al., "Biophysical properties of human antibody variable domains," J Mol Biol. Jan. 17, 2003;325(3):531-53.
Hanes J and Plückthun A., "In vitro selection and evolution of functional proteins by using ribosome display," Proc Natl Acad Sci U S A. May 13, 1997;94(10):4937-42.
Ivanov I et al., 2005, "Development of the Expressed Ig CDR-H3 Repertoire Is Marked by Focusing of Constraints in Length, Amino Acid Use, and Charge That Are First Established in Early B Cell Progenitors," J Immunol 174; 7773-7780.
Knappik A et al., "Fully synthetic human combinatorial antibody libraries (HuCAL) based on modular consensus frameworks and CDRs randomized with trinucleotides," J Mol Biol. Feb. 11, 2000;296(1):57-86.
Lee CV et al., "High-affinity human antibodies from phage-displayed synthetic Fab libraries with a single framework scaffold," J Mol Biol. Jul. 23, 2004;340(5):1073-93.
Lefranc, M.-P. et al., "IMGT, the international ImMunoGeneTics database," 1999 Nucleic Acids Research, 27, 209-212.
Link JM et al., "Despite extensive similarity in germline DH and JH sequence, the adult Rhesus macaque CDR-H3 repertoire differs from human," Molecular Immunol. 2005 42; 943-955.
Lu, "Seamless cloning and gene fusion," Trends in Biotechnology, 2005 vol. 23(4): 200-207.
Marks JD et al., "By-passing immunization. Human antibodies from V-gene libraries displayed on phage," J Mol Biol. Dec. 5, 1991;222(3):581-97.
Persson MA et al., "Generation of diverse high-affinity human monoclonal antibodies by repertoire cloning" Proc Natl Acad Sci U S A. Mar. 15, 1991;88(6):2432-6.
Rock EP et al., "CDR3 Length in Antigen-specific Immune Receptors," J Exp Med 1994 179; 323-328.
Rothe et al., "The human combinatorial antibody library HuCAL GOLD combines diversification of all six CDRs according to the natural immune system with a novel display method for efficient selection of high-affinity antibodies," J Mol Biol. Feb. 29, 2008;376(4):1182-200.
Schoonbroodt S, et al., "Oligonucleotide-assisted cleavage and ligation: a novel directional DNA cloning technology to capture cDNAs. Application in the construction of a human immune antibody phage-display library" Nucleic Acids Res. May 19, 2005;33(9):e81.
Schroeder Jr, HW et al., "Slow, programmed maturation of the immunoglobulin HCDR3 repertoire during the third trimester of fetal life," 2001 Blood 98; 2745-2751.
Sidhu SS et al., "Phage-displayed antibody libraries of synthetic heavy chain complementarity determining regions," J Mol Biol. Apr. 23, 2004;338(2):299-310.
Sidhu SS, et al., "Phage display for selection of novel binding peptides," Methods Enzymol. 2000;328:333-63.
Smith GP., "Filamentous fusion phage: novel expression vectors that display cloned antigens on the virion surface," Science. Jun. 14, 1985;228(4705):1315-7.
Söderling E et al., "Recombining germline-derived CDR sequences for creating diverse single-framework antibody libraries," Nat Biotechnol. Aug. 2000; 18(8):852-6.
Szybalski et al., "Class-IIS Restriction Enzymes—a Review." Gene, vol. 100: 13-26 (1991).
Zemlin M et al., "Expressed murine and human CDR-H3 intervals of equal length exhibit distinct repertoires that differ in their amino acid composition and predicted range of structures," 2003 J Mol Biol 334; 733-749.
Fagete et al., "Specificity tuning of antibody fragments to neutralize two human chemokines with a single agent," mAbs, vol. 1(3): 288-296 (2009).

* cited by examiner

```
VH1-2   QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCAR   SEQ ID NO: 1
VH1-18  QVQLVQSGAEVKKPGASVKVSCKASGYTFTSYGISWVRQAPGQGLEWMGWISAYNGNTNYAQKLQGRVTMTDTSTSTAYMELSRLRSDDTAVYYCAR   SEQ ID NO: 2
VH1-69  QVQLVQSGAEVKKPGSSVKVSCKASGGTFSSYAISWVRQAPGQGLEWMGGIIPIFGTANYAQKFQGRVTITADESTSTAYMELSSLRSEDTAVYYCAR  SEQ ID NO: 3
VH3-30  QVQLVESGGGVVQPGRSLRLSCAASGFTFSSYAMHWVRQAPGKGLEWVAVLSYDGSNKYYADSVKGRFTISRDNSKNTLYLQMNSLRAEDTAVYYCAR  SEQ ID NO: 4
VH3-48  EVQLVESGGGLVQPGGSLRLSCAASGFTFSSYSMNWVRQAPGKGLEWVSYISSSSTIYYADSVKGRFTISRDNAKNSLYLQMNSLRAEDTAVYYCAR   SEQ ID NO: 5
VH3-23  EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAK  SEQ ID NO: 6
VH5-51  EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCAR  SEQ ID NO: 7
VK1-33  DIQMTQSPSSLSASVGDRVTITCQASQDIS  NYLNWYQQKPGKAPKLLIYDASNLETGVPSRFSGSGSGTDFTFTISSLQPEDIATYYCQQYDNLPPTV SEQ ID NO: 8
VK1-39  DIQMTQSPSSLSASVGDRVTITCRASQSIS  SYLNWYQQKPGKAPKLLIYAASSLQSGVPSRFSGSGSGTDFTLTISSLQPEDFATYYCQQSYSTPPTV SEQ ID NO: 9
VK3-11  EIVLTQSPATLSLSPGERATLSCRASQSVS  SYLAWYQQKPGQAPRLLIYDASNRATGIPARFSGSGSGTDFTLTISSLEPEDFAVYYCQQRSNWPPTV SEQ ID NO: 10
VK3-15  EIVMTQSPATLSVSPGERATLSCRASQSVS  SNLAWYQQKPGQAPRLLIYGASTRATGIPARFSGSGSGTEFTLTISSLQPEDFAVYYCQQYNWPPTV  SEQ ID NO: 11
VK3-20  EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPPTV SEQ ID NO: 12
VL1-44  QSVLTQPPSASGTPGQRVTISCSGSSSNIGSNYVNWYQQLPGTAPKLLIYSNNQRPSGVPDRFSGSKSGTSASLAISGLQSEDEADYYCAAWDDSLNG  SEQ ID NO: 13
VL1-51  QSVLTQPPSVSAAPGQKVTISCSGSSSNIGNNYVSWYQQLPGTAPKLLIYENNKRPSGIPDRFSGSKSGTSATLGITGLQTGDEADYYCGTWDSSLSA  SEQ ID NO: 14
```

Fig. 5

```
|550      |2560      |2570      |2580      |2590      |2600      |2610      |2620      |2630      |2640      |2650
TATTACTGTGCGAGAGATGAGACGAATAACGGTAAGGCGTTTACCAGGTTTAAACGCTTTCAAGATTTAGGCGGTTTGGGGAAGGCCGTCTCTTGGGGCCAGGAACCCTGGTCACAGTCTCG  SEQ ID NO: 15
 V L Y C A R . D E . R . R I T V R . G G L P G L N A Y W E G A R L G A R L L G P G N P P G H S L         SEQ ID NO: 16
  Y Y C A R D E M R R I T V K A N N G K A V Y Q V . T R I G K A R L L G P G N P P G H S L                SEQ ID NO: 17
 I T V R D . E T N N G K A V Y Q V . T R I G K A R L L G P G N P P G H S L                               SEQ ID NO: 18

5'...CGTCTCN|NNNNNNN...3' SEQ ID NO: 19
3'...GCAGAGN|NNNN|NNN...5' SEQ ID NO: 20
```

```
gaggtgcagc tgttggagtc tgggggaggc ttggtacagc ctggggggtc cctgagactc tcctgtgcag cctctggatt caccttagc agctatgcca tgagctggt ccgccaggct ccagggaagg
  e  v  q   l  l  e  s   g  g  g   l  v  q   p  g  g  s   l  r  l   s  c  a   a  s  g  f   t  f  s    s  y  a   m  s  w   v  r  q  a   p  g  k
  r  g  a   a  v  g  v   w  g  r   l  g  t   a  w  g  v   p  e  t   l  l  c   s  l  w  i   h  l  -    q  l  c   h  e  l   g  p  p  g   s  r  e
  p  r  c  s  c  w  s   l  g  e   a  w  y  s   l  g  g    p  -  d   s  p  v   q  p  l  d   s  p  l   a  a  m  p  -  a    g  s  a  r    l  g  g  r
> ....VH3-23............................................................................................................................................>
  e  v  q   l  l  e  s   g  g  g   l  v  q   p  g  g  s   l  r  l   s  c  a   a  s  g  f   t  f  s   s  y  a   m  s  w    v  r  q  a   p  g  k ggctgagtg ggctccagct attagtggta gtggtggtag cacatactac gcagactccg tgaaggccg gttccacatc tccagagaca attccaagaa cacgctgtat ctgcaaatga acagcctgag
  g  a  v  g  l  s   y  -  w  -  w   -  w  w  -   h  i  l   r  r  l   r  e  g  p   v  h  h  l  q  r   f  f  t  i   s  r  d   n  s  k   n  t  l  y   l  q  m  n   s  l
  g  l  e   w  v  s   a  i  s  g   s  g  g  s   t  y  y   a  d  s   v  k  g   r  f  t  i   s  r  d   n  s  k   n  t  l  y    l  q  m  n   s  l
  g  w  s   g  s  q   l  l  v  v   v  v  v   a  h  t  t  q  t  p   -  r  a   g  s  p  s   p  e  t  i   p  r  t  r  c  l  k  -  t  a  -
> ....VH3-23............................................................................................................................................>
  g  l  e   w  v  s   a  i  s  g   s  g  g  s   t  y  y   a  d  s   v  k  g   r  f  t  i   s  r  d   n  s  k   n  t  l  y   l  q  m  n   s  l agccgaggac acggccgtat attactgtgc gaaatgagac gaataacggt aaggcggttta accaggttta aggcggttt accaggtttcg aaaggcgc gtctcttggg gccagggaac cctggtcaca gtctcg    SEQ ID NO: 37
  s  r  g   h  g  r  i   l  l  c   e  m  r  i   t  v  r  r  f  t  r  f   k  r  v  i  g  r  r  v  s  w   g  q  g   t  l  v  t    v  s      SEQ ID NO: 38
  r  a  e  d   t  a  v  y  y  c   a  k  -  d   e  -  r  -   g  g  l  p  g  l   n  a  y  w   e  g  a  s  l  g   a  r  e   p  w  s   q  s      SEQ ID NO: 39
  e  p  r   t  r  b  y   i  t  v   r  n  e  t  n  n  g   k  a  v  y   q  v  -   t  r  i   g  k  a  r  l  l   g  p  g  n   p  g  h  s   l      SEQ ID NO: 40
> ............................................................................................>>
  r  a  e  d   t  a  v  y  y  c   a  k  -  d   e  -  r  -  g  g  l  p  g  l   n  a  y  w   e  g  a  s  l  g   a  r  e   p  w  s   q  s      SEQ ID NO: 39
```

```
caggtgcagc tggtggagtc tgggggaggc gtggtccagc ctggggggtc cctgagactc tcctgtgcag cctctggatt cacctttagt agctatgcta tgcactgggt ccgccaggct ccaggcaagg
  q  v  q   l  v  e  s   g  g  g  v   v  q  p  g   g  s  l  r   l  s  c  a   a  s  g  f   t  f  s  s   y  a  m  h   w  v  r  q   a  p  g  k
                                                              .........VH3-30.........
  q  v  q   l  v  e  s   g  g  g  v   v  q  p  g   r  s  l  r   l  s  c  a   a  s  g  f   t  f  s  s   y  a  m  h   w  v  r  q   a  p  g  k ggctggagtg ggtggcagtt atatcatatg atggaagtaa taaatactac gcagactccg tgaagggccg attccaccatc tccagagaca attccaagaa cacgctgtat ctgcaaatga acagcctgag
  g  l  e   w  v  a  v   i  s  y  d   g  s  n  k   y  y  a  d   s  v  k  g   r  f  t  i   s  r  d  n   s  k  n  t   l  y  l  q   m  n  s  l
                                                              .........VH3-30.........
  g  l  e   w  v  a  v   i  s  y  d   g  s  n  k   y  y  a  d   s  v  k  g   r  f  t  i   s  r  d  n   s  k  n  t   l  y  l  q   m  n  s  l agctgaggac acggctgtgt attactgtgc gagatcagac aatactactt gggaaggcgc gtccttcttggg gcaagggaac cctggtcaca gtctcg      SEQ ID NO: 41
  s  l  r   t  a  v  y   y  c  a  r                                                                              SEQ ID NO: 42
                                                                                                                  SEQ ID NO: 43
                                                                                                                  SEQ ID NO: 44
                                                                                                                  SEQ ID NO: 43
```

Fig. 8 Cont.

VH3-48 AF gaggtgcagc tggtggagtc tgggggaggc ttggtacagc ctgggggtc cctgagactc tcctgtgcag cctctggatt caccttcagt agctatagca tgaactgggt ccgccaggct ccagggaagg
  r  g  a  a  g  g  v  W  g  r  l  g  t  a  w  g  v  p  g  g  s  l  r  l  c  s  l  W  i  h  l  q  -  l  -  h  e  l  g  p  p  g  s  r  e
  e  v  q  l  v  e  s  g  g  g  l  v  q  p  g  g  s  l  r  l  s  c  a  a  s  g  f  t  f  s  s  y  s  m  n  W  v  r  q  a  p  g  k
  p  r  c  s  W  W  s  l  g  e  a  W  y  s  l  g  g  g  p  -  d  s  p  v  g  p  l  d  s  p  s  v  a  i  a  -  t  g  s  a  r  l  q  g  r
>..............................VH3-48..............................>
  e  v  q  l  v  e  s  g  g  g  l  v  q  p  g  g  s  -  r  l  s  c  a  a  s  g  f  t  f  s  s  y  s  m  n  W  v  r  q  a  p  g  k ggctggagtg ggtttcatac attagtagta gtagtagtac catatactac gcagactctg tgaagggccg attcaccatc tccagagaca atgccaagaa ctcactgtat ctgcaaatga acagcctgag
  g  a  l  e  W  g  f  i  h  -  -  -  y  h  i  l  r  r  l  c  e  g  p  i  h  h  l  g  r  q  e  l  t  v  s  a  n  e  q  p  e
  g  l  e  W  v  s  Y  i  s  s  -  -  -  s  s  t  i  Y  Y  a  d  s  v  k  g  r  f  t  i  s  r  d  n  a  k  n  s  l  Y  l  q  m  n  s  l
  g  W  s  g  f  h  t  l  v  v  v  v  v  p  Y  t  q  t  -  r  a  d  s  p  s  p  e  t  m  p  r  t  h  c  i  c  k  -  t  a  -
>..............................VH3-48..............................>
  g  l  e  W  v  s  Y  i  s  s  -  -  -  s  s  t  i  Y  Y  a  d  s  v  k  g  r  f  t  i  s  r  d  n  a  k  n  s  l  Y  l  q  m  n  s  l agccgaggac acggctgtgt attactgtgc gagatgagac gaataacggt aagcggttta ccaggttta vrrttrf krv lgrr vsw gqg tlvt vs
  s  r  g  h  g  c  v  l  l  c  e  m  r  r  i  t  v  r  r  f  t  r  f  k  r  v  l  g  r  r  v  s  W  g  q  g  t  l  v  t  v  s
  r  a  e  d  t  a  v  Y  Y  c  a  r  -  d  e  -  r  -  g  g  l  p  g  l  n  a  Y  W  e  g  a  s  l  g  a  r  e  p  W  s  q  q  s
  e  p  r  t  r  l  c  i  t  v  r  d  e  t  n  n  g  k  a  v  Y  q  v  -  t  r  i  g  g  k  a  r  l  l  g  p  g  n  p  g  h  s  l
>..............................VH3-48..............................>
  r  a  e  d  t  a  v  Y  Y  c  a  r  -  d  e  -  r  -  g  g  l  p  g  i  n  a  Y  W  e  g  a  s  l  g  a  r  e  p  W  s  q  q  s

SEQ ID NO: 45
SEQ ID NO: 46
SEQ ID NO: 47
SEQ ID NO: 48

SEQ ID NO: 47

```
gaggtgcagc tggtgcagtc tggagcacag gtgaaaaagc ccggggagtc tctgaagatc tcctgtaagg gttctggata cagctttacc agctactgga tcggctgggt gcgccagatg cccgggaaag
 e  v  q  l  v  q  s  g  a  e  v  k  k  p  g  e  s  l  k  i  s  c  k  g  s  g  y  s  f  t  s  y  w  i  g  w  v  r  q  m  p  g  k
>>...........................................................................................VH5-51.........................................................> gcctggagtg gatgggaatc atctatcctg gtgactctga taccagatac agcccgtcct tccaaggcca gatcaccatc tcagccgaca agtccatcag caccgcctac ctgcagtgga gcagcctgaa
 g  l  e  w  m  g  i  i  y  p  g  d  s  d  t  r  y  s  p  s  f  q  g  q  v  t  i  s  a  d  k  s  i  s  t  a  y  l  q  w  s  s  l
>.............................................................................................VH5-51.........................................................> ggcctcggac accgccatgt attactgcgc gagatgagac gaataacggt aaggcggttt accagtttta aacgcgtatt gggaaggcgc gtctcttggg gccagggaac cctggtcaca gtctcg
 k  a  s  d  t  a  m  y  y  c  a  r  -  d  e  -  r  -  g  g  l  p  g  l  n  a  y  w  e  g  a  s  l  g  a  r  e  p  w  s  g  q  s
>..............................................................................................VH5-51.........................................................>
```

```
VK3-11G AF
gaattgtgt tgacagtc tccagccacc ctgtctttgt ctccagggga agagccacc ctctcctgca gggccagtca ggtgttagc agctacttag cctgtacca acagaaacct ggccaggctc
 g n c v d t v s s h p v f v s p g k s h p l l q g q s e c - g l l s l v p t e t w p g
 e i v l t c s p a t l s l c - h s l q p p c l c l g g   e r a t l s c r a s q s v s s y l a w y q q k p g q a
 r k l c - h s l q p p c l c l g g   k e p p s p a   g p v r v l   a a t -   p g t n r n l a r l
 >>.......................................VK 3-11G..........................................>
 e i v l t g s p a t l s i s p g e r a t l s c r a s q s v s s y l a w y q q k p g g a ccaggctcct catctatgat gcatccaaca gggccactgg catcccagcc aggttcagtg gcagtgggtc tgggacagac ttcactctca ccatcagcag cctagagcct gaagattttg cagtttatta
 s q a P l h l - c i q q g q h w h p s q v q w q w v w d r l h s l f t l t i s P r a - r f c s l l
 P r l l i y d a s n r a t g i P a r f s g s g s g t d f t l t i s s l e P e d f a v y
 p g s s s m h P t g p l a s q p g s v a v g l g g t s l s p s a - s l i k i l q f i
 >.................................................VK 3-11G.......................................>
 P r l l i y d a s n r a t g i P a r f s g s g s g t d f t l t i s s l e P e d f a v y ctgtcagcag cgagacgaat aacgtaagg cgttttacca ggttttaaacg cgtattggga aggcgtct cattcggcca agggaccaag gtggaaatca aagggcggc cgca
 l s a a r r i t v r r f k r v l g r r v s f g q g t k v e i k g a a a
 y c q q r d e - r - g g l p g l n a y w e g a s h s a k g p r w k s k g r p
 t v s s e t n n g k a v y q v - t r i g k a r l i r p r d g g g n q r g g r
 >.......................................VK 3-11G........................................>>
 y c q q r d e - r - g g l p g l n a y w e g a s h s a k g p r w k s k g r p

SEQ ID NO: 69

VH3-11R AF

```
gaaattggtg tgacacagtc tccagccacc ctgtctttgt ctccagggga aagagccacc ctctccctgca ggccagtca gagtgttagc agctacttag cctgtaccaa acagaaacct ggccaggctc
 g n c  v d t v  s s h  p v f  v s r g  k s h  p l l s  p v f  v s r g  k s h  p l l s  p v f  v s r g  k s h  p l l s  p v f  v s r g  k s h  p l l s
 e i v  l t q  s p a t  l s l s  p g e  r a t  l s c  r a s  q s v s  s y l  a w y  q q k p  g q a
 r k l c  - h s  l q p  p c l c  l q g  k e p  p s p a  g p v r l  a a t -  p g t  n r n l  a r l  ..>
 >>..........................VK

| SAMPLE | FW3 | H3 | H3/FW4 | CDR3 LENGTH | | | |
|---|---|---|---|---|---|---|---|
| 1a | CAK | AFRPNWGSRVLYF | DYW | 15 | SEQ | ID NO: | 101 |
| 1b | CAK | LNWGWF | DPW | 8 | SEQ | ID NO: | 102 |
| 1c | CAK | GWEGEY | DYW | 8 | SEQ | ID NO: | 103 |
| 1d | CAK | DLWLDSSSNWF | DPW | 13 | SEQ | ID NO: | 104 |
| 1e | CAK | DLPG | DPHW | 7 | SEQ | ID NO: | 105 |
| 1f | CAK | APPTGYF | DYW | 9 | SEQ | ID NO: | 106 |
| 1g | CAK | VGLTGVHF | DYW | 10 | SEQ | ID NO: | 107 |
| 1h | CAK | DSYGSGSYYN | DYW | 12 | SEQ | ID NO: | 108 |
| 2a | CAK | VAGTWGRVAYYF | DYW | 14 | SEQ | ID NO: | 109 |
| 2b | CAK | VTGVFVGNF | DYW | 11 | SEQ | ID NO: | 110 |
| 2c | CAK | DARNSGSYF | DYW | 11 | SEQ | ID NO: | 111 |
| 2d | CAK | GVRTGVVF | DYW | 10 | SEQ | ID NO: | 112 |
| 2e | CAK | GVVNWGTRRKGWF | DPW | 15 | SEQ | ID NO: | 113 |
| 2f | CAK | WGGWF | DPW | 7 | SEQ | ID NO: | 114 |
| 2g | CAK | RRDNWGSV | DW | 9 | SEQ | ID NO: | 115 |
| 2h | CAK | GSGFSSGWF | DSW | 11 | SEQ | ID NO: | 116 |

SYNTHETIC POLYPEPTIDE LIBRARIES AND METHODS FOR GENERATING NATURALLY DIVERSIFIED POLYPEPTIDE VARIANTS

RELATED APPLICATIONS

This application claims the benefit of U.S. Provisional Application Nos. 61/179,850, filed May 20, 2009, 61/287,336, filed Dec. 17, 2009 and 61/314,794, filed Mar. 17, 2010, the contents of each of which are hereby incorporated by reference in their entirety.

INCORPORATION BY REFERENCE OF SEQUENCE LISTING

The contents of the text file named "418USSeqList.txt," which was created on May 20, 2010 and is 141 KB in size, are hereby incorporated by reference in their entirety.

FIELD OF THE INVENTION

The invention relates to the generation of libraries of DNA sequences encoding homologous polypeptides and to the use of such libraries. This invention in particular relates to the generation of collections of synthetic antibody fragments in which one or several complementary determining regions (CDR) are replaced by a collection of the corresponding CDR captured from a natural source. The invention further relates to the generation of collections of antibody fragments containing CDR derived from an immunized animal and their use as a better source to derive high affinity antibody fragments. The invention further relates to the diversification of a portion of a polypeptide by inserting a diversified sequence of synthetic or natural origin without the need for modification of the original polypeptide coding sequence.

BACKGROUND OF THE INVENTION

An antibody is composed of four polypeptides: two heavy chains and two light chains. The antigen binding portion of an antibody is formed by the light chain variable domain (VL) and the heavy chain variable domain (VH). At one extremity of these domains six loops form the antigen binding site and also referred to as the complementarity determining regions (CDR). Three CDRs are located on the VH domain (H1, H2 and H3) and the three others are on the VL domain (L1, L2 and L3). During B cell development a unique immunoglobulin region is formed by somatic recombination known as V(D)J recombination. The variable region of the immunoglobulin heavy or light chain is encoded by different gene segments. The heavy chain is encoded by three segments called variable (V), diversity (D) and joining (J) segments whereas the light chain variable is formed by the recombination of only two segments V and J. A large number of antibody paratopes can be generated by recombination between one of the multiple copies of the V, D and J segments that are present in the genome. The V segment encodes the CDR1 and CDR2 whereas the CDR3 is generated by the recombination events. During the course of the immune response further diversity is introduced into the antigen binding site by a process called somatic hypermutation (SHM). During this process point mutations are introduced in the variable genes of the heavy and light chains and in particular into the regions encoding the CDRs. This additional variability allows for the selection and expansion of B cells expressing antibody variants with improved affinity for their cognate antigen.

In recent years several display technologies have emerged and allow for the screening of large collections of proteins or peptides. These include phage display, bacterial display, yeast display and ribosome display (Smith G P. Science. 1985 Jun. 14; 228(4705):1315-7; Hanes J and Plückthun A. Proc Natl Acad Sci USA. 1997 May 13; 94(10):4937-42; Daugherty P S et al., Protein Eng. 1998 September; 11(9):825-32; Boder E T and Wittrup K D. Nat. Biotechnol. 1997 June; 15(6):553-7). In particular these methods have been applied extensively to antibodies and fragments thereof. A number of methods have been described to generate libraries of polypeptides and to screen for members with desired binding properties.

A first approach is to capture by gene amplification rearranged immunoglobulin genes from natural repertoires using either tissues or cells from humans or other mammals as a source of genetic diversity. These collections of rearranged heavy and light chains (VH and VL) are then combined to generate libraries of binding pairs that can be displayed on bacteriophage or on other display packages such as bacteria, yeast or mammalian cells. In this case a large fraction of the immunoglobulin repertoire found in the donor is captured. Thus all of the frameworks encoded by the donor germline genes can be found in such repertoires as well as diversity generated both by V(D)J recombination and by somatic hypermutation (Marks J D et al., J Mol. Biol. 1991 Dec. 5; 222(3):581-97; McCaffety U.S. Pat. No. 5,969,108).

A limitation of natural repertoires is that naturally occurring antibodies can be based on frameworks with low intrinsic stability that limit their expression levels, shelf life and their usefulness as reagents or therapeutic molecules. In order to overcome these limitations a number of methods have been developed to generate synthetic antibody libraries. In these approaches, a unique or a limited number of selected antibody framework encoded by their corresponding germline genes are selected. The selection of these frameworks is commonly based on their biochemical stability and/or their frequency of expression in natural antibody repertoires. In order to generate a collection of binding proteins, synthetic diversity is then introduced in all or a subset of CDRs. Typically either the whole or part of the CDR is diversified using different strategies. In some cases diversity was introduced at selected positions within the CDRs (Knappik A et al., J Mol. Biol. 2000 Feb. 11; 296(1):57-86). Targeted residues can be those frequently involved in antigen contact, those displaying maximal diversity in natural antibody repertoires or even residues that would be preferentially targeted by the cellular machinery involved in generating somatic hypermutations during the natural affinity maturation process (Balint R F, Larrick J W. Gene. 1993 Dec. 27; 137(1):109-18.).

Several methods have been used to diversify the antibody CDRs. Overlapping PCR using degenerate oligonucleotides have been extensively used to assemble framework and CDR elements to reconstitute antibody genes. In another approach, unique restriction enzyme sites have been engineered into the framework regions at the boundary of each CDR allowing for the introduction of diversified CDRs by restriction enzyme mediated cloning. In any case, as all the members of the library are based on frameworks with selected and preferred characteristics, it is anticipated that the antibodies derived from these repertoires are more stable and provide a better source of useful reagents. (Knappik, U.S. Pat. No. 6,696,248; Sidhu S S, et al., Methods Enzymol. 2000; 328:333-63; Lee C V et al., J Mol. Biol. 2004 Jul. 23; 340(5):1073-93).

However, an important limitation of these synthetic libraries is that a significant proportion of the library members are not expressed because the randomly diversified sequences do not allow for proper expression and/or folding of the protein.

This problem is particularly significant for the CDR3 of the heavy chain. Indeed, this CDR often contributes to most of the binding energy to the antigen and is highly diverse in length and sequence. While the other CDR (H1, H2, L1, L2 and L3) can only adopt a limited number of three dimensional conformations, known as canonical folds, the number of conformations that can be adopted by the heavy chain CDR3 remains too diverse to be predicted (Al-Lazikani B et al., J Mol. Biol. 1997 Nov. 7; 273(4):927-48). In addition, the use of long degenerate oligonucleotides used to cover long CDR H3 often introduces single base-pair deletions. These factors significantly reduce the functional size of synthetic repertoires.

Both natural and synthetic repertoires have advantages and limitations. On one hand, strategies relying on the capture of naturally rearranged antibody variable genes are not optimal as they include potentially less favorable frameworks within the library. A positive aspect is that these rearranged variable genes include CDRs which are compatible with proper domain folding as they have been expressed in context of a natural antibody. On the other hand, strategies based on selecting frameworks and inserting synthetic diversity benefit from the improved stability of the frameworks but are limited by the large number of CDR sequences that are not compatible with folding and/or expression and can destabilize the overall domain (FIG. 1A). There is therefore a need for novel approaches that could combine the benefits of using selected frameworks with desirable characteristics and combine them with properly folded CDRs for instance derived from natural repertoires.

All described approaches to generate antibody libraries either by capturing naturally rearranged antibody sequences or by generating diversity by synthetic means are limited by the occurrence of frame shift mutations leading to non-functional antibody sequences. These mutations can appear at multiple steps of the molecular handling of the DNA encoding the antibodies such as PCR amplification and DNA fragment assembly as well as molecular cloning. The frequency of non-functional members in antibody libraries typically ranges from 15% to 45% depending of the strategies employed to capture or generate the antibody diversity (Persson M A et al., Proc Natl Acad Sci USA. 1991 Mar. 15; 88(6):2432-6; Schoonbroodt S, et al., Nucleic Acids Res. 2005 May 19; 33(9):e81; Söderling E et al., Nat Biotechnol. 2000 August; 18(8):852-6; Rothe et al., J Mol Biol. 2008 Feb. 29; 376(4):1182-200). The frequency of sequences encoding non functional antibodies has a major impact on the antibody identification process. First, the functional size of the library is reduced and, because non-functional clones often have a growth advantage during the propagation of the libraries, they expand faster and can compromise the identification process of antibody candidates (De Bruin R et al., Nat Biotechnol 1999 Apr. 17: 397-399). These issues are recognized as serious limitations for fully exploiting the potential of antibody libraries. The generation of highly functional libraries remains a challenge in the field and has prompted many efforts to improve the process. For instance, multiple diversification strategies aiming at mimicking the amino acids usage found in natural CDR sequences have been used in order to more effectively sample the huge diversity of possible sequence combination encoded by synthetic CDRs (de Kruif J et al., J Mol Biol. 1995 Apr. 21; 248(1):97-105; Sidhu S S et al., J Mol Biol. 2004 Apr. 23; 338(2):299-310). Another approach is to clean up the initial library in order to remove nonfunctional clones at the potential expense of diversity loss. This has been applied to the pre-selection of synthetic repertoires by binding the antibody library to a generic ligand. This step allowed for the enrichment of library members that are able to express and to fold properly and can be used to recreate a more functional library (Winter and Tomlinson, U.S. Pat. No. 6,696,245 B2). Regardless of the approach the quality of any library is dependent on the efficiency of the molecular biology methods applied to generate the library and generally lead to 15% to 45% non-functional members of the library. There is therefore a need for novel and highly efficient approaches that minimize the frequency on non-functional genes due to frame shifts introduced during the molecular cloning steps and that maximize the functionality of libraries by capturing CDR regions having a high propensity of being correctly folded into antibody frameworks with desirable properties. Furthermore, there is a need for approaches that allow the capture of the CDR sequences from an animal immune repertoire into a therapeutically useful context such as human antibody frameworks in order to improve the generation process of high affinity antibodies.

SUMMARY OF THE INVENTION

The present invention provides methods of generating libraries of nucleic acid sequences that combine the benefits of stable framework selection and the insertion of naturally encoded complementarity determining regions (CDRs) or amino acid sequences that can fulfill the role of a CDR that have been selected in a natural context of a functional polypeptide such as an antibody. The method allows for the recovery of long CDRs or amino acid sequences that can fulfill the role of a CDR that are very difficult to encode using synthetic approaches. This invention, by combining stable frameworks and properly folded CDRs or amino acid sequences that can fulfill the role of a CDR, maximizes the proportion of functional antibodies in the library and therefore the performance of the selection process and the quality of selected clones. The invention provides a method to capture naturally expressed CDRs from different species and to insert them into a human antibody framework. This allows for the use of CDR H3 repertoires that differ significantly in length and composition when compared to the human repertoire. The invention enables the generation of human antibody fragments featuring structural repertoires derived from other species and thus the capacity to sample different structural spaces. The present methods are also used to introduce CDRs of synthetic origin or amino acid sequences that can fulfill the role of a CDR with a higher success frequency than alternative methods introducing fewer errors causing frame shifts in the coding sequence. Libraries generated using the present methods contain a high frequency of functional variants. Libraries of variants generated according to this method are used for selection and screening with any described display, selection and screening technology.

The analysis of immune repertoires from different species or, within a species, at different development stages has revealed some striking differences in the characteristics of CDR H3 composition and length. For instance the average CDRH3 length in humans is longer in adult when compared to fetal life or to newborns (Schroeder Jr, H W et al., 2001 Blood 98; 2745-2751). Interestingly despite large similarities between human and primate antibody germline genes, the evolution of the CDRH3 length during development differs (Link J M et al., Molecular Immunol. 2005 42; 943-955). The comparison of CDR H3 sequences found in mice and humans clearly shows that the average length is significantly shorter in mice (Rock E P et al., J Exp Med 1994 179; 323-328). During early B cell development in the bone marrow, the average CDR H3 length increases in mice whereas it tends to decrease in humans and in addition the amino acid composition of the murine and human CDRH3 repertoires differ (Zemlin M et al., 2003 J Mol Biol 334; 733-749; Ivanov I et al., 2005 J Immunol 174; 7773-7780). These examples indicate that different species express different ranges of CDR H3 repertoires despite the fact that they are globally exposed to similar classes of antigens and the biological significance of these observations remain to be further studied. It has been demonstrated that the shape of the combining site of antibodies directed against small antigens such as haptens or peptides differ from those directed against large proteins and the shape of the combining site is dictated by the length and composition of the CDRs (Collis A et al., J Mol Biol 2003 325; 337-354). From these finding it can be anticipated that the CDR H3 repertoire expressed by different species have varying propensities to react efficiently against different target classes.

The methods and antibody libraries provided herein are designed to exploit the various repertoires expressed by different species for the generation of therapeutic antibodies. These repertoires that explore different tridimensional spaces might allow for the generation of antibodies against a wider variety of target classes and epitopes. Methods to generate libraries form naïve or immunized animals are well described and these methods allow for the capturing of the corresponding repertoires and the generation of antibodies. However, antibodies derived from these libraries are not of human origin and are therefore not well suited for human therapy without performing further engineering work such as humanization. There is therefore a need for novel methods to harness the diversity expressed in the repertoire from different species and to exploit this diversity in the therapeutically useful context of a human antibody.

The methods and antibody libraries provided herein address several of the limitations described above and are an improvement over the current art. First, the methods provided herein combine the benefits of stable framework selection and the insertion of naturally encoded CDRs that have been selected in a natural context of a functional antibody. Second, the methods allow for a highly efficient insertion of synthetic or natural CDRs sequences into an antibody framework that significantly minimizes the number of frame shifts in the library and therefore improves its quality. Finally, the invention allows for a novel way to use naturally occurring antibody structural diversity by capturing naturally expressed CDR H3 repertoires from different species and to insert them into human antibody frameworks. It is thus possible to exploit these structurally diverse repertoires in a productive way for the generation of antibodies for human therapy.

The methods provided herein generate antibodies that contain a stable framework and correctly folded CDRs or amino acid sequences that can fulfill the role of a CDR. The methods capture the natural diversity of sequences in stable frameworks.

In the methods provided herein, the germline sequences for framework regions 1, 2 and 3 (FR1, FR2 and FR3) are selected from the desired organism, for example, from the human genome (see e.g., FIGS. 2 and 6). In one embodiment of this method, selected antibody variable domains are modified by introducing a stuffer sequence that will serve as an integration site for diversified sequences. Diversity is introduced into the sequence outside of the immunoglobulin coding region by introducing restriction enzyme recognition sites, for example, Type IIs restriction sites, at a desired location such as the variable heavy chain complementarity determining region 3 (CDR H3), the variable light chain complementarity determining region 3 (CDR L3), the variable heavy chain complementarity determining region 1 (CDR H1), the variable light chain complementarity determining region 1 (CDR L1), the variable heavy chain complementarity determining region 2 (CDR H2) or the variable light chain complementarity determining region 2 (CDR L2). While the examples provided herein demonstrate diversity at the CDR3 region (in the variable heavy chain region and/or variable light chain region), it is understood that diversity can be achieved at any desired location, such as, but not limited to, the CDR1 region (in the variable heavy chain region and/or variable light chain region) or the CDR2 region (in the variable heavy chain region and/or variable light chain region). Diversified DNA sequences are generated with flanking sequences that include Type IIs restriction sites. In the methods provided herein, the cohesive ends generated by the restriction enzymes are compatible and the reading frame is maintained, thus allowing the diversified DNA fragments to be ligated into an acceptor framework.

The methods provided herein are also useful for generating amino acid sequences having diversified regions encoded therein. For example, in the methods provided herein, the sequences for the non-diversified portions of the encoded amino acid are selected from the desired organism, for example, from the human sequence. A portion of the encoded amino acid sequence is modified by introducing a stuffer sequence that will serve as an integration site for diversified sequences. Diversity is introduced into the sequence at the desired location(s) by introducing restriction enzyme recognition sites, for example, Type IIs restriction sites, at a desired location within the encoded amino acid sequence. Diversified DNA sequences are generated with flanking sequences that include Type IIs recognition sites. In the methods provided herein, the cohesive ends generated by the restriction enzymes are compatible and the reading frame is maintained, thus allowing the diversified DNA fragments to be ligated into an acceptor framework.

In the methods provided herein, an "Acceptor Framework" is generated using a "stuffer fragment" of DNA that contain and are, preferably, bordered by two Type IIs restriction enzyme sites. (See e.g., FIG. 6). Preferably, these two Type IIs restriction enzyme sites digest sequences at the boundary of the site at which diversity is desired, such as, for example, the CDR H3 region, the CDR L3 region, the CDR H1 region, the CDR L1 region, the CDR H2 region or the CDR L2 region. As used herein, the term "Acceptor Framework" refers to a nucleic acid sequence that include the nucleic acid sequences encoding the FR1, FR2, FR3 and FR4 regions, the nucleic acid sequences encoding two CDRs or amino acid sequences that can fulfill the role of these CDRs, and a "stuffer fragment" that serves as the site of integration for diversified nucleic acid sequence. For example, in embodiments where diversity at the CDR3 region (in the variable heavy chain region and/or the variable light chain region) is desired, the Acceptor Framework includes the nucleic acid sequences encoding the FR1, FR2, FR3 and FR4 regions, the nucleic acid sequences encoding the CDR1 and CDR2 regions, and a "stuffer fragment" that serves as the site of integration for diversified nucleic acid sequence. For example, in embodiments where diversity at the CDR2 region (in the variable heavy chain region and/or the variable light chain region) is desired, the Acceptor Framework includes the nucleic acid sequences encoding the FR1, FR2, FR3 and FR4 regions, the nucleic acid sequences encoding the CDR1 and CDR3 regions, and a "stuffer fragment" that serves as the site of integration for diversified nucleic acid sequence. For example, in embodiments where diversity at the CDR1 region (in the variable heavy chain regions and/or the variable light chain regions) is desired, the Acceptor Framework includes the nucleic acid sequences encoding the FR1, FR2, FR3 and FR4 regions, the nucleic acid sequences encoding the CDR2 and CDR3 regions, and a "stuffer fragment" that serves as the site of integration for diversified nucleic acid sequence.

The terms "stuffer fragment", "stuffer DNA fragment" and "stuffer sequence" or any grammatical variation thereof are used interchangeably herein to refer to a nucleic acid sequence that includes at least two Type IIs recognition sites and a diversified sequence. The Acceptor Framework can be a variable heavy chain (VH) Acceptor Framework or a variable light chain (VL) Acceptor Framework. The use of the Acceptor Frameworks and the stuffer fragments contained therein allow for the integration of a CDR sequence (natural or synthetic) or an amino acid sequence that can fulfill the role of the CDR into the acceptor framework with no donor framework nucleotides or residues contained therein or needed for integration. For example, the use of the Acceptor Frameworks and the stuffer fragments contained therein allow for the integration of a CDR sequence (natural or synthetic) selected from CDR H3, CDR L3, CDR H2, CDR L2, CDR H1 and CDR L1, or an amino acid sequence that can fulfill the role of a CDR selected from CDR H3, CDR L3, CDR H2, CDR L2, CDR H1 and CDR L1 into the acceptor framework with no donor framework nucleotides or residues contained therein or needed for integration. Thus, upon integration, the stuffer fragment is removed in full, and the coding region of the acceptor protein and the inserted proteins fragments (i.e., the CDRs) are intact.

The methods provided herein use primers that are designed to contain cleavage sites for Type IIs restriction enzymes at the boundary of the site of at which diversity is desired, for example, the CDR H3 region, the CDR L3 region, the CDR H2 region, the CDR L2, the CDR H1 region or the CDR L1 region. Random, naturally occurring CDR clones (see e.g., FIG. 10) or synthetic CDR sequences (see e.g., Example 6) or amino acid sequences that can fulfill the role of the CDR are captured in the Acceptor Frameworks used herein. For example, in embodiments where diversity at the CDR3 region (in the variable heavy chain region and/or the variable light chain region) is desired, random, naturally occurring CDR3 clones (see e.g., FIG. 10) or synthetic CDR3 sequences (see e.g., Example 6) or amino acid sequences that can fulfill the role of a CDR3 are captured in the Acceptor Frameworks used herein. For example, in embodiments where diversity at the CDR2 region (in the variable heavy chain region and/or the variable light chain region) is desired, random, naturally occurring CDR2 clones (see e.g., methods shown in FIG. 10) or synthetic CDR2 sequences (see e.g., methods shown in Example 6) or amino acid sequences that can fulfill the role of a CDR2 are captured in the Acceptor Frameworks used herein. For example, in embodiments where diversity at the CDR1 region (in the variable heavy chain region and/or the variable light chain region) is desired, random, naturally occurring CDR1 clones (see e.g., methods shown in FIG. 10) or synthetic CDR1 sequences (see e.g., methods shown in Example 6) or amino acid sequences that can fulfill the role of a CDR1 are captured in the Acceptor Frameworks used herein. As an example, oligonucleotides primers specific for flanking regions of the DNA sequence encoding the CDR H3 of immunoglobulins, i.e., specific for the FR3 and FR4 of the variable region, were designed. Oligonucleotide primers specific for flanking regions of the DNA sequences encoding other regions, such as, for example, the CDR L3, CDR H1, CDR L1, CDR H2, or CDR L2, can also be designed. These oligonucleotides contain at their 5' end a site for a Type IIs restriction enzyme whereas their 3' portion matches the targeted DNA sequence.

In some embodiments, the primer is a nucleic acid selected from the group consisting of SEQ ID NOs: 120-254.

The methods provided herein use Type IIs restriction enzymes, such as, for example, FokI, to insert natural CDR sequences, such as, for example, natural CDR H3, CDR L3, CDR H1, CDR L1, CDR H2, or CDR L2 sequences into the acceptor frameworks described herein. The methods provided herein use Type IIs restriction enzymes, such as, for example, FokI, to insert synthetic CDR sequences, such as, for example, synthetic CDR H3, CDR L3, CDR H1, CDR L1, CDR H2, or CDR L2 sequences into the acceptor frameworks described herein. The methods provided herein use Type IIs restriction enzymes, such as, for example, FokI, to insert amino acid sequences that can fulfill the role of a desired CDR region, such as, for example, an amino acid sequence that can fulfill the role of a natural or synthetic CDR H3, CDR L3, CDR H1, CDR L1, CDR H2, or CDR L2 region into the acceptor frameworks described herein. The Type IIs restriction enzymes are enzymes that cleave outside of their recognition sequence to one side. These enzymes are intermediate in size, typically 400-650 amino acids in length, and they recognize sequences that are continuous and asymmetric. Suitable Type IIs restriction enzymes, also known as Type IIs restriction endonucleases, and the sequences they identify are described, for example, in Szybalski et al., "Class-IIS Restriction Enzymes—a Review." Gene, vol. 100: 13-26 (1991), the contents of which are hereby incorporated in their entirety by reference.

Primary Libraries include a VH Acceptor Framework and a fixed VL sequence (also referred to as a "dummy VL" sequence) or a VL Acceptor Framework and a fixed VH sequence (also referred to as a "dummy VH" sequence). Thus, Primary Libraries exhibit diversity in only one of the heavy or light chains. Secondary Libraries are generated by ligating a VH Acceptor Framework and a VL Acceptor Framework together (see e.g., Example 7). Secondary Libraries have diversity in both the heavy and light chains.

The invention provides methods for producing a collection of nucleic acids, wherein each nucleic acid encodes a human immunoglobulin heavy chain variable domain containing a plurality of heavy chain complementarity determining region 3 (CDR H3) isolated from the immunoglobulin variable domain repertoire from a non-human species. In some embodiments, the method includes the steps of: (a) providing a plurality of Acceptor Framework nucleic acid sequences encoding distinct human immunoglobulin heavy chain variable domains, each Acceptor Framework nucleic acid sequence containing a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a stuffer nucleic acid sequence including at least two Type IIs restriction enzyme recognition sites interspaced by a random nucleic acid sequence; (b) providing a plurality of diversified nucleic acid sequences encoding heavy chain complementarity determining region 3 (CDR H3) sequences isolated from a non-human species immunoglobulin repertoire wherein each of the plurality of diversified nucleic acid sequences includes a Type IIs restriction enzyme recognition site at each extremity; (c) digesting each of the plurality of nucleic acid sequences encoding the CDR H3 regions using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and (d) ligating the digested nucleic acid sequences encoding the CDR H3 regions or the amino acid sequences of step (c) into the digested Acceptor Framework of step (c) such that the FR3 and FR4 regions are interspaced by the nucleic acid sequences encoding the CDR H3 region or the amino acid sequence that can fulfill the role of a CDR3 region and a complete immunoglobulin variable domain encoding sequences that do not contain the Type IIs restriction enzyme recognition sites of steps (a) and (b) are restored.

In some embodiments, step (b) as set forth above is performed by amplifying the CDR H3 sequence from a non human species using oligonucleotide primers containing a Type IIs restriction site. In some embodiments, step (b) as set forth above is performed by amplifying the CDR H3 sequence from a non human species using oligonucleotide primers containing a FokI IIs restriction site. In some embodiments, the non-human species is non-human primate, rodent, canine, feline, sheep, goat, cattle, horse, or pig.

The invention provides methods for producing a library of nucleic acids, wherein each nucleic acid encodes an immunoglobulin variable domain by (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a stuffer nucleic acid sequence containing at least two Type IIs restriction enzyme recognition sites interspaced by a random nucleic acid sequence; (b) providing a plurality of diversified nucleic acid sequences encoding complementarity determining region 3 (CDR3) regions or encoding amino acid sequences that can fulfill the role of a CDR3 region, wherein each of the plurality of diversified nucleic acid sequences includes a Type IIs restriction enzyme recognition site at each extremity; (c) digesting each of the plurality of nucleic acid sequences encoding the CDR3 regions or amino acid sequences that can fulfill the role of a CDR3 region using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and (d) ligating the digested nucleic acid sequences encoding the CDR3 regions or the amino acid sequences that can fulfill the role of a CDR3 region of step (c) into the digested Acceptor Framework of step (c) such that the FR3 and FR4 regions are interspaced by the nucleic acid sequences encoding the CDR3 region or the amino acid sequence that can fulfill the role of a CDR3 region and a complete immunoglobulin variable domain encoding sequences that do not contain the Type IIs restriction enzyme recognition sites of steps (a) and (b) are restored.

In some embodiments, the Type IIs restriction enzyme recognition sites of step (a) and step (b) are recognized by the same Type IIs restriction enzyme. In some embodiments, the Type IIs restriction enzyme recognition sites of step (a) and step (b) are recognized by different Type IIs restriction enzymes. For example, the Type IIs restriction enzyme recognition sites are FokI recognition sites, BsaI recognition sites, and/or BsmBI recognition sites.

In some embodiments, the Acceptor Framework nucleic acid sequence is derived from a human gene sequence. For example, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51. In some embodiments, the human sequence is a human kappa light chain variable gene sequence or a sequence derived from a human kappa light chain variable gene sequence. For example, the human kappa light chain variable gene sequence is selected from VK1-33, VK1-39, VK3-11, VK3-15, and VK3-20. In some embodiments, the human sequence is a human lambda light chain variable gene sequence or a sequence derived from a human lambda light chain variable gene sequence. For example, the human lambda light chain variable gene sequence is selected from VL1-44 and VL1-51.

In one embodiment, the plurality of diversified nucleic acids encodes CDR3 regions, and the plurality of diversified nucleic acids includes naturally occurring sequences or sequences derived from immunized animals.

In one embodiment, the plurality of diversified nucleic acids includes or is derived from sequences selected from naturally occurring CDR3 sequences, naturally occurring Ig sequences from humans, naturally occurring Ig sequences from a mammal, naturally occurring sequences from a loop region of a T cell receptor in a mammal, and other naturally diversified polypeptide collections.

In one embodiment, the plurality of diversified nucleic acids encodes CDR3 regions, and the plurality of diversified nucleic acids includes or is derived from immunoglobulin sequences that occur naturally in humans that have been exposed to a particular immunogen or sequences derived from animals that have been identified as having been exposed to a particular antigen.

In one embodiment, the plurality of diversified nucleic acids encodes amino acid sequences that can fulfill the role of a CDR3 region, and the plurality of diversified nucleic acids includes synthetic sequences.

In another embodiment, the plurality of diversified nucleic acids encodes amino acid sequences that can fulfill the role of a CDR3 region, and the plurality of diversified nucleic acids includes synthetic sequences.

In some embodiments, the plurality of Acceptor Framework nucleic acid sequences include a mixture of at least one variable heavy chain (VH) Acceptor Framework nucleic acid sequence and at least one variable light chain Acceptor Framework nucleic acid sequence.

In some embodiments, the methods provided include the additional step of (e) transforming the expression vector of step (d) into a host cell and culturing the host cell under conditions sufficient to express the plurality of Acceptor Framework sequences. For example, the host cell is *E. coli*. In some embodiments, the expression vector is a phagemid vector. For example, the phagemid vector is pNDS1.

The invention also provides methods for producing a library of nucleic acids, wherein each nucleic acid encodes an immunoglobulin variable domain, by (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a stuffer nucleic acid sequence including at least two Type IIs restriction enzyme recognition sites interspaced by a random nucleic acid sequence, the FR2 and FR3 regions are interspaced by a complementarity determining region 2 (CDR2), and the FR3 and FR4 regions are interspaced by a complementarity determining region 3 (CDR3); (b) providing a plurality of diversified nucleic acid sequences encoding complementarity determining region 1 (CDR1) regions or encoding amino acid sequences that can fulfill the role of a CDR1 region, wherein each of the plurality of diversified nucleic acid sequences includes a Type IIs restriction enzyme recognition site at each extremity; (c) digesting each of the plurality of nucleic acid sequences encoding the CDR1 regions or amino acid sequences that can fulfill the role of a CDR1 region using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and (d) ligating the digested nucleic acid sequences encoding the CDR1 regions or the amino acid sequences that can fulfill the role of a CDR1 region of step (c) into the digested Acceptor Framework of step (c) such that the FR1 and FR2 regions are interspaced by the nucleic acid sequences encoding the CDR1 region or the amino acid sequence that can fulfill the role of a CDR1 region and a complete immunoglobulin variable domain encoding sequences that do not contain the Type IIs restriction enzyme recognition sites of steps (a) and (b) are restored.

In some embodiments, the Type IIs restriction enzyme recognition sites of step (a) and step (b) are recognized by the same Type IIs restriction enzyme. In some embodiments, the Type IIs restriction enzyme recognition sites of step (a) and step (b) are recognized by different Type IIs restriction enzymes. For example, the Type IIs restriction enzyme recognition sites are FokI recognition sites, BsaI recognition sites, and/or BsmBI recognition sites.

In some embodiments, the Acceptor Framework nucleic acid sequence is derived from a human gene sequence. For example, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51. In some embodiments, the human sequence is a human kappa light chain variable gene sequence or a sequence derived from a human kappa light chain variable gene sequence. For example, the human kappa light chain variable gene sequence is selected from VK1-33, VK1-39, VK3-11, VK3-15, and VK3-20. In some embodiments, the human sequence is a human lambda light chain variable gene sequence or a sequence derived from a human lambda light chain variable gene sequence. For example, the human lambda light chain variable gene sequence is selected from VL1-44 and VL1-51.

In one embodiment, the plurality of diversified nucleic acids encodes CDR1 regions, and the plurality of diversified nucleic acids include naturally occurring sequences or sequences derived from immunized animals.

In one embodiment, the plurality of diversified nucleic acids includes or is derived from sequences selected from naturally occurring CDR1 sequences, naturally occurring Ig sequences from humans, naturally occurring Ig sequences from a mammal, naturally occurring sequences from a loop region of a T cell receptor in a mammal, and other naturally diversified polypeptide collections.

In one embodiment, the plurality of diversified nucleic acids encodes CDR1 regions, and the plurality of diversified nucleic acids includes or is derived from immunoglobulin sequences that occur naturally in humans that have been exposed to a particular immunogen or sequences derived from animals that have been identified as having been exposed to a particular antigen.

In one embodiment, the plurality of diversified nucleic acids encodes amino acid sequences that can fulfill the role of a CDR1 region, and the plurality of diversified nucleic acids includes synthetic sequences.

In another embodiment, the plurality of diversified nucleic acids encodes amino acid sequences that can fulfill the role of a CDR1 region, and the plurality of diversified nucleic acids includes synthetic sequences.

In some embodiments, the plurality of Acceptor Framework nucleic acid sequences include a mixture of at least one variable heavy chain (VH) Acceptor Framework nucleic acid sequence and at least one variable light chain Acceptor Framework nucleic acid sequence.

In some embodiments, the methods provided include the additional steps of (e) cloning the library of nucleic acids encoding immunoglobulin variable domains of step (d) into an expression vector and (f) transforming the expression vector of step (e) into a host cell and culturing the host cell under conditions sufficient to express a plurality of immunoglobulin variable domain encoded by the library. For example, the host cell is *E. coli*. In some embodiments, the expression vector is a phagemid vector. For example, the phagemid vector is pNDS1.

The invention also provides methods for producing a library of nucleic acids, wherein each nucleic acid encodes an immunoglobulin variable domain, by (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a stuffer nucleic acid sequence including at least two Type IIs restriction enzyme recognition sites interspaced by a random nucleic acid sequence, and the FR3 and FR4 regions are interspaced by a complementarity determining region 3 (CDR3); (b) providing a plurality of diversified nucleic acid sequences encoding complementarity determining region 2 (CDR2) regions or encoding amino acid sequences that can fulfill the role of a CDR2 region, wherein each of the plurality of diversified nucleic acid sequences includes a Type IIs restriction enzyme recognition site at each extremity; (c) digesting each of the plurality of nucleic acid sequences encoding the CDR2 regions or amino acid sequences that can fulfill the role of a CDR2 region using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and (d) ligating the digested nucleic acid sequences encoding the CDR2 regions or the amino acid sequences that can fulfill the role of a CDR2 region of step (c) into the digested Acceptor Framework of step (c) such that the FR2 and FR3 regions are interspaced by the nucleic acid sequences encoding the CDR2 region or the amino acid sequence that can fulfill the role of a CDR2 region and a complete immunoglobulin variable domain encoding sequences that do not contain the Type IIs restriction enzyme recognition sites of steps (a) and (b) are restored.

In some embodiments, the Type IIs restriction enzyme recognition sites of step (a) and step (b) are recognized by the same Type IIs restriction enzyme. In some embodiments, the Type IIs restriction enzyme recognition sites of step (a) and step (b) are recognized by different Type IIs restriction enzymes. For example, the Type IIs restriction enzyme recognition sites are FokI recognition sites, BsaI recognition sites, and/or BsmBI recognition sites.

In some embodiments, the Acceptor Framework nucleic acid sequence is derived from a human gene sequence. For example, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51. In some embodiments, the human sequence is a human kappa light chain variable gene sequence or a sequence derived from a human kappa light chain variable gene sequence. For example, the human kappa light chain variable gene sequence is selected from VK1-33, VK1-39, VK3-11, VK3-15, and VK3-20. In some embodiments, the human sequence is a human lambda light chain variable gene sequence or a sequence derived from a human lambda light chain variable gene sequence. For example, the human lambda light chain variable gene sequence is selected from VL1-44 and VL1-51.

In one embodiment, the plurality of diversified nucleic acids encodes CDR2 regions, and the plurality of diversified nucleic acids includes naturally occurring sequences or sequences derived from immunized animals.

In one embodiment, the plurality of diversified nucleic acids includes or is derived from sequences selected from naturally occurring CDR2 sequences, naturally occurring Ig sequences from humans, naturally occurring Ig sequences from a mammal, naturally occurring sequences from a loop region of a T cell receptor in a mammal, and other naturally diversified polypeptide collections.

In one embodiment, the plurality of diversified nucleic acids encode CDR2 regions, and the plurality of diversified nucleic acids includes or is derived from immunoglobulin sequences that occur naturally in humans that have been exposed to a particular immunogen or sequences derived from animals that have been identified as having been exposed to a particular antigen.

In another embodiment, the plurality of diversified nucleic acids encodes amino acid sequences that can fulfill the role of a CDR2 region, and the plurality of diversified nucleic acids include synthetic sequences.

In some embodiments, the plurality of Acceptor Framework nucleic acid sequences include a mixture of at least one variable heavy chain (VH) Acceptor Framework nucleic acid sequence and at least one variable light chain Acceptor Framework nucleic acid sequence.

In some embodiments, the methods provided include the additional steps of (e) cloning the library of nucleic acids encoding immunoglobulin variable domains of step (d) into an expression vector and (f) transforming the expression vector of step (e) into a host cell and culturing the host cell under conditions sufficient to express a plurality of immunoglobulin variable domain encoded by the library. For example, the host cell is E. coli. In some embodiments, the expression vector is a phagemid vector. For example, the phagemid vector is pNDS1.

The invention also provides methods for making a target-specific antibody, antibody variable region or a portion thereof, by (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a stuffer nucleic acid sequence including at least two Type IIs restriction enzyme recognition sites interspaced by a random nucleic acid sequence; (b) providing a plurality of diversified nucleic acid sequences encoding complementarity determining region 3 (CDR3) regions or encoding amino acid sequences that can fulfill the role of a CDR3 region, wherein each of the plurality of diversified nucleic acid sequences includes a Type IIs restriction enzyme recognition site at each extremity; (c) digesting each of the plurality of nucleic acid sequences encoding the CDR3 regions or amino acid sequences that can fulfill the role of a CDR3 region using a Type IIs restriction enzyme that binds to the Type IIs restriction enzyme recognition site of step (b) and digesting the stuffer nucleic acid sequence of step (a) using a Type IIs restriction enzyme that binds to the Type IIs restriction enzyme recognition site of step (a); (d) cloning the digested nucleic acid sequences encoding the CDR3 regions or the amino acid sequences that can fulfill the role of a CDR3 region into an expression vector and ligating the digested nucleic acid sequences encoding the CDR3 regions or the amino acid sequences that can fulfill the role of a CDR3 region of step (c) into the Acceptor Framework such that the FR3 and FR4 regions are interspaced by the nucleic acid sequences encoding the CDR3 region or the amino acid sequence that can fulfill the role of a CDR3 region and a complete immunoglobulin variable gene encoding sequence is restored; (e) transforming the expression vector of step (e) into a host cell and culturing the host cell under conditions sufficient to express the plurality of Acceptor Framework sequences; (f) contacting the host cell with a target antigen; and (g) determining which expressed Acceptor Framework sequences bind to the target antigen.

In some embodiments, the Type IIs restriction enzyme recognition sites of step (a) and step (b) are recognized by the same Type IIs restriction enzyme. In some embodiments, the Type IIs restriction enzyme recognition sites of step (a) and step (b) are recognized by different Type IIs restriction enzymes. For example, the Type IIs restriction enzyme recognition sites are FokI recognition sites, BsaI recognition sites, and/or BsmBI recognition sites.

In some embodiments, the Acceptor Framework nucleic acid sequence is derived from a human gene sequence. For example, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51. In some embodiments, the human sequence is a human kappa light chain variable gene sequence or a sequence derived from a human kappa light chain variable gene sequence. For example, the human kappa light chain variable gene sequence is selected from VK1-33, VK1-39, VK3-11, VK3-15, and VK3-20. In some embodiments, the human sequence is a human lambda light chain variable gene sequence or a sequence derived from a human lambda light chain variable gene sequence. For example, the human lambda light chain variable gene sequence is selected from VL1-44 and VL1-51.

In one embodiment, the plurality of diversified nucleic acids encodes CDR3 regions, and the plurality of diversified nucleic acids includes naturally occurring sequences or sequences derived from immunized animals.

In one embodiment, the plurality of diversified nucleic acids includes or is derived from sequences selected from naturally occurring CDR3 sequences, naturally occurring Ig sequences from humans, naturally occurring Ig sequences from a mammal, naturally occurring sequences from a loop region of a T cell receptor in a mammal, and other naturally diversified polypeptide collections.

In one embodiment, the plurality of diversified nucleic acids encodes CDR3 regions, and the plurality of diversified nucleic acids includes or is derived from immunoglobulin sequences that occur naturally in humans that have been exposed to a particular immunogen or sequences derived from animals that have been identified as having been exposed to a particular antigen.

In another embodiment, the plurality of diversified nucleic acids encodes amino acid sequences that can fulfill the role of a CDR3 region, and the plurality of diversified nucleic acids include synthetic sequences.

In some embodiments, the plurality of Acceptor Framework nucleic acid sequences include a mixture of at least one variable heavy chain (VH) Acceptor Framework nucleic acid sequence and at least one variable light chain Acceptor Framework nucleic acid sequence.

In some embodiments, the expression vector is a phagemid vector. For example, the phagemid vector is pNDS1. In some embodiments, the host cell is E. coli.

In some embodiments, the method includes the additional step of (i) sequencing the immunoglobulin variable domain encoding sequences that bind the target antigen.

The invention also provides methods for making a target-specific antibody, antibody variable region or a portion thereof, by (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a stuffer nucleic acid sequence including at least two Type IIs restriction enzyme recognition sites interspaced by a random nucleic acid sequence, the FR2 and FR3 regions are interspaced by a complementarity determining region 2 (CDR2), and the FR3 and FR4 regions are interspaced by a complementarity determining region 3 (CDR3); (b) providing a plurality of diversified nucleic acid sequences encoding complementarity determining region 1 (CDR1) regions or encoding amino acid sequences that can fulfill the role of a CDR1 region, wherein each of the plurality of diversified nucleic acid sequences includes a Type IIs restriction enzyme recognition site at each extremity; (c) digesting each of the plurality of nucleic acid sequences encoding the CDR1 regions or amino acid sequences that can fulfill the role of a CDR1 region using a Type IIs restriction enzyme that binds to the Type IIs restriction enzyme recognition site of step (b) and digesting the stuffer nucleic acid sequence of step (a) using a Type IIs restriction enzyme that binds to the Type IIs restriction enzyme recognition site of step (a); (d) cloning the digested nucleic acid sequences encoding the CDR1 regions or the amino acid sequences that can fulfill the role of a CDR1 region into an expression vector and ligating the digested nucleic acid sequences encoding the CDR1 regions or the amino acid sequences that can fulfill the role of a CDR1 region of step (c) into the Acceptor Framework such that the FR1 and FR2 regions are interspaced by the nucleic acid sequences encoding the CDR1 region or the amino acid sequence that can fulfill the role of a CDR1 region and a complete immunoglobulin variable gene encoding sequence is restored; (e) transforming the expression vector of step (e) into a host cell and culturing the host cell under conditions sufficient to express the plurality of Acceptor Framework sequences; (f) contacting the host cell with a target antigen; and (g) determining which expressed Acceptor Framework sequences bind to the target antigen.

In some embodiments, the Type IIs restriction enzyme recognition sites of step (a) and step (b) are recognized by the same Type IIs restriction enzyme. In some embodiments, the Type IIs restriction enzyme recognition sites of step (a) and step (b) are recognized by different Type IIs restriction enzymes. For example, the Type IIs restriction enzyme recognition sites are FokI recognition sites BsaI recognition sites, and/or BsmBI recognition sites.

In some embodiments, the Acceptor Framework nucleic acid sequence is derived from a human gene sequence. For example, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51. In some embodiments, the human sequence is a human kappa light chain variable gene sequence or a sequence derived from a human kappa light chain variable gene sequence. For example, the human kappa light chain variable gene sequence is selected from VK1-33, VK1-39, VK3-11, VK3-15, and VK3-20. In some embodiments, the human sequence is a human lambda light chain variable gene sequence or a sequence derived from a human lambda light chain variable gene sequence. For example, the human lambda light chain variable gene sequence is selected from VL1-44 and VL1-51.

In one embodiment, the plurality of diversified nucleic acids encodes CDR1 regions, and the plurality of diversified nucleic acids includes naturally occurring sequences or sequences derived from immunized animals.

In one embodiment, the plurality of diversified nucleic acids includes or is derived from sequences selected from naturally occurring CDR1 sequences, naturally occurring Ig sequences from humans, naturally occurring Ig sequences from a mammal, naturally occurring sequences from a loop region of a T cell receptor in a mammal, and other naturally diversified polypeptide collections.

In one embodiment, the plurality of diversified nucleic acids encodes CDR1 regions, and the plurality of diversified nucleic acids includes or is derived from immunoglobulin sequences that occur naturally in humans that have been exposed to a particular immunogen or sequences derived from animals that have been identified as having been exposed to a particular antigen.

In another embodiment, the plurality of diversified nucleic acids encodes amino acid sequences that can fulfill the role of a CDR1 region, and the plurality of diversified nucleic acids includes synthetic sequences.

In some embodiments, the plurality of Acceptor Framework nucleic acid sequences include a mixture of at least one variable heavy chain (VH) Acceptor Framework nucleic acid sequence and at least one variable light chain Acceptor Framework nucleic acid sequence.

In some embodiments, the expression vector is a phagemid vector. For example, the phagemid vector is pNDS1. In some embodiments, the host cell is *E. coli*.

In some embodiments, the method includes the additional step of (i) sequencing the immunoglobulin variable domain encoding sequences that bind the target antigen.

The invention provides methods for making a target-specific antibody, antibody variable region or a portion thereof, by (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a stuffer nucleic acid sequence including at least two Type IIs restriction enzyme recognition sites interspaced by a random nucleic acid sequence, and the FR3 and FR4 regions are interspaced by a complementarity determining region 3 (CDR3); (b) providing a plurality of diversified nucleic acid sequences encoding complementarity determining region 2 (CDR2) regions or encoding amino acid sequences that can fulfill the role of a CDR2 region, wherein each of the plurality of diversified nucleic acid sequences includes a Type IIs restriction enzyme recognition site at each extremity; (c) digesting each of the plurality of nucleic acid sequences encoding the CDR2 regions or amino acid sequences that can fulfill the role of a CDR2 region using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); (d) ligating the digested nucleic acid sequences encoding the CDR2 regions or the amino acid sequences that can fulfill the role of a CDR2 region of step (c) into the digested Acceptor Framework of step (c) such that the FR2 and FR3 regions are interspaced by the nucleic acid sequences encoding the CDR2 region or the amino acid sequence that can fulfill the role of a CDR2 region and complete immunoglobulin variable domain encoding sequences that do not contain the Type IIs restriction enzyme recognition sites of steps (a) and (b) are restored; (e) cloning the library of nucleic acids encoding immunoglobulin variable domains of step (d) into an expression vector; (f) transforming the expression vector of step (e) into a host cell and culturing the host cell under conditions sufficient to express a plurality of immunoglobulin variable domains encoded by the library; (g) contacting the plurality of immunoglobulin variable domains of step (f) with a target antigen; and (h) determining which expressed immunoglobulin variable domain encoding sequences bind to the target antigen.

In some embodiments, the Type IIs restriction enzyme recognition sites of step (a) and step (b) are recognized by the same Type IIs restriction enzyme. In some embodiments, the Type IIs restriction enzyme recognition sites of step (a) and step (b) are recognized by different Type IIs restriction enzymes. For example, the Type IIs restriction enzyme recognition sites are FokI recognition sites, BsaI recognition sites, and/or BsmBI recognition sites.

In some embodiments, the Acceptor Framework nucleic acid sequence is derived from a human gene sequence. For example, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51. In some embodiments, the human sequence is a human kappa light chain variable gene sequence or a sequence derived from a human kappa light chain variable gene sequence. For example, the human kappa light chain variable gene sequence is selected from VK1-33, VK1-39, VK3-11, VK3-15, and VK3-20. In some embodiments, the human sequence is a human lambda light chain variable gene sequence or a sequence derived from a human lambda light chain variable gene sequence. For example, the human lambda light chain variable gene sequence is selected from VL1-44 and VL1-51.

In one embodiment, the plurality of diversified nucleic acids encodes CDR2 regions, and the plurality of diversified nucleic acids includes naturally occurring sequences or sequences derived from immunized animals.

In one embodiment, the plurality of diversified nucleic acids includes or is derived from sequences selected from naturally occurring CDR2 sequences, naturally occurring Ig sequences from humans, naturally occurring Ig sequences from a mammal, naturally occurring sequences from a loop region of a T cell receptor in a mammal, and other naturally diversified polypeptide collections.

In one embodiment, the plurality of diversified nucleic acids encodes CDR2 regions, and the plurality of diversified nucleic acids includes or is derived from immunoglobulin sequences that occur naturally in humans that have been exposed to a particular immunogen or sequences derived from animals that have been identified as having been exposed to a particular antigen.

In one embodiment, the plurality of diversified nucleic acids encodes amino acid sequences that can fulfill the role of a CDR2 region, and the plurality of diversified nucleic acids includes synthetic sequences.

In another embodiment, the plurality of diversified nucleic acids encodes amino acid sequences that can fulfill the role of a CDR2 region, and the plurality of diversified nucleic acids includes synthetic sequences.

In some embodiments, the plurality of Acceptor Framework nucleic acid sequences include a mixture of at least one variable heavy chain (VH) Acceptor Framework nucleic acid sequence and at least one variable light chain Acceptor Framework nucleic acid sequence.

In some embodiments, the host cell is *E. coli*. In some embodiments, the expression vector is a phagemid vector. For example, the phagemid vector is pNDS1.

In some embodiments, the method includes the additional step of (i) sequencing the immunoglobulin variable domain encoding sequences that bind the target antigen.

The invention also provides methods for producing a library of nucleic acids, wherein each nucleic acid encodes an immunoglobulin variable domain. These methods include the steps of (a) providing a plurality of Ig Acceptor Framework nucleic acid sequences into which a source of diversity is introduced at a single complementarity determining region (CDR) selected from the group consisting of complementarity determining region 1 (CDR1), complementarity determining region 2 (CDR2), and complementarity determining region 3 (CDR3), wherein the Ig Acceptor Framework sequence includes a stuffer nucleic acid sequence including at least two Type IIs restriction enzyme recognition sites, and wherein the source of diversity is a CDR selected from naturally occurring CDR sequences that contain Type IIs restriction enzyme recognition sites outside the CDR region, (b) introducing the source of diversity within each Ig Acceptor Framework by digesting both the source of diversity and the Ig Acceptor Frameworks with a Type IIs restriction enzyme; and (c) ligating the digested source of diversity into the Ig Acceptor Framework such that a complete immunoglobulin variable domain encoding sequences that do not contain the Type IIs restriction enzyme recognition sites of steps (a) and (b) are restored.

The naturally occurring CDR region sequences are substantially unaltered from their wild-type, i.e., natural state. These naturally occurring CDR region sequences are flanked by amino acid sequences that have been engineered (or otherwise artificially manipulated) to contain two Type IIs restriction enzyme recognition sites, with one Type IIs restriction enzyme recognition site on each of side of the naturally occurring CDR region sequence. The Type IIS restriction enzyme recognition sites are outside the CDR encoding region. The sequence of CDR regions are unaltered at the boundaries of the CDR encoding region—the restriction enzymes recognize and splice at a region that is up to the boundary of the CDR encoding region, but does not splice within the CDR encoding region.

In some embodiments, the Type IIs restriction enzyme recognition sites within the stuffer nucleic acid sequences and flanking the naturally occurring CDR sequences are recognized by the same Type IIs restriction enzyme. In some embodiments, the Type IIs restriction enzyme recognition sites within the stuffer nucleic acid sequences and flanking the naturally occurring CDR sequences are recognized by different Type IIs restriction enzymes. For example, the Type IIs restriction enzyme recognition sites are FokI recognition sites, BsaI recognition sites, and/or BsmBI recognition sites.

In some embodiments, the Ig Acceptor Framework nucleic acid sequence is derived from a human gene sequence. For example, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51. In some embodiments, the human sequence is a human kappa light chain variable gene sequence or a sequence derived from a human kappa light chain variable gene sequence. For example, the human kappa light chain variable gene sequence is selected from VK1-33, VK1-39, VK3-11, VK3-15, and VK3-20. In some embodiments, the human sequence is a human lambda light chain variable gene sequence or a sequence derived from a human lambda light chain variable gene sequence. For example, the human lambda light chain variable gene sequence is selected from VL1-44 and VL1-51.

In some embodiments, the set of naturally occurring nucleic acids includes or is derived from sequences selected from naturally occurring CDR3 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the set of naturally occurring nucleic acids encode CDR3 regions, and the set of naturally occurring nucleic acids include immunoglobulin sequences that occur naturally in humans that have been exposed to a particular immunogen or sequences derived from animals that have been identified as having been exposed to a particular antigen.

In some embodiments, the set of naturally occurring nucleic acids includes or is derived from sequences selected from naturally occurring CDR1 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the set of naturally occurring nucleic acids encode CDR1 regions, and the set of naturally occurring nucleic acids includes or is derived from immunoglobulin sequences that occur naturally in humans that have been exposed to a particular immunogen or sequences derived from animals that have been identified as having been exposed to a particular antigen.

In some embodiments, the set of naturally occurring nucleic acids includes or is derived from sequences selected from naturally occurring CDR2 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the set of naturally occurring nucleic acids encodes CDR2 regions, and the set of naturally occurring nucleic acids includes immunoglobulin sequences that occur naturally in humans that have been exposed to a particular immunogen or sequences derived from animals that have been identified as having been exposed to a particular antigen.

In some embodiments, the plurality of Ig Acceptor Framework nucleic acid sequences include a mixture of at least one variable heavy chain (VH) Acceptor Framework nucleic acid sequence and at least one variable light chain (VL) Acceptor Framework nucleic acid sequence.

In some embodiments, the methods provided include the additional steps of (e) cloning the library of nucleic acids encoding immunoglobulin variable domains of step (d) into an expression vector and (f) transforming the expression vector of step (e) into a host cell and culturing the host cell under conditions sufficient to express a plurality of immunoglobulin variable domain encoded by the library. For example, the host cell is *E. coli*. In some embodiments, the expression vector is a phagemid vector. For example, the phagemid vector is pNDS1.

The invention also provides methods for producing a library of nucleic acids, wherein each nucleic acid encodes an immunoglobulin variable domain. These methods include the steps of (a) providing a plurality of Ig Acceptor Framework nucleic acid sequences into which a source of diversity is introduced at a single complementarity determining region (CDR) selected from the group consisting of complementarity determining region 1 (CDR1), complementarity determining region 2 (CDR2), and complementarity determining region 3 (CDR3), where the Ig Acceptor Framework sequence includes a stuffer nucleic acid sequence including at least two Type IIs restriction enzyme recognition sites, and wherein the source of diversity is a CDR selected from synthetically produced CDR sequences that contain Type IIs restriction enzyme recognition sites outside the CDR region, (b) introducing the source of diversity within each Ig Acceptor Framework by digesting both the source of diversity and the Ig Acceptor Framework with a Type IIs restriction enzyme; and (c) ligating the digested source of diversity into the Ig Acceptor Framework such that a complete immunoglobulin variable domain encoding sequences that do not contain the Type IIs restriction enzyme recognition sites of steps (a) and (b) are restored.

In some embodiments, the Type IIs restriction enzyme recognition sites within the stuffer nucleic acid sequences and the synthetically produced CDR sequences are recognized by the same Type IIs restriction enzyme. In some embodiments, the Type IIs restriction enzyme recognition sites within the stuffer nucleic acid sequences and the synthetically produced CDR sequences are recognized by different Type IIs restriction enzymes. For example, the Type IIs restriction enzyme recognition sites are FokI recognition sites, BsaI recognition sites, and/or BsmBI recognition sites.

In some embodiments, the Ig Acceptor Framework nucleic acid sequence is derived from a human sequence. For example, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51. In some embodiments, the human sequence is a human kappa light chain variable gene sequence or a sequence derived from a human kappa light chain variable gene sequence. For example, the human kappa light chain variable gene sequence is selected from VK1-33, VK1-39, VK3-11, VK3-15, and VK3-20. In some embodiments, the human sequence is a human lambda light chain variable gene sequence or a sequence derived from a human lambda light chain variable gene sequence. For example, the human lambda light chain variable gene sequence is selected from VL1-44 and VL1-51.

In some embodiments, the plurality of diversified nucleic acids encodes amino acid sequences that can fulfill the role of a CDR3 region, and the plurality of diversified nucleic acids includes synthetic sequences.

In some embodiments, the plurality of diversified nucleic acids encodes amino acid sequences that can fulfill the role of a CDR1 region, and the plurality of diversified nucleic acids includes synthetic sequences.

In some embodiments, the plurality of diversified nucleic acids encode amino acid sequences that can fulfill the role of a CDR2 region, and the plurality of diversified nucleic acids includes synthetic sequences.

In some embodiments, the plurality of Ig Acceptor Framework nucleic acid sequences includes a mixture of at least one variable heavy chain (VH) Acceptor Framework nucleic acid sequence and at least one variable light chain Acceptor Framework nucleic acid sequence.

In some embodiments, the methods provided include the additional steps of (e) cloning the library of nucleic acids encoding immunoglobulin variable domains of step (d) into an expression vector and (f) transforming the expression vector of step (e) into a host cell and culturing the host cell under conditions sufficient to express a plurality of immunoglobulin variable domain encoded by the library. For example, the host cell is *E. coli*. In some embodiments, the expression vector is a phagemid vector. For example, the phagemid vector is pNDS1.

The invention also provides methods for making an immunoglobulin polypeptide. These methods include the steps of (a) providing a plurality of Ig Acceptor Framework nucleic acid sequences into which a source of diversity is introduced at a single complementarity determining region (CDR) selected from the group consisting of complementarity determining region 1 (CDR1), complementarity determining region 2 (CDR2), and complementarity determining region 3 (CDR3), wherein the Ig Acceptor Framework sequence includes a stuffer nucleic acid sequence including at least two Type IIs restriction enzyme recognition sites, and wherein the source of diversity is a CDR selected from naturally occurring CDR sequences that contain Type IIs restriction enzyme recognition sites outside the CDR region, (b) introducing the source of diversity within each Ig Acceptor Framework by digesting both the source of diversity and the Ig Acceptor Frameworks with a Type IIs restriction enzyme; (c) ligating the digested source of diversity into the Ig Acceptor Framework such that a complete immunoglobulin variable gene encoding sequence is restored; and (d) cloning the complete immunoglobulin variable gene encoding sequence from step (c) into an expression vector; and (e) transforming the expression vector of step (d) into a host cell and culturing the host cell under conditions sufficient to express the complete immunoglobulin gene encoding sequences that do not contain the Type IIs restriction enzyme recognition sites are restored.

In these embodiments, the naturally occurring CDR region sequences are substantially unaltered from their wild-type, i.e., natural state. These naturally occurring CDR region sequences are flanked by amino acid sequences that have been engineered (or otherwise artificially manipulated) to contain two Type IIs restriction enzyme recognition sites, with one Type IIs restriction enzyme recognition site on each of side of the naturally occurring CDR region sequence.

In some embodiments, the Type IIs restriction enzyme recognition sites within the stuffer nucleic acid sequences and flanking the naturally occurring CDR sequences are recognized by the same Type IIs restriction enzyme. In some embodiments, the Type IIs restriction enzyme recognition sites within the stuffer nucleic acid sequences and flanking the naturally occurring CDR sequences are recognized by different Type IIs restriction enzymes. For example, the Type IIs restriction enzyme recognition sites are FokI recognition sites, BsaI recognition sites, and/or BsmBI recognition sites.

In some embodiments, the Acceptor Framework nucleic acid sequence is derived from a human gene sequence. For example, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51. In some embodiments, the human sequence is a human kappa light chain variable gene sequence or a sequence derived from a human kappa light chain variable gene sequence. For example, the human kappa light chain variable gene sequence is selected from VK1-33, VK1-39, VK3-11, VK3-15, and VK3-20. In some embodiments, the human sequence is a human lambda light chain variable gene sequence or a sequence derived from a human lambda light chain variable gene sequence. For example, the human lambda light chain variable gene sequence is selected from VL1-44 and VL1-51.

In some embodiments, the set of naturally occurring nucleic acids includes or is derived from sequences selected from naturally occurring CDR3 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the set of naturally occurring nucleic acids encode CDR3 regions, and the set of naturally occurring nucleic acids include immunoglobulin sequences that occur naturally in humans that have been exposed to a particular immunogen or sequences derived from animals that have been identified as having been exposed to a particular antigen.

In some embodiments, the set of naturally occurring nucleic acids includes or is derived from sequences selected from naturally occurring CDR1 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the set of naturally occurring nucleic acids encode CDR1 regions, and the set of naturally occurring nucleic acids includes or is derived from immunoglobulin sequences that occur naturally in humans that have been exposed to a particular immunogen or sequences derived from animals that have been identified as having been exposed to a particular antigen.

In some embodiments, the set of naturally occurring nucleic acids includes or is derived from sequences selected from naturally occurring CDR2 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the set of naturally occurring nucleic acids encodes CDR2 regions, and the set of naturally occurring nucleic acids includes immunoglobulin sequences that occur naturally in humans that have been exposed to a particular immunogen or sequences derived from animals that have been identified as having been exposed to a particular antigen.

In some embodiments, the plurality of Acceptor Framework nucleic acid sequences include a mixture of at least one variable heavy chain (VH) Acceptor Framework nucleic acid sequence and at least one variable light chain Acceptor Framework nucleic acid sequence.

In some embodiments, the expression vector is a phagemid vector. In some embodiments, the host cell is $E.\ coli$.

In some embodiments, the method also includes the steps of contacting the host cell with a target antigen, and determining which expressed complete Ig variable gene encoding sequences bind to the target antigen, thereby identifying target specific antibodies, antibody variable regions or portions thereof. In some embodiments, the method includes the additional step of (i) sequencing the immunoglobulin variable domain encoding sequences that bind the target antigen.

The invention also provides methods for making an immunoglobulin polypeptide. These methods include the steps of (a) providing a plurality of Ig Acceptor Framework nucleic acid sequences into which a source of diversity is introduced at a single complementarity determining region (CDR) selected from the group consisting of complementarity determining region 1 (CDR1), complementarity determining region 2 (CDR2), and complementarity determining region 3 (CDR3), wherein the Ig Acceptor Framework sequence includes a stuffer nucleic acid sequence including at least two Type IIs restriction enzyme recognition sites, and wherein the source of diversity is a CDR selected from synthetically produced CDR sequences that contain Type IIs restriction enzyme recognition sites outside the CDR region, (b) introducing the source of diversity within each Ig Acceptor Framework by digesting both the source of diversity and the Ig Acceptor Framework with a Type IIs restriction enzyme; (c) ligating the digested source of diversity into the Ig Acceptor Framework such that a complete immunoglobulin variable gene encoding sequence is restored; (d) cloning the ligated Ig Acceptor Framework from step (c) into an expression vector; and (e) transforming the expression vector of step (d) into a host cell and culturing the host cell under conditions sufficient to express the complete immunoglobulin gene encoding sequences that do not contain the Type IIs restriction enzyme recognition sites are restored.

In some embodiments, the Type IIs restriction enzyme recognition sites within the stuffer nucleic acid sequences and the synthetically produced CDR sequences are recognized by the same Type IIs restriction enzyme. In some embodiments, the Type IIs restriction enzyme recognition sites within the stuffer nucleic acid sequences and the synthetically produced CDR sequences are recognized by different Type IIs restriction enzymes. For example, the Type IIs restriction enzyme recognition sites are FokI recognition sites, BsaI recognition sites, and/or BsmBI recognition sites.

In some embodiments, the Ig Acceptor Framework nucleic acid sequence is derived from a human gene sequence. For example, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51. In some embodiments, the human sequence is a human kappa light chain variable gene sequence or a sequence derived from a human kappa light chain variable gene sequence. For example, the human kappa light chain variable gene sequence is selected from VK1-33, VK1-39, VK3-11, VK3-15, and VK3-20. In some embodiments, the human sequence is a human lambda light chain variable gene sequence or a sequence derived from a human lambda light chain variable gene sequence. For example, the human lambda light chain variable gene sequence is selected from VL1-44 and VL1-51.

In some embodiments, the plurality of diversified nucleic acids encodes amino acid sequences that can fulfill the role of a CDR3 region, and the plurality of diversified nucleic acids includes synthetic sequences.

In some embodiments, the plurality of diversified nucleic acids encodes amino acid sequences that can fulfill the role of a CDR1 region, and the plurality of diversified nucleic acids includes synthetic sequences.

In some embodiments, the plurality of diversified nucleic acids encode amino acid sequences that can fulfill the role of a CDR2 region, and the plurality of diversified nucleic acids includes synthetic sequences.

In some embodiments, the plurality of Ig Acceptor Framework nucleic acid sequences includes a mixture of at least one variable heavy chain (VH) Acceptor Framework nucleic acid sequence and at least one variable light chain Acceptor Framework nucleic acid sequence.

In some embodiments, the expression vector is a phagemid vector. In some embodiments, the host cell is $E.\ coli$.

In some embodiments, the method also includes the steps of contacting the host cell with a target antigen, and determining which expressed complete Ig variable gene encoding sequences bind to the target antigen, thereby identifying target specific antibodies, antibody variable regions or portions thereof. In some embodiments, the method includes the additional step of (i) sequencing the immunoglobulin variable domain encoding sequences that bind the target antigen.

The invention provides methods for producing a collection of nucleic acids, wherein each nucleic acid encodes a human immunoglobulin variable domain including a plurality of complementarity determining region 3 (CDR3) sequences isolated separately from the immunoglobulin variable domain repertoire from a mammalian species. The invention also provides methods for producing a collection of nucleic acids, wherein each nucleic acid encodes a human immunoglobulin variable domain including a plurality of complementarity determining region 2 (CDR2) sequences isolated separately from the immunoglobulin variable domain repertoire from a mammalian species. The invention also provides methods for producing a collection of nucleic acids, wherein each nucleic acid encodes a human immunoglobulin variable domain including a plurality of complementarity determining region 1 (CDR1) sequences isolated separately from the immunoglobulin variable domain repertoire from a mammalian species.

The invention provides methods for producing a collection of nucleic acids, wherein each nucleic acid encodes a human immunoglobulin variable domain including a plurality of complementarity determining region 3 (CDR3) sequences isolated separately from the immunoglobulin variable domain repertoire from a non-human mammalian species. The invention also provides methods for producing a collection of nucleic acids, wherein each nucleic acid encodes a human immunoglobulin variable domain including a plurality of complementarity determining region 2 (CDR2) sequences isolated separately from the immunoglobulin variable domain repertoire from a non-human mammalian species. The invention also provides methods for producing a collection of nucleic acids, wherein each nucleic acid encodes a human immunoglobulin variable domain including a plurality of complementarity determining region 1 (CDR1) sequences isolated separately from the immunoglobulin variable domain repertoire from a non-human mammalian species.

In some embodiments, the non-human species is non-human primate, rodent, canine, feline, sheep, goat, cattle, horse, a member of the Camelidae family, llama, camel, dromedary, or pig.

The invention provides methods for producing a collection of nucleic acids, wherein each nucleic acid encodes a human immunoglobulin variable domain including a plurality of complementarity determining region 3 (CDR3) sequences isolated separately from the immunoglobulin variable domain repertoire from a human. The invention provides methods for producing a collection of nucleic acids, wherein each nucleic acid encodes a human immunoglobulin variable domain including a plurality of complementarity determining region 2 (CDR2) sequences isolated separately from the immunoglobulin variable domain repertoire from a human. The invention provides methods for producing a collection of nucleic acids, wherein each nucleic acid encodes a human immunoglobulin variable domain including a plurality of complementarity determining region 1 (CDR1) sequences isolated separately from the immunoglobulin variable domain repertoire from a human.

The invention provides methods for producing a collection of nucleic acids, wherein each nucleic acid encodes a human immunoglobulin variable domain including a plurality of complementarity determining region 3 (CDR3) sequences isolated separately from the immunoglobulin variable domain repertoire from a non-human species.

In some embodiments, these methods includes the steps of (a) providing a plurality of Acceptor Framework nucleic acid sequences encoding distinct human immunoglobulin variable domains, each Acceptor Framework nucleic acid sequence comprising a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a stuffer nucleic acid sequence comprising at least two Type IIs restriction enzyme recognition sites interspaced by a random nucleic acid sequence; (b) providing a plurality of diversified nucleic acid sequences encoding complementarity determining region 3 (CDR3) sequences isolated from the mammalian species immunoglobulin repertoire wherein each of the plurality of diversified nucleic acid sequences comprises a Type IIs restriction enzyme recognition site at each extremity; (c) digesting each of the plurality of nucleic acid sequences encoding the CDR3 regions using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and (d) ligating the digested nucleic acid sequences encoding the CDR3 regions or the amino acid sequences of step (c) into the digested Acceptor Framework of step (c) such that the FR3 and FR4 regions are interspaced by the nucleic acid sequences encoding the CDR3 region or the amino acid sequence that can fulfill the role of a CDR3 region and a complete immunoglobulin variable domain encoding sequences that do not contain the Type IIs restriction enzyme recognition sites of steps (a) and (b) are restored. These steps may also be performed using a plurality of diversified nucleic acid sequences encoding complementarity determining region 2 (CDR2) sequences isolated from the mammalian species immunoglobulin repertoire. These steps may also be performed using a plurality of diversified nucleic acid sequences encoding complementarity determining region 1 (CDR1) sequences isolated from the mammalian species immunoglobulin repertoire.

In some embodiments, step (b) is performed by amplifying the CDR3 sequence from a mammalian species using oligonucleotide primers containing a Type IIs restriction site. In some embodiments, the oligonucleotide primer is designed to enhance compatibility between the mammalian CDR3 sequence and the Acceptor Framework encoding a human immunoglobulin variable domain. In some embodiments, the oligonucleotide primer is designed to modify the sequence at the boundaries of the mammalian CDR3 sequences to allow efficient ligation via compatible cohesive ends into the Acceptor Framework encoding a human immunoglobulin variable domain. In some embodiments the mammalian DNA sequences flanking the CDR3 regions might not upon cleavage by Type IIS restriction enzymes generate cohesive ends compatible with the cohesive ends of the digested Acceptor Frameworks. In such cases the oligonucleotides used for amplification are designed to modify the target mammalian sequence so that after cleavage with a Type IIS restriction enzyme, the cohesive ends are compatible and efficient ligation can occur. These steps can also be performed by amplifying the CDR2 sequence from a mammalian species using oligonucleotide primers containing a Type IIs restriction site. These steps can also be performed by amplifying the CDR1 sequence from a mammalian species using oligonucleotide primers containing a Type IIs restriction site.

In some embodiments, step (b) is performed by amplifying the CDR3 sequence from a non human species using oligonucleotide primers containing a FokI IIs restriction site. These steps can also be performed by amplifying the CDR2 sequence from a mammalian species using oligonucleotide primers containing a FokI IIs restriction site. These steps can also be performed by amplifying the CDR1 sequence from a mammalian species using oligonucleotide primers containing a FokI IIs restriction site.

In some embodiments, the Type IIs restriction enzyme recognition sites of step (a) and step (b) are recognized by a different Type IIs restriction enzyme. In some embodiments, the Type IIs restriction enzyme recognition sites are BsmBI recognition sites, BsaI recognition sites, FokI recognition sites or a combination thereof.

In some embodiments, the diversified nucleic acid sequences encoding CDR3 sequences encode heavy chain CDR3 (CDR H3) sequences. In some embodiments, the diversified nucleic acid sequences encoding CDR3 sequences encode light chain CDR3 (CDR L3) sequences. In some embodiments, the diversified nucleic acid sequences encoding CDR2 sequences encode heavy chain CDR2 (CDR H2) sequences. In some embodiments, the diversified nucleic acid sequences encoding CDR2 sequences encode light chain CDR2 (CDR L2) sequences. In some embodiments, the diversified nucleic acid sequences encoding CDR1 sequences encode heavy chain CDR1 (CDR H1) sequences. In some embodiments, the diversified nucleic acid sequences encoding CDR1 sequences encode light chain CDR1 (CDR L1) sequences.

In some embodiments, the Acceptor Framework nucleic acid sequence includes or is derived from at least a portion of a human heavy chain variable gene sequence selected from VH1-2, VH1-69, VH1-18, VH3-30, VH3-48, VH3-23, and VH5-51. In some embodiments, the Acceptor Framework nucleic acid sequence includes is derived from at least a portion of a human kappa light chain variable gene sequence. For example, the human kappa light chain variable gene sequence is selected from VK1-33, VK1-39, VK3-11, VK3-15, and VK3-20. In some embodiments, the Acceptor Framework nucleic acid sequence includes or is derived from at least a portion of a human lambda light chain variable gene sequence. For example, the human lambda light chain variable gene sequence is selected from VL1-44 and VL1-51.

In some embodiments, the plurality of Acceptor Framework nucleic acid sequences comprises a mixture of at least one variable heavy chain (VH) Acceptor Framework nucleic acid sequence and at least one variable light chain Acceptor Framework nucleic acid sequence.

In some embodiments, the methods described herein also include the steps of (e) cloning the library of nucleic acids encoding immunoglobulin variable domains of step (d) into an expression vector and (f) transforming the expression vector of step (e) into a host cell and culturing the host cell under conditions sufficient to express a plurality of immunoglobulin variable domain encoded by the library. In some embodiments, the expression vector is a phagemid or phage vector. In some embodiments, the host cell is E. coli.

The invention provides methods for producing a collection of nucleic acids, wherein each nucleic acid encodes a human immunoglobulin variable domain including a plurality of complementarity determining region 3 (CDR3) sequences isolated separately from immunoglobulin variable domains from an immunized non-human mammal or non-human species. The invention also provides methods for producing a collection of nucleic acids, wherein each nucleic acid encodes a human immunoglobulin variable domain including a plurality of complementarity determining region 2 (CDR2) sequences isolated separately from immunoglobulin variable domains from an immunized non-human mammal. The invention also provides methods for producing a collection of nucleic acids, wherein each nucleic acid encodes a human immunoglobulin variable domain including a plurality of complementarity determining region 1 (CDR1) sequences isolated separately from immunoglobulin variable domains from an immunized non-human mammal.

In some embodiments, the non-human species is non-human primate, rodent, canine, feline, sheep, goat, cattle, horse, a member of the Camelidae family, llama, camel, dromedary, or pig.

In some embodiments, the methods include the steps of (a) providing a plurality of Acceptor Framework nucleic acid sequences encoding distinct human immunoglobulin variable domains, each Acceptor Framework nucleic acid sequence comprising a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a stuffer nucleic acid sequence comprising at least two Type IIs restriction enzyme recognition sites interspaced by a random nucleic acid sequence; (b) providing a plurality of diversified nucleic acid sequences encoding complementarity determining region 3 (CDR3) sequences isolated from the immunized non-human mammal wherein each of the plurality of diversified nucleic acid sequences comprises a Type IIs restriction enzyme recognition site at each extremity; (c) digesting each of the plurality of nucleic acid sequences encoding the CDR3 regions using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and (d) ligating the digested nucleic acid sequences encoding the CDR3 regions or the amino acid sequences of step (c) into the digested Acceptor Framework of step (c) such that the FR3 and FR4 regions are interspaced by the nucleic acid sequences encoding the CDR3 region or the amino acid sequence that can fulfill the role of a CDR3 region and a complete immunoglobulin variable domain encoding sequences that do not contain the Type IIs restriction enzyme recognition sites of steps (a) and (b) are restored. These steps may also be performed using a plurality of diversified nucleic acid sequences encoding complementarity determining region 2 (CDR2) sequences isolated from the immunized non-human mammal. These steps may also be performed using a plurality of diversified nucleic acid sequences encoding complementarity determining region 1 (CDR1) sequences isolated from the immunized non-human mammal.

In some embodiments, step (b) is performed by amplifying the CDR3 sequence from the immunized non-human mammal using oligonucleotide primers containing a Type IIs restriction site. In some embodiments, the oligonucleotide primer is designed to enhance compatibility between the mammalian CDR3 sequence and the Acceptor Framework encoding a human immunoglobulin variable domain. In some embodiments, the oligonucleotide primer is designed to modify the sequence at the boundaries of the mammalian CDR3 sequences to allow efficient ligation via compatible cohesive ends into the Acceptor Framework encoding a human immunoglobulin variable domain. In some embodiments the mammalian DNA sequences flanking the CDR3 regions might not upon cleavage by Type IIS restriction enzymes generate cohesive ends compatible with the cohesive ends of the digested Acceptor Frameworks. In such cases the oligonucleotides used for amplification are designed to modify the target mammalian sequence so that after cleavage with a Type IIS restriction enzyme, the cohesive ends are compatible and efficient ligation can occur. These steps can also be performed by amplifying the CDR2 sequence from the immunized non-human mammal using oligonucleotide primers containing a Type IIs restriction site. These steps can also be performed by amplifying the CDR1 sequence from the immunized non-human mammal using oligonucleotide primers containing a Type IIs restriction site.

In some embodiments, step (b) is performed by amplifying the CDR H3 sequence from the non-human mammal using oligonucleotide primers containing a FokI IIs restriction site. These steps can also be performed by amplifying the CDR2 sequence from the non-human mammal using oligonucleotide primers containing a FokI IIs restriction site. These steps can also be performed by amplifying the CDR1 sequence from the non-human mammal using oligonucleotide primers containing a FokI IIs restriction site.

In some embodiments, the Type IIs restriction enzyme recognition sites of step (a) and step (b) are recognized by a different Type IIs restriction enzyme. In some embodiments, the Type IIs restriction enzyme recognition sites are BsmBI recognition sites, BsaI recognition sites, FokI recognition sites or a combination thereof.

In some embodiments, the diversified nucleic acid sequences encoding CDR3 sequences encode heavy chain CDR3 (CDR H3) sequences. In some embodiments, the diversified nucleic acid sequences encoding CDR3 sequences encode light chain CDR3 (CDR L3) sequences. In some embodiments, the diversified nucleic acid sequences encoding CDR2 sequences encode heavy chain CDR2 (CDR H2) sequences. In some embodiments, the diversified nucleic acid sequences encoding CDR2 sequences encode light chain CDR2 (CDR L2) sequences. In some embodiments, the diversified nucleic acid sequences encoding CDR1 sequences encode heavy chain CDR1 (CDR H1) sequences. In some embodiments, the diversified nucleic acid sequences encoding CDR1 sequences encode light chain CDR1 (CDR L1) sequences.

In some embodiments, the Acceptor Framework nucleic acid sequence includes or is derived from at least a portion of a human heavy chain variable gene sequence selected from VH1-2, VH1-69, VH1-18, VH3-30, VH3-48, VH3-23, and VH5-51.

In some embodiments, the Acceptor Framework nucleic acid sequence includes or is derived from at least a portion of a human kappa light chain variable gene sequence. For example, the human kappa light chain variable gene sequence is selected from VK1-33, VK1-39, VK3-11, VK3-15, and VK3-20. In some embodiments, the Acceptor Framework nucleic acid sequence includes or is derived from at least a portion of a human lambda light chain variable gene sequence. For example, the human lambda light chain variable gene sequence is selected from VL1-44 and VL1-51.

In some embodiments, the plurality of Acceptor Framework nucleic acid sequences comprises a mixture of at least one variable heavy chain (VH) Acceptor Framework nucleic acid sequence and at least one variable light chain Acceptor Framework nucleic acid sequence.

In some embodiments, the methods also include the steps of (e) cloning the library of nucleic acids encoding immunoglobulin variable domains of step (d) into an expression vector and (f) transforming the expression vector of step (e) into a host cell and culturing the host cell under conditions sufficient to express a plurality of immunoglobulin variable domain encoded by the library. In some embodiments, the host cell is *E. coli*. In some embodiments, the expression vector is a phagemid or phage vector.

BRIEF DESCRIPTION OF THE DRAWINGS

FIG. 5 is an illustration depicting the germline gene sequences of the variable heavy and light chain domain selected for the generation of Acceptor Frameworks.

FIG. 7, top panel, is an illustration depicting the sequence detail of Stuffer fragments of VH acceptor Framework. DNA sequences recognized and cleaved by the restriction enzyme BsmBI are boxed in red and black respectively and indicated in the lower panel of the figure. The reading frame corresponding to the antibody variable sequence is underlined.

FIG. 8 is an illustration depicting the sequences of the 20 Acceptor Frameworks.

FIG. 10 is a table depicting the sequences of CDRH3 sequences that were retrieved from a human cDNA source and inserted into human Acceptor Frameworks.

FIG. 11 is a table representing the design of synthetic CDR sequences for VH, VK and Vλ. The positions are numbered according to the Kabat numbering scheme. The theoretical diversity of the CDR using a defined codon diversification strategy (NNS, DVK, NVT, DVT) is indicated. The strategies adopted for VH CDR synthesis are boxed.

DETAILED DESCRIPTION OF THE INVENTION

Figure 1A:
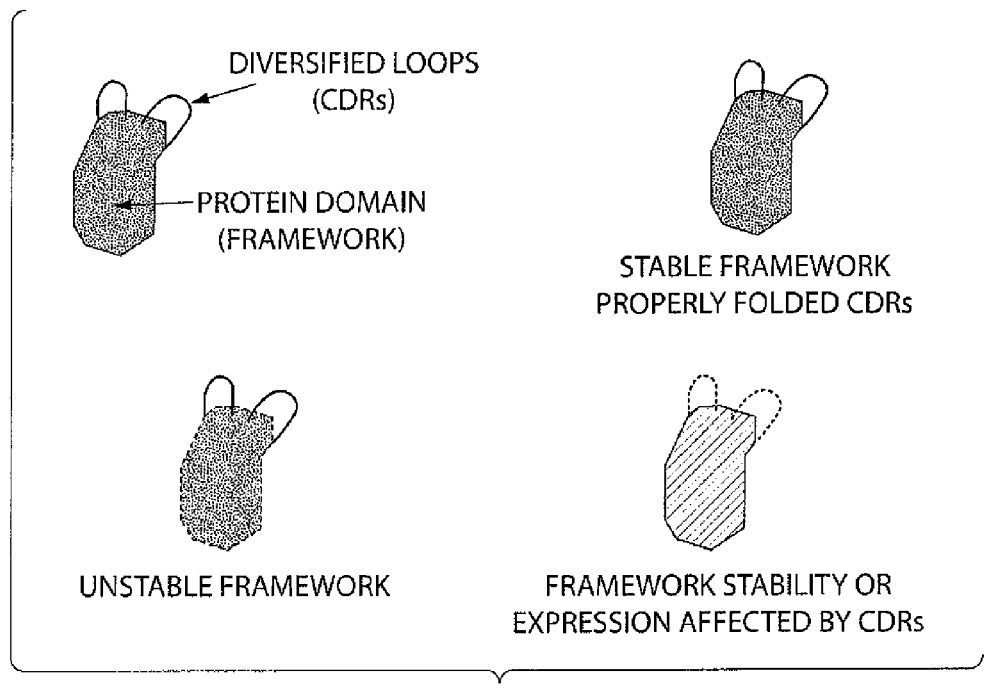
FIG. 1A is a schematic representation of a protein domain with a framework and loops providing contact residues with another protein or molecule. Several situations are depicted: A stable protein domain with properly folded loop regions; properly folded loops inserted into a domain of limited intrinsic stability; an intrinsically stable protein domain which stability is affected by the loop regions.
Figure 1B:
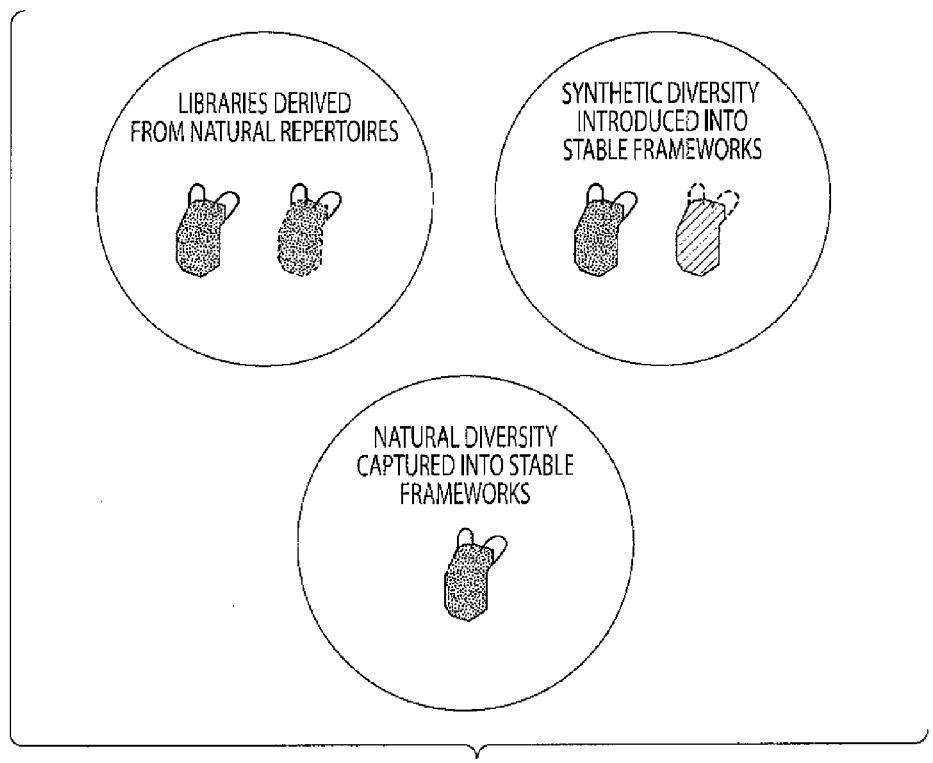
FIG. 1B is a schematic representation of different types of libraries of protein repertoires generated using different diversification strategies.

Synthetic protein libraries and in particular synthetic antibody libraries are attractive as it is possible during the library generation process to select the building blocks composing these synthetic proteins and include desired characteristics. An important limitation, however, is that the randomization of portions of these synthetic proteins to generate a collection of variants often leads to non-functional proteins and thus can dramatically decrease the functional library size and its performance. Another limitation of synthetic diversity is that the library size needed to cover the theoretical diversity of randomized amino acid stretches cannot be covered because of practical limitations. Even with display systems such as ribosome display a diversity of $10^{13}$ to $10^{14}$ can be generated and sampled which can maximally cover the complete randomization of stretches of 9 amino acids. As the average size of natural CDR H3 (also referred to herein as the heavy chain CDR3 or VH CDR3) is above 9 and can be over 20 amino acids in length, synthetic diversity is not a practicable approach to generate such CDRs.

The combination of methods generally used for DNA handling and that are used in the course of the generation of a library of protein variants introduces errors in the DNA sequences. These errors can lead to alterations in the reading frame of the DNA that will no longer encode a functional polypeptide. Typically, antibody libraries generated using assembly of DNA fragments by PCR and/or restriction cloning contain between 15% and 45% sequences that are not in the correct reading frame for protein translation. These non-functional library members can compromise the efficiency of the antibody selection and identification process and are thus recognized as a limitation in the field. The methods described allow for a more robust introduction of diversity into an antibody library by using an alternative cloning strategy. Typically the frequency of in-frame sequences is approximately 90%. Another advantage of the invention is that it combines selected acceptor antibody variable frameworks with CDR loops that have a high probability of correct folding. It allows for the capture of long CDRs that are difficult to cover with synthetic randomization approaches. Furthermore the methods described do not employ any modification within the coding region of acceptor antibody variable for cloning of the diversified sequences. Another advantage of this method is that several sources of diversity can be captured into the same set of acceptor antibody frameworks. These sources include but are not limited to: natural antibody CDRs of human or other mammal origin, CDR from chicken antibodies, CDRs of antibody-like molecules such as VHH from camelids, IgNARs from sharks, variable loops from T cell receptors. In addition, natural CDRs can be derived from naïve or immunized animals. In the latter case, the CDRs retrieved are enriched in sequences that were involved in recognition of the antigen used for immunization.

A unique feature of the methods described herein is the efficient capture of heavy chain CDR3 coding sequences from non-human species and their insertion into human immunoglobulin frameworks. Using these methods, it is therefore possible to generate different antibody combining sites that are shaped by the captured CDRH3 repertoire from another species and allow for the sampling of a different tri dimensional space. These methods allow for the generation of human antibodies with novel specificities targeting a different range of target classes and epitopes than those accessible to a human CDRH3 repertoire. Furthermore, these novel antibodies encode human framework as well as CDR1 and CDR2 regions and thus are suitable for human therapy.

In this method selected protein domains, as exemplified by antibody variable domains, are modified by introducing a stuffer sequence that will serve as an integration site for diversified sequences. Upon integration, the stuffer fragment is removed in full, thus leaving intact the coding region of the acceptor protein and the inserted proteins fragments (i.e., the CDRs). This integration event is mediated by a the use of Type IIs restriction enzyme that recognizes a defined site in the DNA sequence but cleave the DNA at a defined distance from this site. This approach has two major advantages: (1) it allows for the digestion of acceptors framework without affecting their coding sequences (no need to engineer silent restrictions sites); and (2) it allows for the digestion and cloning of naturally diversified sequences that by definition do not possess compatible restriction sites.

As described above, prior attempts to generate libraries and/or displays of antibody sequences differ from the methods provided herein. For example, some methods require the grafting of each CDR, as described for example by U.S. Pat.

No. 6,300,064, in which restriction enzyme sites are engineered at the boundary of each CDR, not just the CDR H3 region. In other methods, CDR sequences from natural sources are amplified and rearranged, as described in, e.g., U.S. Pat. No. 6,989,250. In some methods, such as those described in US Patent Application Publication No. 20060134098, sequences from a mouse (or other mammal) is added to a human framework, such that the resulting antibody has CDR1 and CDR2 regions of murine origin and a CDR3 region of human origin. Other methods, such as those described in US Patent Application Publication No. 20030232333, generate antibodies that have synthetic CDR1 and/or CDR1/CDR2 regions along with a natural CDR3 region. However, these methods fail to provide libraries that contain stable framework regions and correctly folded CDRs.

Figure 2:
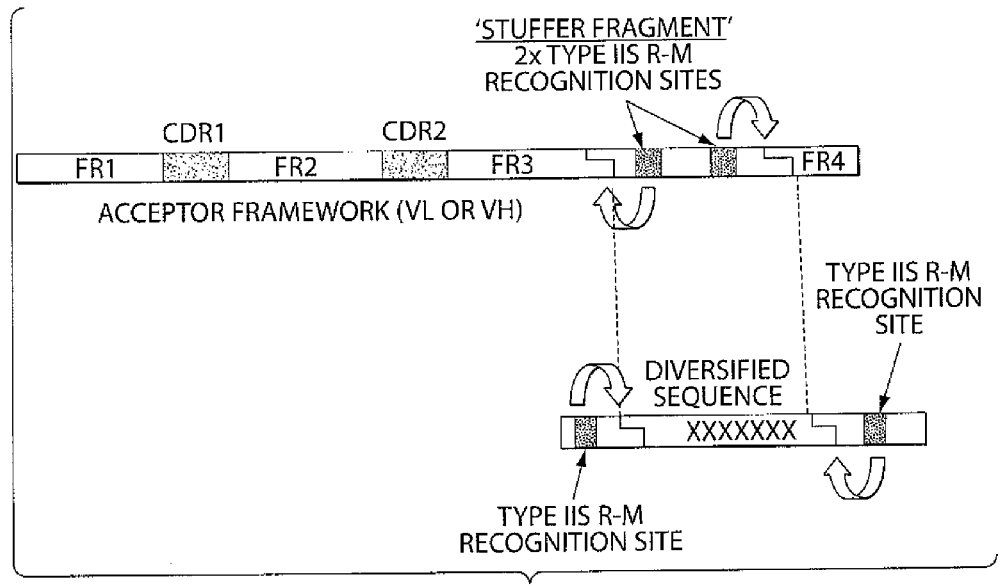
FIG. 2 is a schematic representation of an antibody variable Acceptor Framework. Framework regions, CDRs and type IIS-RM restriction site are indicated.

The methods provided herein design the antibody acceptor frameworks for diversity cloning. A strategy was designed to introduce diversity into the CDR3 of selected human antibody domains that avoids the modification of the sequence of the original framework. The strategy relies on the introduction outside of the immunoglobulin coding region of Type IIs restriction sites. This class of restriction enzymes recognizes asymmetric and uninterrupted sequence of 4-7 base pairs but cleave DNA at a defined distance of up to 20 bases independently of the DNA sequence found at the cleavage site. In order to take advantage of this system for cloning of diversified sequences into selected frameworks, acceptor frameworks containing a stuffer DNA fragment, instead of the CDR3, that includes two Type IIs restriction sites were designed. Similarly, diversified DNA sequences are generated with flanking sequences that include Type IIs. Provided that the cohesive ends generated by the restriction enzymes are compatible and that reading frame is maintained, the DNA fragments can be ligated into the acceptor framework and restore the encoded CDR3 in the new context of the acceptor antibody framework (FIG. 2).

Figure 3:
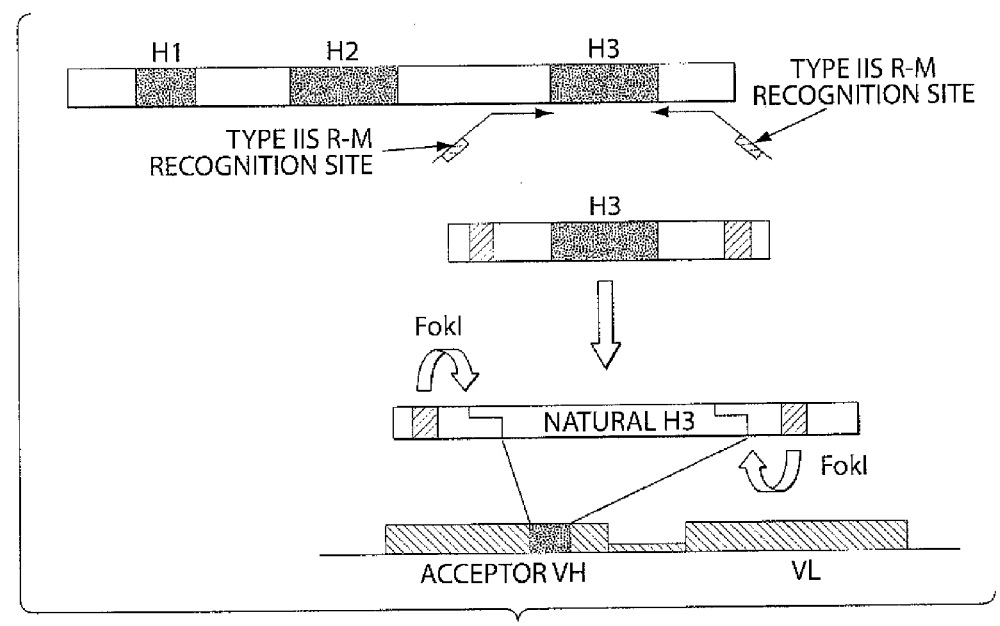
FIG. 3 is a schematic representation of a strategy used for capturing CDRH3 sequences from natural repertoires.
Figure 4:
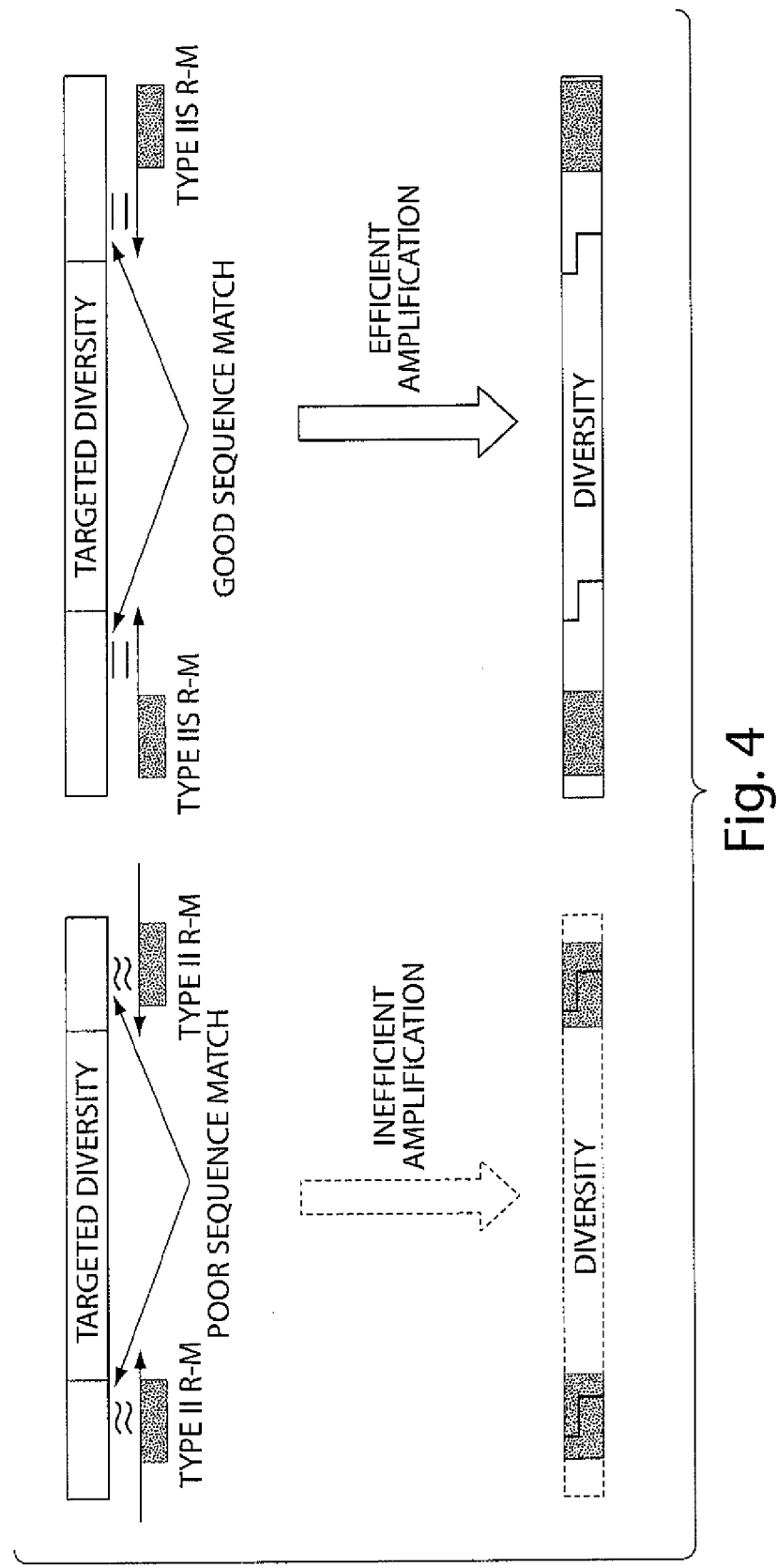
FIG. 4 is a schematic representation of the benefit of using primers containing Type IIS-RM restriction enzymes for the amplification and insertion of natural CDR regions into Acceptor Frameworks.

The methods provided herein capture natural CDR diversity. The strategy that was developed to capture naturally diversified protein fragments as a source of diversity also takes advantage of Type IIs restriction enzymes. As an example, oligonucleotides primers specific for flanking regions of the DNA sequence encoding the CDR H3 of immunoglobulins, i.e., specific for the FR3 and FR4 of the variable region, were designed. These oligonucleotides contain at their 5' end a site for a Type IIs restriction enzyme whereas their 3' portion matches the targeted DNA sequence. The restriction enzyme site used is preferably an enzyme that cleaves DNA far away from the DNA recognition site such as FokI. This is a key element of the method as it allows for the efficient amplification of natural DNA sequences as it maintains a good match between the 3' end of the primer and the DNA flanking the CDR H3 while allowing for excision of the CDRH3 coding sequence by DNA cleavage at the boundary between the CDR and framework regions (FIG. 3). This precise excision of the CDR coding sequence is very difficult using Type II enzymes that cleave DNA at their recognition site as the corresponding restriction site is not present in the natural DNA sequences and that introduction of such sites during amplification would be difficult due poor primer annealing. Thus this method allows for the amplification of diversified protein sequences and their insertion into any the acceptor antibody framework regardless of origin of amplified diversity (FIG. 4).

The methods described herein produce a library of nucleic acids, wherein each nucleic acid encodes an immunoglobulin variable domain by: (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a stuffer nucleic acid sequence containing at least two Type IIs restriction enzyme recognition sites interspaced by a random nucleic acid sequence; (b) providing a plurality of diversified nucleic acid sequences encoding complementarity determining region 3 (CDR3) regions or encoding amino acid sequences that can fulfill the role of a CDR3 region, wherein each of the plurality of diversified nucleic acid sequences includes a Type IIs restriction enzyme recognition site at each extremity; (c) digesting each of the plurality of nucleic acid sequences encoding the CDR3 regions or amino acid sequences that can fulfill the role of a CDR3 region using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and (d) ligating the digested nucleic acid sequences encoding the CDR3 regions or the amino acid sequences that can fulfill the role of a CDR3 region of step (c) into the digested Acceptor Framework of step (c) such that the FR3 and FR4 regions are interspaced by the nucleic acid sequences encoding the CDR3 region or the amino acid sequence that can fulfill the role of a CDR3 region and a complete immunoglobulin variable domain encoding sequences that do not contain the Type IIs restriction enzyme recognition sites of steps (a) and (b) are restored.

The methods provided herein produce a method for producing a library of nucleic acids, wherein each nucleic acid encodes an immunoglobulin variable domain by: (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a stuffer nucleic acid sequence containing at least two Type IIs restriction enzyme recognition sites interspaced by a random nucleic acid sequence, the FR2 and FR3 regions are interspaced by a complementarity determining region 2 (CDR2), and the FR3 and FR4 regions are interspaced by a complementarity determining region 3 (CDR3); (b) providing a plurality of diversified nucleic acid sequences encoding complementarity determining region 1 (CDR1) regions or encoding amino acid sequences that can fulfill the role of a CDR1 region, wherein each of the plurality of diversified nucleic acid sequences includes a Type IIs restriction enzyme recognition site at each extremity; (c) digesting each of the plurality of nucleic acid sequences encoding the CDR1 regions or amino acid sequences that can fulfill the role of a CDR1 region using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and (d) ligating the digested nucleic acid sequences encoding the CDR1 regions or the amino acid sequences that can fulfill the role of a CDR1 region of step (c) into the digested Acceptor Framework of step (c) such that the FR1 and FR2 regions are interspaced by the nucleic acid sequences encoding the CDR1 region or the amino acid sequence that can fulfill the role of a CDR1 region and a complete immunoglobulin variable domain encoding sequences that do not contain the Type IIs restriction enzyme recognition sites of steps (a) and (b) are restored.

The methods provided herein produce a library of nucleic acids, wherein each nucleic acid encodes an immunoglobulin variable domain, by: (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a stuffer nucleic acid sequence including at least two Type IIs restriction enzyme recognition sites interspaced by a random nucleic acid sequence, and the FR3 and FR4 regions are interspaced by a complementarity determining region 3 (CDR3); (b) providing a plurality of diversified nucleic acid sequences encoding complementarity determining region 2 (CDR2) regions or encoding amino acid sequences that can fulfill the role of a CDR2 region, wherein each of the plurality of diversified nucleic acid sequences includes a Type IIs restriction enzyme recognition site at each extremity; (c) digesting each of the plurality of nucleic acid sequences encoding the CDR2 regions or amino acid sequences that can fulfill the role of a CDR2 region using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and (d) ligating the digested nucleic acid sequences encoding the CDR2 regions or the amino acid sequences that can fulfill the role of a CDR2 region of step (c) into the digested Acceptor Framework of step (c) such that the FR2 and FR3 regions are interspaced by the nucleic acid sequences encoding the CDR2 region or the amino acid sequence that can fulfill the role of a CDR2 region and a complete immunoglobulin variable domain encoding sequences that do not contain the Type IIs restriction enzyme recognition sites of steps (a) and (b) are restored.

In some embodiments, the Type IIs restriction enzyme recognition sites of step (a) and step (b) in the methods set forth above are recognized by a different Type IIs restriction enzyme. For example, in some embodiments, the Type IIs restriction enzyme recognition sites are BsmBI recognition sites, BsaI recognition sites, FokI recognition sites or a combination thereof.

In some embodiments, the Acceptor Framework nucleic acid sequence is derived from a human gene sequence. For example, in some embodiments, the human sequence is a human heavy chain variable gene sequence or a sequence derived from a human heavy chain variable gene sequence. In some embodiments, the human heavy chain variable gene sequence is selected from VH1-2, VH1-69, VH1-18, VH3-30, VH3-48, VH3-23, and VH5-51.

In some embodiments, the human sequence is a human kappa light chain variable gene sequence or a sequence derived from a human kappa light chain variable gene sequence. For example, in some embodiments, the human kappa light chain variable gene sequence is selected from VK1-33, VK1-39, VK3-11, VK3-15, and VK3-20.

In some embodiments, the human sequence is a human lambda light chain variable gene sequence or a sequence derived from a human lambda light chain variable gene sequence. For example, in some embodiments, the human lambda light chain variable gene sequence is selected from VL1-44 and VL1-51.

In some embodiments, the plurality of diversified nucleic acids includes or is derived from sequences selected from naturally occurring CDR3 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the plurality of diversified nucleic acids encodes CDR3 regions, and the plurality of diversified nucleic acids includes or is derived from immunoglobulin sequences that occur naturally in humans that have been exposed to a particular immunogen or sequences derived from animals that have been identified as having been exposed to a particular antigen.

In some embodiments, the plurality of diversified nucleic acids encodes amino acid sequences that can fulfill the role of a CDR3 region, and the plurality of diversified nucleic acids includes synthetic sequences.

In some embodiments, the plurality of diversified nucleic acids includes or is derived from sequences selected from naturally occurring CDR1 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the plurality of diversified nucleic acids encodes CDR1 regions, and the plurality of diversified nucleic acids includes or is derived from immunoglobulin sequences that occur naturally in humans that have been exposed to a particular immunogen or sequences derived from animals that have been identified as having been exposed to a particular antigen.

In some embodiments, the plurality of diversified nucleic acids encodes amino acid sequences that can fulfill the role of a CDR1 region, and the plurality of diversified nucleic acids includes synthetic sequences.

In some embodiments, the plurality of diversified nucleic acids includes or is derived from sequences selected from naturally occurring CDR2 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the plurality of diversified nucleic acids encodes CDR2 regions, and the plurality of diversified nucleic acids includes or is derived from immunoglobulin sequences that occur naturally in humans that have been exposed to a particular immunogen or sequences derived from animals that have been identified as having been exposed to a particular antigen.

In some embodiments, the plurality of diversified nucleic acids encodes amino acid sequences that can fulfill the role of a CDR2 region, and the plurality of diversified nucleic acids includes synthetic sequences.

In some embodiments, the plurality of Acceptor Framework nucleic acid sequences includes a mixture of at least one variable heavy chain (VH) Acceptor Framework nucleic acid sequence and at least one variable light chain Acceptor Framework nucleic acid sequence.

In some embodiments, the methods provided herein further include the steps of (e) cloning the library of nucleic acids encoding immunoglobulin variable domains of step (d) into an expression vector and (f) transforming the expression vector of step (e) into a host cell and culturing the host cell under conditions sufficient to express a plurality of immunoglobulin variable domain encoded by the library.

In some embodiments, the host cell is *E. coli*. In some embodiments, the expression vector is a phagemid vector.

The methods provided herein generate or otherwise produce a target-specific antibody, antibody variable region or a portion thereof, by: (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a stuffer nucleic acid sequence having at least two Type IIs restriction enzyme recognition sites interspaced by a random nucleic acid sequence; (b) providing a plurality of diversified nucleic acid sequences encoding complementarity determining region 3 (CDR3) regions or encoding amino acid sequences that can fulfill the role of a CDR3 region, wherein each of the plurality of diversified nucleic acid sequences includes a Type IIs restriction enzyme recognition site at each extremity; (c) digesting each of the plurality of nucleic acid sequences encoding the CDR3 regions or amino acid sequences that can fulfill the role of a CDR3 region using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); (d) ligating the digested nucleic acid sequences encoding the CDR3 regions or the amino acid sequences that can fulfill the role of a CDR3 region of step (c) into the digested Acceptor Framework of step (c) such that the FR3 and FR4 regions are interspaced by the nucleic acid sequences encoding the CDR3 region or the amino acid sequence that can fulfill the role of a CDR3 region and complete immunoglobulin variable domain encoding sequences that do not contain the Type IIs restriction enzyme recognition sites of steps (a) and (b) are restored; (e) cloning the library of nucleic acids encoding immunoglobulin variable domains of step (d) into an expression vector; (f) transforming the expression vector of step (e) into a host cell and culturing the host cell under conditions sufficient to express a plurality of immunoglobulin variable domains encoded by the library; (g) contacting the plurality of immunoglobulin domains of step (f) with a target antigen; and (h) determining which expressed immunoglobulin variable domain encoding sequences bind to the target antigen.

The methods provided herein generate or otherwise produce a target-specific antibody, antibody variable region or a portion thereof, by: (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a stuffer nucleic acid sequence including at least two Type IIs restriction enzyme recognition sites interspaced by a random nucleic acid sequence, the FR2 and FR3 regions are interspaced by a complementarity determining region 2 (CDR2), and the FR3 and FR4 regions are interspaced by a complementarity determining region 3 (CDR3); (b) providing a plurality of diversified nucleic acid sequences encoding complementarity determining region 1 (CDR1) regions or encoding amino acid sequences that can fulfill the role of a CDR1 region, wherein each of the plurality of diversified nucleic acid sequences includes a Type IIs restriction enzyme recognition site at each extremity; (c) digesting each of the plurality of nucleic acid sequences encoding the CDR1 regions or amino acid sequences that can fulfill the role of a CDR1 region using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); (d) ligating the digested nucleic acid sequences encoding the CDR1 regions or the amino acid sequences that can fulfill the role of a CDR1 region of step (c) into the digested Acceptor Framework of step (c) such that the FR1 and FR2 regions are interspaced by the nucleic acid sequences encoding the CDR1 region or the amino acid sequence that can fulfill the role of a CDR1 region and complete immunoglobulin variable domain encoding sequences that do not contain the Type IIs restriction enzyme recognition sites of steps (a) and (b) are restored; (e) cloning the library of nucleic acids encoding immunoglobulin variable domains of step (d) into an expression vector; (f) transforming the expression vector of step (e) into a host cell and culturing the host cell under conditions sufficient to express a plurality of immunoglobulin variable domains encoded by the library; (g) contacting the plurality of immunoglobulin domains of step (f) with a target antigen; and (g) determining which expressed immunoglobulin variable domain encoding sequences bind to the target antigen.

The methods provided herein generate or otherwise produce a target-specific antibody, antibody variable region or a portion thereof, by: (a) providing a plurality of Acceptor Framework nucleic acid sequences encoding distinct immunoglobulin variable domains, each Acceptor Framework nucleic acid sequence including a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a stuffer nucleic acid sequence including at least two Type IIs restriction enzyme recognition sites interspaced by a random nucleic acid sequence, and the FR3 and FR4 regions are interspaced by a complementarity determining region 3 (CDR3); (b) providing a plurality of diversified nucleic acid sequences encoding complementarity determining region 2 (CDR2) regions or encoding amino acid sequences that can fulfill the role of a CDR2 region, wherein each of the plurality of diversified nucleic acid sequences includes a Type IIs restriction enzyme recognition site at each extremity; (c) digesting each of the plurality of nucleic acid sequences encoding the CDR2 regions or amino acid sequences that can fulfill the role of a CDR2 region using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); (d) ligating the digested nucleic acid sequences encoding the CDR2 regions or the amino acid sequences that can fulfill the role of a CDR2 region of step (c) into the digested Acceptor Framework of step (c) such that the FR2 and FR3 regions are interspaced by the nucleic acid sequences encoding the CDR2 region or the amino acid sequence that can fulfill the role of a CDR2 region and complete immunoglobulin variable domain encoding sequences that do not contain the Type IIs restriction enzyme recognition sites of steps (a) and (b) are restored; (e) cloning the library of nucleic acids encoding immunoglobulin variable domains of step (d) into an expression vector; (f) transforming the expression vector of step (e) into a host cell and culturing the host cell under conditions sufficient to express a plurality of immunoglobulin variable domains encoded by the library; (g) contacting the plurality of immunoglobulin variable domains of step (f) with a target antigen; and (h) determining which expressed immunoglobulin variable domain encoding sequences bind to the target antigen.

In some embodiments, the methods provided herein further include the step of (i) sequencing the immunoglobulin variable domain encoding sequences that bind the target antigen.

In some embodiments, the Type IIs restriction enzyme recognition sites of step (a) and step (b) are recognized by a different Type IIs restriction enzyme.

In some embodiments, the Type IIs restriction enzyme recognition sites are BsmBI recognition sites, BsaI recognition sites, FokI recognition sites or a combination thereof.

In some embodiments, the Acceptor Framework nucleic acid sequence is derived from a human gene sequence. For example, in some embodiments, the human sequence is a human heavy chain variable gene sequence or a sequence derived from a human heavy chain variable gene sequence. For example, in some embodiments, the human heavy chain variable gene sequence is selected from VH1-2, VH1-69, VH1-18, VH3-30, VH3-48, VH3-23, and VH5-51.

In some embodiments, the human sequence is a human kappa light chain variable gene sequence or a sequence derived from a human kappa light chain variable gene sequence. For example, in some embodiments, the human kappa light chain variable gene sequence is selected from VK1-33, VK1-39, VK3-11, VK3-15, and VK3-20.

In some embodiments, the human sequence is a human lambda light chain variable gene sequence or a sequence derived from a human lambda light chain variable gene sequence. For example, in some embodiments, the human lambda light chain variable gene sequence is selected from VL1-44 and VL1-51.

In some embodiments, the plurality of diversified nucleic acids includes or is derived from sequences selected from naturally occurring CDR3 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the plurality of diversified nucleic acids encodes CDR3 regions, and the plurality of diversified nucleic acids includes or is derived from immunoglobulin sequences that occur naturally in humans that have been exposed to a particular immunogen or sequences derived from animals that have been identified as having been exposed to a particular antigen.

In some embodiments, the plurality of diversified nucleic acids encodes amino acid sequences that can fulfill the role of a CDR3 region, and the plurality of diversified nucleic acids includes synthetic sequences.

In some embodiments, the plurality of diversified nucleic acids includes or is derived from sequences selected from naturally occurring CDR1 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the plurality of diversified nucleic acids encodes CDR1 regions, and the plurality of diversified nucleic acids includes or is derived from immunoglobulin sequences that occur naturally in humans that have been exposed to a particular immunogen or sequences derived from animals that have been identified as having been exposed to a particular antigen.

In some embodiments, the plurality of diversified nucleic acids encodes amino acid sequences that can fulfill the role of a CDR1 region, and the plurality of diversified nucleic acids includes synthetic sequences.

In some embodiments, the plurality of diversified nucleic acids included or is derived from sequences selected from naturally occurring CDR2 sequences, naturally occurring Ig sequences from humans, naturally occurring Ig sequences from a mammal, naturally occurring sequences from a loop region of a T cell receptor in a mammal, and other naturally diversified polypeptide collections.

In some embodiments, the plurality of diversified nucleic acids encodes CDR2 regions, and the plurality of diversified nucleic acids includes or is derived from immunoglobulin sequences that occur naturally in humans that have been exposed to a particular immunogen or sequences derived from animals that have been identified as having been exposed to a particular antigen.

In some embodiments, the plurality of Acceptor Framework nucleic acid sequences includes a mixture of at least one variable heavy chain (VH) Acceptor Framework nucleic acid sequence and at least one variable light chain Acceptor Framework nucleic acid sequence.

In some embodiments, the expression vector is a phagemid vector. In some embodiments, the host cell is *E. coli*.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; e.g., ≤100 nM, preferably ≤10 nM and more preferably ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to its target, when the equilibrium binding constant ($K_d$) is ≤1 µM, e.g., ≤100 nM, preferably ≤10 nM, and more preferably ≤1 nM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules, and nucleic acid molecules encoding the light chain immunoglobulin molecules described herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules, and the light chain immunoglobulin molecules described herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The invention will be further described in the following examples, which do not limit the scope of the invention described in the claims.

EXAMPLES

Example 1

Cloning of Immunoglobulin Variable Germline Genes

Seven human heavy chain variable germline genes (VH1-2, VH1-69, VH1-18, VH3-30, VH3-48, VH3-23, VH5-51), five human kappa light chain variable germline genes (VK1-33, VK1-39, VK3-11, VK3-15, VK3-20) and two human lambda light chain variable germline genes (VL1-44, VL1-51) were selected to construct the libraries (Lefranc, M.-P. et al., 1999 Nucleic Acids Research, 27, 209-212). These genes were selected because they are often used in human expressed antibody repertoires and the frameworks they encode show favorable stability and expression profiles as individual domains or in the context of a VH/VL pair (Ewert S et al., J Mol. Biol. 2003 Jan. 17; 325(3):531-53). Two sets of specific primers were used to amplify these genes from human genomic DNA by nested PCR. This approach was necessary as the 5' sequences of germline genes of the same family are identical or very similar. For each gene, a first pair of primers, called genomic locators, was designed to be specific to the 5' and 3' untranslated regions flanking the germline gene. The second pair was designed to be specific for the beginning of the framework 1 region (FR1) and the end of the FR2. The 14 independent PCR products were cloned into pGEMT-easy (Promega, Madison Wis.) and their identity and integrity were verified by sequencing. The amino acid sequence of the selected germline genes is shown in FIG. 5.

The primers and primer combination used are indicated below.

Genomic Locators

| | | | |
|---|---|---|---|
| 5 K1-33 | TGTTTCTAATCGCAGGTGCCAGATG | (SEQ ID NO: 120) |
| 3 K1-33 | ATTTATGTTATGACTTGTTACACTG | (SEQ ID NO: 121) |
| 5 K1-39 | TATTTGTTTTTATGTTTCCAATCTC | (SEQ ID NO: 122) |
| 3 K1-39 | CCTTGGAGGTTTATGTTATGACTTG | (SEQ ID NO: 123) |
| 5 K3-11 | TTATTTCCAATTTCAGATACCACCG | (SEQ ID NO: 124) |
| 3 K3-11 | TTGTTGGGGTTTTTGTTTCATGTGG | (SEQ ID NO: 125) |
| 5 K3-15 | TATTTCCAATTTCAGATACCACTGG | (SEQ ID NO: 126) |
| 3 K3-15 | ATGTTGAATCACTGTGGGAGGCCAG | (SEQ ID NO: 127) |
| 5 K3-20 | TTATTTCCAATCTCAGATACCACCG | (SEQ ID NO: 128) |
| 3 K3-20 | TTTTGTTTCAAGCTGAATCACTGTG | (SEQ ID NO: 129) |
| 5 L1-44 | ATGTCTGTGTCTCTCTCACTTCCAG | (SEQ ID NO: 130) |
| 3 L1-44 | TTCCCCATTGGCCTGGAGCACTGTG | (SEQ ID NO: 131) |
| 5 L1-51 | GTGTCTGTGTCTCTCCTGCTTCCAG | (SEQ ID NO: 132) |
| 3 L1-51 | CTTGTCTCAGTTCCCCATTGGGCTG | (SEQ ID NO: 133) |
| 5 H1-2 | ATCTCATCCACTTCTGTGTTCTCTC | (SEQ ID NO: 134) |
| 3 H1-2 | TTGGGTTTCTGACACCCTCAGGATG | (SEQ ID NO: 135) |
| 5 H1-18 | CAGGCCAGTCATGTGAGACTTCACC | (SEQ ID NO: 136) |

```
3 H1-18    CTGCCTCCTCCCTGGGGTTTCTGAA      (SEQ ID NO: 137)

5 H1-69    CCCCTGTGTCCTCTCCACAGGTGTC      (SEQ ID NO: 138)

3 H1-69    CCGGCACAGCTGCCTTCTCCCTCAG      (SEQ ID NO: 139)

5 DP-47    GAGGTGCAGCTGTTGGAG             (SEQ ID NO: 140)

5 H3-23    TCTGACCAGGGTTTCTTTTTGTTTGC     (SEQ ID NO: 141)

3 H3-23    TTGTGTCTGGGCTCACAATGACTTC      (SEQ ID NO: 142)

5 H3-30    TGGCATTTTCTGATAACGGTGTCC       (SEQ ID NO: 143)

3 H3-30    CTGCAGGGAGGTTTGTGTCTGGGCG      (SEQ ID NO: 144)

5 H3-48    ATATGTGTGGCAGTTTCTGACCTTG      (SEQ ID NO: 145)

3 H3-48    GGTTTGTGTCTGGTGTCACACTGAC      (SEQ ID NO: 146)

5 H5-a     GAGTCTGTGCCGGAAGTGCAGCTGG      (SEQ ID NO: 147)
```

```
5 DPK21
TATGAAATAGTGATGACGCAGTCT              (SEQ ID NO: 159)

3 DPK21
ATAGGAGGCCAGTTATTATACTG               (SEQ ID NO: 160)

3 L6
CAGCGTAGCAACTGGCCTCCTAT               (SEQ ID NO: 161)

5 DPL2
TACAGTCTGTGCTGACTCAG                  (SEQ ID NO: 162)

3 DPL2
ATAGGACCATTCAGGCTGTCATC               (SEQ ID NO: 163)

5 DPL5
TATCAGTCTGTGTTGACGCAG                 (SEQ ID NO: 164)

3 DPL5
ATAGGAGCACTCAGGCTGCTAT                (SEQ ID NO: 165)
```

Primer Combinations Used to Amplify Selected Germline Genes.

| Family | germline | 1st PCR 5' | 1st PCR 3' | 2nd PCR 5' | 2nd PCR 3' |
|---|---|---|---|---|---|
| VH1 | DP-8/75 HV 1-2 | 5 H1-2 | 3 H1-2 | 5 VH1 | 3 VH1/3 |
|  | DP-10 HV 1-69 | 5 H1-69 | 3 H1-69 | 5 VH1 | 3 VH1/3 |
|  | DP-14 HV 1-18 | 5 H1-18 | 3 H1-18 | 5 VH1 | 3 VH1/3 |
| VH3 | DP-49 HV 3-30 | 5 H3-30 | 3 H3-30 | 5 VH3 | 3 VH1/3 |
|  | DP-51 HV 3-48 | 5 H3-48 | 3 H3-48 | 5 VH3 | 3 VH1/3 |
|  | DP-47 HV 3-23 | 5 H3-23 | 3 H3-23 | 5 VH3 | 3 VH3 |
| VH5 | HV 5a | 5 H5a | 3 VH5 | 5 VH5 | 3 VH5 |
| VKI | DPK-1 KV 1-33 | 5 K 1-33 | 3 K 1-33 | 5 VK1 | 3 DPK-1 |
|  | DPK-9 KV 1-39 | 5 K 1-39 | 3 K 1-39 | 5 VK1 | 3 DPK-9 |
| VKIII | L6 KV 3-11 | 5 K3-11 | 3 K3-11 | 5 DPK22_L6 | 3 L6 |
|  | DPK-21 KV 3-15 | 5 K3-15 | 3 K3-15 | 5 DPK21 | 3 DPK21 |
|  | DPK-22 KV 3-20 | 5 K3-20 | 3 K3-20 | 5 DPK22_L6 | 3 DPK22 |
| VL1 | DPL-2 LV 1-44 | 5 L1-44 | 3 L1-44 | 5 DPL2 | 3 DPL2 |
|  | DPL-5 LV 1-51 | 5 L1-51 | 3 L1-51 | 5 DPL5 | 3 DPL5 |

Specific for Coding Sequence

```
5 VH1
TATCAGGTGCAGCTGGTGCAG                 (SEQ ID NO: 148)

5 VH3
TATCAGGTGCAGCTGGTGGAG                 (SEQ ID NO: 149)

5 VH5
TATGAGGTGCAGCTGGTGCAG                 (SEQ ID NO: 150)

3 VH1/3
ATATCTCTCGCACAGTAATACAC               (SEQ ID NO: 151)

3 VH3
ATATCTCTCGCACAGTAATATAC               (SEQ ID NO: 152)

3 VH5
ATATGTCTCGCACAGTAATACAT               (SEQ ID NO: 153)

5 VK1
TATGACATCCAGATGACCCAGTCTCCATCCTC      (SEQ ID NO: 154)

3 DPK9
ATAGGAGGGGTACTGTAACT                  (SEQ ID NO: 155)

3 DPK1
ATAGGAGGGAGATTATCATA                  (SEQ ID NO: 156)

5 DPK22_L6
TATGAAATTGTGTTGACGCAGTCT              (SEQ ID NO: 157)

3 DPK22
ATAGGAGGTGAGCTACCATACTG               (SEQ ID NO: 158)
```

Example 2

Generation of Acceptor Frameworks

The sequences of the selected germline genes were analyzed for the presence of Type IIs restriction sites. No BsmBI site was present in the selected antibody variable germline genes. Two BsmBI sites were found in the backbone of pNDS1, the phagemid vector in which the Acceptor Framework would be cloned. These two sites were removed by site-directed mutagenesis so that unique BsmBI sites could be introduced into the stuffer DNA sequences of the Acceptor Frameworks. Each germline gene was amplified by multiple nested PCR in order to add a stuffer DNA sequence at the 3' end of the FR3 sequence followed by a sequence encoding FR4 which is specific for each corresponding variable segment (VH, Vk, Vλ). The amino acid sequence of VH FR4 corresponds to the FR4 region encoded by the germline J genes JH1, JH3, JH4 and JH5. The amino acid sequence of VK FR4 corresponds to the FR4 region encoded by the germline J genes JK1. The amino acid sequence of Vλ FR4 corresponds to the FR4 region encoded by the germline J genes JL2 and JL3. Two variants of the Vk FR4 sequence were generated with a single amino acid substitution at position 106 (Arginine or Glycine). For the Acceptor Framework based on the germline gene VH3-23, two variants were also constructed differing by a single amino acid (Lysine to Arginine) at position 94, the last residue of FR3. During the final amplification step SfiI/NcoI and XhoI sites were introduced at the 5' and 3' end of the VH, respectively.

Figure 6:
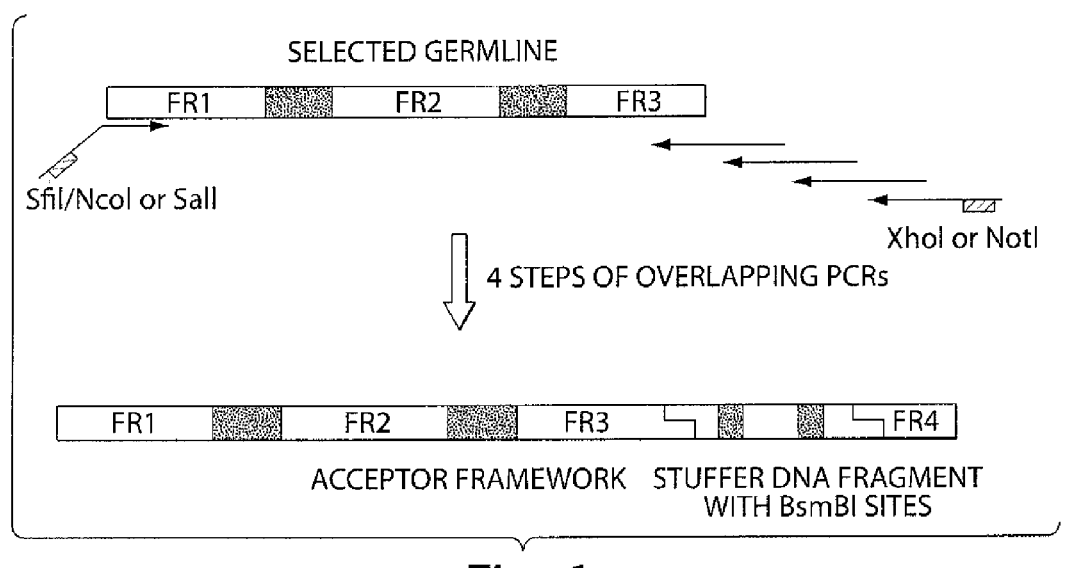
FIG. 6 is a schematic representation of an amplification strategy used for the generation of Acceptor Frameworks by addition to the germline sequences of a stuffer fragment and a FR4 region.

Similarly, SalI and NotI sites were introduced at the 5' and 3' end of the VL, respectively (FIG. 6). The stuffer fragment was designed so that the translation reading frame was shifted thus preventing the expression of any functional protein from the Acceptor Frameworks (FIG. 7). The primers used in this process are listed below.

VH
5 VH1
(SEQ ID NO: 166)
CAGCCGGCCATGGCCCAGGTGCAGCTGGTGCAG

5 VH3-30
(SEQ ID NO: 167)
CAGCCGGCCATGGCCCAGGTGCAGCTGGTGGAG

5 VH3-23
(SEQ ID NO: 168)
CAGCCGGCCATGGCCGAGGTGCAGCTGTTGGAG

5 VH3-48
(SEQ ID NO: 169)
CAGCCGGCCATGGCCGAGGTGCAGCTGGTGGAGTCTGGGGGAG

5 VH5-51
(SEQ ID NO: 170)
CAGCCGGCCATGGCCGAGGTGCAGCTGGTGCAG

3 VH1/3
(SEQ ID NO: 171)
CTTACCGTTATTCGTCTCATCTCGCACAGTAATACAC

3 VH3-23
(SEQ ID NO: 172)
CTTACCGTTATTCGTCTCATTTCGCACAGTAATATAC

3 VH3-48
(SEQ ID NO: 173)
CTCGCACAGTAATACACAGCCGTGTCCTCGGCTCTCAGGCTG

3 VH5-51
(SEQ ID NO: 174)
CTTACCGTTATTCGTCTCATCTCGCACAGTAATACAT

3 VHext1
(SEQ ID NO: 175)
CAATACGCGTTTAAACCTGGTAAACCGCCTTACCGTTATTCGTCTCA

3 VHext2
(SEQ ID NO: 176)
GTTCCCTGGCCCCAAGAGACGCGCCTTCCCAATACGCGTTTAAACCTG

3 VHext3
(SEQ ID NO: 177)
CCTCCACCGCTCGAGACTGTGACCAGGGTTCCCTGGCCCCAAGAG

VK
5 VK1
(SEQ ID NO: 178)
CGGGTCGACGGACATCCAGATGACCCAGTC

5 VK3-11
(SEQ ID NO: 179)
CGGGTCGACGGAAATTGTGTTGACACAGTCTCCAGC

5 VK3-15
(SEQ ID NO: 180)
CGGGTCGACGGAAATAGTGATGACGCAGTCTCCAGC

5 VK3-20
(SEQ ID NO: 181)
CGGGTCGACGGAAATTGTGTTGACGCAGTCTCCAGG

3 VK1-33
(SEQ ID NO: 182)
CCTTACCGTTATTCGTCTCGCTGCTGACAGTAATATGTTGCAATA

3 VK1-39
(SEQ ID NO: 183)
CCTTACCGTTATTCGTCTCGCTGCTGACAGTAGTAAGTTGCAAAA

3 VK3
(SEQ ID NO: 184)
CCTTACCGTTATTCGTCTCGCTGCTGACAGTAATAAACTGCAAATC

3 VKext1
(SEQ ID NO: 185)
CCAATACGCGTTTAAACCTGGTAAACCGCCTTACCGTTATTCGTCTC

3 VKext2
(SEQ ID NO: 186)
GGTCCCTTGGCCGAATGAGACGCGCCTTCCCAATACGCGTTTAAAC

3 VKext3R
(SEQ ID NO: 187)
GTGCGGCCGCCCGTTTGATTTCCACCTTGGTCCCTTGGCCGAATG

3 VKext3G
(SEQ ID NO: 188)
GTGCGGCCGCCCCTTTGATTTCCACCTTGGTCCCTTGGCCGAATG

Vλ
5 VL1-44
(SEQ ID NO: 189)
CGGGTCGACGCAGTCTGTGCTGACTCAGCCAC

5 VL1-51
(SEQ ID NO: 190)
CGGGTCGACGCAGTCTGTGTTGACGCAGCCGC

3 VL1-44
(SEQ ID NO: 191)
CCTTACCGTTATTCGTCTCCTGCTGCACAGTAATAATC

3 VL1-51
(SEQ ID NO: 192)
CCTTACCGTTATTCGTCTCCTGTTCCGCAGTAATAATC

3 Vlext2
(SEQ ID NO: 193)
CCCTCCGCCGAACACAGAGACGCGCCTTCCCAATACGCGTTTAAAC

3 Vlext3
(SEQ ID NO: 194)
GTGCGGCCGCCCCTAGGACGGTCAGCTTGGTCCCTCCGCCGAACACAGA

Figure 8:
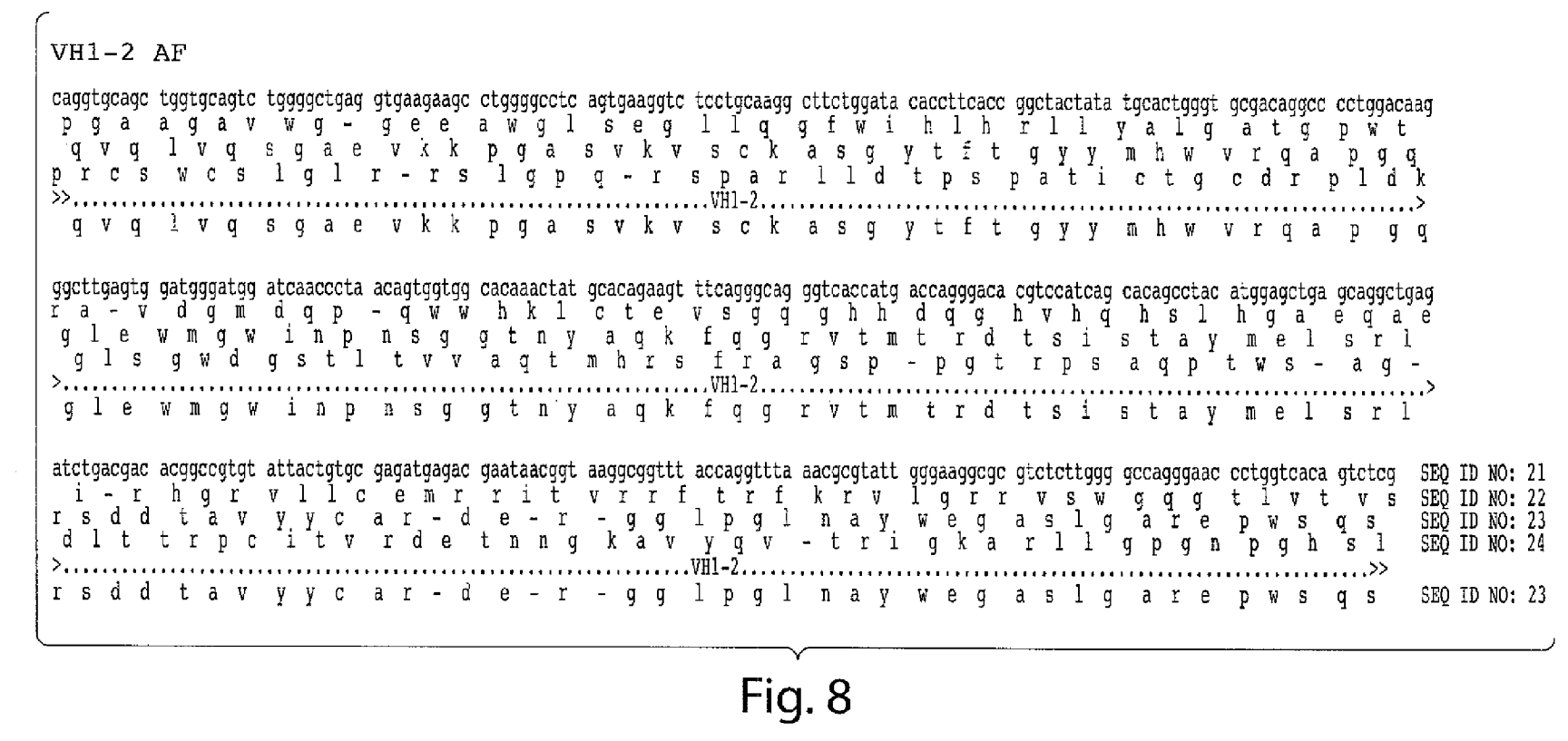
Figure 8:
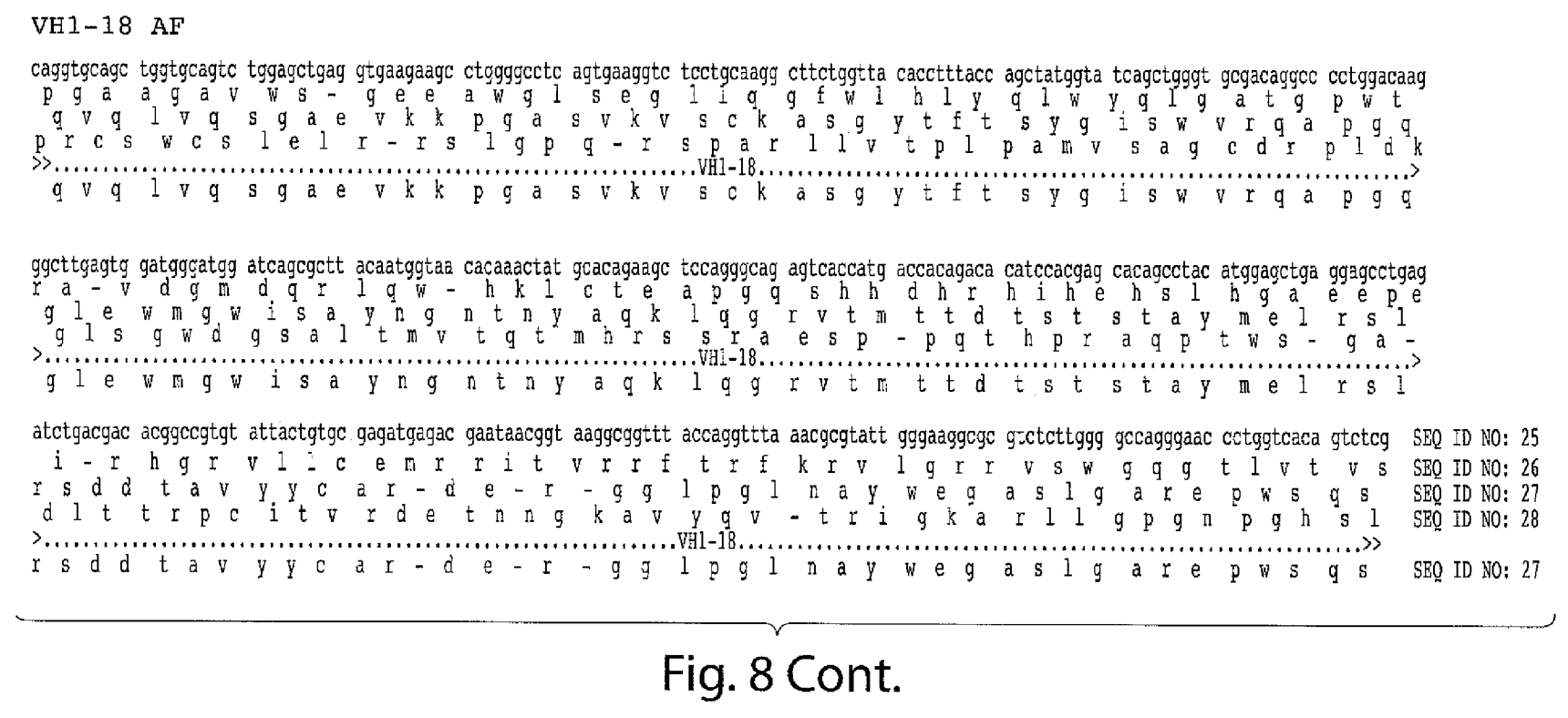
Figure 8:
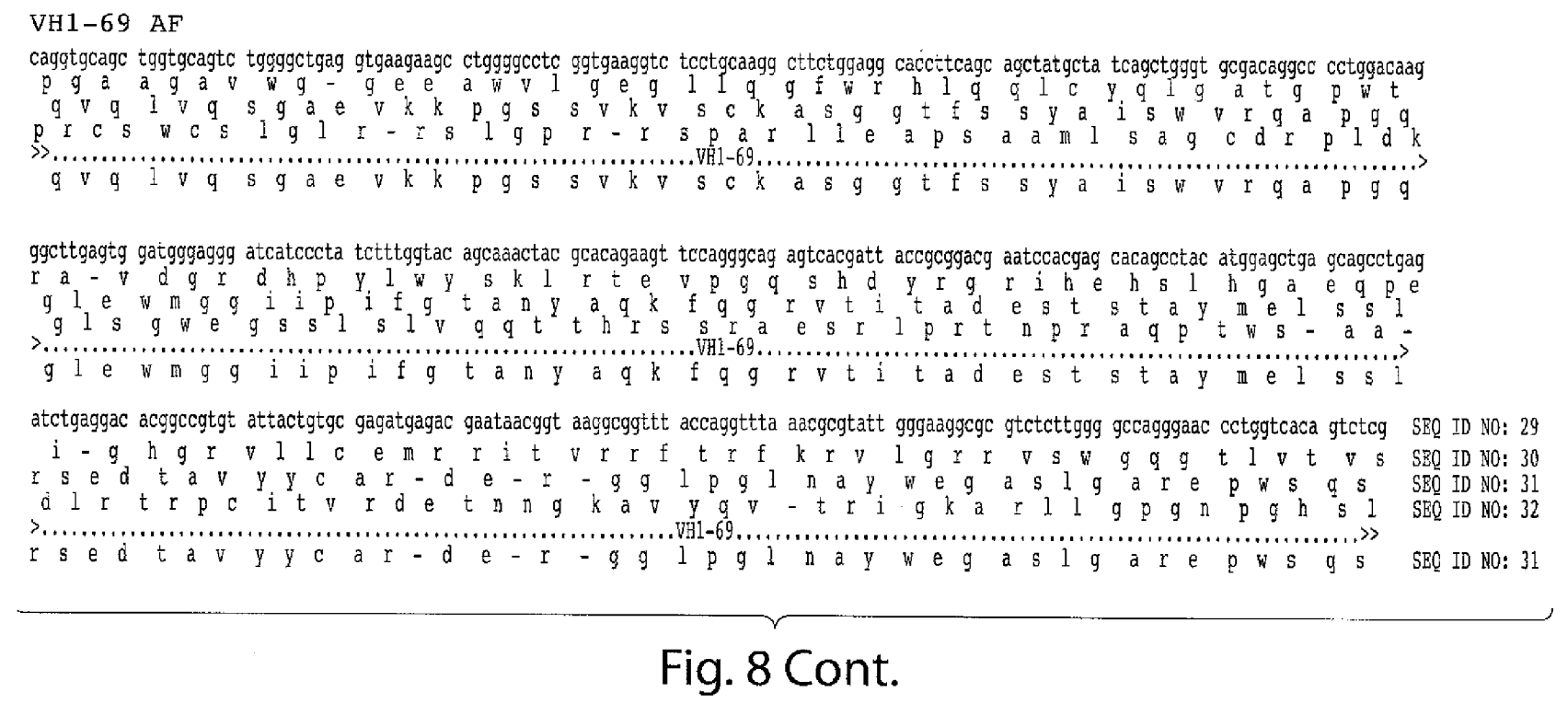
Figure 8:
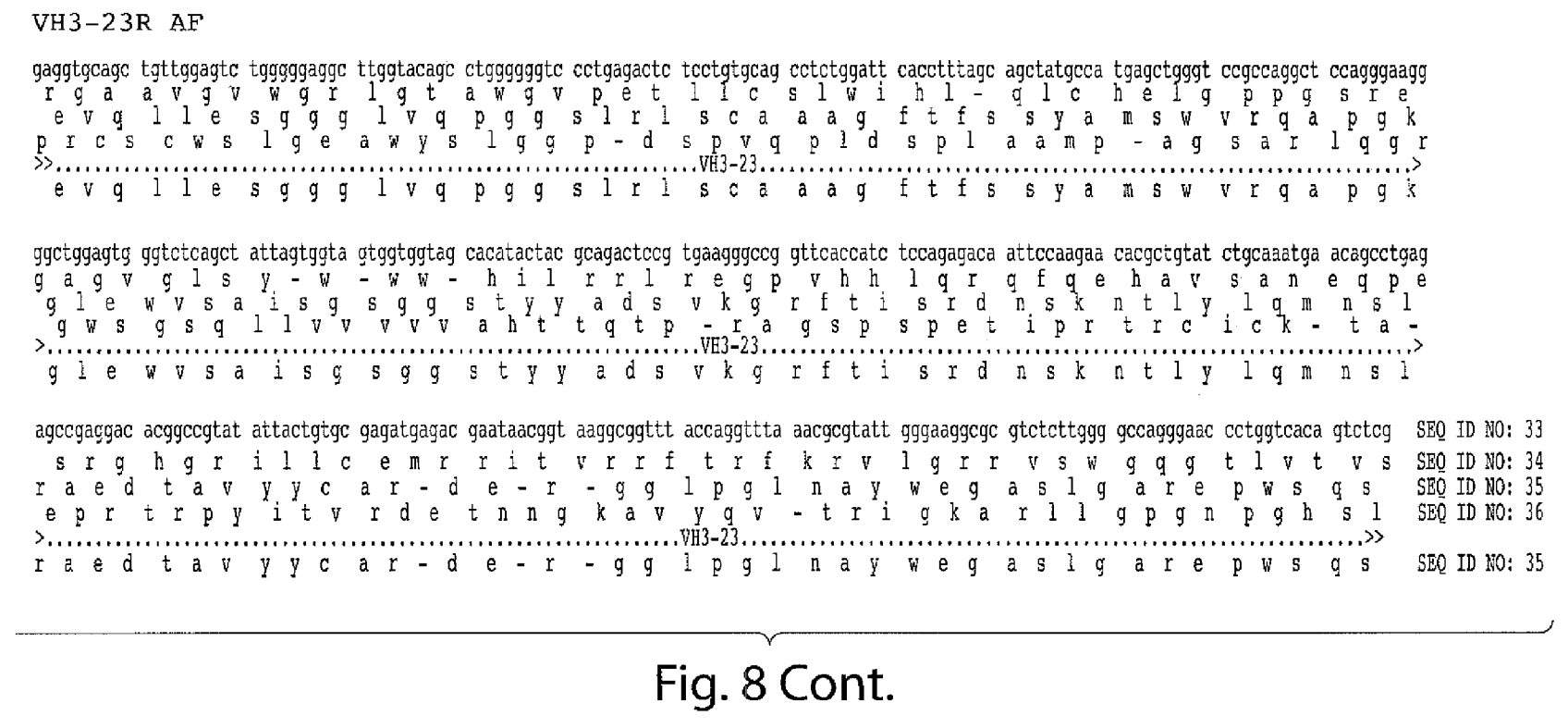
Figure 8:
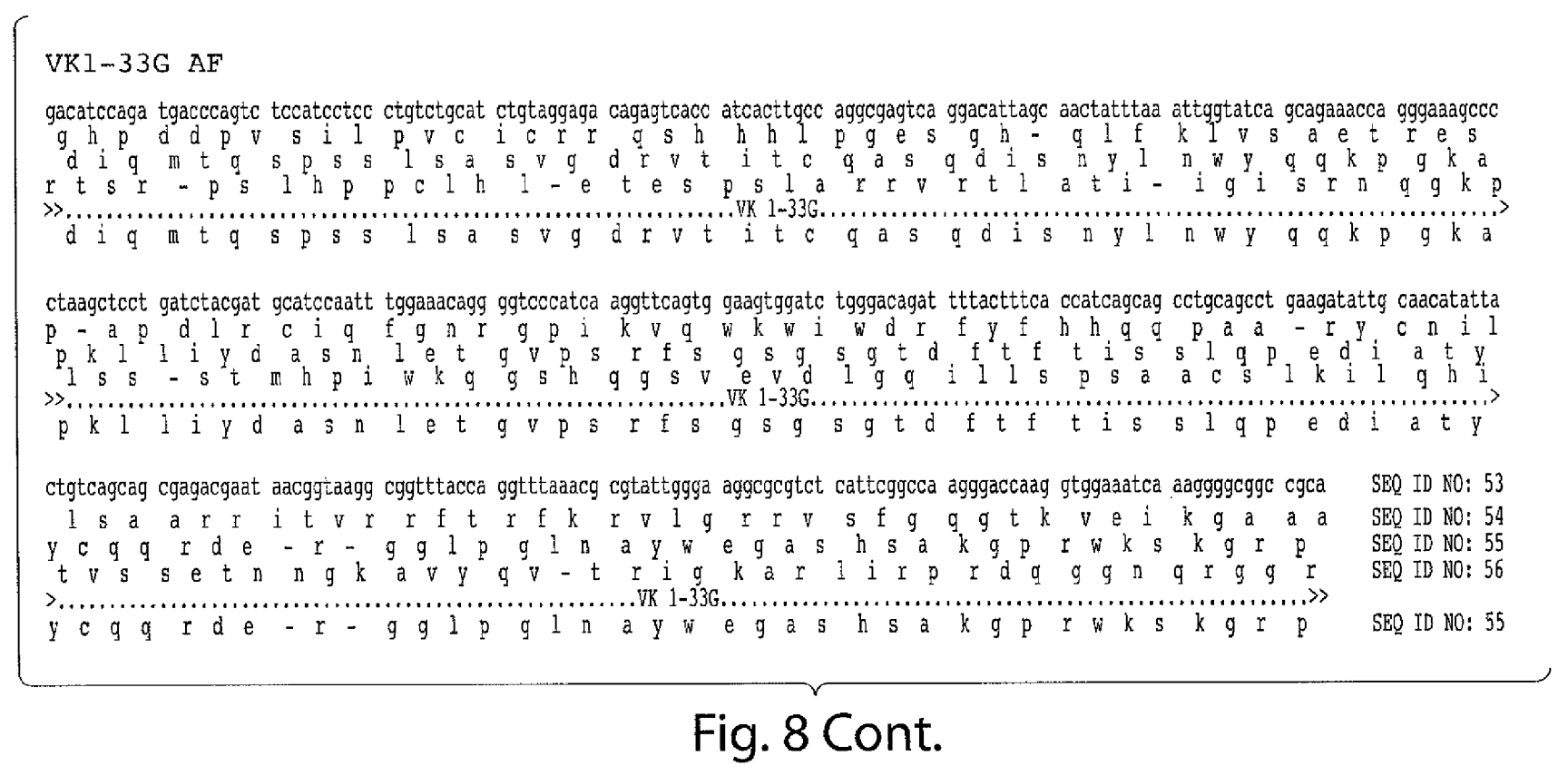
Figure 8:
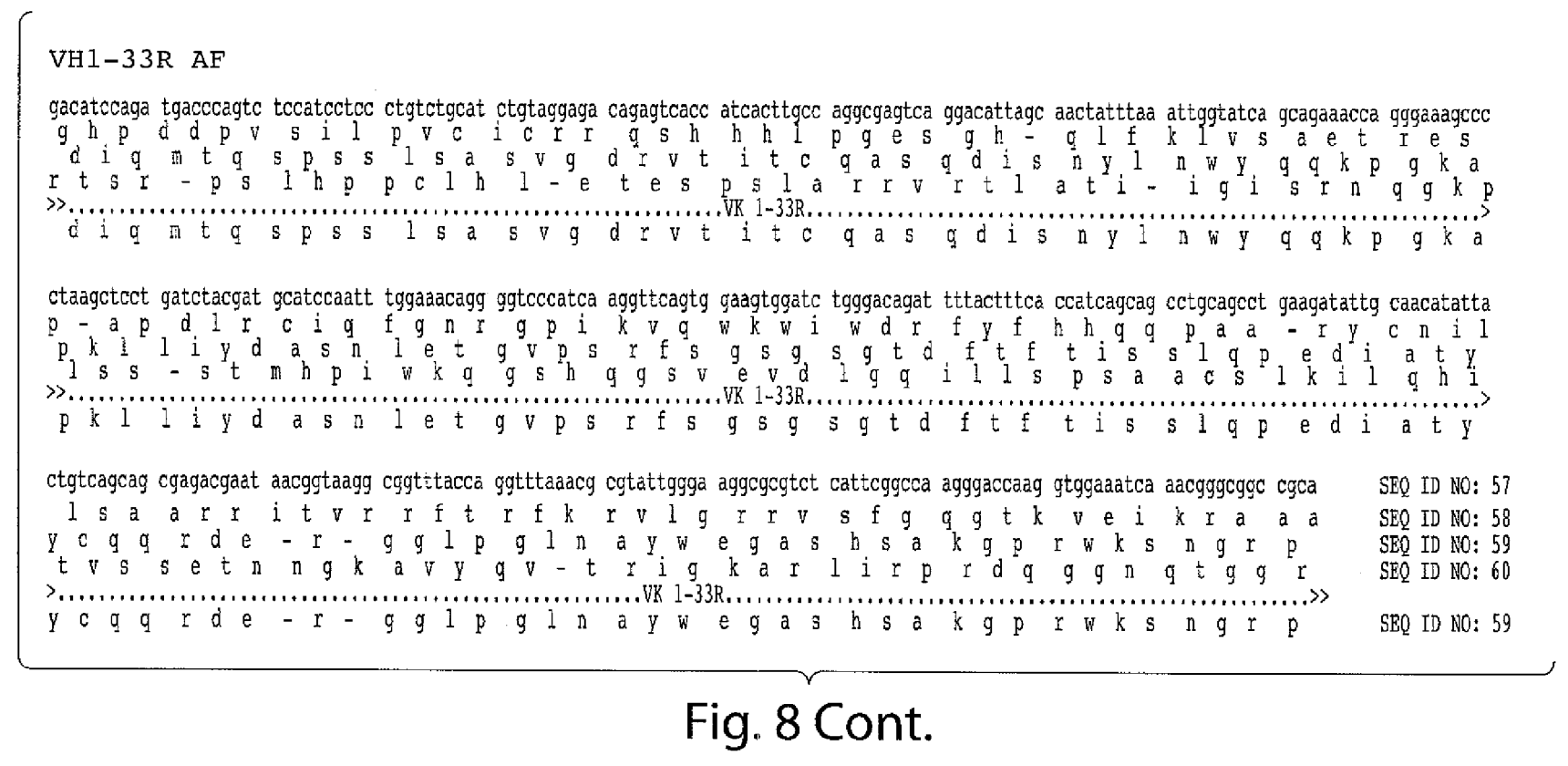
Figure 8:
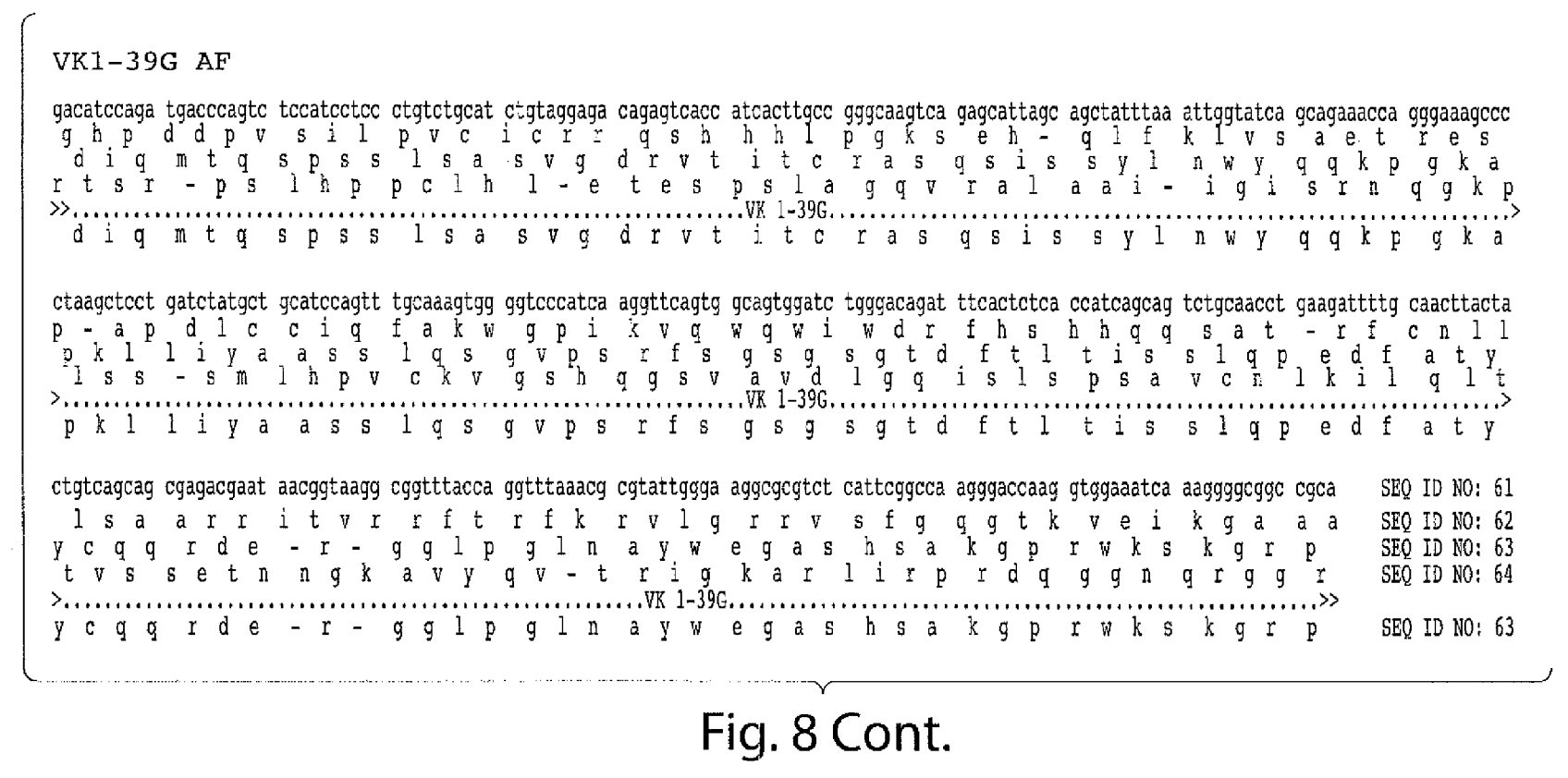
Figure 8:
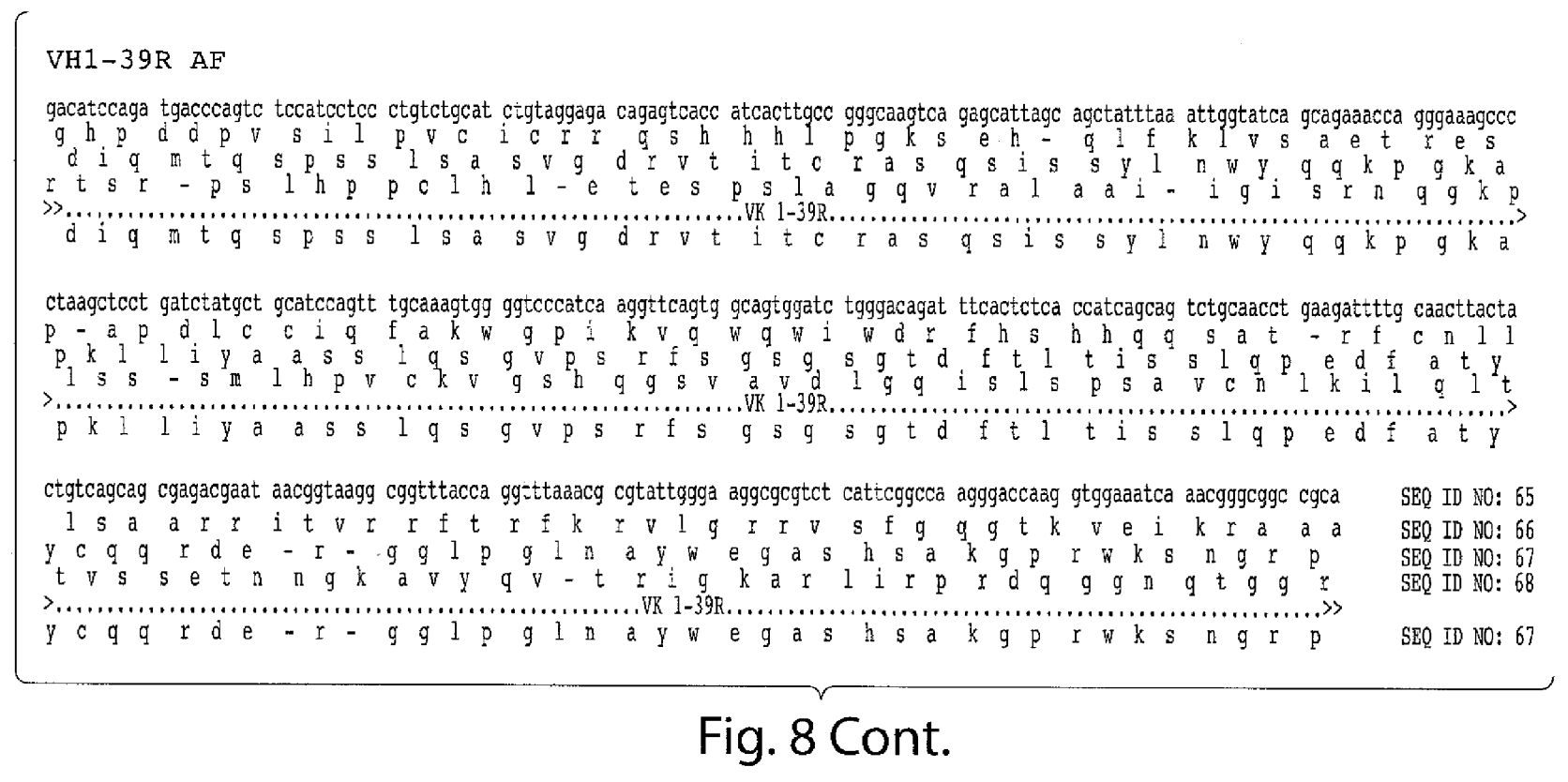
Figure 8:
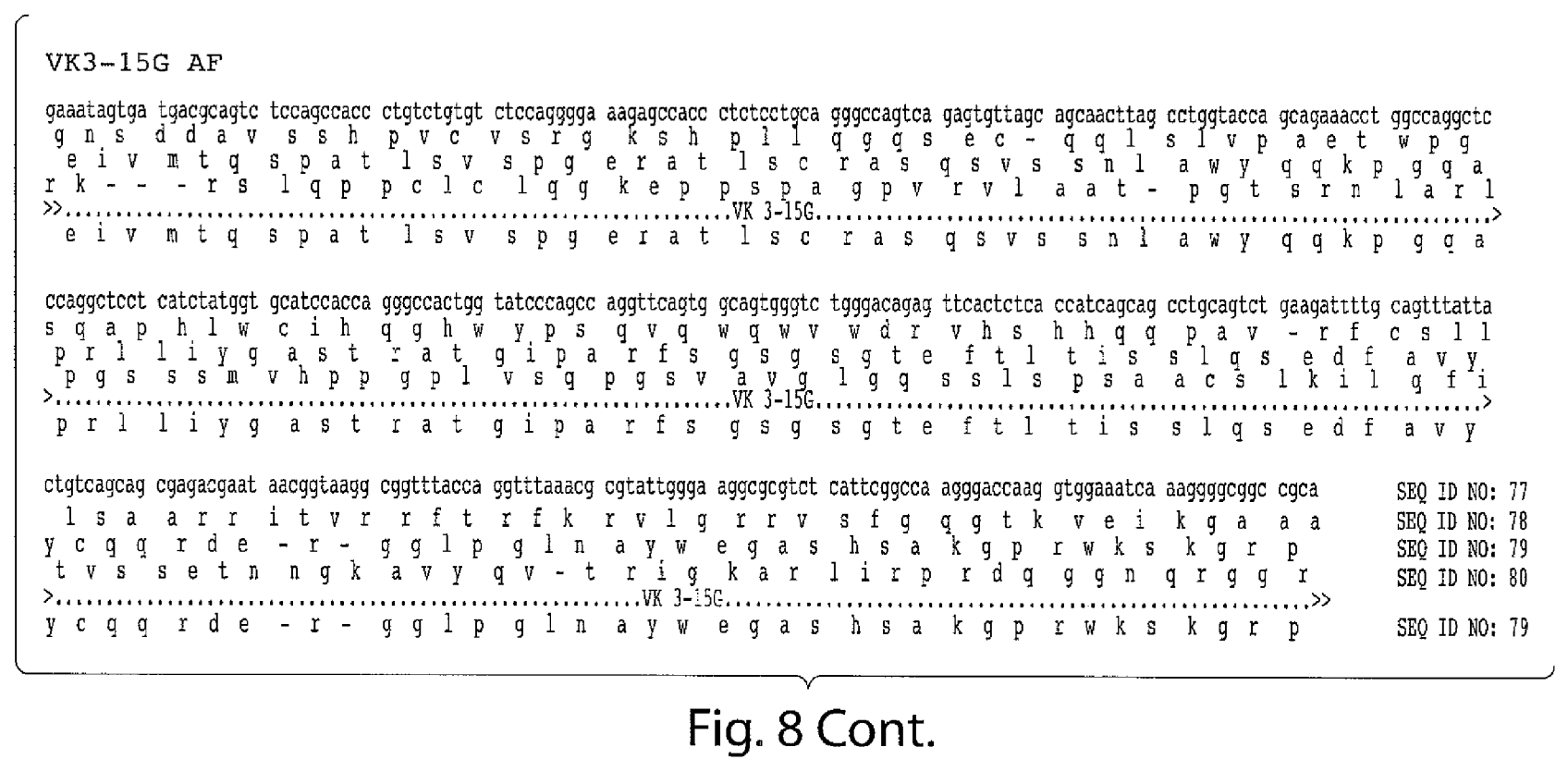
Figure 8:
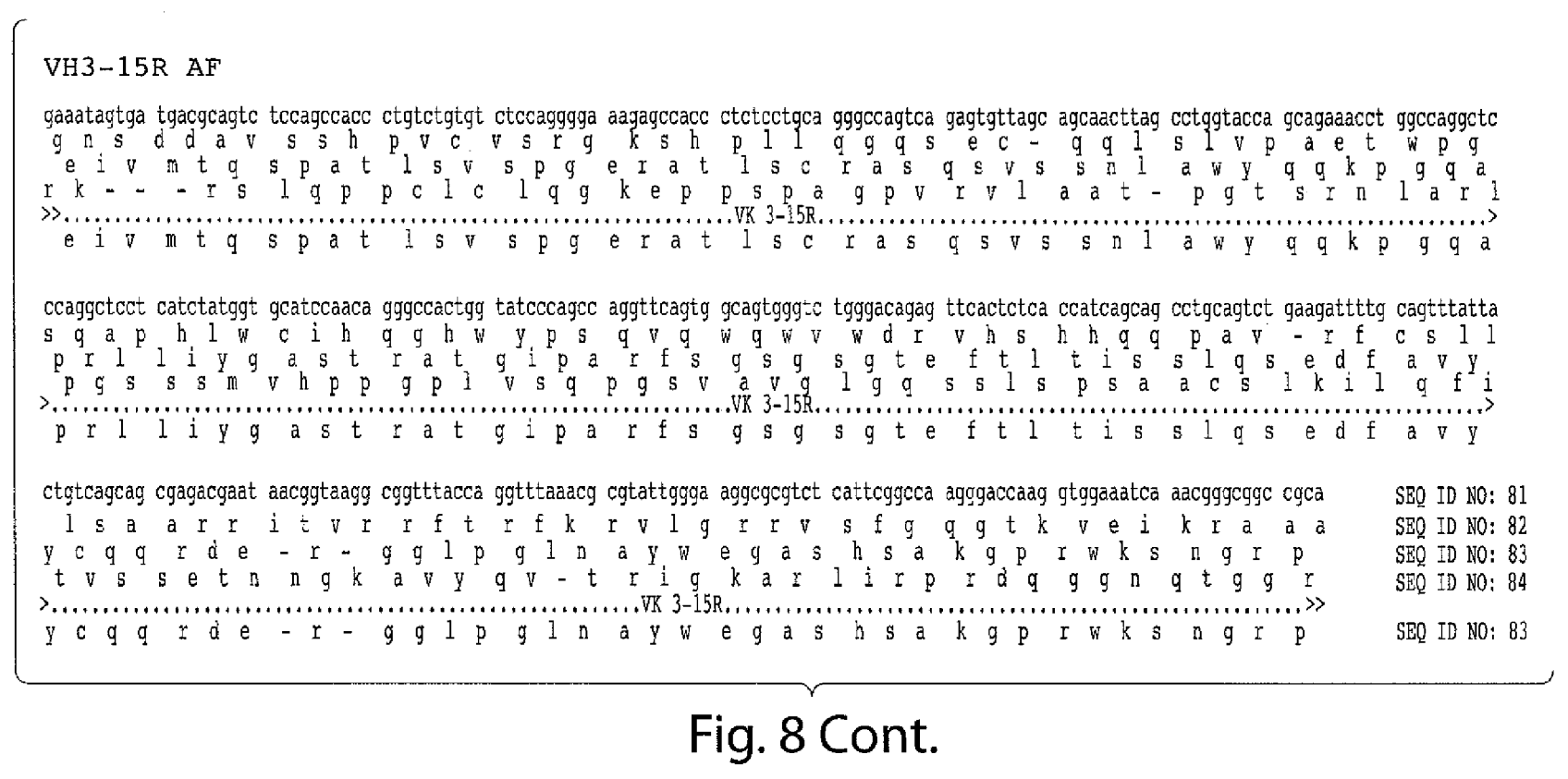
Figure 8:
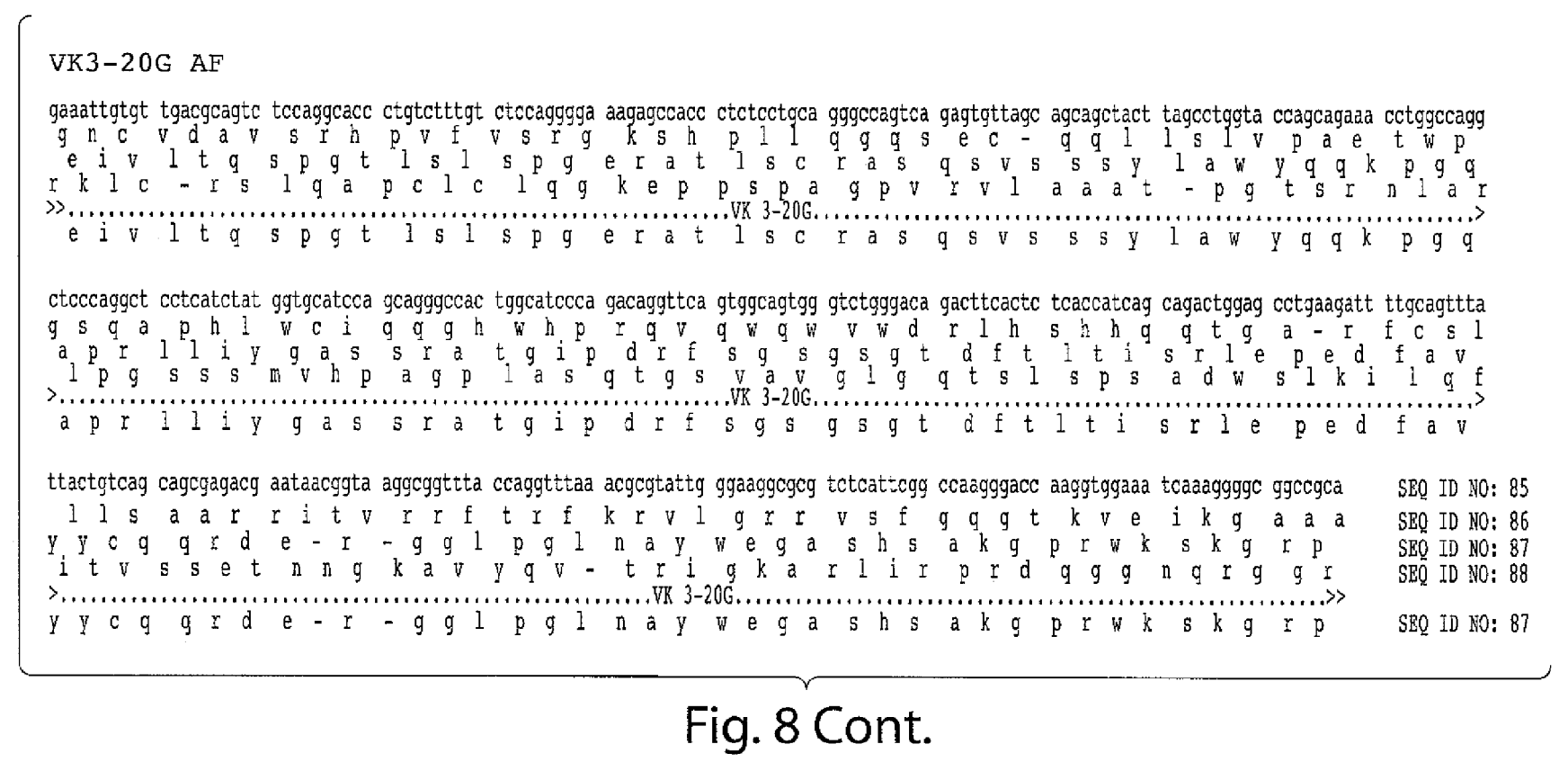
Figure 8:
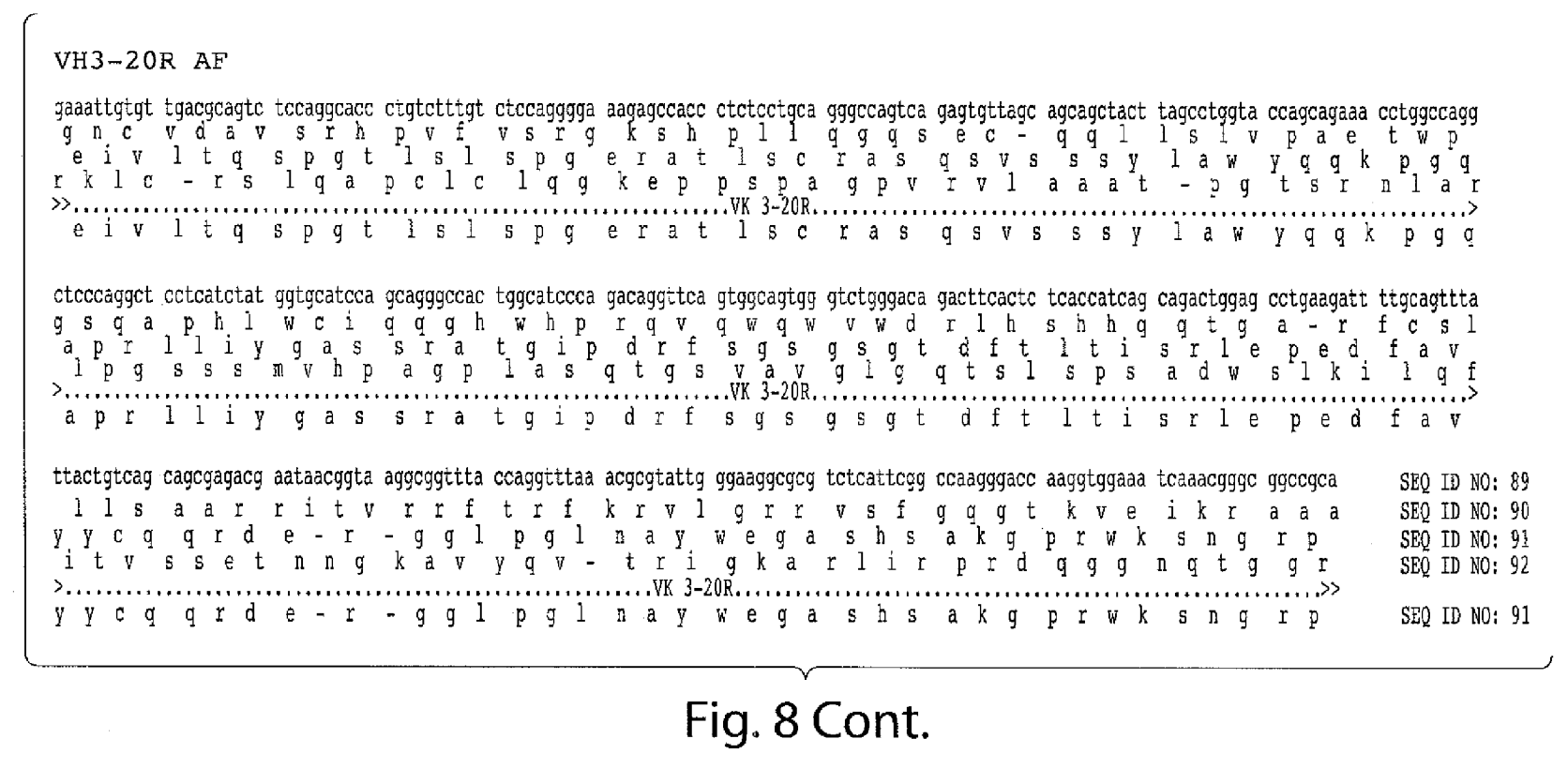
Figure 8:
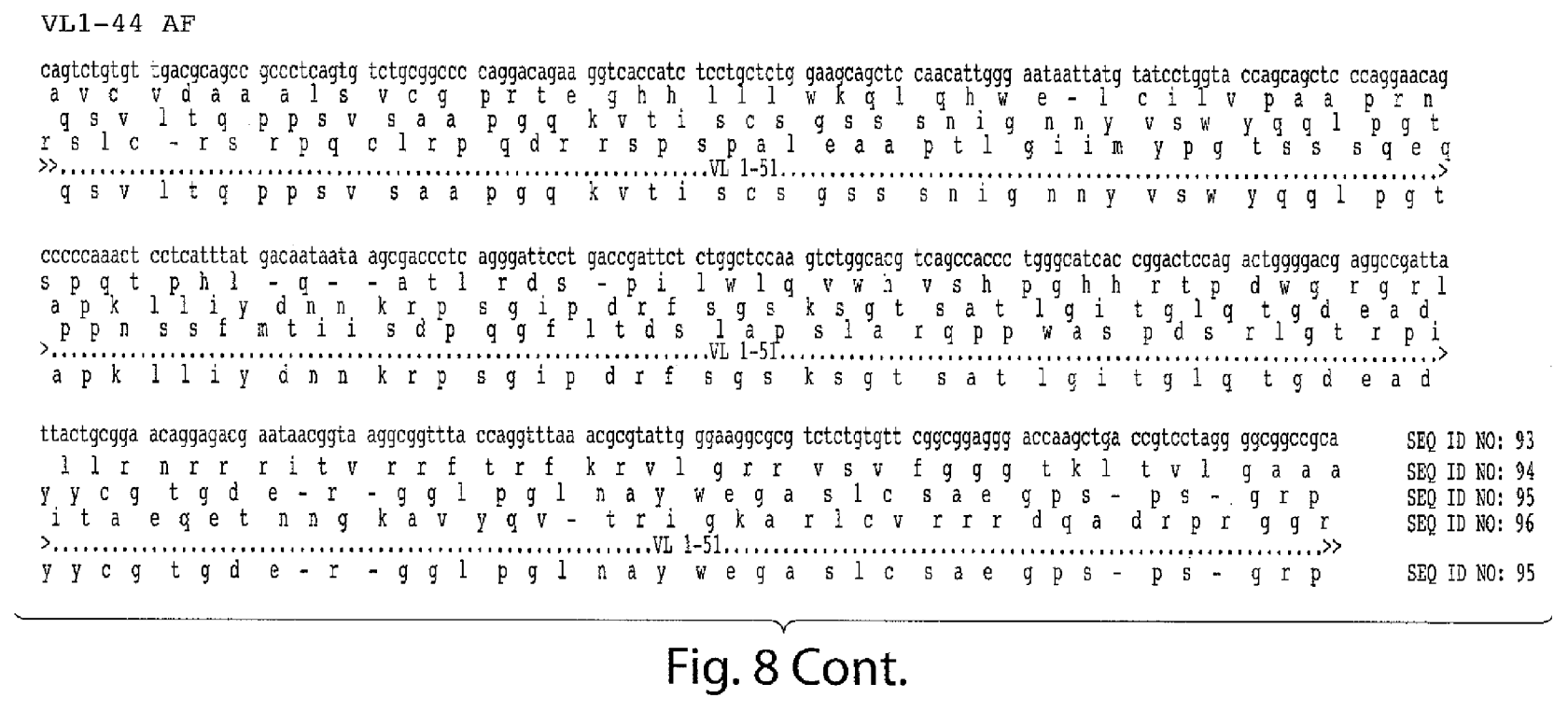
Figure 8:
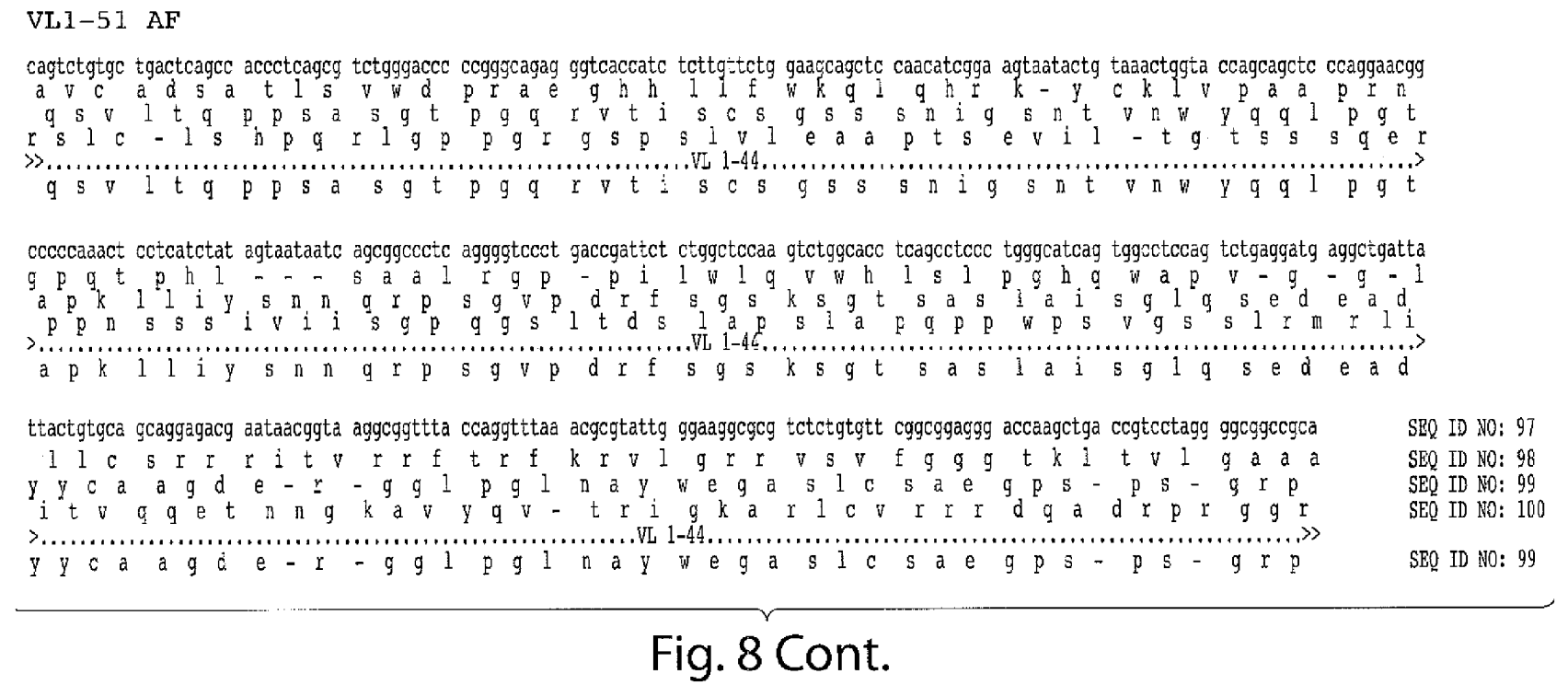

The sequences of the 20 final assembled Acceptor Frameworks are shown in FIG. 8.

Example 3

Generation of Phagemid Acceptor Vectors Containing an Invariant Variable Domain

Figure 9:
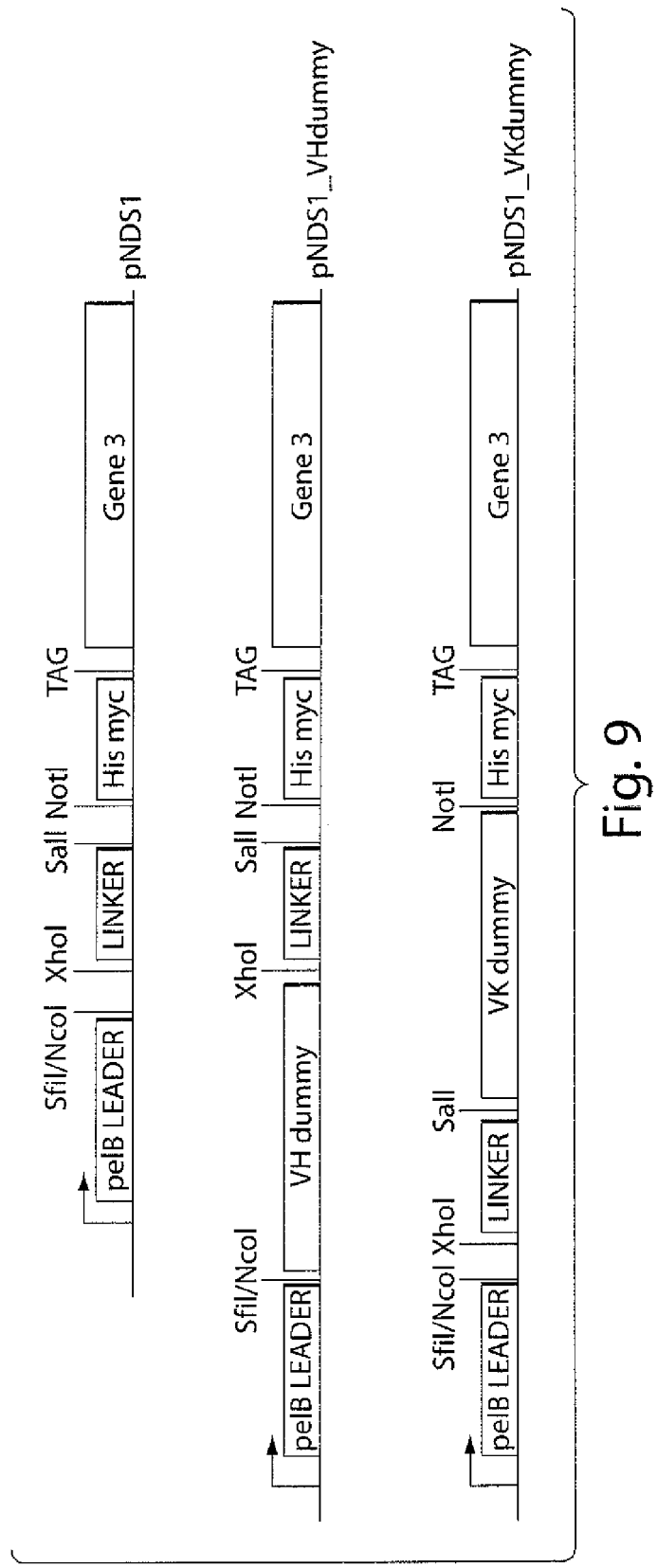
FIG. 9 is a schematic representation of the pNDS1 vector alone or combined with a dummy heavy chain variable region or a dummy light chain variable region.

The phagemid vector pNDS1 used for the expression of scFv was first modified to remove two BsmBI sites. A VH3-23 domain containing a defined CDR3 sequence was cloned into the modified pNDS1 using the SfiI and XhoI restriction sites to obtain the phagemid vector pNDS_VHdummy. This domain contained a BsmBI site in the FR4 region, which was corrected by silent site directed mutagenesis. In parallel, a VK1-39 domain containing a defined CDR3 sequence was then cloned into the modified pNDS1 using the SalI and NotI restriction sites to obtain the phagemid vector pNDS_VKdummy (FIG. 9). The 8 VH Acceptor Frameworks were cloned into pNDS_VKdummy using the SalI and NotI restrictions sites. The 12 VL Acceptor Frameworks were cloned into pNDS_VHdummy using the SfiI and XhoI restrictions sites. The resulting 20 pNDS phagemid vectors that are listed below could at this stage be used for cloning of diversified CDR3 using the BsmBI sites present in the stuffer DNA fragments.

VH Acceptors: pNDS_VH1-2_VKd; pNDS_VH1-18_VKd; pNDS_VH1-69_VKd; pNDS_VH3-23R_VKd; pNDS_VH3-23K_VKd; pNDS_VH3-30_VKd; pNDS_VH5-51_VKd; pNDS_VH3-48_VKd.

VL Acceptors: pNDS_VHd_VK1-33G; pNDS_VHd_VK1-33R; pNDS_VHd_VK1-39G; pNDS_VHd_VK1-39R; pNDS_VHd_VK3-11G; pNDS_VHd_VK3-11R; pNDS_VHd_VK3-15G; pNDS_VHd_VK3-15R; pNDS_VHd_VK3-20G; pNDS_VHd_VK3-20R; pNDS_VHd_VL1-44; pNDS_VHd_VK1-51.

Example 4

Capturing Natural CDR H3 Diversity from Human Repertoires

Multiple sources of human cDNA were used as a template for amplification of CDR H3 sequences. These sources included human fetal spleen as well as pools of male and female normal adult peripheral blood purified cells. Several strategies for amplification have been used in order to recover CDR H3 sequences originating from rearranged VH cDNA encoded by a specific germline gene or CDR H3 sequences originating from any VH cDNA.

First, mixtures of primers matching the 5' coding regions of the majority of human VH families were used in combination with primer mixtures matching all the human JH regions. This allowed for PCR amplification a majority of heavy chain immunoglobulin variable genes. The expected amplification products of approximately 400 base pairs (bp) were isolated by agarose gel electrophoresis and purified. This DNA served as template in a second PCR step using primers with a 13 bp and 14 bp match for the end FR3 region and the beginning of FR4, respectively. In most cases, the last residue of the FR3 is either an arginine or a lysine. As the last bp matches are critical for primer extension by the polymerase, two different 5' primers were used: 5 VHR_FOK (SEQ ID NO: 205 shown below) and 5 VHK_FOK (SEQ ID NO: 206 shown below). Importantly, these primers also contain a FokI restriction site for excision of the CDR H3 sequence (FIG. 4). The primers used in the second PCR step were biotinylated at their 5' end to facilitate downstream purification steps (see example 5). This two step approach allows for an efficient amplification of the CDR H3 sequences despite the limited number of base pairs matches. Amplifications were performed at varying annealing temperatures (between 30° C. and 70° C.) and with several thermostable DNA polymerases to establish optimal conditions. An annealing temperature of 55-58° C. in combination with GoTaq polymerase (Promega) was found to be optimal for this set of primers. The second amplification product was separated on a 2% agarose gel and resulted in a smear in the lower part of the gel corresponding to CDR H3 of different length. Either the complete DNA smear was extracted from the gel or a region corresponding to larger DNA fragments in order to enrich for long CDR H3.

Alternatively, the first amplification step was performed using the 5' primer 5 VH3-23H2 (SEQ ID NO: 201 shown below), which is specific for the sequence encoding the CDR H2 of the germline VH3-23. As the different germline genes are diverse in this CDR, VH cDNAs encoded by the selected germline gene can be preferentially amplified. The subsequent purification and amplification steps were identical. In this way, it is possible to retrieve CDRs originating from a specific framework environment and to re-introduce them into the same, a similar or different framework.

Below is a list of primers used for the amplification of natural human CDR H3 repertoires.

1st PCR step
5 VH1/5
(SEQ ID NO: 195)
CCGCACAGCCGGCCATGGCCCAGGTGCAGCTGGTGCAGTCTGG

5 VH3
(SEQ ID NO: 196)
CCGCACAGCCGGCCATGGCCGAGGTGCAGCTGGTGGAGTCTGG

5 VH2
(SEQ ID NO: 197)
CCGCACAGCCGGCCATGGCCCAGRTCACCTTGCTCGAGTCTGG

5 VH4
(SEQ ID NO: 198)
CCGCACAGCCGGCCATGGCCCAGGTGCAGCTGCAGGAGTCGGG

5 VH4DP64
(SEQ ID NO: 199)
CCGCACAGCCGGCCATGGCCCAGCTGCAGCTGCAGGAGTCCGG

5 VH4DP63
(SEQ ID NO: 200)
CCGCACAGCCGGCCATGGCCCAGGTGCAGCTACAGCAGTGGGG

5 VH3-23H2
(SEQ ID NO: 201)
TGGAGTGGGTCTCAGCTATTAGTGGTAGTGGT

3 HJ1/2
(SEQ ID NO: 202)
CGATGGGCCCTTGGTGGAGGCTGAGGAGACRGTGACCAGGGTGCC

3 HJ3/6
(SEQ ID NO: 203)
CGATGGGCCCTTGGTGGAGGCTGAAGAGACGGTGACCRTKGTCCC

3 HJ4/5
(SEQ ID NO: 204)
CGATGGGCCCTTGGTGGAGGCTGAGGAGACGGTGACCAGGGTTCC

2nd PCR step
5 VHR_FOK
(SEQ ID NO: 205)
GAGCCGAGGACACGGCCGGATGTTACTGTGCGAGA

5 VHK_FOK
(SEQ ID NO: 206)
GAGCCGAGGACACGGCCGGATGTTACTGTGCGAAA

3 JH1_FOK
(SEQ ID NO: 207)
GAGGAGACGGTGACGGATGTGCCCTGGCCCCA

3 JH2_FOK
(SEQ ID NO: 208)
GAGGAGACGGTGACGGATGTGCCACGGCCCCA

3 JH3456_FOK
(SEQ ID NO: 209)
GAGGAGACGGTGACGGATGTYCCTTGGCCCCA

Example 5

Generation of Primary Libraries by Cloning Natural Human CDR H3 into Acceptor Frameworks The amplified CDR H3 were digested with FokI, and the cleaved extremities as well as undigested DNA was removed using streptavidin coated magnetic beads. In parallel, pNDS VH Acceptor vectors were digested using BsmBI. As the overhangs generated by these digestions are compatible, the collection of natural CDR H3 was able to be ligated into the VH Acceptor Framework restoring the appropriate reading frame. The ligated DNA was purified and concentrated for transformation into competent *E. coli* XL1 Blue cells, and random clones analyzed by sequencing in order to check that CDR H3 sequence had been reconstituted and that junctions between the CDR and the Framework region are correct (FIG. 10). The results indicated that all the clones contained CDR H3 sequences and that the reading frame was restored, thus encoding an immunoglobulin variable heavy chain. In addition, all the CDRs were different, indicating that a large diversity of naturally occurring sequences had been captured by this approach. The length of the CDR H3 was also variable and relatively long CDRs of 10 to 15 residues were found, thus underscoring the advantage of this approach for sampling long CDR sequences that are difficult to cover using synthetic diversity.

Using this method, natural CDR H3 sequences, derived either from pooled human peripheral blood purified cells or human fetal spleen, were cloned into each of the pNDS VH Acceptor Frameworks and transformed into electrocompetent *E. coli* TG1 cells and plated on 2×TYAG Bioassay plates (2×TY media containing 100 µg/ml ampicillin and 2% glucose). After overnight incubation at 30° C., 10 ml of 2×TYAG liquid medium was added to the plates and the cells were scraped from the surface and transferred to a 50 ml polypropylene tube. 2×TYAG containing 50% glycerol was added to the cell suspension to obtain a final concentration of 17% glycerol. Aliquots of the libraries were stored at −80° C. In this process, 14 primary libraries were generated representing a total of $8.1 \times 10^9$ transformants. 180 randomly picked clones were sequenced to determine the quality and diversity of the libraries. All clones encoded different VH sequences and >89% were in frame. These primary libraries contain diversity in the CDR H3 only as they are combined with a dummy VL domain.

Example 6

Figure 11:
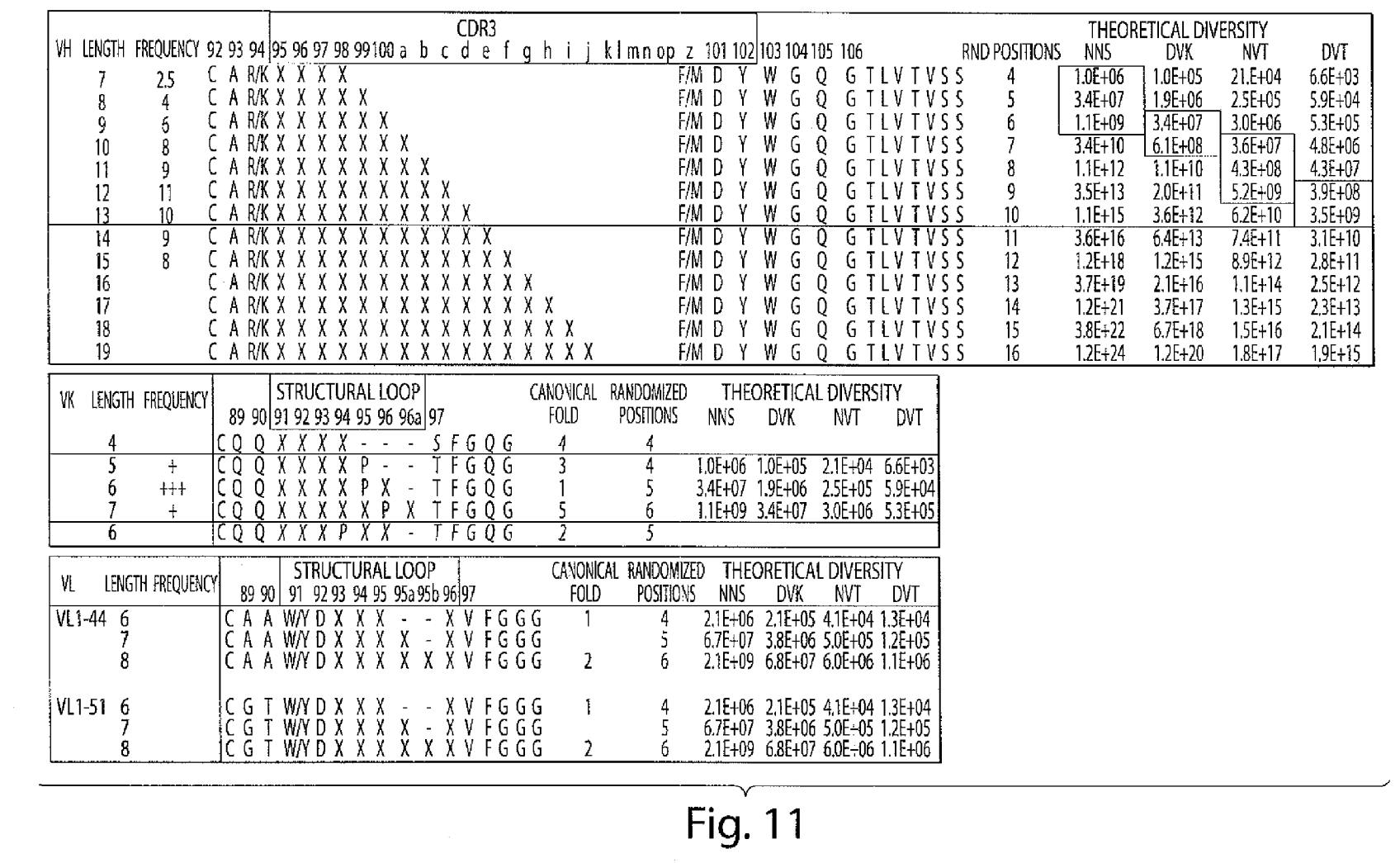

Generation of Primary Libraries by Cloning Synthetic CDR3 into Acceptor Frameworks Although the method is of particular interest for retrieving natural diversity, it can also be applied for the integration of synthetic diversity into Acceptor Frameworks. Synthetic CDR3 sequences were designed for both the VH and VL. The design took into account the frequency of CDRs with a given length and the diversification strategy (NNS, DVK, NVT or DVT codons) that would allow a complete coverage of the theoretical diversity within a reasonable number of transformants in a library (~$5 \times 10^9$ transformants) (FIG. 11). Key residues to maintain the canonical structure of the CDR were kept constant in the design of CDR3 for VK and Vλ chains. For the heavy chain, only CDR3 with up to 10 diversified positions were generated as the number of clones required to cover the diversity encoded by longer CDRs is beyond practical limits of transformation efficiency.

Figure 12:
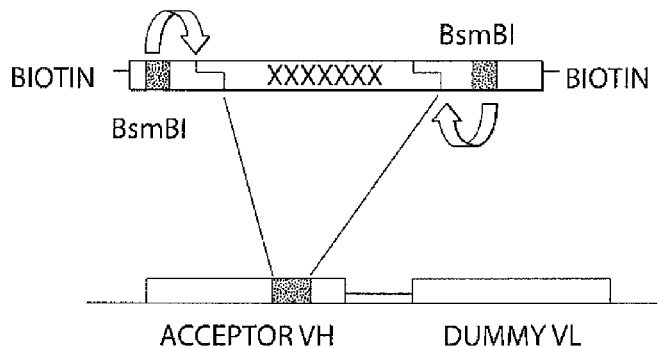
FIG. 12 is a schematic representation and sequence detail of synthetic CDR insertion into an Acceptor Framework.

Degenerate oligonucleotides of different length were synthesized using NNS, NVT, DVK or DVT randomized codons. For each CDR H3, two oligonucleotides were synthesized encoding either a methionine or a phenylalanine at position 100z (FIG. 11). Each oligonucleotide was extended and amplified with two external biotinylated primers to generate double stranded DNA fragments encoding the designed CDRs. These external primers contain BsmBI restriction sites for subsequent excision of the CDR sequence and insertion into the Acceptor Frameworks (FIG. 12). The assembled DNA fragments were processed without gel purification and digested with BsmBI. The cleaved extremities as well as undigested DNA was removed using streptavidin coated magnetic beads. The digested DNA fragments were concentrated by ethanol precipitation and ligated into the corresponding pNDS VH, VK or Vλ Acceptor vectors. Ligation products were purified and concentrated for transformation into electrocompetent *E. coli* TG1 cells and plated on 2×TYAG Bioassay plates (2×TY media containing 100 µg/ml ampicillin and 2% glucose). After overnight incubation at 30° C., 10 ml of 2×TYAG liquid medium was added to the plates and the cells were scraped from the surface and transferred to a 50 ml polypropylene tube. 2×TYAG containing 50% glycerol was added to the cell suspension to obtain a final concentration of 17% glycerol Aliquots of the libraries were stored at −80° C. A total of 24 primary heavy chain libraries were generated representing a total of $1.6 \times 10^{10}$ transformants. Similarly, 13 primary light chain libraries were generated representing a total of $6.9 \times 10^9$ transformants. These primary libraries contain diversity in the CDR H3 only as they are combined with a dummy VL domain. A total of 330 randomly picked clones were sequenced to determine the quality and diversity of the libraries. All clones encoded different variable domain sequences and >90% were in frame. This low frequency of sequences containing shifts in the reading frame is in sharp contrast with results traditionally obtained during the construction of synthetic antibody fragment libraries using overlapping PCR approaches which are more prone to the introduction of insertion, and significant loss of functional clones (15-45%) has frequently been reported.

The diversity in these primary libraries was restricted to the CDR H3 or CDR L3 as they are combined with a dummy VL or VH chain, respectively.

Primers used for synthetic CDR assembly are listed below.

```
5 H3_R_biot    ATGATGCTGCTGGCACGTCTCCGAGA                                    (SEQ ID NO: 210)

3 H3_M_biot    CCACGTCATCCGATCCGTCTCCCCCAATAATCCAT                           (SEQ ID NO: 211)

3 H3_F_biot    CCACGTCATCCGATCCGTCTCCCCCAATAATCAAA                           (SEQ ID NO: 212)

H3_4nnsF       GCTGGCACGTCTCCGAGANNSNNSNNSNNSTTTGATTATTGGGGGAGACG            (SEQ ID NO: 213)

H3_4nnsM       GCTGGCACGTCTCCGAGANNSNNSNNSNNSATGGATTATTGGGGGAGACG            (SEQ ID NO: 214)

H3_5nnsF       GCTGGCACGTCTCCGAGANNSNNSNNSNNSNNSTTTGATTATTGGGGGAGACG         (SEQ ID NO: 215)

H3_5nnsM       GCTGGCACGTCTCCGAGANNSNNSNNSNNSNNSATGGATTATTGGGGGAGACG         (SEQ ID NO: 216)

H3_6nnsF       GCTGGCACGTCTCCGAGANNSNNSNNSNNSNNSNNSTTTGATTATTGGGGGAGACG      (SEQ ID NO: 217)

H3_6nnsM       GCTGGCACGTCTCCGAGANNSNNSNNSNNSNNSNNSATGGATTATTGGGGGAGACG      (SEQ ID NO: 218)

H3_6dvkF       GCTGGCACGTCTCCGAGADVKDVKDVKDVKDVKDVKTTTGATTATTGGGGGAGACG      (SEQ ID NO: 219)
```

| | | |
|---|---|---|
| H3_6dvkM | GCTGGCACGTCTCCGAGADVKDVKDVKDVKDVKDVKATGGATTATTGGGGGAGACG | (SEQ ID NO: 220) |
| H3_7dvkF | GCTGGCACGTCTCCGAGADVKDVKDVKDVKDVKDVKDVKTTTGATTATTGGGGGAGACG | (SEQ ID NO: 221) |
| H3_7dvkM | GCTGGCACGTCTCCGAGADVKDVKDVKDVKDVKDVKDVKATGGATTATTGGGGGAGACG | (SEQ ID NO: 222) |
| H3_7nvtF | GCTGGCACGTCTCCGAGANVTNVTNVTNVTNVTNVTNVTTTTGATTATTGGGGGAGACG | (SEQ ID NO: 223) |
| H3_7nvtM | GCTGGCACGTCTCCGAGANVTNVTNVTNVTNVTNVTNVTATGGATTATTGGGGGAGACG | (SEQ ID NO: 224) |
| H3_8nvtF | GCTGGCACGTCTCCGAGANVTNVTNVTNVTNVTNVTNVTNVTTTTGATTATTGGGGGAGACG | (SEQ ID NO: 225) |
| H3_8nvtM | GCTGGCACGTCTCCGAGANVTNVTNVTNVTNVTNVTNVTNVTATGGATTATTGGGGGAGACG | (SEQ ID NO: 226) |
| H3_9nvtF | GCTGGCACGTCTCCGAGANVTNVTNVTNVTNVTNVTNVTNVTNVTTTTGATTATTGGGGGAGACG | (SEQ ID NO: 227) |
| H3_9nvtM | GCTGGCACGTCTCCGAGANVTNVTNVTNVTNVTNVTNVTNVTNVTATGGATTATTGGGGGAGACG | (SEQ ID NO: 228) |
| H3_9dvtF | GCTGGCACGTCTCCGAGADVTDVTDVTDVTDVTDVTDVTDVTDVTTTTGATTATTGGGGGAGACG | (SEQ ID NO: 229) |
| H3_9dvtM | GCTGGCACGTCTCCGAGADVTDVTDVTDVTDVTDVTDVTDVTDVTATGGATTATTGGGGGAGACG | (SEQ ID NO: 230) |
| H3_10dvtF | GCTGGCACGTCTCCGAGADVTDVTDVTDVTDVTDVTDVTDVTDVTDVTTTTGATTATTGGGGGAGACG | (SEQ ID NO: 231) |
| H3_10dvtM | GCTGGCACGTCTCCGAGADVTDVTDVTDVTDVTDVTDVTDVTDVTDVTATGGATTATTGGGGGAGACG | (SEQ ID NO: 232) |
| 5 KL3_biot | CCGGTGTAGCGAAGGCGTCTCAGCAG | (SEQ ID NO: 233) |
| 3 KL3_biot | TAGGGTCGCCTTGATCGTCTCCCGAAGGTCGG | (SEQ ID NO: 234) |
| K_4nns | GAAGGCGTCTCAGCAGNNSNNSNNSNNSCCGACCTTCGGGAGACG | (SEQ ID NO: 235) |
| K_5nns | GAAGGCGTCTCAGCAGNNSNNSNNSNNSCCGNNSACCTTCGGGAGACG | (SEQ ID NO: 236) |
| K_6nns | GAAGGCGTCTCAGCAGNNSNNSNNSNNSNNSCCGNNSACCTTCGGGAGACG | (SEQ ID NO: 237) |
| 5 L44W_biot | CGGTCAGTCGCAATACGTCTCCAGCATGGGAT | (SEQ ID NO: 238) |
| 5 L44Y_biot | CGGTCAGTCGCAATACGTCTCCAGCATATGAT | (SEQ ID NO: 239) |
| 3 L_biot | CAGGACCAGTCTCGTGAGGATCGTCTCAACAC | (SEQ ID NO: 240) |
| L44W_4nns | CGTCTCCAGCATGGGATNNSNNSNNSNNSGTGTTGAGACGATCCTC | (SEQ ID NO: 241) |
| L44Y_4nns | CGTCTCCAGCATATGATNNSNNSNNSNNSGTGTTGAGACGATCCTC | (SEQ ID NO: 242) |
| L44W_5nns | CGTCTCCAGCATGGGATNNSNNSNNSNNSNNSGTGTTGAGACGATCCTC | (SEQ ID NO: 243) |
| L44Y_5nns | CGTCTCCAGCATATGATNNSNNSNNSNNSNNSGTGTTGAGACGATCCTC | (SEQ ID NO: 244) |
| L44W_6nns | CGTCTCCAGCATGGGATNNSNNSNNSNNSNNSNNSGTGTTGAGACGATCCTC | (SEQ ID NO: 245) |
| L44Y_6nns | CGTCTCCAGCATATGATNNSNNSNNSNNSNNSNNSGTGTTGAGACGATCCTC | (SEQ ID NO: 246) |
| 5 L51W_biot | CGGTCAGTCGCAATACGTCTCGAACATGGGAT | (SEQ ID NO: 247) |
| 5 L51Y_biot | CGGTCAGTCGCAATACGTCTCGAACATATGAT | (SEQ ID NO: 248) |
| L51W_4nns | CGTCTCGAACATGGGATNNSNNSNNSNNSGTGTTGAGACGATCCTC | (SEQ ID NO: 249) |
| L51Y_4nns | CGTCTCGAACATATGATNNSNNSNNSNNSGTGTTGAGACGATCCTC | (SEQ ID NO: 250) |
| L51W_5nns | CGTCTCGAACATGGGATNNSNNSNNSNNSNNSGTGTTGAGACGATCCTC | (SEQ ID NO: 251) |
| L51Y_5nns | CGTCTCGAACATATGATNNSNNSNNSNNSNNSGTGTTGAGACGATCCTC | (SEQ ID NO: 252) |
| L51W_6nns | CGTCTCGAACATGGGATNNSNNSNNSNNSNNSNNSGTGTTGAGACGATCCTC | (SEQ ID NO: 253) |
| L51Y_6nns | CGTCTCGAACATATGATNNSNNSNNSNNSNNSNNSGTGTTGAGACGATCCTC | (SEQ ID NO: 254) |

Example 7

Generation of Secondary Libraries

Figure 13:
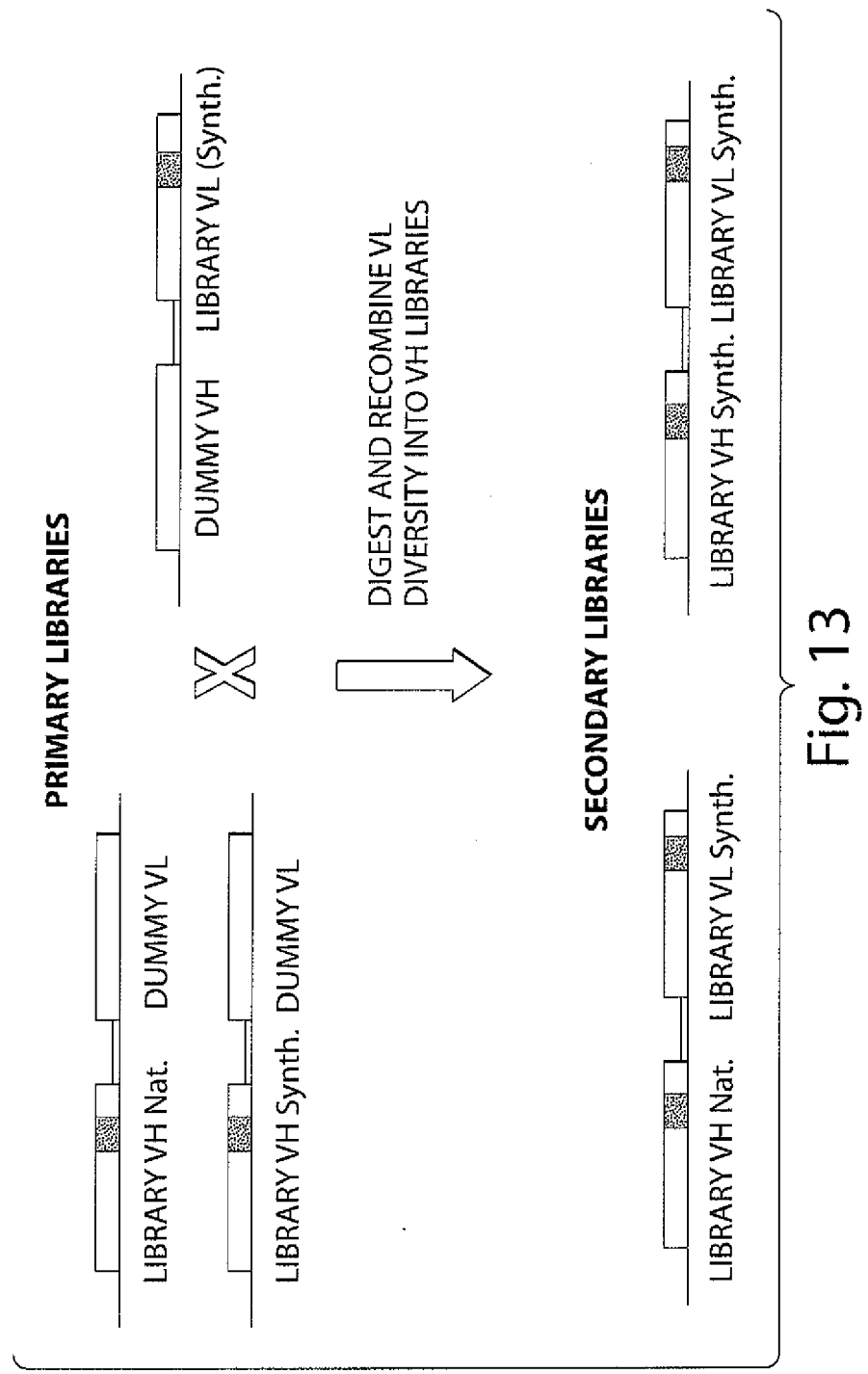
FIG. 13 is a schematic representation of Primary libraries and the chain recombination performed to generate Secondary libraries.

In order to generate libraries of scFv carrying diversity in both the heavy and light chains, the Primary synthetic light chain libraries were combined with either the Primary synthetic heavy chain libraries or the Primary natural heavy chain libraries (FIG. 13). Phagemid DNA was prepared from each primary library and digested with XhoI/NotI restriction enzymes. The DNA fragments corresponding to the linker and light chains from the Primary synthetic libraries were inserted by ligation into the digested Primary natural or synthetic heavy chain vectors. Alternatively the Linker-VL sequence was also amplified with specific primers before digestion with XhoI/NotI and ligation. The ligation products were purified by phenol/chloroform extraction and precipitation before transformation into electrocompetent E. coli TG1 cells and plating on 2×TYAG Bioassay plates (2×TY media containing 100 µg/ml ampicillin and 2% glucose). After overnight incubation at 30° C., 10 ml of 2×TYAG liquid medium was added to the plates and the cells were scraped from the surface and transferred to a 50 ml polypropylene tube. 2×TYAG containing 50% glycerol was added to the cell suspension to obtain a final concentration of 17% glycerol. Aliquots of the libraries were stored at −80° C. To limit the number of libraries to be recombined, they were pooled by chain subclasses (i.e., VH1, VH3, VH5, VK1, VK3, Vλ1) and thus 9 library combination were performed for (i.e., VH1×VK1, VH1×VK3, VH1×Vλ1, VH3×VK1, VH3×VK3, VH3×Vλ1, VH5×VK1, VH5×VK3, VH5×Vλ1). The total size of the Secondary synthetic libraries (carrying synthetic diversity in both the VH and VL) was 7.3×10$^9$ transformants. The total size of the Secondary natural libraries (carrying natural diversity in the VH and synthetic diversity in the VL) was 1.5×10$^{10}$ transformants.

Example 8

Generation of Human Antibody Libraries Displaying a CDRH3 Repertoire Derived from a Non-Human Species In order to utilize alternative sources of diversity that would allow exploring a different tri-dimensional space within the antibody combining site, a library was created by capturing the CDRH3 of mice and introduced them into a collection of human antibody frameworks. For this approach an acceptor library containing a collection of VL genes with synthetic CDR L3 diversity was constructed and combined with a collection of acceptor sequences containing a stuffer DNA sequence ready suitable for Type IIS restriction cloning as described in Example 2. This library represents the starting point for rapid generation of secondary libraries with multiple sources of natural (human as well as non-human) or synthetic CDR H3. In this example, natural CDR H3 diversity was captured from naïve Balb/c mice and mice that had been immunized with hIFNγ or hCCL5 (hRANTES).

Figure 14:
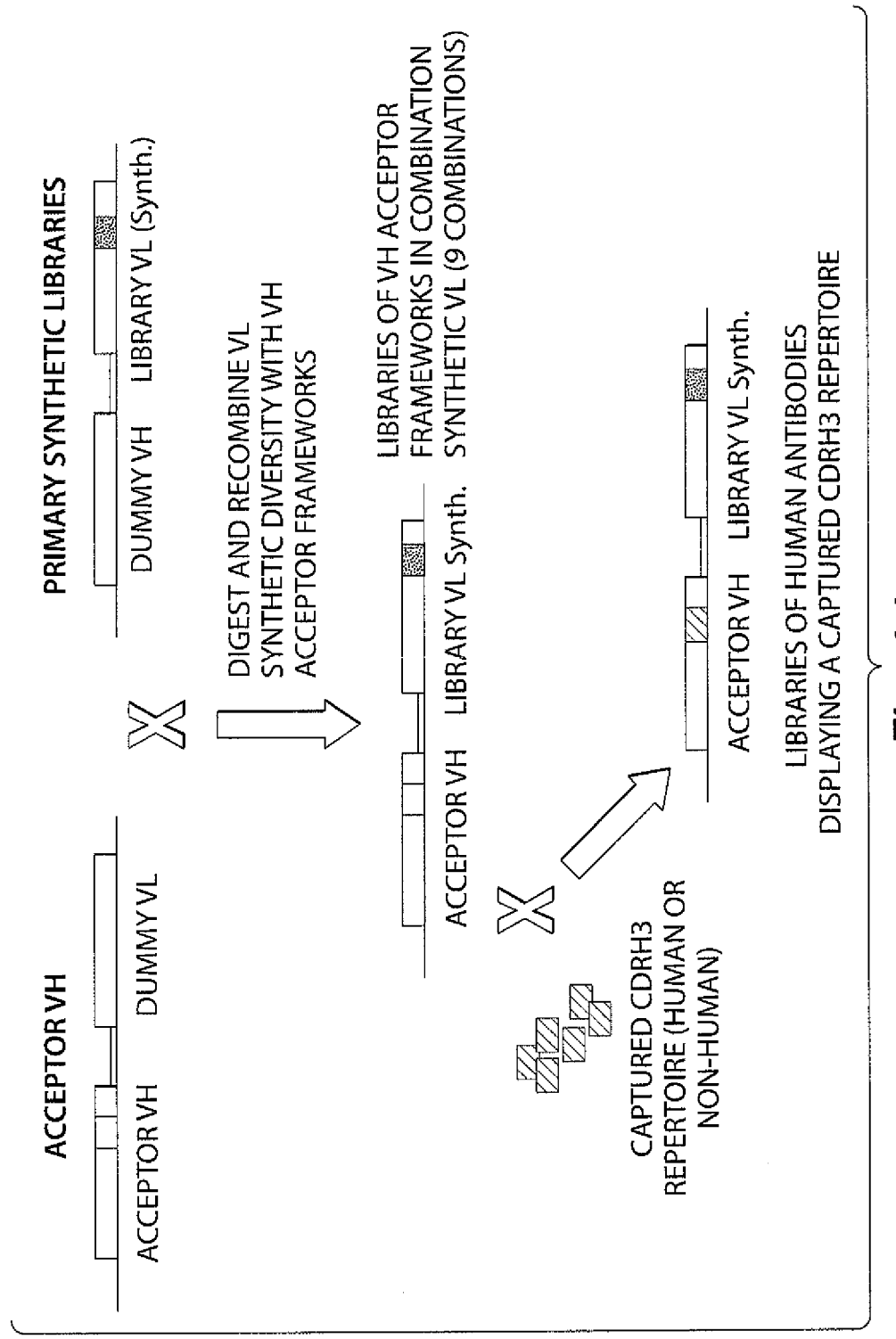
FIG. 14 is a schematic representation of the generation of Acceptor VH libraries combined with VL synthetic libraries and the capture of CDRH3 repertoires of human or non-human origin.

The first step was the generation of acceptor libraries by cloning a collection of VL containing synthetic CDR L3 diversity into acceptor VH framework vectors (FIG. 14). The VL sequences were derived from the seven Primary Synthetic Libraries described in Example 6 by PCR amplification using primers 5' biot-VHdummy and 3' biot-fdtseq. The resulting VL containing fragments of approximately 400 bp were digested using XhoI/NotI and purified on spin columns to remove primers and enzymes. Similarly the pNDS VH acceptor vectors containing a CDRH3 stuffer and a dummy light chain were digested with XhoI/NotI and SwaI (SwaI cutting inside the VL dummy) and purified on Chroma Spin TE columns with a cutoff of 1000 bp to get rid of the VL dummy fragment. The digested VL fragments were then ligated into the VH acceptor vectors (FIG. 14). To limit the number of libraries to be recombined, VH acceptor vectors and VL fragments were pooled by chain subclasses (i.e., VH1, VH3, VH5, VK1, VK3, Vλ1) and thus nine library combinations were performed (i.e., VH1×VK1, VH1×VK3, VH1×Vλ1, VH3×VK1, VH3×VK3, VH3×Vλ1, VH5×VK1, VH5×VK3, VH5×Vλ1). The ligation products were transformed into electrocompetent E. coli TG1 cells and plated on 2×TYAG Bioassay plates (2×TY medium containing 100 µg/ml ampicillin and 2% glucose). After overnight incubation at 30° C., 6 ml of 2×TYAG liquid medium was added to the plates and the cells were scraped from the surface and transferred to a 50 ml polypropylene tube. Glycerol 50% was added to the cell suspension to obtain a final concentration of 17% glycerol. Aliquots of the libraries were stored at −80° C. The total size of this acceptor library, carrying synthetic diversity in the CDR L3, was 1.9×10$^9$ transformants.

The next step was to isolate CDRH3 sequences from a non-human source. Cells were isolated from the spleen of five naïve or immunized Balb/c mice and total RNA was purified. cDNA was obtained from the extracted RNA by RT-PCR. This cDNA was used as template to isolate and amplify mouse VH by PCR. A series of PCRs were performed using 15 different 5' primers (one for each mouse VH subgroup) specific for the beginning of the FR1 region and a pool of 3' primers (four primers covering the JH region). These first PCRs were pooled and purified on a 2% agarose gel. The purified DNA served as template to perform a second PCR to isolate the mouse CDR H3 region.

The 5' and 3' primers for this second PCR target the FR3 and FR4 regions of mouse VH, respectively. These primers added a FokI restriction site in order to allow for precise excision of the CDR H3 and cloning into the human acceptor vectors. However, alignments of murine VH sequences revealed that sequence at the 5' boundary of murine CDR-H3 and that are located at the cleavage site of FokI almost always differ from human sequence by one base, whereas the 3' end matched between these two species. The sequences cleaved by FokI are boxed in Table below:

|  | 5' sequences |  |  |  | 3' sequences |  |  |  |
|---|---|---|---|---|---|---|---|---|
| (SEQ ID NO: 281) | Human:<br>Mouse: | TTACTGTGC | GAGA |  | Human:<br>Mouse: | TGGG | GCCAGGGAA | (SEQ ID NO: 286) |
| (SEQ ID NO: 282) | VH1 | TTACTGTGC | AAGA |  | JH1 | TGGG | GCGCAGGGA | (SEQ ID NO: 287) |
| (SEQ ID NO: 283) |  | TTTCTGTGC | AAGA |  | JH2 | TGGG | GCCAAGGCA | (SEQ ID NO: 288) |
| (SEQ ID NO: 284) | VH2 | CTACTGTGC | CAGA |  | JH3 | TGGG | GCCAGGGCA | (SEQ ID NO: 289) |
| (SEQ ID NO: 285) | VH3-16 | TTACTGTGC | AAGA |  | JH4 | TGGG | GTCAGGGCA | (SEQ ID NO: 290) |

Consequently the base had to be corrected during the second amplification step in order to generate cohesive ends that are compatible with the cohesive ends generated upon digestion of the Acceptor Frameworks. Efficient amplification was observed suggesting that this conversion occurred readily. At the 3' end, mouse and human sequences that will be cut by the Type IIS restriction enzymes are identical thus avoiding any correction issues.

Primers for the second amplification were biotinylated at their 5' ends to facilitate downstream purification steps. The acceptor vectors were digested with BsmBI and purified on Chroma Spin TE columns having a cutoff of 1000 bp. After digestion and purification, the nine different library combinations were pooled in equimolar ratio for ligation of the captured mouse CDRH3.

Figure 15:
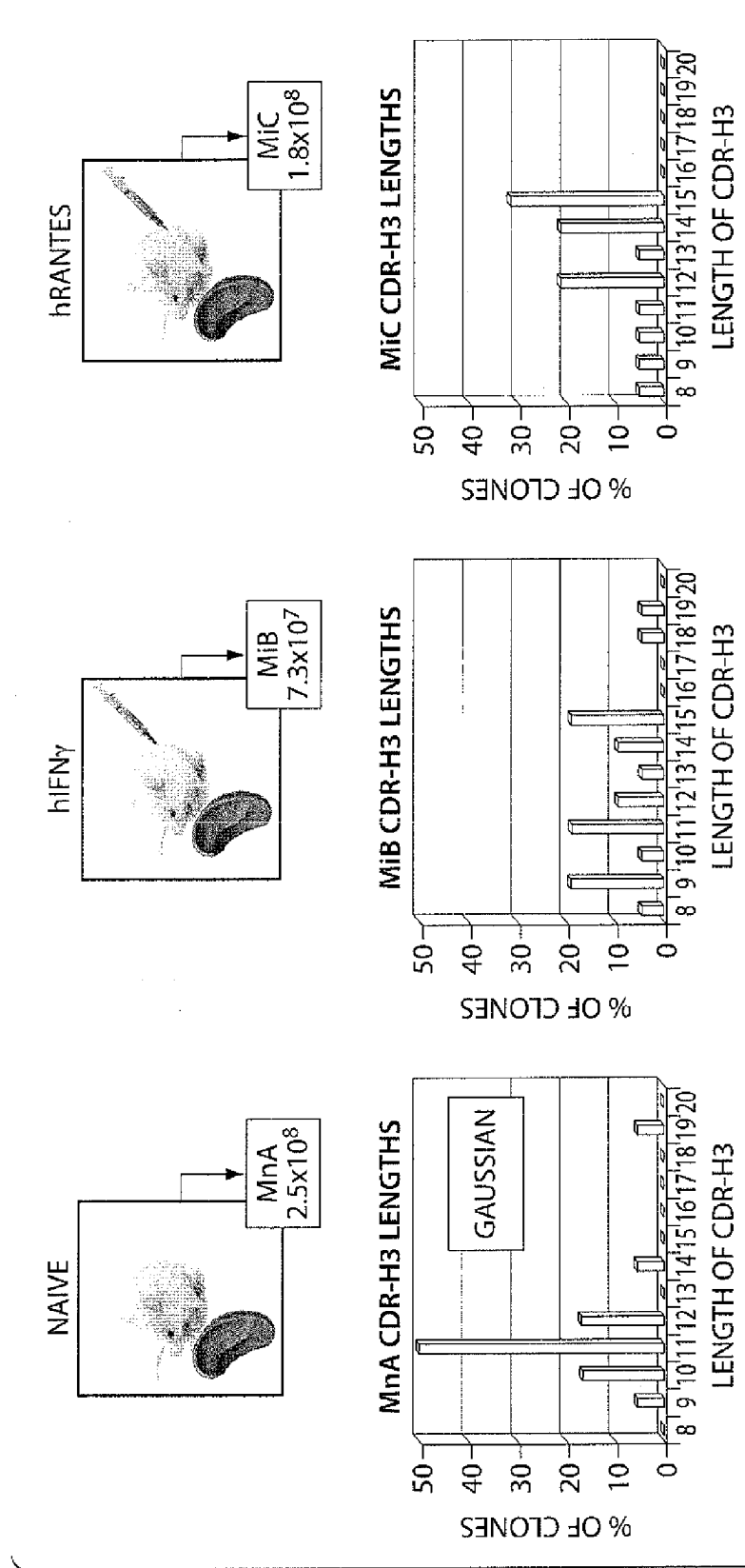
FIG. 15 is a schematic representation of the MnA, MiB and MiC library generation using the CDRH3 repertoire from naïve mice or mice immunized with hIFNγ or hCCL5/RANTES as a source of diversity. The size of the libraries is indicated in the top panels. The bottom panels show the distribution of CDRH3 lengths found in these libraries.

The ligated DNA was purified by phenol/chloroform extractions and concentrated by precipitation before transformation into competent *E. coli* TG1 cells and plated on 2×TYAG Bioassay plates (2×TY medium containing 100 μg/ml ampicillin and 2% glucose). After overnight incubation at 30° C., 6 ml of 2×TYAG liquid medium was added to the plates and the cells were scraped from the surface and transferred to a 50 ml polypropylene tube. Glycerol 50% was added to the cell suspension to obtain a final concentration of 17% glycerol. Aliquots of the libraries were stored at −80° C. Three libraries of similar size were obtained: MnA, $2.5 \times 10^8$ transformants (carrying a restricted natural human framework diversity, naïve mouse diversity in the CDR H3 and synthetic diversity in the CDR L3); MiB, $7.3 \times 10^7$ transformants (carrying a restricted natural human framework diversity, immune mouse diversity against hIFNγ in the CDR H3 and synthetic diversity in the CDR L3) and MiC, $1.8 \times 10^8$ transformants (carrying a restricted natural human framework diversity, immune mouse diversity against hCCL5 in the CDR H3 and synthetic diversity in the CDR L3). Random clones were analyzed by sequencing in order to check that CDR H3 sequence had been reconstituted and that junctions between the CDR and the Framework regions were correct. The results indicated that all the clones contained CDR H3 sequences and that the reading frame was restored, thus encoding an immunoglobulin variable heavy chain. All the CDRs were different and resembled typical mouse CDR H3 sequences indicating that a large diversity of naturally occurring mouse CDRH3 sequences had been captured by this approach. In addition, the analysis of the CDRH3 length profiles indicated that a Gaussian distribution was captured in the naïve library that corresponds to the expected distribution of lengths in normal mouse repertoire. In contrast, in the two immune libraries the profiles were different suggesting that a different CDRH3 repertoire had been captured (FIG. 15).

Primers Used for CDRH3 Amplification from Mice

```
1st PCR
5' primers:
m5 VH1
                                        (SEQ ID NO: 256)
ATGCGGCCCAGCCGGCCATGGCCSAGGTYCAGCTBCAGCAGTC m5 VH2
                                        (SEQ ID NO: 257)
ATGCGGCCCAGCCGGCCATGGCCCAGGTTCACCTGCAGCARTC m5 VH3
                                        (SEQ ID NO: 258)
ATGCGGCCCAGCCGGCCATGGCCCAGGTRCAGCTGAAGGAGTC m5 VH4
                                        (SEQ ID NO: 259)
ATGCGGCCCAGCCGGCCATGGCCCAGGTCCAACTVCAGCARCC m5 VH5
                                        (SEQ ID NO: 260)
ATGCGGCCCAGCCGGCCATGGCCCAGATCCAGTTGGTVCAGTC m5 VH6
                                        (SEQ ID NO: 261)
ATGCGGCCCAGCCGGCCATGGCCCAGGTGCAGCTGAAGSASTC m5 VH7
                                        (SEQ ID NO: 262)
ATGCGGCCCAGCCGGCCATGGCCGAGGTGCAGSKGGTGGAGTC m5 VH8
                                        (SEQ ID NO: 263)
ATGCGGCCCAGCCGGCCATGGCCGAAGTGAARSTTGAGGAGTC m5 VH9
                                        (SEQ ID NO: 264)
ATGCGGCCCAGCCGGCCATGGCCGAKGTSVAGCTTCAGGAGTC
```

-continued
```
m5 VH10
                                        (SEQ ID NO: 265)
ATGCGGCCCAGCCGGCCATGGCCGAGGTGAASSTGGTGGAATC m5 VH11
                                        (SEQ ID NO: 266)
ATGCGGCCCAGCCGGCCATGGCCGAGGTGAAGCTGRTGGARTC m5 VH12
                                        (SEQ ID NO: 267)
ATGCGGCCCAGCCGGCCATGGCCGARGTGAAGCTGRTGGAGTC m5 VH13
                                        (SEQ ID NO: 268)
ATGCGGCCCAGCCGGCCATGGCCGAAGTGCAGCTGTTGGAGAC m5 VH14
                                        (SEQ ID NO: 269)
ATGCGGCCCAGCCGGCCATGGCCGARGTGAAGCTTCTCSAGTC m5 VH15
                                        (SEQ ID NO: 270)
ATGCGGCCCAGCCGGCCATGGCCCARGTTACTCTGAAAGAGT 3' primers:
m3 HJ1
                                        (SEQ ID NO: 271)
CCTGAACCGCCGCCTCCGCTCGAGACGGTGACCGTGGTCCC m3 HJ2
                                        (SEQ ID NO: 272)
CCTGAACCGCCGCCTCCGCTCGAGACTGTGAGAGTGGTGCC m3 HJ3
                                        (SEQ ID NO: 273)
CCTGAACCGCCGCCTCCGCTCGAGACAGTGACCAGAGTCCC m3 HJ4
                                        (SEQ ID NO: 274)
CCTGAACCGCCGCCTCCGCTCGAGACGGTGACTGAGGTTCC 2nd PCR
5' primers:
5 VHR_FOK_Biot
                                        (SEQ ID NO: 275)
GAGCCGAGGACACGGCCGGATGTTACTGTGCGAGA 3' primers:
3'mJH1_Fok_Biot
                                        (SEQ ID NO: 276)
GGGGCGCAGGGACATCCGTCACCGTCTCCTC 3'mJH2_Fok_Biot
                                        (SEQ ID NO: 277)
GAGGAGACTGTGAGGGATGTGCCTTGGCCCCA 3'JH1_Fok
                                        (SEQ ID NO: 278)
GAGGAGACGGTGACGGATGTGCCCTGGCCCCA 3'mJH4_Fok_biot
                                        (SEQ ID NO: 279)
GAGGAGACGGTGACGGATGTTCCTTGACCCCA
```

Example 9

Phage Rescue of the Libraries

Each Primary and Secondary library was rescued independently according to standard phage display procedures briefly summarized hereafter. A volume of cell from the frozen library aliquots sufficient to cover at least 10 times the theoretical diversity of the library was added to 500 ml of 2×TYAG and grown at 37° C. with agitation (240 rpm) until an OD600 of 0.3 to 0.5 was reached. The culture was then super-infected with MK13K07 helper phage and incubated for one hour at 37° C. (150 rpm). The medium was then changed by centrifuging the cells at 2000 rpm for 10 minutes, removing the medium and resuspending the pellet in 500 ml of 2×TY-AK (100 μm/ml ampicillin; 50 μg/ml kanamycin). The culture was then grown overnight at 30° C. (240 rpm). The culture was centrifuged at 4000 rpm for 20 minutes to pellet the cells. The supernatant was collected and 30% (vol/vol) of PEG 8000 (20%)/2.5M NaCl was added to precipitate the phage particles by incubating the mixture 1 hour on ice. The phage particles were collected by centrifugation at 10,000 rpm for 30 minutes and resuspended in 10 ml of TE buffer (10 mM tris-HCl pH 8.0; 1 mM EDTA). The resuspended solution was centrifuged at 10,000 rpm to clear the bacterial debris and the precipitation procedure was repeated. After final resuspension, phage was titrated by infection of E. coli and absorption at 280 nm. The display level of scFv at the surface of phage was also evaluated by Western blot analysis using an anti-c-myc monoclonal antibody. Purified phage from different libraries was stored frozen at −80° C. after addition of glycerol to a final concentration of 15% (w/v).

In order to use a manageable number of libraries during selection procedures, the purified phage was pooled into 4 working libraries: AA1—Phage from all Primary synthetic VH libraries; AB1—Phage from all Primary synthetic VL libraries; AC1—Phage from all Primary natural VH libraries; AD1—Phage from all Secondary natural libraries; AE1—Phage from all Secondary synthetic libraries; MnA—Libraries with diversity captured from naïve mice; MiB—Libraries with diversity captured from mice immunized with hIFNγ; MiC—Libraries with diversity captured from mice immunized with hCCL5/RANTES.

Example 10

High Throughput Sequencing of Antibody Libraries

The quality and diversity of a library can be evaluated by DNA sequencing of random library members. In most cases a few hundred clones are sequenced which represent only a very small fraction of the library (less than 1 in 10,000,000 library members). In order to analyze the performance of the methods provide herein, next generation sequencing technology was used to analyze a more representative number of library members. DNA isolated from the library AE1 was used as a template for high throughput sequencing using an illumina Genome Analyzer instrument. This next-generation DNA sequencing system allows for billions of bases to be read in a few days. The sequencing reads are relatively short (about 70 bases) but perfectly compatible with our library design. As the diversity is confined to the CDR3 regions a 70 base read is sufficient to cover the CDRH3 and part of the framework 3 region for VH family identification. This technology has been applied to sequence several millions of CDRH3 regions from the AE1 library. 5,078,705 sequences were obtained for a total of 365,666,760 bases. Analysis of the data indicated that 5,007,022 sequences (98.6% of the total) were unique. A total of 4,680,882 sequences could be unambiguously ascribed to a VH family (VH1, VH3 and VH5) and the representation of the VH families in the AE1 library determined (41% VH1; 30% VH3; 29% VH5). An important finding was that the proportion of in frame inserts ranged between 88 and 91%. This data confirmed in a far more statistical manner the sequencing results of the 24 primary VH synthetic libraries described in Example 6. This combined set of sequencing data demonstrates that the type IIs restriction cloning process used in this method is very robust, leading to an efficient and productive insertion in the 24 independent library constructions performed to generate the VH diversity of the AE1 library.

The sequencing of millions of library members represents an unprecedented quality control step for an antibody library. The results demonstrate that the method allows for the generation of high quality and high diversity libraries in a reproducible and robust manner.

Example 11

Phage Display Selections Using Secondary Libraries

Figure 16:
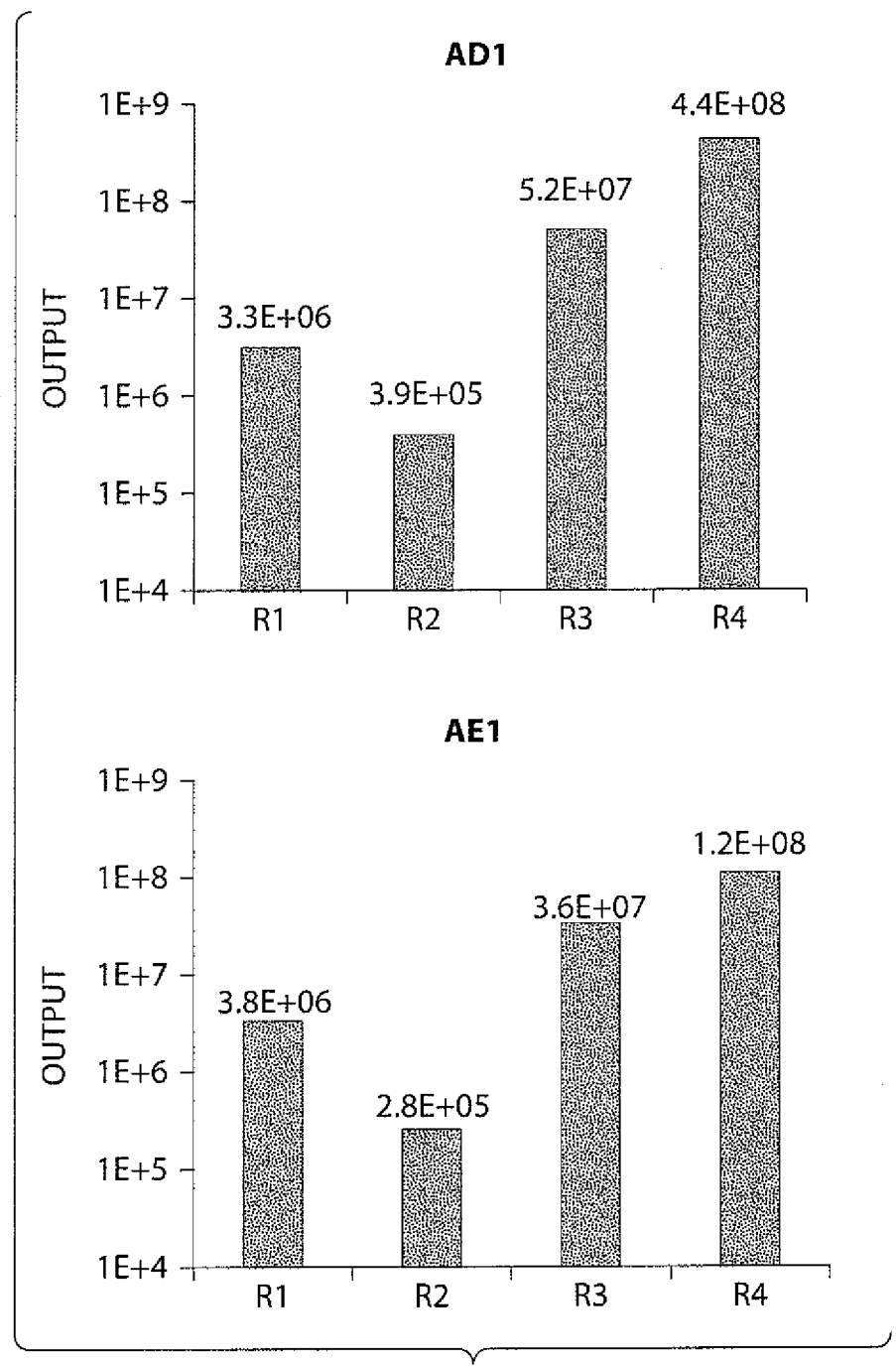
FIG. 16 is a series of graphs depicting phage output titration during selection against hIFNγ with the secondary libraries AD1 and AE1.

Liquid phase selections against human interferon gamma (hIFNγ): Aliquots of AD1 and AE1 phage libraries ($10^{11}$-$10^{12}$ Pfu) were blocked with PBS containing 3% (w/v) skimmed milk for one hour at room temperature on a rotary mixer. Blocked phage was then deselected on streptavidin magnetic beads (Dynal M-280) for one hour at room temperature on a rotary mixer. Deselected phage was then incubated with in vivo biotinylated hIFNγ (100 nM) for two hours at room temperature on a rotary mixer. Beads were captured using a magnetic stand followed by four washes with PBS/0.1% Tween 20 and 3 washes with PBS. Beads were then directly added to 10 ml of exponentially growing TG1 cells and incubated for one hour at 37° C. with slow shaking (100 rpm). An aliquot of the infected TG1 was serial diluted to titer the selection output. The remaining infected TG1 were spun at 3000 rpm for 15 minutes and re-suspended in 0.5 ml 2×TYAG (2×TY media containing 100 μg/ml ampicillin and 2% glucose) and spread on 2×TYAG agar Bioassay plates. After overnight incubation at 30° C., 10 ml of 2×TYAG was added to the plates and the cells were scraped from the surface and transferred to a 50 ml polypropylene tube. 2×TYAG containing 50% glycerol was added to the cell suspension to obtain a final concentration of 17% glycerol. Aliquots of the selection round were kept at −80° C. Phage outputs were titrated after each round and the progressive increase in outputs indicated that the enrichment of clones specific for the target was occurring (FIG. 16).

Figure 17:
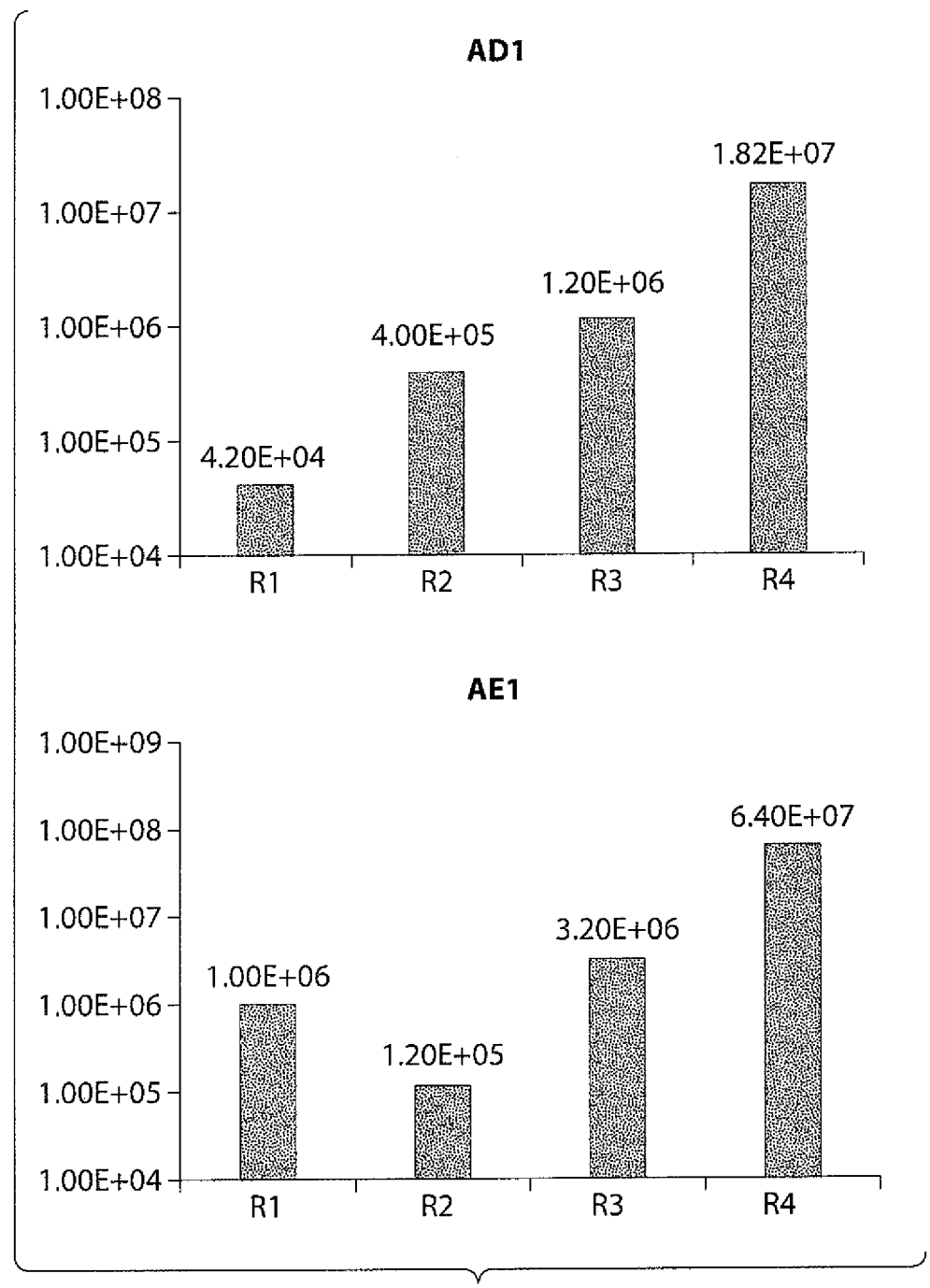
FIG. 17 is a series of graphs depicting phage output titration during selection against monoclonal antibody 5E3 with the secondary libraries AD1 and AE1.

Selections by panning against the rat monoclonal antibody 5E3: Immunotubes were coated with 5E3 at 10 μg/ml in PBS over night at 4° C. and immunotubes for phage deselection were coated with an irrelevant rat antibody under the same conditions. After washing immunotubes were blocked with PBS containing 3% (w/v) skimmed milk for one hour at room temperature. Aliquots of AD1 and AE1 phage libraries ($10^{11}$-$10^{12}$ Pfu) were blocked with PBS containing 3% (w/v) skimmed milk for one hour at room temperature on a rotary mixer. Blocked phage was then deselected in the immunotubes coated with an irrelevant rat antibody for one hour at room temperature on a rotary mixer. Deselected phage was then transferred to the immunotubes coated with 5E3 and incubated for two hours at room temperature on a rotary mixer. Tubes were washed five times with PBS/0.1% Tween 20 and 3 times with PBS. Phage was eluted with TEA 100 mM for 10 minutes and neutralized with 1M Tris HCl pH 7.5. Phage was added to 10 ml of exponentially growing TG1 cells and incubated for one hour at 37° C. with slow shaking (100 rpm). An aliquot of the infected TG1 was serial diluted to titer the selection output. The remaining infected TG1 were spun at 3000 rpm for 15 minutes and re-suspended in 0.5 ml 2×TYAG (2×TY media containing 100 μg/ml ampicillin and 2% glucose) and spread on 2×TYAG agar Bioassay plates. After overnight incubation at 30° C., 10 ml of 2×TYAG was added to the plates and the cells were scraped from the surface and transferred to a 50 ml polypropylene tube. 2×TYAG containing 50% glycerol was added to the cell suspension to obtain a final concentration of 17% glycerol. Aliquots of the selection round were kept at −80° C. Rounds of selection were performed by alternating between rat 5E3 and a chimeric version of 5E3 in which the variable region was fused to mouse constant domains. These alternating rounds were performed in order to enrich for clones specific for the variable region of 5E3 and generate anti-idiotypic antibodies. Phage outputs were titrated after each round and the progressive increase in outputs indicated that the enrichment of clones specific for the target was occurring (FIG. 17).

Phage Rescue:

100 µA of cell suspension obtained from previous selection rounds were added to 20 ml of 2×TYAG and grown at 37° C. with agitation (240 rpm) until an OD600 of 0.3 to 0.5 was reached. The culture was then super-infected with $3.3 \times 10^{10}$ MK13K07 helper phage and incubated for one hour at 37° C. (150 rpm). The medium was then changed by centrifuging the cells at 2000 rpm for 10 minutes, removing the medium and resuspending the pellet in 20 ml of 2×TY-AK (100 µg/ml ampicillin; 50 µg/ml kanamycin). The culture was then grown overnight at 30° C. (240 rpm).

Monoclonal Phage Rescue for ELISA:

Single clones were picked into a microtiter plate containing 150 µl of 2×TYAG media (2% glucose) per well and grown at 37° C. (100-120 rpm) for 5-6 h. M13KO7 helper phage was added to each well to obtain a multiplicity of infection (MOI) of 10 (i.e., 10 phage for each cell in the culture) and incubated at 37° C. (100 rpm) for 1 h. Following growth, plates were centrifuged at 3,200 rpm for 10 min. Supernatant was carefully removed, cells resuspended in 150 µl 2×TYAK medium and grown overnight at 30° C. (120 rpm). For the ELISA, the phage are blocked by adding 150 µl of 2× concentration PBS containing 5% skimmed milk powder followed by one hour incubation at room temperature. The plates were then centrifuged 10 minutes at 3000 rpm and the phage containing supernatant used for the ELISA.

Phage ELISA:

ELISA plates (Maxisorb, NUNC) were coated overnight with 2 µg/ml hIFNγ in PBS or 2 µg/ml rat 5E3 in PBs. Control plates were coated with 2 µg/ml BSA or an irrelevant rat monoclonal antibody. Plates were then blocked with 3% skimmed milk/PBS at room temperature for 1 h. Plates were washed 3 times with PBS 0.05% Tween 20 before transferring the pre-blocked phage supernatants and incubation for one hour at room temperature. Plates were then washed 3 times with PBS 0.05% Tween 20. 50 µl of 3% skimmed milk/PBS containing (HRP)-conjugated anti-M13 antibody (Amersham, diluted 1:10,000) to each well. Following incubation at room temperature for 1 hr, the plates were washed 5 times with PBS 0.05% Tween 20. The ELISA was then revealed by adding 50 µl of TMB (Sigma) and 50 µl of 2N $H_2SO_4$ to stop the reaction. Absorption intensity was read at 450 nm. Clones specific for hIFNγ could be identified and the hit rates ranged between 10% and 30% after the third round of selection. Clones specific for the variable region of 5E3 could also be identified and the hit rates ranged between 7 and 48% after the third round of selection.

Phage Clone Sequencing:

Single clones were grown in 5 ml of 2×TYAG media (2% glucose) per well and grown at 37° C. (120 rpm) overnight. The next day phagemid DNA was purified and used for DNA sequencing using a primer specific for pNDS1: mycseq, 5'-CTCTTCTGAGATGAGTTTTTG. (SEQ ID NO: 255).

Large Scale scFv Purification:

A starter culture of 1 ml of 2×TYAG was inoculated with a single colony from a freshly streaked 2×TYAG agar plate and incubated with shaking (240 rpm) at 37° C. for 5 hours. 0.9 ml of this culture was used to inoculate a 400 ml culture of the same media and was grown overnight at 30° C. with vigorous shaking (300 rpm).

The next day the culture was induced by adding 400 µl of 1M IPTG and incubation was continued for an additional 3 hours. The cells were collected by centrifugation at 5,000 rpm for 10 minutes at 4° C. Pelleted cells were resuspended in 10 ml of ice-cold TES buffer complemented with protease inhibitors as described above. Osmotic shock was achieved by adding 15 ml of 1:5 diluted TES buffer and incubation for 1 hour on ice. Cells were centrifuged at 10,000 rpm for 20 minutes at 4° C. to pellet cell debris. The supernatant was carefully transferred to a fresh tube. Imidazole was added to the supernatant to a final concentration of 10 mM. 1 ml of Ni-NTA resin (Qiagen), equilibrated in PBS was added to each tube and incubated on a rotary mixer at 4° C. (20 rpm) for 1 hour. The tubes were centrifuged at 2,000 rpm for 5 minutes and the supernatant carefully removed. The pelleted resin was resuspended in 10 ml of cold (4° C.) Wash buffer 1 (50 mM $NaH_2PO_4$, 300 mM NaCl, 10 mM imidazole, pH to 8.0). The suspension was added to a polyprep column (Biorad). 8 ml of cold Wash Buffer 2 (50 mM $NaH_2PO_4$, 300 mM NaCl, 20 mM imidazole, pH to 8.0) were used to wash the column by gravity flow. The scFv were eluted from the column with 2 ml of Elution buffer (50 mM $NaH_2PO_4$, 300 mM NaCl, 250 mM imidazole, pH to 8.0). Fractions were analyzed by absorption at 280 nm and protein containing fractions were pooled before buffer exchange on a PD10 desalting column (Amersham) equilibrated with PBS. The scFv in PBS were analyzed by SDS-PAGE and quantified by absorption at 280 nm. The purified scFv were aliquoted and stored at −20° C. and at 4° C.

Example 12

Figure 18:
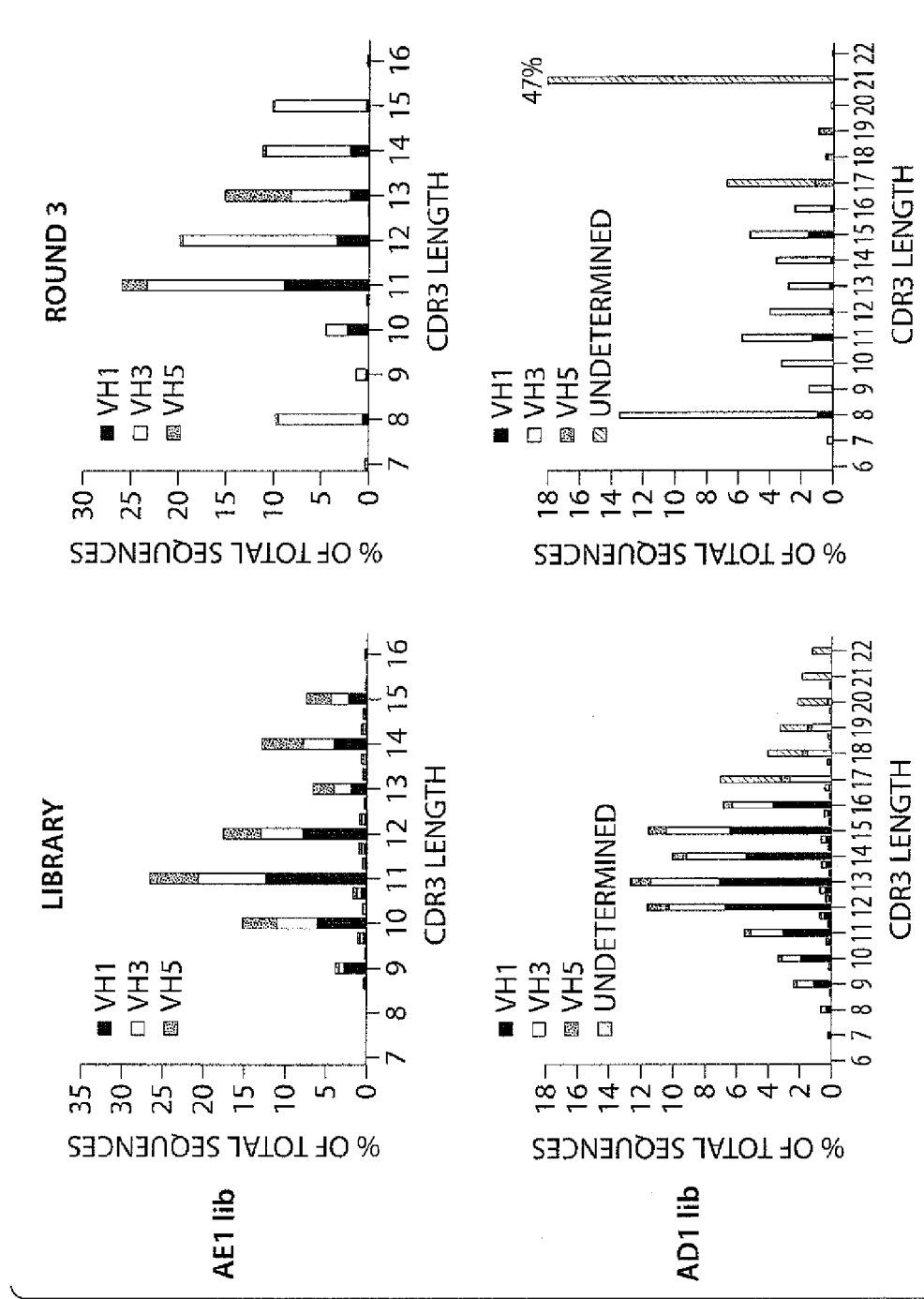
FIG. 18 is a series of graphs depicting the frequency of CDR H3 lengths found in the AE1 and AD1 libraries and after three rounds of selection against the monoclonal antibody 5E3. The distribution of each CDR H3 length within the different VH families is indicated. However, when CDR H3 are longer than 16 amino acids, the 70 bp sequences delivered by the Illumina Sequencing platform do not cover enough framework sequence to unambiguously identify the VH1 family and therefore the VH family is indicated as undetermined.

Analysis of CDR3 Profiles Obtained after Selection Using High Throughput Sequencing Using next generation sequencing technology as described in Example 10, the distribution of CDR H3 lengths within each VH family in the AE1 and AD1 libraries as well as in the output obtained after the third round of selection was analyzed. The profiles of the AE1 and AD1 libraries are clearly different (FIG. 18). The CDR H3 length distribution in the AE1 library corresponds to the intended library design, with lengths ranging between 9-15 amino acids. In contrast, much longer CDR H3 of up to 22 amino acids are found in the AD1 library, and the profile corresponds to the length distribution observed in human natural repertoires. These results confirm that a human natural CDR H3 repertoire has been captured during the construction of the AD1 library. A similar analysis performed after three rounds of selection against 5E3 revealed that completely different CDR H3 length profiles were selected. In particular, a dramatic enrichment of CDR H3 of 8 and 21 amino acids in length could be observed in the selection performed with the AD1 library. This set of data demonstrated that different CDR H3 profiles were enriched from the two libraries after selection against the same target. Furthermore, this analysis demonstrates that, using the present invention, long CDR H3 that are very difficult to cover using synthetic diversity could be captured into selected human frameworks and selected.

Example 13

Evaluating Identified scFvs in Binding Assays

Figure 19:
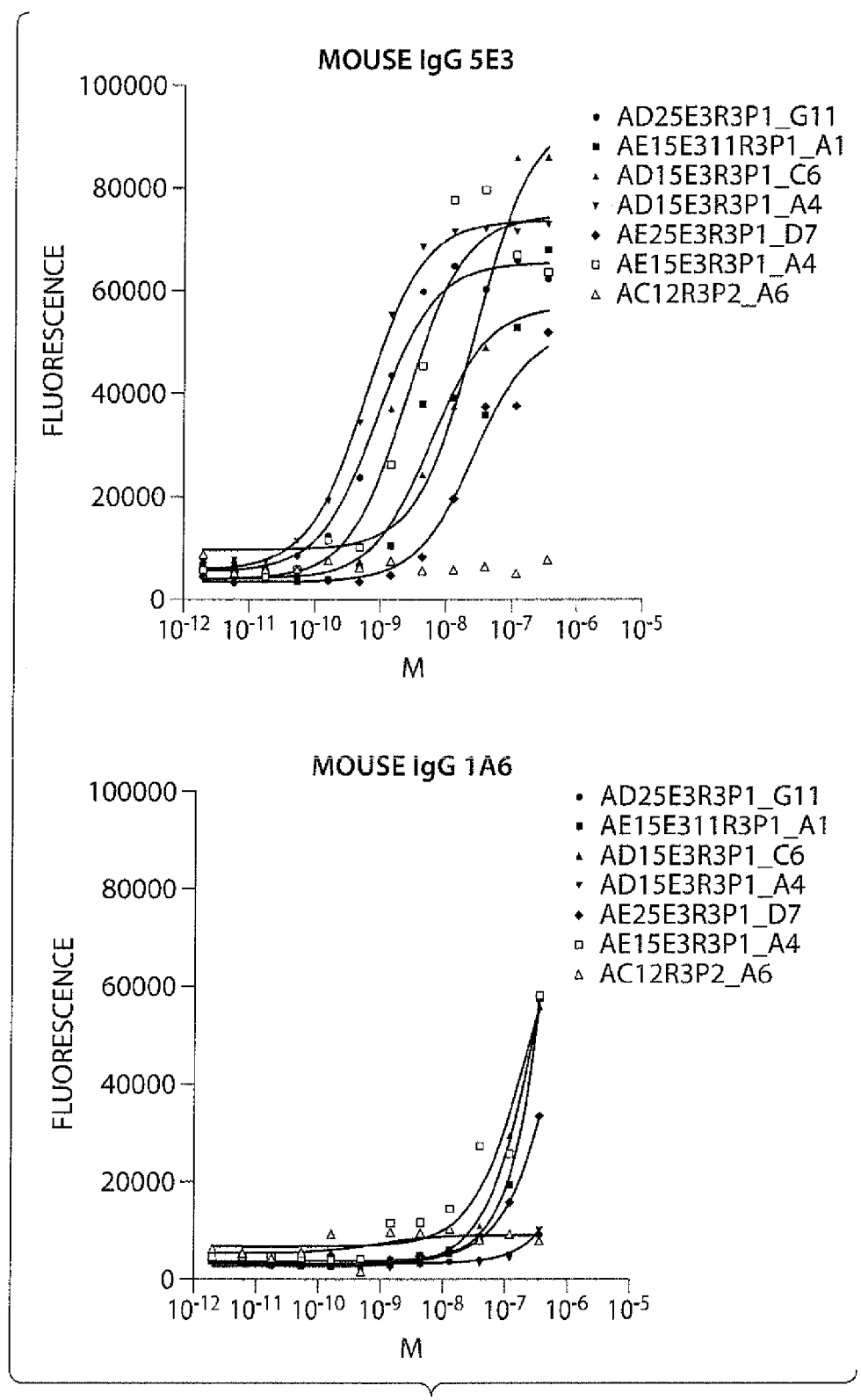
FIG. 19 is a series of graphs depicting dose response ELISA using purified 6 scFv preparations against mouse 5E3 or an irrelevant mouse antibody 1A6. The seven clones encode different scFvs. Clone A6 is a scFv specific for hIFNγ and was used as a negative control.
Figure 20:
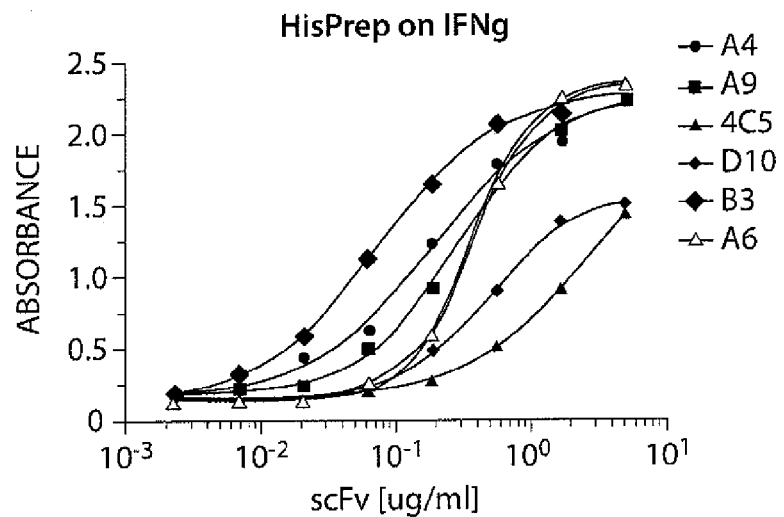
FIG. 20 is a graph that depicts dose response ELISA using purified scFv preparations against hIFNγ and compared to a positive scFv specific for hIFNγ (A6).
Figure 21:
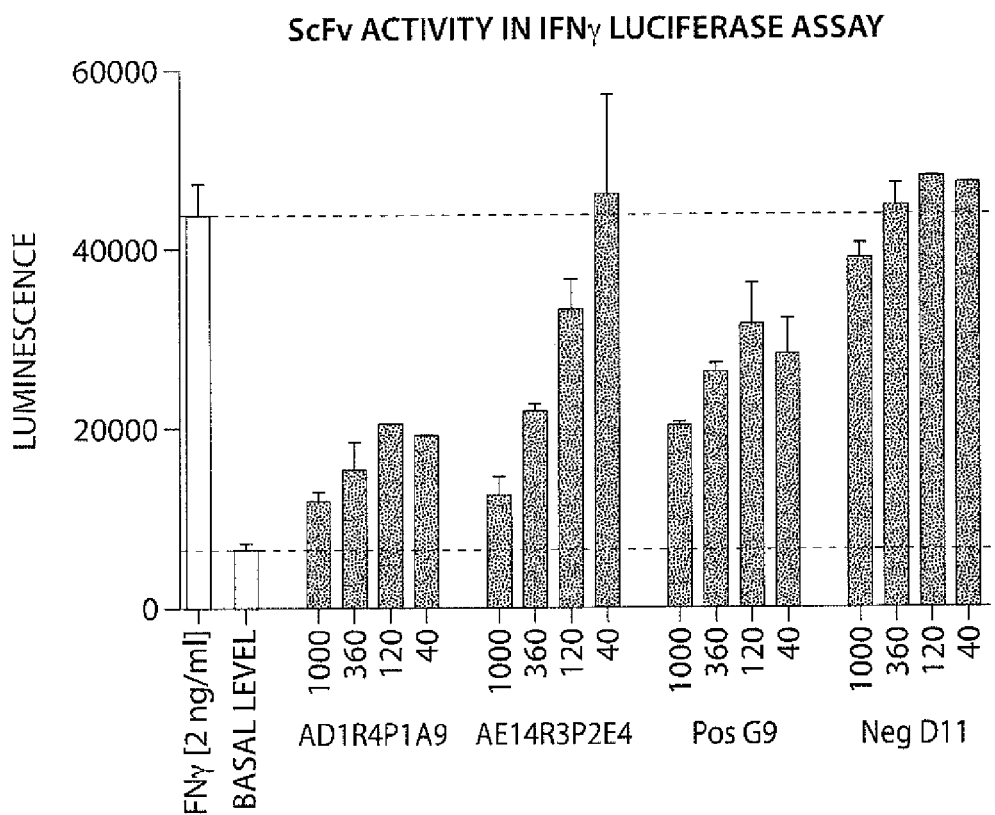
FIG. 21 is a graph that depicts the inhibitory effect of purified scFv preparations in a luciferase reporter gene assay driven by hIFNγ. The neutralizing activity of two scFv candidates (AD1R4P1A9 and AE14R3P2E4) was compared to the activity of a positive control scFv (G9) and a negative control scFv (D11).
Figure 22:
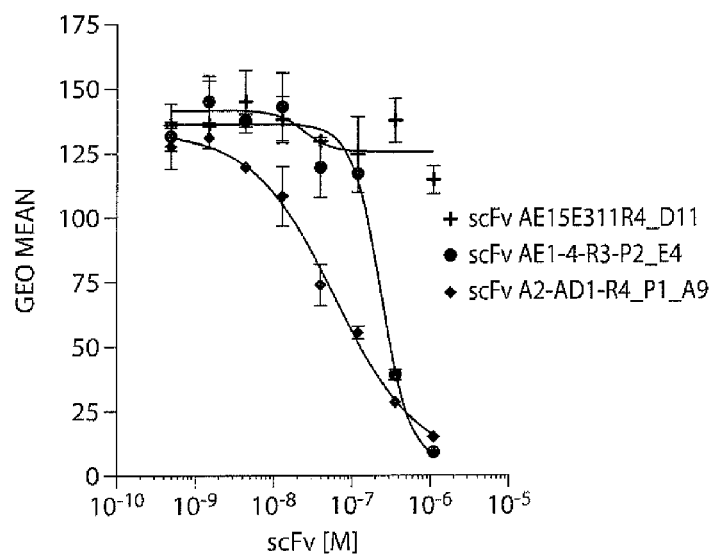
FIG. 22 is a graph that depicts the inhibitory effect of purified scFv preparations in a MHCII induction assay in response to hIFNγ. The neutralizing activity of two scFv candidates (AD1R4P1A9 and AE14R3P2E4) was compared to the activity of a negative control scFv (D11).

Purified scFvs preparations of clones having different sequences and that were identified positive against the variable region of 5E3 were tested for binding against chimeric 5E3 in a dose response ELISA. These preparations were also tested against an irrelevant mouse antibody (1A6). ELISA plates (Maxisorb, NUNC) were coated overnight with 2 µg/ml mouse 5E3 in PBS. Control plates were coated with 2 µg/ml 1A6 monoclonal antibody. Plates were then blocked with 3% skimmed milk/PBS at room temperature for 1 h. Plates were washed 3 times with PBS 0.05% Tween 20 before adding different concentrations of purified scFv and incubation for one hour at room temperature. Plates were then washed 3 times with PBS 0.05% Tween 20. 50 µl of 3% skimmed milk/PBS containing (HRP)-conjugated anti-myc antibody to each well. Following incubation at room temperature for 1 hr, the plates were washed 5 times with PBS 0.05% Tween 20. The ELISA was then revealed by adding 50 µl of Amplex Red fluorescent substrate and the signal was read on fluorescence spectrophotometer. The data shows that most of the clones are highly specific for 5E3 as they do not recognize 1A6 and that they are directed against the variable regions of 5E3 (FIG. 19).

Similarly, purified scFvs preparations of clones having different sequences and that were identified in phage ELISA as binders against hIFNγ were tested for binding against hIFNγ in a dose response experiment. ELISA plates (Maxisorb, NUNC) were coated overnight with 2 μg/ml hIFNγ in PBS and control plates were coated with 2 μg/ml BSA in PBS. Plates were then blocked with 3% skimmed milk/PBS at room temperature for 1 h. Plates were washed 3 times with PBS 0.05% Tween 20 before adding different concentration of purified scFv and incubation for one hour at room temperature. Plates were then washed 3 times with PBS 0.05% Tween 20. 50 μl of 3% skimmed milk/PBS containing (HRP)-conjugated anti-myc antibody to each well. Following incubation at room temperature for 1 hr, the plates were washed 5 times with PBS 0.05% Tween 20. The ELISA was then revealed by adding 50 μl TMB substrate and 50 μl of 2N $H_2SO_4$ to stop the reaction. The signal was read on an absorbance spectrophotometer at 450 nm. The data shows that the selected clones are binding to hIFNγ in a dose dependent manner and gave a very good signal when compared to a positive control scFv A6 that has a high affinity for hIFNγ (FIG. 20).

Example 14

ScFv Inhibition of Interferon Gamma-Induced Reporter Gene Expression

A panel of selected scFv specific for hIFNγ was produced and purified as described above and tested for the capacity to block the biological activity of hIFNγ. A reporter gene (firefly luciferase), driven by the IFNγ-inducible GBP1 promoter, was transfected into the human melanoma cell line, Me67.8. Various concentrations of scFv were incubated with 2 ng/ml of hIFNγ and then added to the cell culture. Following a 6 hour incubation time, the luciferase reporter assay was performed and the intensity of the luminescence measured. The activity was compared to a scFv isolated from another human scFv antibody library constructed by traditional capturing of the VH/VL repertoires form human donors (clone G9). The data shows that scFv isolated either from synthetic or natural human diversity libraries (AE1 and AD1) were capable of neutralizing the biological activity of hIFNγ in a dose dependent manner (FIG. 21). The neutralization potential of these scFv was superior to the benchmark scFv clone G9.

Example 15 scFv Inhibition of Interferon Gamma-Induced MHC Class II Expression

A flow cytometric assay was implemented to identify fully human IgG antibodies, or fragments thereof, capable of blocking the expression of IFNγ-induced MHC class II molecules. Following the plating of Me67.8 cells, 5 ng/ml recombinant human IFNγ was added to cultures in the presence of various concentrations of candidate fully human anti-IFNγ monoclonal antibodies. Following 48 h in culture, cells were stained with fluorescently labeled anti-human MHC class II antibody (HLA-DR) and analyzed using a FACSCalibur®. Thus, the $IC_{50}$ (where 50% of the IFNγ-induced MHC class II expression is inhibited, i.e., 50% inhibitory concentration), for each candidate antibody is measured.

Purified fully human scFv were produced as described above. The effect of selected scFv on IFNγ-induced MHC class II expression on melanoma cells was evaluated using the flow cytometric cell-based assay described above. These scFv inhibited IFNγ-induced MHC II expression on melanoma cells (FIG. 22).

Example 16

Reformatting scFv into IgG Format

The $V_H$ and $V_L$ sequence of selected scFv were amplified with specific oligonucleotides introducing a leader sequence and a HindIII restriction site at the 5' end. An ApaI site was introduced at the 3' end of the heavy whereas an AvrII and a BsiWI site were introduced at the 3' end of the lambda or kappa light chain sequences, respectively. The amplified $V_H$ sequences were digested HindIII/ApaI and cloned into the pCon_gamma1 expression vector (LONZA, Basel, Switzerland). The amplified $V_L$ lambda sequences were digested HindIII/AvrII and cloned into the pCon_lambda2 expression vector and the amplified $V_L$ kappa sequences were digested HindIII/BsiWI and cloned into the pCon_kappa expression vector (LONZA, Basel, Switzerland). The constructions were verified by sequencing before transfection into mammalian cells.

The $V_H$ and $V_L$ cDNA sequences in their appropriate expression vectors were transfected into mammalian cells using the Fugene 6 Transfection Reagent (Roche, Basel, Switzerland). Briefly, Peak cells were cultured in 6-well plates at a concentration of $6\times10^5$ cells per well in 2 ml culture media containing fetal bovine serum. The expression vectors, encoding the candidate $V_H$ and $V_L$ sequences, were co-transfected into the cells using the Fugene 6 Transfection Reagent according to manufacturer's instructions. One day following transfection, the culture media was aspirated, and 3 ml of fresh serum-free media was added to cells and cultured for three days at 37° C. Following three days culture period, the supernatant was harvested for IgG purified on protein G-Sepharose 4B fast flow columns (Sigma, St. Louis, Mo.) according to manufacturer's instructions. Briefly, supernatants from transfected cells were incubated overnight at 4° C. with ImmunoPure (G) IgG binding buffer (Pierce, Rockford Ill.). Samples were then passed over Protein G-Sepharose 4B fast flow columns and the IgG consequently purified using elution buffer. The eluted IgG fraction was then dialyzed against PBS and the IgG content quantified by absorption at 280 nm. Purity and IgG integrity were verified by SDS-PAGE.

Example 17

IgG Inhibition of Interferon Gamma Biological Activity

Figure 23:
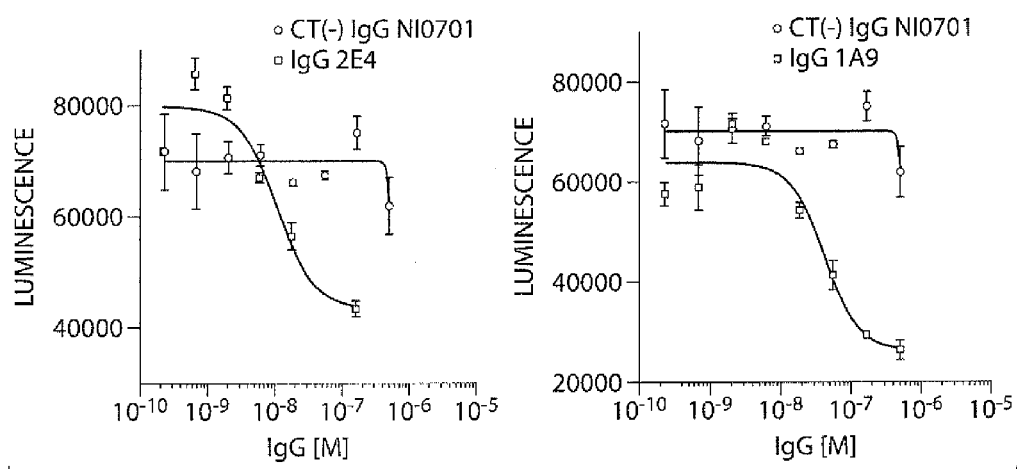
FIG. 23 is a series of graphs depicting the inhibitory effect of the two candidates AD1R4P1A9 and AE14R3P2E4 reformatted into IgG in a luciferase reporter gene assay driven by hIFNγ. The neutralizing activity of two IgGs was compared to the activity of an irrelevant IgG directed against human RANTES (NI-0701).

Two scFv, AE1-4-R3-P2E4 (2E4) and A2-AD1-R4P1A9 (1A9), that had confirmed inhibitory activity against hIFNγ in functional assays were reformatted into IgG as described in Example 16 and tested in the interferon gamma-induced reporter gene assay described in Example 14. The results shown in FIG. 23 indicate that in a IgG format both 1A9 and 2E4 could neutralize the activity of hIFNγ with $IC_{50}$ of 42 nM and 10 nM, respectively whereas a negative control IgG (NI-0701) had no effect in this assay. Thus these two candidates isolated from both synthetic and natural diversity libraries could be reformatted into full IgG and feature neutralizing activity against the selected target.

Example 18

Development of a Pharmacokinetic Assay for the Detection of 5E3 in Mouse Serum

Figure 24:
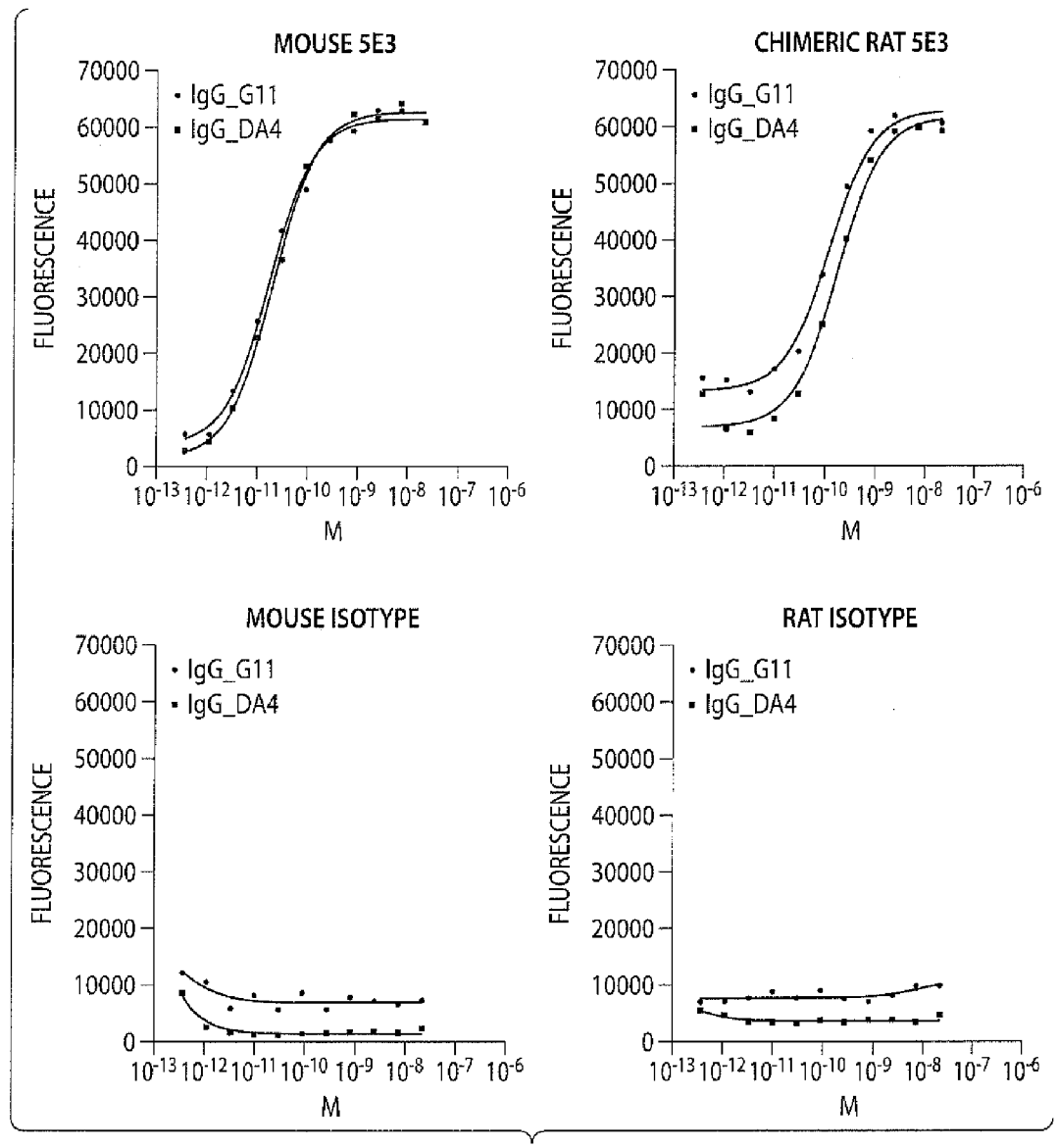
FIG. 24 is a series of graphs depicting a dose response ELISA using the IgG G11 and DA4 against mouse 5E3, chimeric rat 5E3 and the corresponding mouse and rat isotype antibodies.
Figure 25:
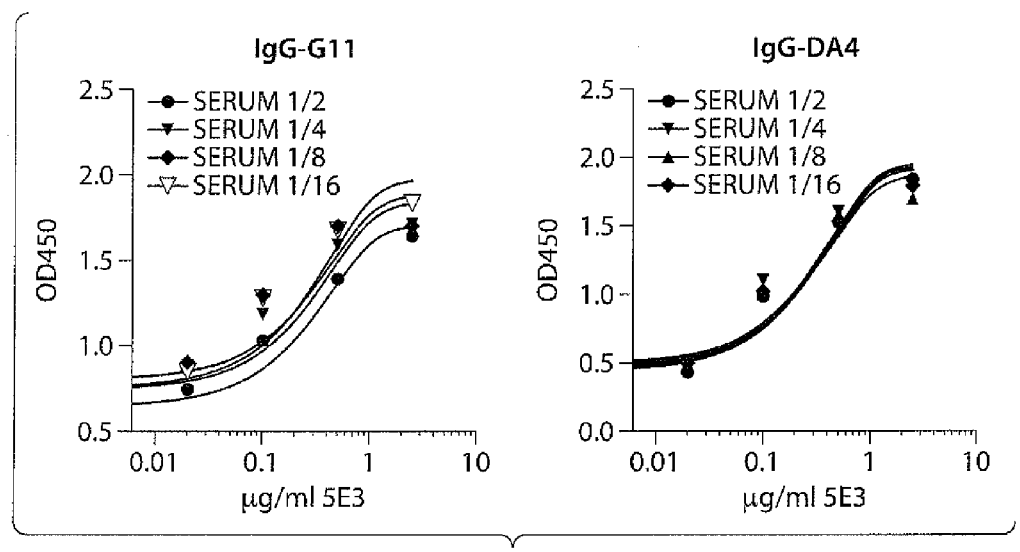
FIG. 25 is a series of graphs depicting an ELISA for the detection of mouse 5E3 in different dilutions of mouse serum using the anti-idiotypic IgGs G11 and DA4 as capture antibodies.

Two scFv candidates AD15E3R3P1_A4 and AD25E3R3P1_G11 that bind specifically to mouse monoclonal antibody 5E3 (FIG. 19) were reformatted into full human IgG as described in Example 16. The specificity of the corresponding IgGs DA4 and G11 was confirmed in ELISA against mouse 5E3 and a chimeric version of this monoclonal antibody in which the mouse variable regions have been fused to rat constant IgG regions. The results shown in FIG. 24 demonstrate that the IgG DA4 and G11 are specific for the variable region of 5E3 as they bind to both mouse and chimeric rat 5E3 and not to mouse and rat isotype controls. These two monoclonals antibodies were used to develop an assay for the quantification of 5E3 in mouse serum for pharmacokinetic studies. Several dilutions of mouse serum were spiked with 5 µg/ml of mouse 5E3 antibody and serially diluted in such a way that serum concentration was maintained constant throughout the dilution series. Maxisorb plates (Nunc, Denmark) were coated overnight with 1 µg/ml of IgG DA4 or IgG G11. After blocking with PBS; 1% BSA dilution series of the spiked serum preparations were added to the wells. After incubation and washing, the signal was revealed using an anti-mouse Kappa light chain monoclonal antibody coupled to horse radish peroxydase (HRP) and a fluorescent substrate (Amplex red; Invitrogen). The results show that both antibodies can be used to specifically detect the mouse monoclonal 5E3 antibody in mouse serum (FIG. 25). The detection limit of mouse 5E3 in serum was about 200 ng/ml and the assay was not significantly affected by the serum concentration indicating that IgG DA4 and IgG G11 are highly specific for mouse 5E3 and do not bind to other mouse immunoglobulin. These experiments demonstrate that highly specific anti-idiotypic antibodies could be isolated from the natural or synthetic libraries AE1 and AD1.

Example 19

Figure 26:
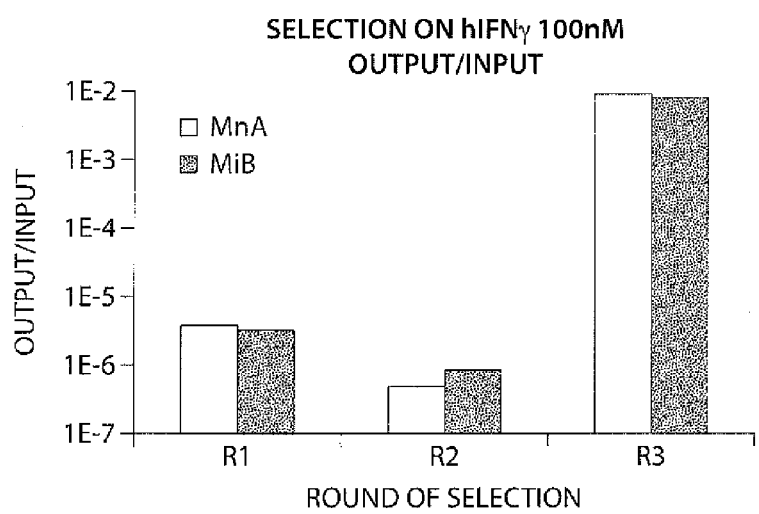
FIG. 26 is a graph that depicts phage output/input ratios during selection against hIFNγ with the libraries MnA and MiB.
Figure 27:
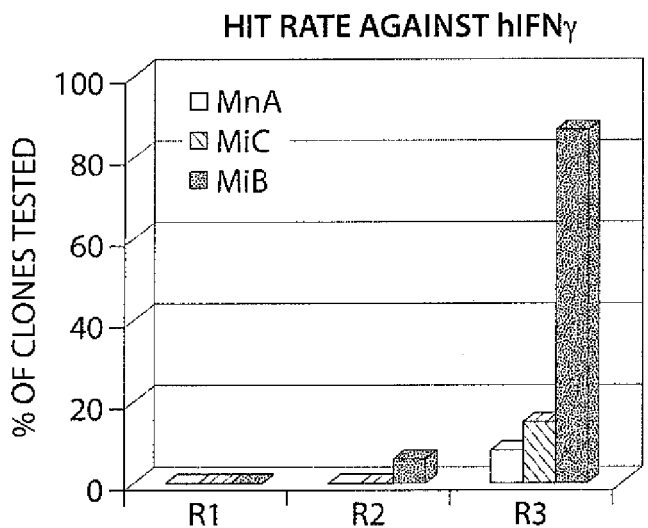
FIG. 27 is a graph depicting the hit rates obtained in a scFv ELISA screening with clones derived from the MnA, MiB and MiC libraries after each round of selection against hIFNγ. The threshold was set to half the signal obtained with the A6 control scFv.
Figure 28:
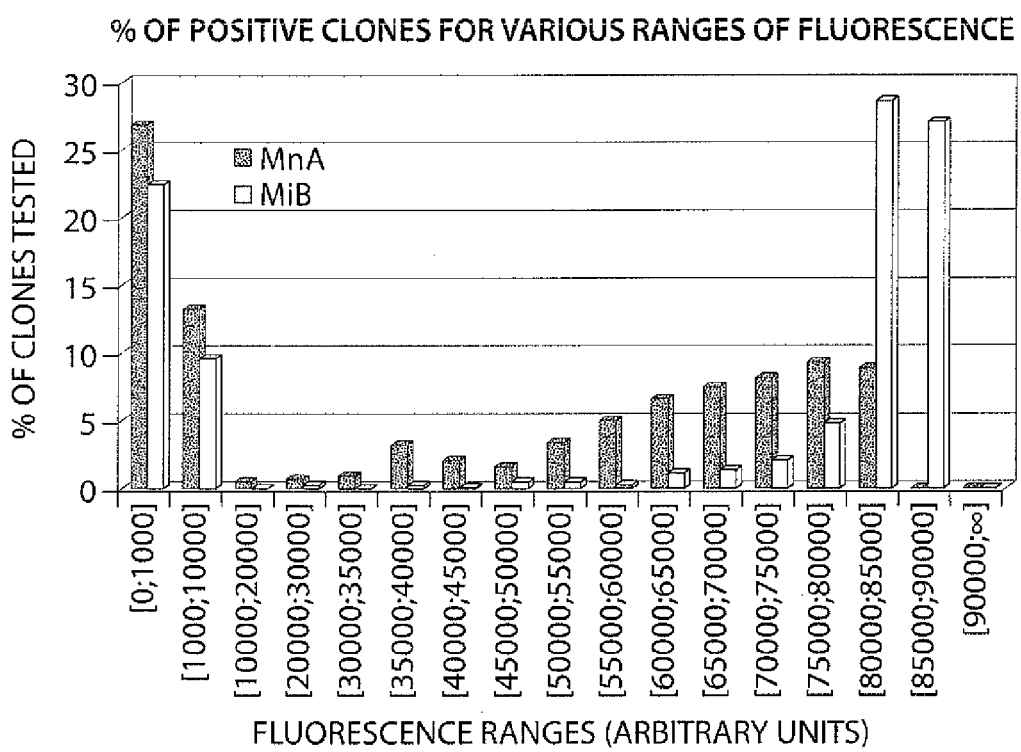
FIG. 28 is a graph that represents the distribution frequency of scFv giving different levels of signal in binding experiments against hIFNγ obtained with clones derived from the MnA and MiB libraries.
Figure 29:
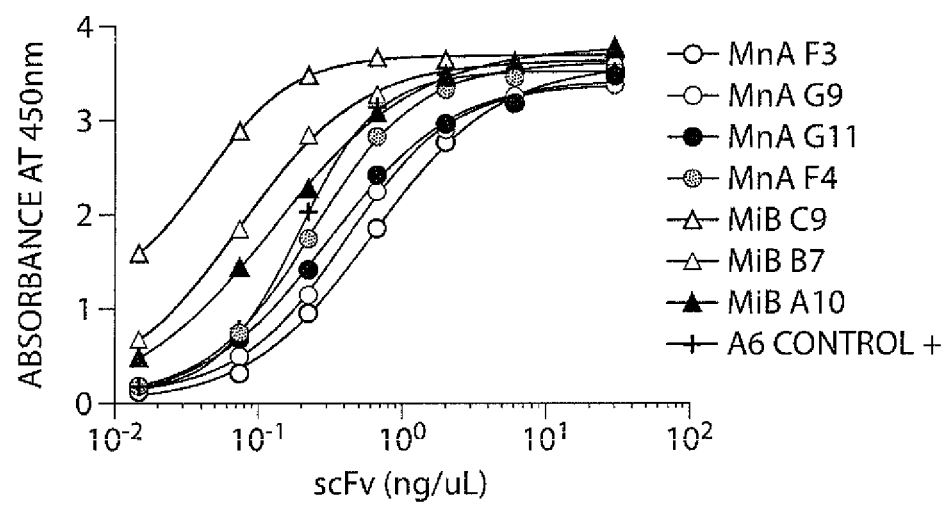
FIG. 29 is a graph that depicts dose response ELISA using purified scFv preparations from clones derived from the MnA and MiB libraries against hIFNγ and compared to a positive scFv specific for hIFNγ (A6).

Phage Selection Using Libraries Containing CDRH3 Diversity Captured from Naïve and Immunized Mice The MnA, MiB and MiC libraries described in Examples 8 and 9 were used in parallel for phage selections against hIFNγ following the procedure described in Example 11. During the selection process a similar enrichment of phage was observed (FIG. 26).

scFv Expression in Microtiter Plate Format:

Single clones were picked into a microtiter plate containing 150 µl of 2×TYAG media (2% glucose) per well and grown at 37° C. (100-120 rpm) for 5-6 h. Plates were centrifuged at 280 rpm, the medium discarded and the cell pellets resuspended in 100 µl of 2×TYA medium containing 1 mM IPTG. The plates were incubated overnight at 30° C. with shaking (100 rpm). Following growth, plates were centrifuged at 3,200 rpm for 10 min and the supernatant carefully transferred to a plate containing 2× concentrated PBS containing 5% skimmed milk powder for blocking.

scFv ELISA:

ELISA plates (Maxisorb, NUNC) were coated overnight with 2 µg/ml hIFNγ in PBS. Control plates were coated with 2 µg/ml recombinant BSA (Sigma). Plates were then blocked with 3% skimmed milk/PBS at room temperature for 1 h. Plates were washed 3 times with PBS 0.05% Tween 20 before transferring the pre-blocked scFv supernatants and incubation for one hour at room temperature. Plates were then washed 3 times with PBS 0.05% Tween 20. 50 µl of 3% skimmed milk/PBS containing (HRP)-conjugated anti-cMyc antibody (diluted 1:5,000) to each well. Following incubation at room temperature for 1 hr, the plates were washed 5 times with PBS 0.05% Tween 20. The ELISA was then revealed by adding 50 µl of Amplex Red (Invitrogen). Fluorescence intensity was measured at 590 nm upon excitation at 530 nm. The frequency of hits giving a signal of half the intensity of the control A6 clone was evaluated after each round of selection for the three libraries (FIG. 27). The hit rate obtained with the MiB library was dramatically higher compared to the two other libraries and the average level of signal was superior for the clones derived from the MiB library, indicating that higher affinity scFv were enriched (FIG. 28). In order to confirm this observation, positive clones were sequenced, expressed in larger scale and purified to be tested in dose response binding experiments according to Example 13. The scFv derived from the MiB library all had a higher apparent affinity for hIFNγ than those isolated from the naïve MnA library (FIG. 29). The results indicate that the CDRH3 repertoire from mice immunized with a protein could be captured into a human antibody framework context in a productive way to generate at higher frequency high affinity human antibody fragments. Libraries generated using the present invention thus represent a powerful mean of generating antibodies with therapeutic potential.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for producing a collection of nucleic acids, wherein each nucleic acid encodes a human immunoglobulin variable domain comprising a plurality of complementarity determining region 3 (CDR3) sequences isolated separately from the immunoglobulin variable domain repertoire from a mammalian species, the method comprising:
  (a) providing a plurality of Acceptor Framework nucleic acid sequences encoding distinct human immunoglobulin variable domains, each Acceptor Framework nucleic acid sequence comprising a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a stuffer nucleic acid sequence comprising at least two Type IIs restriction enzyme recognition sites interspaced by a random nucleic acid sequence;
  (b) providing a plurality of diversified nucleic acid sequences encoding complementarity determining region 3 (CDR3) sequences isolated from the mammalian species immunoglobulin repertoire wherein each of the plurality of diversified nucleic acid sequences comprises a Type IIs restriction enzyme recognition site at each extremity and wherein each of the plurality of diversified nucleic acid sequences encode a complete CDR3;
  (c) digesting each of the plurality of nucleic acid sequences encoding the complete CDR3 using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and
  (d) ligating the digested nucleic acid sequences encoding the complete CDR3 of step (c) into the digested Acceptor Framework of step (c) such that the FR3 and FR4 regions are interspaced by the nucleic acid sequences encoding the complete CDR3 and wherein the complete immunoglobulin variable domain encoding sequences do not contain the Type IIs restriction enzyme recognition sites of steps (a) and (b).

2. The method of claim 1, wherein step (b) is performed by amplifying the CDR3 sequence from a mammalian species using oligonucleotide primers containing a Type IIs restriction site.

3. The method of claim 2, wherein the oligonucleotide primer is designed to enhance compatibility between the mammalian CDR3 sequence and the Acceptor Framework encoding a human immunoglobulin variable domain.

4. The method of claim 3, wherein the oligonucleotide primer is designed to modify a nucleic acid sequence at a boundary of the mammalian CDR3 sequence to produce a compatible cohesive nucleotide sequence in the Acceptor Framework encoding a human immunoglobulin variable domain.

5. The method of claim 2, wherein step (b) is performed by amplifying the CDR3 sequence from a non-human mammalian species using oligonucleotide primers containing a FokI IIs restriction site.

6. The method of claim 5, wherein the non-human mammalian species is non-human primate, rodent, canine, feline, sheep, goat, cattle, horse, a member of the Camelidae family, llama, camel, dromedary, or pig.

7. The method of claim 1, wherein the Type IIs restriction enzyme recognition sites of step (a) and step (b) are recognized by a different Type IIs restriction enzyme.

8. The method of claim 7, wherein the Type IIs restriction enzyme recognition sites are BsmBI recognition sites, BsaI recognition sites, FokI recognition sites or a combination thereof.

9. The method of claim 1, wherein the diversified nucleic acid sequences encoding CDR3 sequences encode heavy chain CDR3 (CDR H3) sequences.

10. The method of claim 1, wherein the diversified nucleic acid sequences encoding CDR3 sequences encode light chain CDR3 (CDR L3) sequences.

11. The method of claim 1, wherein the Acceptor Framework nucleic acid sequence comprises a human heavy chain variable gene sequence selected from VH1-2, VH1-69, VH1-18, VH3-30, VH3-48, VH3-23, and VH5-51.

12. The method of claim 1, wherein the Acceptor Framework nucleic acid sequence comprises a human kappa light chain variable gene sequence.

13. The method of claim 12, wherein the human kappa light chain variable gene sequence is selected from VK1-33, VK1-39, VK3-11, VK3-15, and VK3-20.

14. The method of claim 1, wherein the Acceptor Framework nucleic acid sequence comprises a human lambda light chain variable gene sequence.

15. The method of claim 14, wherein the human lambda light chain variable gene sequence is selected from VL1-44 and VL1-51.

16. The method of claim 1, wherein the plurality of Acceptor Framework nucleic acid sequences comprises a mixture of at least one variable heavy chain (VH) Acceptor Framework nucleic acid sequence and at least one variable light chain Acceptor Framework nucleic acid sequence.

17. The method of claim 1, further comprising the steps of (e) cloning the library of nucleic acids encoding immunoglobulin variable domains of step (d) into an expression vector and (f) transforming the expression vector of step (e) into a host cell and culturing the host cell under conditions sufficient to express a plurality of immunoglobulin variable domain encoded by the library.

18. The method of claim 17, wherein the host cell is *E. coli*.

19. The method according to claim 17, wherein the expression vector is a phagemid or a phage vector.

20. A method for producing a collection of nucleic acids, wherein each nucleic acid encodes a human immunoglobulin variable domain comprising a plurality of complementarity determining region 3 (CDR3) sequences isolated separately from immunoglobulin variable domains from an immunized non-human mammal, the method comprising:
  (a) providing a plurality of Acceptor Framework nucleic acid sequences encoding distinct human immunoglobulin variable domains, each Acceptor Framework nucleic acid sequence comprising a first framework region (FR1), a second framework region (FR2), a third framework region (FR3), and a fourth framework region (FR4), wherein the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a stuffer nucleic acid sequence comprising at least two Type IIs restriction enzyme recognition sites interspaced by a random nucleic acid sequence;

(b) providing a plurality of diversified nucleic acid sequences encoding complementarity determining region 3 (CDR3) sequences isolated from the mammalian species immunoglobulin repertoire wherein each of the plurality of diversified nucleic acid sequences comprises a Type IIs restriction enzyme recognition site at each extremity and wherein each of the plurality of diversified nucleic acid sequences encode a complete CDR3;

(c) digesting each of the plurality of nucleic acid sequences encoding the complete CDR3 using a Type IIs restriction enzyme that binds to the Type IIs restriction enzyme recognition site of step (b) and digesting the stuffer nucleic acid sequence of step (a) from the Acceptor Framework using a Type IIs restriction enzyme that binds to the Type IIs restriction enzyme recognition site of step (a); and (d) ligating the digested nucleic acid sequences encoding the complete CDR3 of step (c) into the digested Acceptor Framework of step (c) such that the FR3 and FR4 regions are interspaced by the nucleic acid sequences encoding the complete CDR3 and wherein the complete immunoglobulin variable domain encoding sequences do not contain the Type IIs restriction enzyme recognition sites of steps (a) and (b).

21. The method of claim 20, wherein step (b) is performed by amplifying the CDR3 sequence from the immunized non-human mammal using oligonucleotide primers containing a Type IIs restriction site.

22. The method of claim 21, wherein the oligonucleotide primer is designed to enhance compatibility between the mammalian CDR3 sequence and the Acceptor Framework encoding a human immunoglobulin variable domain.

23. The method of claim 22, wherein the oligonucleotide primer is designed to modify a nucleic acid sequence at a boundary of the mammalian CDR3 sequence to produce a compatible cohesive nucleotide sequence in the Acceptor Framework encoding a human immunoglobulin variable domain.

24. The method of claim 21, wherein step (b) is performed by amplifying the CDR H3 sequence from the non-human mammal using oligonucleotide primers containing a FokI IIs restriction site.

25. The method of claim 20, wherein the non-human mammal is non-human primate, rodent, canine, feline, sheep, goat, cattle, horse, llama, camel, dromedary, or pig.

26. The method of claim 20, wherein the Type IIs restriction enzyme recognition sites of step (a) and step (b) are recognized by a different Type IIs restriction enzyme.

27. The method of claim 26, wherein the Type IIs restriction enzyme recognition sites are BsmBI recognition sites, BsaI recognition sites, FokI recognition sites or a combination thereof.

28. The method of claim 20, wherein the diversified nucleic acid sequences encoding CDR3 sequences encode heavy chain CDR3 (CDR H3) sequences.

29. The method of claim 20, wherein the diversified nucleic acid sequences encoding CDR3 sequences encode light chain CDR3 (CDR L3) sequences.

30. The method of claim 20, wherein the Acceptor Framework nucleic acid sequence comprises a human heavy chain variable gene sequence selected from VH1-2, VH1-69, VH1-18, VH3-30, VH3-48, VH3-23, and VH5-51.

31. The method of claim 20, wherein the Acceptor Framework nucleic acid sequence comprises a human kappa light chain variable gene sequence.

32. The method of claim 31, wherein the human kappa light chain variable gene sequence is selected from VK1-33, VK1-39, VK3-11, VK3-15, and VK3-20.

33. The method of claim 20, wherein the Acceptor Framework nucleic acid sequence comprises a human lambda light chain variable gene sequence.

34. The method of claim 33, wherein the human lambda light chain variable gene sequence is selected from VL1-44 and VL1-51.

35. The method of claim 20, wherein the plurality of Acceptor Framework nucleic acid sequences comprises a mixture of at least one variable heavy chain (VH) Acceptor Framework nucleic acid sequence and at least one variable light chain Acceptor Framework nucleic acid sequence.

36. The method of claim 20, further comprising the steps of (e) cloning the library of nucleic acids encoding immunoglobulin variable domains of step (d) into an expression vector and (f) transforming the expression vector of step (e) into a host cell and culturing the host cell under conditions sufficient to express a plurality of immunoglobulin variable domain encoded by the library.

37. The method of claim 36, wherein the host cell is *E. coli*.

38. The method according to claim 36, wherein the expression vector is a phagemid or a phage vector.

* * * * *

SEQUENCE LISTING

<160> NUMBER OF SEQ ID NOS: 289

<210> SEQ ID NO 1
<211> LENGTH: 98
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 2
<211> LENGTH: 98
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 3
<211> LENGTH: 98
<212> TYPE: PRT
<213> ORGANISM: Homo sapiens

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg

<210> SEQ ID NO 4
<211> LENGTH: 98
<212> TYPE: PRT
<213> ORGANISM: Homo sapiens

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 5
<211> LENGTH: 98
<212> TYPE: PRT
<213> ORGANISM: Homo sapiens

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 6
<211> LENGTH: 98
<212> TYPE: PRT
<213> ORGANISM: Homo sapiens

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 7
<211> LENGTH: 98
<212> TYPE: PRT
<213> ORGANISM: Homo sapiens

<400> SEQUENCE: 7

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 8
<211> LENGTH: 98
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Pro
                 85                  90                  95

Thr Val

<210> SEQ ID NO 9
<211> LENGTH: 98
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
 1               5                  10                  15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Thr Val

<210> SEQ ID NO 10
<211> LENGTH: 98
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Val

<210> SEQ ID NO 11
<211> LENGTH: 98
<212> TYPE: PRT
<213> ORGANISM: Homo sapiens

<400> SEQUENCE: 11

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Pro
                 85                  90                  95

Thr Val

<210> SEQ ID NO 12
<211> LENGTH: 99
<212> TYPE: PRT
<213> ORGANISM: Homo sapiens
```

```
<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Thr Val

<210> SEQ ID NO 13
<211> LENGTH: 98
<212> TYPE: PRT
<213> ORGANISM: Homo sapiens

<400> SEQUENCE: 13

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 14
<211> LENGTH: 98
<212> TYPE: PRT
<213> ORGANISM: Homo sapiens

<400> SEQUENCE: 14

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala
```

-continued

```
<210> SEQ ID NO 15
<211> LENGTH: 107
<212> TYPE: DNA
<213> ORGANISM: Homo sapiens

<400> SEQUENCE: 15
tattactgtg cgagatgaga cgaataacgg taaggcggtt taccaggttt aaacgcgtat        60
tgggaaggcg cgtctcttgg ggccagggaa ccctggtcac agtctcg                     107

<210> SEQ ID NO 16
<211> LENGTH: 36
<212> TYPE: PRT
<213> ORGANISM: Homo sapiens

<400> SEQUENCE: 16

Val Leu Leu Cys Glu Met Arg Arg Ile Thr Val Arg Arg Phe Thr Arg
1               5                   10                  15

Phe Lys Arg Val Leu Gly Arg Arg Val Ser Trp Gly Gln Gly Thr Leu
            20                  25                  30

Val Thr Val Ser
        35

<210> SEQ ID NO 17
<211> LENGTH: 33
<212> TYPE: PRT
<213> ORGANISM: Homo sapiens

<400> SEQUENCE: 17

Tyr Tyr Cys Ala Arg Asp Glu Arg Gly Gly Leu Pro Gly Leu Asn Ala
1               5                   10                  15

Tyr Trp Glu Gly Ala Ser Leu Gly Ala Arg Glu Pro Trp Ser Gln Ser
            20                  25                  30

Arg

<210> SEQ ID NO 18
<211> LENGTH: 35
<212> TYPE: PRT
<213> ORGANISM: Homo sapiens

<400> SEQUENCE: 18

Ile Thr Val Arg Asp Glu Thr Asn Asn Gly Lys Ala Val Tyr Gln Val
1               5                   10                  15

Thr Arg Ile Gly Thr Lys Ala Arg Leu Leu Gly Pro Gly Asn Pro Gly
            20                  25                  30

His Ser Leu
        35

<210> SEQ ID NO 19
<211> LENGTH: 14
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (7)..(14)
<223> OTHER INFORMATION: n is a, t, c or g

<400> SEQUENCE: 19
cgtctcnnnn nnnn                                                          14

<210> SEQ ID NO 20
```

```
<211> LENGTH: 14
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (7)..(14)
<223> OTHER INFORMATION: n is a, t, c or g

<400> SEQUENCE: 20
gcagagnnnn nnnn                                                           14

<210> SEQ ID NO 21
<211> LENGTH: 386
<212> TYPE: DNA
<213> ORGANISM: Homo sapiens

<400> SEQUENCE: 21
caggtgcagc tggtgcagtc tggggctgag gtgaagaagc ctggggcctc agtgaaggtc          60
tcctgcaagg cttctggata caccttcacc ggctactata tgcactgggt gcgacaggcc         120
cctggacaag gcttgagtg gatgggatgg atcaaccct a acagtggtgg cacaaactat         180
gcacagaagt ttcagggcag ggtcaccatg accagggaca cgtccatcag cacagcctac         240
atggagctga gcaggctgag atctgacgac acggccgtgt attactgtgc gagatgagac         300
gaataacggt aaggcggttt accaggttta acgcgtatt gggaaggcgc gtctcttggg         360
gccagggaac cctggtcaca gtctcg                                             386

<210> SEQ ID NO 22
<211> LENGTH: 125
<212> TYPE: PRT
<213> ORGANISM: Homo sapiens

<400> SEQUENCE: 22

Pro Gly Ala Ala Gly Ala Val Trp Gly Gly Glu Glu Ala Trp Gly Leu
1               5                   10                  15

Ser Glu Gly Leu Leu Gln Gly Phe Trp Ile His Leu His Arg Leu Leu
            20                  25                  30

Tyr Ala Leu Gly Ala Thr Gly Pro Trp Thr Arg Ala Val Asp Gly Met
        35                  40                  45

Asp Gln Pro Gln Trp Trp His Lys Leu Cys Thr Glu Val Ser Gly Gln
    50                  55                  60

Gly His His Asp Gln Gly His Val His Gln His Ser Leu His Gly Ala
65                  70                  75                  80

Glu Gln Ala Glu Ile Arg His Gly Arg Val Leu Leu Cys Glu Met Arg
                85                  90                  95

Arg Ile Thr Val Arg Arg Phe Thr Arg Phe Lys Arg Val Leu Gly Arg
            100                 105                 110

Arg Val Ser Trp Gly Gln Gly Thr Leu Val Thr Val Ser
        115                 120                 125

<210> SEQ ID NO 23
<211> LENGTH: 125
<212> TYPE: PRT
<213> ORGANISM: Homo sapiens

<400> SEQUENCE: 23

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Glu Arg Gly Gly Leu Pro Gly Leu Asn Ala Tyr Trp Glu
            100                 105                 110

Gly Ala Ser Leu Gly Ala Arg Glu Pro Trp Ser Gln Ser
            115                 120                 125

<210> SEQ ID NO 24
<211> LENGTH: 123
<212> TYPE: PRT
<213> ORGANISM: Homo sapiens

<400> SEQUENCE: 24

Pro Arg Cys Ser Trp Cys Ser Leu Gly Leu Arg Ser Leu Gly Pro
1               5                   10                  15

Gln Arg Ser Pro Ala Arg Leu Leu Asp Thr Pro Ser Pro Ala Thr Ile
            20                  25                  30

Cys Thr Gly Cys Asp Arg Pro Leu Asp Lys Gly Leu Ser Gly Trp Asp
         35                  40                  45

Gly Ser Thr Leu Thr Val Val Ala Gln Thr Met His Arg Ser Phe Arg
 50                  55                  60

Ala Gly Ser Pro Pro Gly Thr Arg Pro Ser Ala Gln Pro Thr Trp Ser
 65                  70                  75                  80

Ala Gly Asp Leu Thr Thr Arg Pro Cys Ile Thr Val Arg Asp Glu Thr
                 85                  90                  95

Asn Asn Gly Lys Ala Val Tyr Gln Val Thr Arg Ile Gly Lys Ala Arg
            100                 105                 110

Leu Leu Gly Pro Gly Asn Pro Gly His Ser Leu
            115                 120

<210> SEQ ID NO 25
<211> LENGTH: 386
<212> TYPE: DNA
<213> ORGANISM: Homo sapiens

<400> SEQUENCE: 25
caggtgcagc tggtgcagtc tggagctgag gtgaagaagc ctggggcctc agtgaaggtc      60
tcctgcaagg cttctggtta cacctttacc agctatggta tcagctgggt gcgacaggcc    120
cctggacaag gcttgagtg gatgggatgg atcagcgctt acaatggtaa cacaaactat     180
gcacagaagc tccagggcag agtcaccatg accacagaca tccacgag cacagcctac      240 atggagctga ggagcctgag atctgacgac acggccgtgt attactgtgc gagatgagac    300
gaataacggt aaggcggttt accaggttta acgcgtatt gggaaggcgc gtctcttggg     360
gccagggaac cctggtcaca gtctcg                                         386

<210> SEQ ID NO 26
<211> LENGTH: 125
<212> TYPE: PRT

<213> ORGANISM: Homo sapiens

<400> SEQUENCE: 26

Pro Gly Ala Ala Gly Ala Val Trp Ser Gly Glu Glu Ala Trp Gly Leu
1               5                   10                  15

Ser Glu Gly Leu Leu Gln Gly Phe Trp Leu His Leu Tyr Gln Leu Trp
            20                  25                  30

Tyr Gln Leu Gly Ala Thr Gly Pro Trp Thr Arg Ala Val Asp Gly Met
        35                  40                  45

Asp Gln Arg Leu Gln Trp His Lys Leu Cys Thr Glu Ala Pro Gly Gln
50                  55                  60

Ser His His Asp His Arg His Ile His Glu His Ser Leu His Gly Ala
65                  70                  75                  80

Glu Glu Pro Glu Ile Arg His Gly Arg Val Leu Leu Cys Glu Met Arg
                85                  90                  95

Arg Ile Thr Val Arg Arg Phe Thr Arg Phe Lys Val Arg Leu Gly Arg
            100                 105                 110

Arg Val Ser Trp Gly Gln Gly Thr Leu Val Thr Val Ser
        115                 120                 125

<210> SEQ ID NO 27
<211> LENGTH: 125
<212> TYPE: PRT
<213> ORGANISM: Homo sapiens

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Glu Arg Gly Gly Leu Pro Gly Leu Asn Ala Tyr Trp Glu
            100                 105                 110

Gly Ala Ser Leu Gly Ala Arg Glu Pro Trp Ser Gln Ser
        115                 120                 125

<210> SEQ ID NO 28
<211> LENGTH: 122
<212> TYPE: PRT
<213> ORGANISM: Homo sapiens

<400> SEQUENCE: 28

Pro Arg Cys Ser Trp Cys Ser Leu Glu Leu Arg Arg Ser Leu Gly Pro
1               5                   10                  15

Gln Arg Ser Pro Ala Arg Leu Leu Val Thr Pro Leu Pro Ala Met Val
            20                  25                  30

Ser Ala Gly Cys Asp Arg Pro Leu Asp Lys Gly Leu Ser Gly Trp Asp
        35                  40                  45

Gly Ser Ala Leu Thr Met Val Thr Gln Thr Met His Arg Ser Ser Arg
50                  55                  60

Ala Glu Ser Pro Pro Gln Thr His Pro Arg Ala Gln Pro Thr Trp Ser
65                  70                  75                  80

Gly Ala Asp Leu Thr Thr Arg Pro Cys Ile Thr Val Arg Asp Glu Thr
                85                  90                  95

Asn Asn Gly Lys Ala Val Tyr Gln Val Thr Arg Ile Gly Lys Ala Arg
            100                 105                 110

Leu Leu Gly Pro Gly Asn Pro His Ser Leu
            115                 120

<210> SEQ ID NO 29
<211> LENGTH: 386
<212> TYPE: DNA
<213> ORGANISM: Homo sapiens

<400> SEQUENCE: 29
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatggagggg atcatcccta tctttggtac agcaaactac   180
gcacagaagt tccagggcag agtcacgatt accgcggacg aatccacgag cacagcctac   240
atggagctga gcagcctgag atctgaggac acggccgtgt attactgtgc gagatgagac   300
gaataacggt aaggcggttt accaggttta aacgcgtatt gggaaggcgc gtctcttggg   360
gccagggaac cctggtcaca gtctcg                                        386

<210> SEQ ID NO 30
<211> LENGTH: 126
<212> TYPE: PRT
<213> ORGANISM: Homo sapiens

<400> SEQUENCE: 30

Pro Gly Ala Ala Gly Ala Val Trp Gly Gly Glu Ala Trp Val Leu
1               5                   10                  15

Gly Glu Gly Leu Leu Gln Gly Phe Trp Arg His Leu Gln Gln Leu Cys
                20                  25                  30

Tyr Gln Leu Gly Ala Thr Gly Pro Trp Thr Arg Ala Val Asp Gly Arg
            35                  40                  45

Asp His Pro Tyr Leu Trp Tyr Ser Lys Leu Arg Thr Glu Val Pro Gly
50                  55                  60

Gln Ser His Asp Tyr Arg Gly Arg Ile His Glu His Ser Leu His Gly
65                  70                  75                  80

Ala Glu Gln Pro Glu Ile Gly His Gly Arg Val Leu Leu Cys Glu Met
                85                  90                  95

Arg Arg Ile Thr Val Arg Arg Phe Thr Arg Phe Lys Arg Val Leu Gly
            100                 105                 110

Arg Arg Val Ser Trp Gly Gln Gly Thr Leu Val Thr Val Ser
            115                 120                 125

<210> SEQ ID NO 31
<211> LENGTH: 125
<212> TYPE: PRT
<213> ORGANISM: Homo sapiens

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Glu Arg Gly Gly Leu Pro Gly Leu Asn Ala Tyr Trp Glu
            100                 105                 110

Gly Ala Ser Leu Gly Ala Arg Glu Pro Trp Ser Gln Ser
            115                 120                 125

<210> SEQ ID NO 32
<211> LENGTH: 123
<212> TYPE: PRT
<213> ORGANISM: Homo sapiens

<400> SEQUENCE: 32

Pro Arg Cys Ser Trp Cys Ser Leu Gly Leu Arg Arg Ser Leu Gly Pro
1               5                   10                  15

Arg Arg Ser Pro Ala Arg Leu Leu Glu Ala Pro Ser Ala Ala Met Leu
            20                  25                  30

Ser Ala Gly Cys Asp Arg Pro Leu Asp Lys Gly Leu Ser Gly Trp Glu
        35                  40                  45

Gly Ser Ser Leu Ser Val Gln Gln Thr Thr His Arg Ser Ser Arg Ala
    50                  55                  60

Glu Ser Arg Leu Pro Arg Thr Asn Pro Arg Ala Gln Pro Thr Trp Ser
65                  70                  75                  80

Ala Ala Asp Leu Arg Thr Arg Pro Cys Ile Thr Val Arg Asp Glu Thr
                85                  90                  95

Asn Asn Gly Lys Ala Val Tyr Gln Val Thr Arg Ile Gly Lys Ala Arg
            100                 105                 110

Leu Leu Gly Pro Gly Asn Pro Gly His Ser Leu
            115                 120

<210> SEQ ID NO 33
<211> LENGTH: 386
<212> TYPE: DNA
<213> ORGANISM: Homo sapiens

<400> SEQUENCE: 33
gaggtgcagc tgttggagtc tgggggaggc ttggtacagc ctgggggtc cctgagactc     60 tcctgtgcag cctctggatt cacctttagc agctatgcca tgagctgggt ccgccaggct    120
ccagggaagg gctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac acggccgtat attactgtgc gagatgagac    300
gaataacggt aaggcggttt accaggttta aacgcgtatt gggaaggcgc gtctcttggg    360
gccagggaac ctggtcaca gtctcg                                          386

<210> SEQ ID NO 34
<211> LENGTH: 126
<212> TYPE: PRT
<213> ORGANISM: Homo sapiens

```
<400> SEQUENCE: 34

Arg Gly Ala Ala Val Gly Val Trp Gly Arg Leu Gly Thr Ala Trp Gly
1               5                   10                  15

Val Pro Glu Thr Leu Leu Cys Ser Leu Trp Ile His Leu Gln Leu Cys
                20                  25                  30

His Glu Leu Gly Pro Pro Gly Ser Arg Glu Gly Ala Gly Val Gly Leu
            35                  40                  45

Ser Tyr Trp Trp Trp His Ile Leu Arg Arg Leu Arg Glu Gly Pro Val
    50                  55                  60

His His Leu Gln Arg Gln Phe Gln His Ala Val Ser Ser Ala Asn
65                  70                  75                  80

Glu Gln Pro Glu Ser Arg Gly His Gly Arg Ile Leu Leu Cys Glu Met
                85                  90                  95

Arg Arg Ile Thr Val Arg Arg Phe Thr Arg Phe Lys Arg Val Leu Gly
            100                 105                 110

Arg Arg Val Ser Trp Gly Gln Gly Thr Leu Val Thr Val Ser
            115                 120                 125

<210> SEQ ID NO 35
<211> LENGTH: 125
<212> TYPE: PRT
<213> ORGANISM: Homo sapiens

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Arg Gly Gly Leu Pro Gly Leu Asn Ala Tyr Trp Glu
            100                 105                 110

Gly Ala Ser Leu Gly Ala Arg Glu Pro Trp Ser Gln Ser
            115                 120                 125

<210> SEQ ID NO 36
<211> LENGTH: 123
<212> TYPE: PRT
<213> ORGANISM: Homo sapiens

<400> SEQUENCE: 36

Pro Arg Cys Ser Cys Trp Ser Leu Gly Glu Ala Trp Tyr Ser Leu Gly
1               5                   10                  15

Gly Pro Asp Ser Pro Val Gln Pro Leu Asp Ser Pro Leu Ala Ala Met
                20                  25                  30

Pro Ala Gly Ser Ala Arg Leu Gln Gly Arg Gly Trp Ser Gly Ser Gln
            35                  40                  45

Leu Leu Val Val Val Val Ala His Thr Thr Gln Thr Pro Arg Ala
    50                  55                  60

Gly Ser Pro Ser Pro Glu Thr Ile Pro Arg Thr Arg Cys Ile Cys Lys
```

```
                65                  70                  75                  80
Thr Ala Glu Pro Arg Thr Arg Pro Tyr Ile Thr Val Arg Asp Glu Thr
                        85                  90                  95

Asn Asn Gly Lys Ala Val Tyr Gln Val Thr Arg Ile Gly Lys Ala Arg
            100                 105                 110

Leu Leu Gly Pro Gly Asn Pro Gly His Ser Leu
            115                 120

<210> SEQ ID NO 37
<211> LENGTH: 385
<212> TYPE: DNA
<213> ORGANISM: Homo sapiens

<400> SEQUENCE: 37
gaggtgcagc tgttggagtc tgggggaggc ttggtacagc ctggggggtc cctgagactc        60
tcctgtgcag cctctggatt cacctttagc agctatgcca tgagctgggt ccgccaggct       120
ccagggaagg ggctggagtg ggtctcagct attagtggta gtggtggtag cacatactac       180
gcagactccg tgaagggccg gttcacatct ccagagacaa ttccaagaac acgctgtatc       240
tgcaaatgaa cagcctgaga gccgaggaca cggccgtata ttactgtgcg aaatgagacg       300
aataacggta aggcggttta ccaggtttaa acgcgtattg ggaaggcgcg tctcttgggg       360
ccagggaacc ctggtcacag tctcg                                             385

<210> SEQ ID NO 38
<211> LENGTH: 125
<212> TYPE: PRT
<213> ORGANISM: Homo sapiens

<400> SEQUENCE: 38

Arg Gly Ala Ala Val Gly Val Trp Gly Arg Leu Gly Thr Ala Trp Gly
1               5                   10                  15

Val Pro Glu Thr Leu Leu Cys Ser Leu Trp Ile His Leu Gln Leu Cys
            20                  25                  30

His Glu Leu Gly Pro Pro Gly Ser Arg Glu Gly Ala Gly Val Gly Leu
        35                  40                  45

Ser Tyr Trp Trp Trp His Ile Leu Arg Arg Leu Arg Glu Gly Pro Val
    50                  55                  60

His His Leu Gln Arg Gln Phe Gln Glu His Ala Val Ser Ala Asn Glu
65                  70                  75                  80

Gln Pro Glu Ser Arg Gly His Gly Arg Ile Leu Leu Cys Glu Met Arg
                85                  90                  95

Arg Ile Thr Val Arg Arg Phe Thr Arg Phe Lys Arg Val Leu Gly Arg
            100                 105                 110

Arg Val Ser Trp Gly Gln Gly Thr Leu Val Thr Val Ser
        115                 120                 125

<210> SEQ ID NO 39
<211> LENGTH: 125
<212> TYPE: PRT
<213> ORGANISM: Homo sapiens

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Glu Arg Gly Gly Leu Pro Gly Leu Asn Ala Tyr Trp Glu
                100                 105                 110

Gly Ala Ser Leu Gly Ala Arg Glu Pro Trp Ser Gln Ser
                115                 120                 125

<210> SEQ ID NO 40
<211> LENGTH: 123
<212> TYPE: PRT
<213> ORGANISM: Homo sapiens

<400> SEQUENCE: 40

Pro Arg Cys Ser Cys Trp Ser Leu Gly Glu Ala Trp Tyr Ser Leu Gly
 1               5                  10                  15

Gly Pro Asp Ser Pro Val Gln Pro Leu Asp Ser Pro Leu Ala Ala Met
                 20                  25                  30

Pro Ala Gly Ser Ala Arg Leu Gln Gly Arg Gly Trp Ser Gly Ser Gln
                 35                  40                  45

Leu Leu Val Val Val Val Ala His Thr Thr Gln Thr Pro Arg Ala
 50                  55                  60

Gly Ser Pro Ser Pro Glu Thr Ile Pro Arg Thr Arg Cys Ile Cys Lys
 65                  70                  75                  80

Thr Ala Glu Pro Arg Thr Arg Pro Tyr Ile Thr Val Arg Asn Glu Thr
                 85                  90                  95

Asn Asn Gly Lys Ala Val Tyr Gln Val Thr Arg Ile Gly Lys Ala Arg
                100                 105                 110

Leu Leu Gly Pro Gly Asn Pro Gly His Ser Leu
                115                 120

<210> SEQ ID NO 41
<211> LENGTH: 386
<212> TYPE: DNA
<213> ORGANISM: Homo sapiens

<400> SEQUENCE: 41
caggtgcagc tggtggagtc tgggggaggc gtggtccagc ctgggaggtc cctgagactc        60
tcctgtgcag cctctggatt caccttcagt agctatgcta tgcactgggt ccgccaggct       120
ccaggcaagg ggctggagtg ggtggcagtt atatcatatg atggaagtaa taaatactac       180
gcagactccg tgaagggccg attcaccatc tccagagaca attccaagaa cacgctgtat       240
ctgcaaatga acagcctgag agctgaggac acggctgtgt attactgtgc gagatgagac       300
gaataacggt aaggcggttt accaggttta acgcgtatt gggaaggcgc gtctcttggg       360
gccagggaac cctggtcaca gtctcg                                             386

<210> SEQ ID NO 42
<211> LENGTH: 124
<212> TYPE: PRT
<213> ORGANISM: Homo sapiens

<400> SEQUENCE: 42

Pro Gly Ala Ala Gly Gly Val Trp Gly Arg Gly Pro Ala Trp Glu
1               5                   10                  15

Val Pro Glu Thr Leu Leu Cys Ser Leu Trp Ile His Leu Gln Leu Cys
            20                  25                  30

Tyr Ala Leu Gly Pro Pro Gly Ser Arg Gln Gly Ala Gly Val Gly Gly
                35                  40                  45

Ser Tyr Ile Ile Trp Lys Ile Leu Arg Arg Leu Arg Glu Gly Pro Ile
50                  55                  60

His His Leu Gln Arg Gln Phe Gln Glu His Ala Val Ser Ala Asn Glu
65                  70                  75                  80

Gln Pro Glu Ser Gly His Gly Cys Val Leu Leu Cys Glu Met Arg Arg
                85                  90                  95

Ile Thr Val Arg Arg Phe Thr Arg Phe Lys Arg Val Leu Gly Arg Arg
                100                 105                 110

Val Ser Trp Gly Gln Gly Thr Leu Val Thr Val Ser
            115                 120

<210> SEQ ID NO 43
<211> LENGTH: 125
<212> TYPE: PRT
<213> ORGANISM: Homo sapiens

<400> SEQUENCE: 43

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Arg Gly Gly Leu Pro Gly Leu Asn Ala Tyr Trp Glu
                100                 105                 110

Gly Ala Ser Leu Gly Ala Arg Glu Pro Trp Ser Gln Ser
            115                 120                 125

<210> SEQ ID NO 44
<211> LENGTH: 124
<212> TYPE: PRT
<213> ORGANISM: Homo sapiens

<400> SEQUENCE: 44

Pro Arg Cys Ser Trp Trp Ser Leu Gly Glu Ala Trp Ser Ser Leu Gly
1               5                   10                  15

Gly Pro Asp Ser Pro Val Gln Pro Leu Asp Ser Pro Ser Val Ala Met
            20                  25                  30

Leu Cys Thr Gly Ser Ala Arg Leu Gln Ala Arg Gly Trp Ser Gly Trp
        35                  40                  45

Gln Leu Tyr His Met Met Glu Val Ile Asn Thr Thr Gln Thr Pro Arg
    50                  55                  60

Ala Asp Ser Pro Ser Pro Glu Thr Ile Pro Arg Thr Arg Cys Ile Cys
65                  70                  75                  80

Lys Thr Ala Glu Leu Arg Thr Arg Leu Cys Ile Thr Val Arg Asp Glu
                85                  90                  95

Thr Asn Asn Gly Lys Ala Val Tyr Gln Val Thr Arg Ile Gly Lys Ala
            100                 105                 110

Arg Leu Leu Gly Pro Gly Asn Pro Gly His Ser Leu
        115                 120

<210> SEQ ID NO 45
<211> LENGTH: 386
<212> TYPE: DNA
<213> ORGANISM: Homo sapiens

<400> SEQUENCE: 45
gaggtgcagc tggtggagtc tgggggaggc ttggtacagc ctgggggtc cctgagactc      60 tcctgtgcag cctctggatt caccttcagt agctatagca tgaactgggt ccgccaggct    120
ccagggaagg gctggagtg gtttcatac attagtagta gtagtagtac catatactac      180
gcagactctg tgaagggccg attcaccatc tccagagaca atgccaagaa ctcactgtat    240
ctgcaaatga acagcctgag agccgaggac acggctgtgt attactgtgc gagatgagac    300
gaataacggt aaggcggttt accaggttta aacgcgtatt gggaaggcgc gtctcttggg    360
gccagggaac cctggtcaca gtctcg                                         386

<210> SEQ ID NO 46
<211> LENGTH: 122
<212> TYPE: PRT
<213> ORGANISM: Homo sapiens

<400> SEQUENCE: 46

Arg Gly Ala Ala Gly Gly Val Trp Gly Arg Leu Gly Thr Ala Trp Gly
1               5                   10                  15

Val Pro Glu Thr Leu Leu Cys Ser Leu Trp Ile His Leu Gln Leu His
            20                  25                  30

Glu Leu Gly Pro Pro Gly Ser Arg Glu Gly Ala Gly Val Gly Phe Ile
        35                  40                  45

His Tyr His Ile Leu Arg Arg Leu Cys Glu Gly Pro Ile His His Leu
    50                  55                  60

Gln Arg Gln Cys Gln Glu Leu Thr Val Ser Ala Asn Glu Gln Pro Glu
65                  70                  75                  80

Ser Arg Gly His Gly Cys Val Leu Leu Cys Glu Met Arg Arg Ile Thr
                85                  90                  95

Val Arg Arg Phe Thr Arg Phe Lys Arg Val Leu Gly Arg Arg Val Ser
            100                 105                 110

Trp Gly Gln Gly Thr Leu Val Thr Val Ser
        115                 120

<210> SEQ ID NO 47
<211> LENGTH: 125
<212> TYPE: PRT
<213> ORGANISM: Homo sapiens

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val

```
                    35                  40                  45
Ser Tyr Ile Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Glu Arg Gly Gly Leu Pro Gly Leu Asn Ala Tyr Trp Glu
            100                 105                 110

Gly Ala Ser Leu Gly Ala Arg Glu Pro Trp Ser Gln Ser
            115                 120                 125

<210> SEQ ID NO 48
<211> LENGTH: 123
<212> TYPE: PRT
<213> ORGANISM: Homo sapiens

<400> SEQUENCE: 48

Pro Arg Cys Ser Trp Trp Ser Leu Gly Glu Ala Trp Tyr Ser Leu Gly
 1               5                  10                  15

Gly Pro Asp Ser Pro Val Gln Pro Leu Asp Ser Pro Val Ala Ile
             20                  25                  30

Ala Thr Gly Ser Ala Arg Leu Gln Gly Arg Gly Trp Ser Gly Phe His
             35                  40                  45

Thr Leu Val Val Val Val Pro Tyr Thr Thr Gln Thr Leu Arg Ala
 50                  55                  60

Asp Ser Pro Ser Pro Glu Thr Met Pro Arg Thr His Cys Ile Cys Lys
 65                  70                  75                  80

Thr Ala Glu Pro Arg Thr Arg Leu Cys Ile Thr Val Arg Asp Glu Thr
                 85                  90                  95

Asn Asn Gly Lys Ala Val Tyr Gln Val Thr Arg Ile Gly Lys Ala Arg
            100                 105                 110

Leu Leu Gly Pro Gly Asn Pro Gly His Ser Leu
            115                 120

<210> SEQ ID NO 49
<211> LENGTH: 290
<212> TYPE: DNA
<213> ORGANISM: Homo sapiens

<400> SEQUENCE: 49
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac      240 ctgcagtgga gcagcctgaa ggcctcggac accgccatgt attactgtgc                290

<210> SEQ ID NO 50
<211> LENGTH: 126
<212> TYPE: PRT
<213> ORGANISM: Homo sapiens

<400> SEQUENCE: 50

Arg Gly Ala Ala Gly Ala Val Trp Ser Arg Gly Glu Lys Ala Arg Gly
 1               5                  10                  15

Val Ser Glu Asp Leu Leu Gly Phe Trp Ile Gln Leu Tyr Gln Leu Leu
```

```
            20                  25                  30

Asp Arg Leu Gly Ala Pro Asp Ala Arg Glu Arg Pro Gly Val Asp Gly
                35                  40                  45

Asp His Leu Ser Trp Leu Tyr Gln Ile Gln Pro Val Leu Pro Arg Pro
 50                  55                  60

Gly His His Leu Ser Arg Gln Val His Gln His Arg Leu Pro Ala Val
 65                  70                  75                  80

Glu Gln Pro Glu Gly Leu Gly His Arg His Val Leu Leu Cys Glu Met
                85                  90                  95

Arg Arg Ile Thr Val Arg Arg Phe Thr Arg Phe Lys Arg Val Leu Gly
                100                 105                 110

Arg Arg Val Ser Trp Gly Gln Gly Thr Leu Val Thr Val Ser
                115                 120                 125

<210> SEQ ID NO 51
<211> LENGTH: 125
<212> TYPE: PRT
<213> ORGANISM: Homo sapiens

<400> SEQUENCE: 51

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
                35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Asp Glu Arg Gly Gly Leu Pro Gly Leu Asn Ala Tyr Trp Glu
                100                 105                 110

Gly Ala Ser Leu Gly Ala Arg Glu Pro Trp Ser Gln Ser
                115                 120                 125

<210> SEQ ID NO 52
<211> LENGTH: 125
<212> TYPE: PRT
<213> ORGANISM: Homo sapiens

<400> SEQUENCE: 52

Pro Arg Cys Ser Trp Cys Ser Leu Glu Gln Arg Lys Ser Pro Gly Ser
 1               5                  10                  15

Leu Arg Ser Pro Val Arg Val Leu Asp Thr Ala Leu Pro Ala Thr Gly
                20                  25                  30

Ser Ala Gly Cys Ala Arg Cys Pro Gly Lys Ala Trp Ser Gly Trp Gly
                35                  40                  45

Ser Ser Ile Leu Val Thr Leu Ile Pro Asp Thr Ala Arg Pro Ser Lys
 50                  55                  60

Ala Arg Ser Pro Ser Gln Pro Thr Ser Pro Ala Pro Pro Thr Cys
 65                  70                  75                  80

Ser Gly Ala Ala Arg Pro Arg Thr Pro Pro Cys Ile Thr Val Arg Asp
                85                  90                  95

Glu Thr Asn Asn Gly Lys Ala Val Tyr Gln Val Thr Arg Ile Gly Lys
```

```
                    100                 105                 110
Ala Arg Leu Leu Gly Pro Gly Asn Pro Gly His Ser Leu
            115                 120                 125

<210> SEQ ID NO 53
<211> LENGTH: 374
<212> TYPE: DNA
<213> ORGANISM: Homo sapiens

<400> SEQUENCE: 53
gacatccaga tgacccagtc tccatcctcc ctgtctgcat ctgtaggaga cagagtcacc       60
atcacttgcc aggcgagtca ggacattagc aactatttaa attggtatca gcagaaacca      120
gggaaagccc ctaagctcct gatctacgat gcatccaatt tggaaacagg ggtcccatca      180
aggttcagtg aagtggatc tgggacagat tttactttca ccatcagcag cctgcagcct      240
gaagatattg caacatatta ctgtcagcag cgagacgaat aacggtaagg cggtttacca      300
ggtttaaacg cgtattggga aggcgcgtct cattcggcca agggaccaag gtggaaatca      360
aaggggcggc cgca                                                       374

<210> SEQ ID NO 54
<211> LENGTH: 122
<212> TYPE: PRT
<213> ORGANISM: Homo sapiens

<400> SEQUENCE: 54

Gly His Pro Asp Asp Pro Val Ser Ile Leu Pro Val Cys Ile Cys Arg
1               5                   10                  15

Arg Gln Ser His His Leu Pro Gly Glu Ser Gly His Gln Leu Phe
            20                  25                  30

Lys Leu Val Ser Ala Glu Thr Arg Glu Ser Pro Ala Pro Asp Leu Arg
        35                  40                  45

Cys Ile Gln Phe Gly Asn Arg Gly Pro Ile Lys Val Gln Trp Lys Trp
    50                  55                  60

Ile Trp Asp Arg Phe Tyr Phe His His Gln Gln Pro Ala Ala Arg Tyr
65                  70                  75                  80

Cys Asn Ile Leu Leu Ser Ala Ala Arg Arg Ile Thr Val Arg Arg Phe
                85                  90                  95

Thr Arg Phe Lys Arg Val Leu Gly Arg Arg Val Ser Phe Gly Gln Gly
            100                 105                 110

Thr Lys Val Glu Ile Lys Gly Ala Ala Ala
        115                 120

<210> SEQ ID NO 55
<211> LENGTH: 122
<212> TYPE: PRT
<213> ORGANISM: Homo sapiens

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60
```

-continued

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Arg Asp Glu Arg Gly Gly
                 85                  90                  95

Leu Pro Gly Leu Asn Ala Tyr Trp Glu Gly Ala Ser His Ser Ala Lys
            100                 105                 110

Gly Pro Arg Trp Lys Ser Lys Gly Arg Pro
        115                 120

<210> SEQ ID NO 56
<211> LENGTH: 120
<212> TYPE: PRT
<213> ORGANISM: Homo sapiens

<400> SEQUENCE: 56

Arg Thr Ser Arg Pro Ser Leu His Pro Pro Cys Leu His Leu Glu Thr
 1               5                  10                  15

Glu Ser Pro Ser Leu Ala Arg Arg Val Arg Thr Leu Ala Thr Ile Ile
                20                  25                  30

Gly Ile Ser Arg Asn Gln Gly Lys Pro Leu Ser Ser Ser Thr Met His
            35                  40                  45

Pro Ile Trp Lys Gln Gly Ser His Gly Ser Val Glu Val Asp Leu
 50                  55                  60

Gly Gln Ile Leu Leu Ser Pro Ser Ala Ala Cys Ser Leu Lys Ile Leu
 65                  70                  75                  80

Gln His Ile Thr Val Ser Ser Glu Thr Asn Asn Gly Lys Ala Val Tyr
                 85                  90                  95

Gln Val Thr Arg Ile Gly Lys Ala Arg Leu Ile Arg Pro Arg Asp Gln
            100                 105                 110

Gly Gly Asn Gln Arg Gly Gly Arg
        115                 120

<210> SEQ ID NO 57
<211> LENGTH: 374
<212> TYPE: DNA
<213> ORGANISM: Homo sapiens

<400> SEQUENCE: 57
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg gtcccatca     180 aggttcagtg gaagtggatc tgggacagat tttactttca ccatcagcag cctgcagcct     240
gaagatattg caacatatta ctgtcagcag cgagacgaat aacggtaagg cggtttacca     300
ggtttaaacg cgtattggga aggcgcgtct cattcggcca agggaccaag gtggaaatca     360
aacgggcggc cgca                                                      374

<210> SEQ ID NO 58
<211> LENGTH: 122
<212> TYPE: PRT
<213> ORGANISM: Homo sapiens

<400> SEQUENCE: 58

Gly His Pro Asp Asp Pro Val Ser Ile Leu Pro Val Cys Ile Cys Arg
 1               5                  10                  15

Arg Gln Ser His His His Leu Pro Gly Glu Ser Gly His Gln Leu Phe
                20                  25                  30

```
Lys Leu Val Ser Ala Glu Thr Arg Glu Ser Pro Ala Pro Asp Leu Arg
            35                  40                  45

Cys Ile Gln Phe Gly Asn Arg Gly Pro Ile Lys Val Gln Trp Lys Trp
 50                  55                  60

Ile Trp Asp Arg Phe Tyr Phe His His Gln Gln Pro Ala Ala Arg Tyr
 65                  70                  75                  80

Cys Asn Ile Leu Leu Ser Ala Ala Arg Arg Ile Thr Val Arg Arg Phe
                85                  90                  95

Thr Arg Phe Lys Arg Val Leu Gly Arg Arg Val Ser Phe Gly Gln Gly
            100                 105                 110

Thr Lys Val Glu Ile Lys Arg Ala Ala Ala
            115                 120

<210> SEQ ID NO 59
<211> LENGTH: 122
<212> TYPE: PRT
<213> ORGANISM: Homo sapiens

<400> SEQUENCE: 59

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Arg Asp Glu Arg Gly Gly
                 85                  90                  95

Leu Pro Gly Leu Asn Ala Tyr Trp Glu Gly Ala Ser His Ser Ala Lys
            100                 105                 110

Gly Pro Arg Trp Lys Ser Asn Gly Arg Pro
            115                 120

<210> SEQ ID NO 60
<211> LENGTH: 120
<212> TYPE: PRT
<213> ORGANISM: Homo sapiens

<400> SEQUENCE: 60

Arg Thr Ser Arg Pro Ser Leu His Pro Pro Cys Leu His Leu Glu Thr
  1               5                  10                  15

Glu Ser Pro Ser Leu Ala Arg Arg Val Arg Thr Leu Ala Thr Ile Ile
                 20                  25                  30

Gly Ile Ser Arg Asn Gln Gly Lys Pro Leu Ser Ser Ser Thr Met His
             35                  40                  45

Pro Ile Trp Lys Gln Gly Ser His Gln Gly Ser Val Glu Val Asp Leu
 50                  55                  60

Gly Gln Ile Leu Leu Ser Pro Ser Ala Ala Cys Ser Leu Lys Ile Leu
 65                  70                  75                  80

Gln His Ile Thr Val Ser Ser Glu Thr Asn Asn Gly Lys Ala Val Tyr
                 85                  90                  95

Gln Val Thr Arg Ile Gly Lys Ala Arg Leu Ile Arg Pro Arg Asp Gln
            100                 105                 110
```

```
Gly Gly Asn Gln Thr Gly Gly Arg
        115             120

<210> SEQ ID NO 61
<211> LENGTH: 374
<212> TYPE: DNA
<213> ORGANISM: Homo sapiens

<400> SEQUENCE: 61
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat tcactctcac ccatcagcag tctgcaacct     240
gaagattttg caacttacta ctgtcagcag cgagacgaat aacggtaagg cggtttacca     300
ggtttaaacg cgtattggga aggcgcgtct cattcggcca agggaccaag gtggaaatca     360
aaggggcggc cgca                                                      374

<210> SEQ ID NO 62
<211> LENGTH: 122
<212> TYPE: PRT
<213> ORGANISM: Homo sapiens

<400> SEQUENCE: 62

Gly His Pro Asp Asp Pro Val Ser Ile Leu Pro Val Cys Ile Cys Arg
1               5                   10                  15

Arg Gln Ser His His Leu Pro Gly Lys Ser Glu His Gln Leu Phe
            20                  25                  30

Lys Leu Val Ser Ala Glu Thr Arg Glu Ser Pro Ala Pro Asp Leu Cys
        35                  40                  45

Cys Ile Gln Phe Ala Lys Trp Gly Pro Ile Lys Val Gln Trp Gln Trp
    50                  55                  60

Ile Trp Asp Arg Phe His Ser His His Gln Gln Ser Ala Thr Arg Phe
65                  70                  75                  80

Cys Asn Leu Leu Leu Ser Ala Ala Arg Arg Ile Thr Val Arg Arg Phe
                85                  90                  95

Thr Arg Phe Lys Arg Val Leu Gly Arg Arg Val Ser Phe Gly Gln Gly
            100                 105                 110

Thr Lys Val Glu Ile Lys Gly Ala Ala Ala
        115                 120

<210> SEQ ID NO 63
<211> LENGTH: 123
<212> TYPE: PRT
<213> ORGANISM: Homo sapiens

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
```

```
                65                  70                  75                  80
Pro Glu Asp Phe Ala Thr Tyr Tyr Cys Gln Gln Arg Asp Glu Arg Gly
                    85                  90                  95

Gly Leu Pro Gly Leu Asn Ala Tyr Trp Glu Gly Ala Ser His Ser Ala
                100                 105                 110

Lys Gly Pro Arg Trp Lys Ser Lys Gly Arg Pro
                115                 120

<210> SEQ ID NO 64
<211> LENGTH: 120
<212> TYPE: PRT
<213> ORGANISM: Homo sapiens

<400> SEQUENCE: 64

Arg Thr Ser Arg Pro Ser Leu His Pro Pro Cys Leu His Leu Glu Thr
1               5                  10                  15

Glu Ser Pro Ser Leu Ala Gly Gln Val Arg Ala Leu Ala Ala Ile Ile
                20                  25                  30

Gly Ile Ser Arg Asn Gln Gly Lys Pro Leu Ser Ser Ser Met Leu His
                35                  40                  45

Pro Val Cys Lys Val Gly Ser His Gln Gly Ser Val Ala Val Asp Leu
                50                  55                  60

Gly Gln Ile Ser Leu Ser Pro Ser Ala Val Cys Asn Leu Lys Ile Leu
65                  70                  75                  80

Gln Leu Thr Thr Val Ser Ser Glu Thr Asn Asn Gly Lys Ala Val Tyr
                85                  90                  95

Gln Val Thr Arg Ile Gly Lys Ala Arg Leu Ile Arg Pro Arg Asp Gln
                100                 105                 110

Gly Gly Asn Gln Arg Gly Gly Arg
                115                 120

<210> SEQ ID NO 65
<211> LENGTH: 374
<212> TYPE: DNA
<213> ORGANISM: Homo sapiens

<400> SEQUENCE: 65
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag cgagacgaat aacggtaagg cggtttacca   300
ggtttaaacg cgtattggga aggcgcgtct cattcggcca agggaccaag gtggaaatca   360
aacgggcggc cgca                                                     374

<210> SEQ ID NO 66
<211> LENGTH: 122
<212> TYPE: PRT
<213> ORGANISM: Homo sapiens

<400> SEQUENCE: 66

Gly His Pro Asp Asp Pro Val Ser Ile Leu Pro Val Cys Ile Cys Arg
1               5                  10                  15

Arg Gln Ser His His Leu Pro Gly Lys Ser Glu His Gln Leu Phe
                20                  25                  30
```

```
Lys Leu Val Ser Ala Glu Thr Arg Glu Ser Pro Ala Pro Asp Leu Cys
            35                  40                  45

Cys Ile Gln Phe Ala Lys Trp Gly Pro Ile Lys Val Gln Trp Gln Trp
 50                  55                  60

Ile Trp Asp Arg Phe His Ser His Gln Gln Ser Ala Thr Arg Phe
 65              70                  75                  80

Cys Asn Leu Leu Ser Ala Ala Arg Arg Ile Thr Val Arg Arg Phe
                85                  90                  95

Thr Arg Phe Lys Arg Val Leu Gly Arg Val Ser Phe Gly Gln Gly
            100                 105                 110

Thr Lys Val Glu Ile Lys Arg Ala Ala Ala
            115                 120
```

<210> SEQ ID NO 67
<211> LENGTH: 122
<212> TYPE: PRT
<213> ORGANISM: Homo sapiens

<400> SEQUENCE: 67

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Gln Arg Asp Glu Arg Gly Gly
                85                  90                  95

Leu Pro Gly Leu Asn Ala Tyr Trp Glu Gly Ala Ser His Ser Ala Lys
            100                 105                 110

Gly Pro Arg Trp Lys Ser Asn Gly Arg Pro
            115                 120
```

<210> SEQ ID NO 68
<211> LENGTH: 120
<212> TYPE: PRT
<213> ORGANISM: Homo sapiens

<400> SEQUENCE: 68

```
Arg Thr Ser Arg Pro Ser Leu His Pro Pro Cys Leu His Leu Glu Thr
 1               5                  10                  15

Glu Ser Pro Ser Leu Ala Gly Gln Val Arg Ala Leu Ala Ala Ile Ile
                20                  25                  30

Gly Ile Ser Arg Asn Gln Gly Lys Pro Leu Ser Ser Ser Met Leu His
            35                  40                  45

Pro Val Cys Lys Val Gly Ser His Gln Gly Ser Val Ala Val Asp Leu
 50                  55                  60

Gly Gln Ile Ser Leu Ser Pro Ser Ala Val Cys Asn Leu Lys Ile Leu
 65              70                  75                  80

Gln Leu Thr Thr Val Ser Ser Glu Thr Asn Asn Gly Lys Ala Val Tyr
                85                  90                  95

Gln Val Thr Arg Ile Gly Lys Ala Arg Leu Ile Arg Pro Arg Asp Gln
            100                 105                 110
```

```
Gly Gly Asn Gln Thr Gly Gly Arg
        115                 120
```

<210> SEQ ID NO 69
<211> LENGTH: 374
<212> TYPE: DNA
<213> ORGANISM: Homo sapiens

<400> SEQUENCE: 69

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgagacgaat aacggtaagg cggtttacca   300
ggtttaaacg cgtattggga aggcgcgtct cattcggcca agggaccaag gtggaaatca   360
aaggggcggc cgca                                                     374
```

<210> SEQ ID NO 70
<211> LENGTH: 122
<212> TYPE: PRT
<213> ORGANISM: Homo sapiens

<400> SEQUENCE: 70

```
Gly Asn Cys Val Asp Thr Val Ser Ser His Pro Val Phe Val Ser Arg
1               5                   10                  15
Gly Lys Ser His Pro Leu Leu Gln Gly Gln Ser Glu Cys Gln Leu Leu
            20                  25                  30
Ser Leu Val Pro Thr Glu Thr Trp Pro Gly Ser Gln Ala Pro His Leu
        35                  40                  45
Cys Ile Gln Gln Gly His Trp His Pro Ser Gln Val Gln Trp Gln Trp
    50                  55                  60
Val Trp Asp Arg Leu His Ser His His Gln Gln Pro Arg Ala Arg Phe
65                  70                  75                  80
Cys Ser Leu Leu Leu Ser Ala Ala Arg Arg Ile Thr Val Arg Arg Phe
                85                  90                  95
Thr Arg Phe Lys Arg Val Leu Gly Arg Arg Val Ser Phe Gly Gln Gly
            100                 105                 110
Thr Lys Val Glu Ile Lys Gly Ala Ala Ala
            115                 120
```

<210> SEQ ID NO 71
<211> LENGTH: 122
<212> TYPE: PRT
<213> ORGANISM: Homo sapiens

<400> SEQUENCE: 71

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
```

-continued

Glu Asp Phe Ala Val Tyr Tyr Cys Gln Gln Arg Asp Glu Arg Gly Gly
                85                  90                  95

Leu Pro Gly Leu Asn Ala Tyr Trp Glu Ala Ser His Ser Ala Lys
            100                 105                 110

Gly Pro Arg Trp Lys Ser Lys Gly Arg Pro
        115                 120

<210> SEQ ID NO 72
<211> LENGTH: 121
<212> TYPE: PRT
<213> ORGANISM: Homo sapiens

<400> SEQUENCE: 72

Arg Lys Leu Cys His Ser Leu Gln Pro Pro Cys Leu Cys Leu Gln Gly
1               5                   10                  15

Lys Glu Pro Pro Ser Pro Ala Gly Pro Val Arg Val Leu Ala Ala Thr
            20                  25                  30

Pro Gly Thr Asn Arg Asn Leu Ala Arg Leu Pro Gly Ser Ser Ser Met
        35                  40                  45

Met His Pro Thr Gly Pro Leu Ala Ser Gln Pro Gly Ser Val Ala Val
    50                  55                  60

Gly Leu Gly Gln Thr Ser Leu Ser Pro Ser Ala Ala Ser Leu Lys Ile
65                  70                  75                  80

Leu Gln Phe Ile Thr Val Ser Ser Glu Thr Asn Asn Gly Lys Ala Val
                85                  90                  95

Tyr Gln Val Thr Arg Ile Gly Lys Ala Arg Leu Ile Arg Pro Arg Asp
            100                 105                 110

Gln Gly Gly Asn Gln Arg Gly Gly Arg
        115                 120

<210> SEQ ID NO 73
<211> LENGTH: 374
<212> TYPE: DNA
<213> ORGANISM: Homo sapiens

<400> SEQUENCE: 73
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgagacgaat aacggtaagg cggtttacca     300
ggtttaaacg cgtattggga aggcgcgtct cattcggcca agggaccaag gtggaaatca     360
aacgggcggc cgca                                                       374

<210> SEQ ID NO 74
<211> LENGTH: 122
<212> TYPE: PRT
<213> ORGANISM: Homo sapiens

<400> SEQUENCE: 74

Gly Asn Cys Val Asp Thr Val Ser Ser His Pro Val Phe Val Ser Arg
1               5                   10                  15

Gly Lys Ser His Pro Leu Leu Gln Gly Gln Ser Glu Cys Gln Leu Leu
            20                  25                  30

Ser Leu Val Pro Thr Glu Thr Trp Pro Gly Ser Gln Ala Pro His Leu

-continued

```
                35                  40                  45
Cys Ile Gln Gln Gly His Trp His Pro Ser Gln Val Gln Trp Gln Trp
     50                  55                  60
Val Trp Asp Arg Leu His Ser His His Gln Gln Pro Arg Ala Arg Phe
 65                  70                  75                  80
Cys Ser Leu Leu Leu Ser Ala Ala Arg Arg Ile Thr Val Arg Arg Phe
                 85                  90                  95
Thr Arg Phe Lys Arg Val Leu Gly Arg Arg Val Ser Phe Gly Gln Gly
                100                 105                 110
Thr Lys Val Glu Ile Lys Arg Ala Ala Ala
            115                 120

<210> SEQ ID NO 75
<211> LENGTH: 122
<212> TYPE: PRT
<213> ORGANISM: Homo sapiens

<400> SEQUENCE: 75

Glu Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Val Ser Ser Tyr
             20                  25                  30
Leu Ala Trp Tyr Gln Gln Lys Pro Gly Gln Ala Pro Arg Leu Leu Ile
         35                  40                  45
Tyr Asp Ala Ser Asn Arg Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Asp Glu Arg Gly Gly
                 85                  90                  95
Leu Pro Gly Leu Asn Ala Tyr Trp Glu Gly Ala Ser His Ser Ala Lys
                100                 105                 110
Gly Pro Arg Trp Lys Ser Asn Gly Arg Pro
            115                 120

<210> SEQ ID NO 76
<211> LENGTH: 121
<212> TYPE: PRT
<213> ORGANISM: Homo sapiens

<400> SEQUENCE: 76

Arg Lys Leu Cys His Ser Leu Gln Pro Cys Leu Cys Leu Gln Gly
 1               5                  10                  15
Lys Glu Pro Pro Ser Pro Ala Gly Pro Val Arg Val Leu Ala Ala Thr
             20                  25                  30
Pro Gly Thr Asn Arg Asn Leu Ala Arg Leu Pro Gly Ser Ser Ser Met
         35                  40                  45
Met His Pro Thr Gly Pro Leu Ala Ser Gln Pro Gly Ser Val Ala Val
         50                  55                  60
Gly Leu Gly Gln Thr Ser Leu Ser Pro Ser Ala Ala Ser Leu Lys Ile
 65                  70                  75                  80
Leu Gln Phe Ile Thr Val Ser Ser Glu Thr Asn Asn Gly Lys Ala Val
                 85                  90                  95
Tyr Gln Val Thr Arg Ile Gly Lys Ala Arg Leu Ile Arg Pro Arg Asp
                100                 105                 110
Gln Gly Gly Asn Gln Thr Gly Gly Arg
```

<210> SEQ ID NO 77
<211> LENGTH: 374
<212> TYPE: DNA
<213> ORGANISM: Homo sapiens

<400> SEQUENCE: 77

```
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag cgagacgaat aacggtaagg cggtttacca     300
ggtttaaacg cgtattggga aggcgcgtct cattcggcca agggaccaag gtggaaatca     360
aaggggcggc cgca                                                       374
```

<210> SEQ ID NO 78
<211> LENGTH: 123
<212> TYPE: PRT
<213> ORGANISM: Homo sapiens

<400> SEQUENCE: 78

Gly Asn Ser Asp Asp Ala Val Ser Ser His Pro Val Cys Val Ser Arg
1               5                   10                  15

Gly Lys Ser His Pro Leu Leu Gln Gly Gln Ser Glu Cys Gln Gln Leu
            20                  25                  30

Ser Leu Val Pro Ala Glu Thr Trp Pro Gly Ser Gln Ala Pro His Leu
        35                  40                  45

Trp Cys Ile His Gln Gly His Trp Tyr Pro Ser Gln Val Gln Trp Gln
    50                  55                  60

Trp Val Trp Asp Arg Val His Ser His His Gln Gln Pro Ala Val Arg
65                  70                  75                  80

Phe Cys Ser Leu Leu Leu Ser Ala Ala Arg Arg Ile Thr Val Arg Arg
                85                  90                  95

Phe Thr Arg Phe Lys Arg Val Leu Gly Arg Arg Val Ser Phe Gly Gln
            100                 105                 110

Gly Thr Lys Val Glu Ile Lys Gly Ala Ala Ala
        115                 120

<210> SEQ ID NO 79
<211> LENGTH: 122
<212> TYPE: PRT
<213> ORGANISM: Homo sapiens

<400> SEQUENCE: 79

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Arg Asp Glu Arg Gly Gly
                85                  90                  95

Leu Pro Gly Leu Asn Ala Tyr Trp Glu Gly Ala Ser His Ser Ala Lys
            100                 105                 110

Gly Pro Arg Trp Lys Ser Lys Gly Arg Pro
        115                 120

<210> SEQ ID NO 80
<211> LENGTH: 120
<212> TYPE: PRT
<213> ORGANISM: Homo sapiens

<400> SEQUENCE: 80

Arg Lys Arg Ser Leu Gln Pro Pro Cys Leu Cys Leu Gln Gly Lys Glu
1               5                   10                  15

Pro Pro Ser Pro Ala Gly Pro Val Arg Val Leu Ala Ala Thr Pro Gly
            20                  25                  30

Thr Ser Arg Asn Leu Ala Arg Leu Pro Gly Ser Ser Met Val His
        35                  40                  45

Pro Pro Gly Pro Leu Val Ser Gln Pro Gly Ser Val Ala Val Gly Leu
    50                  55                  60

Gly Gln Ser Ser Leu Ser Pro Ser Ala Ala Cys Ser Leu Lys Ile Leu
65                  70                  75                  80

Gln Phe Ile Thr Val Ser Ser Glu Thr Asn Asn Gly Lys Ala Val Tyr
                85                  90                  95

Gln Val Thr Arg Ile Gly Lys Ala Arg Leu Ile Arg Pro Arg Asp Gln
            100                 105                 110

Gly Gly Asn Gln Arg Gly Gly Arg
        115                 120

<210> SEQ ID NO 81
<211> LENGTH: 374
<212> TYPE: DNA
<213> ORGANISM: Homo sapiens

<400> SEQUENCE: 81
gaaatagtga tgacgcagtc tccagccacc ctgtctgtgt ctccagggga agagccacc      60 ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag cgagacgaat aacggtaagg cggtttacca    300
ggtttaaacg cgtattggga aggcgcgtct cattcggcca agggaccaag gtggaaatca    360
aacgggcggc cgca                                                     374

<210> SEQ ID NO 82
<211> LENGTH: 123
<212> TYPE: PRT
<213> ORGANISM: Homo sapiens

<400> SEQUENCE: 82

Gly Asn Ser Asp Asp Ala Val Ser His Pro Val Cys Val Ser Arg
1               5                   10                  15

Gly Lys Ser His Pro Leu Leu Gln Gly Gln Ser Glu Cys Gln Gln Leu
            20                  25                  30

Ser Leu Val Pro Ala Glu Thr Trp Pro Gly Ser Gln Ala Pro His Leu
        35                  40                  45

```
Trp Cys Ile His Gln Gly His Trp Tyr Pro Ser Gln Val Gln Trp Gln
         50                  55                  60

Trp Val Trp Asp Arg Val His Ser His His Gln Pro Ala Val Arg
 65                  70                  75                  80

Phe Cys Ser Leu Leu Leu Ser Ala Ala Arg Ile Thr Val Arg Arg
                 85                  90                  95

Phe Thr Arg Phe Lys Arg Val Leu Gly Arg Arg Val Ser Phe Gly Gln
                100                 105                 110

Gly Thr Lys Val Glu Ile Lys Arg Ala Ala Ala
                115                 120

<210> SEQ ID NO 83
<211> LENGTH: 122
<212> TYPE: PRT
<213> ORGANISM: Homo sapiens

<400> SEQUENCE: 83

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Arg Asp Glu Arg Gly Gly
                 85                  90                  95

Leu Pro Gly Leu Asn Ala Tyr Trp Glu Gly Ala Ser His Ser Ala Lys
                100                 105                 110

Gly Pro Arg Trp Lys Ser Asn Gly Arg Pro
                115                 120

<210> SEQ ID NO 84
<211> LENGTH: 119
<212> TYPE: PRT
<213> ORGANISM: Homo sapiens

<400> SEQUENCE: 84

Arg Lys Arg Ser Leu Gln Pro Pro Cys Leu Cys Leu Gln Gly Lys Glu
 1               5                  10                  15

Pro Pro Ser Pro Ala Gly Pro Val Arg Val Leu Ala Ala Thr Pro Gly
             20                  25                  30

Thr Ser Arg Asn Leu Ala Arg Leu Pro Gly Ser Ser Met Val His
         35                  40                  45

Pro Pro Gly Pro Leu Val Ser Gln Pro Gly Ser Val Ala Val Gly Leu
     50                  55                  60

Gly Gln Ser Ser Leu Ser Pro Ser Ala Ala Cys Ser Leu Lys Ile Leu
 65                  70                  75                  80

Gln Phe Ile Thr Val Ser Ser Glu Thr Asn Asn Gly Lys Ala Val Tyr
                 85                  90                  95

Gln Val Thr Arg Ile Gly Lys Ala Arg Leu Ile Arg Pro Asp Gln Gly
                100                 105                 110

Gly Asn Gln Thr Gly Gly Arg
                115
```

<210> SEQ ID NO 85
<211> LENGTH: 377
<212> TYPE: DNA
<213> ORGANISM: Homo sapiens

<400> SEQUENCE: 85

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagttta ttactgtcag cagcgagacg aataacggta aggcggttta     300
ccaggtttaa acgcgtattg ggaaggcgcg tctcattcgg ccaagggacc aaggtggaaa     360
tcaaaggggc ggccgca                                                    377
```

<210> SEQ ID NO 86
<211> LENGTH: 124
<212> TYPE: PRT
<213> ORGANISM: Homo sapiens

<400> SEQUENCE: 86

```
Gly Asn Cys Val Asp Ala Val Ser Arg His Pro Val Phe Val Ser Arg
1               5                   10                  15

Gly Lys Ser His Pro Leu Ile Gln Gly Gln Ser Glu Cys Gln Gln Leu
            20                  25                  30

Leu Ser Leu Val Pro Ala Glu Thr Trp Pro Gly Ser Gln Ala Pro His
        35                  40                  45

Leu Trp Cys Ile Gln Gln Gly His Trp His Pro Arg Gln Val Gln Trp
    50                  55                  60

Gln Trp Val Trp Asp Arg Leu His Ser His Gln Gln Thr Gly Ala
65                  70                  75                  80

Arg Phe Cys Ser Leu Leu Leu Ser Ala Ala Arg Arg Ile Thr Val Arg
                85                  90                  95

Arg Phe Thr Arg Phe Lys Arg Val Leu Gly Arg Val Ser Phe Gly
            100                 105                 110

Gln Gly Thr Lys Val Glu Ile Lys Gly Ala Ala Ala
        115                 120
```

<210> SEQ ID NO 87
<211> LENGTH: 123
<212> TYPE: PRT
<213> ORGANISM: Homo sapiens

<400> SEQUENCE: 87

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Arg Asp Glu Arg Gly
```

85                  90                  95
Gly Leu Pro Gly Leu Asn Ala Tyr Trp Glu Gly Ala Ser His Ser Ala
                100                 105                 110
Lys Gly Pro Arg Trp Lys Ser Lys Gly Arg Pro
                115                 120

<210> SEQ ID NO 88
<211> LENGTH: 123
<212> TYPE: PRT
<213> ORGANISM: Homo sapiens

<400> SEQUENCE: 88

Arg Lys Leu Cys Arg Ser Leu Gln Ala Pro Cys Leu Cys Leu Gln Gly
1               5                   10                  15
Lys Glu Pro Pro Ser Pro Ala Gly Pro Val Arg Val Leu Ala Ala Ala
                20                  25                  30
Thr Pro Gly Thr Ser Arg Asn Leu Ala Arg Leu Pro Gly Ser Ser Ser
            35                  40                  45
Met Val His Pro Ala Gly Pro Leu Ala Ser Gln Thr Gly Ser Val Ala
        50                  55                  60
Val Gly Leu Gly Gln Thr Ser Leu Ser Pro Ser Ala Asp Trp Ser Leu
65                  70                  75                  80
Lys Ile Leu Gln Phe Ile Thr Val Ser Ser Glu Thr Asn Asn Gly Lys
                85                  90                  95
Ala Val Tyr Gln Val Thr Arg Ile Gly Lys Ala Arg Leu Ile Arg Pro
                100                 105                 110
Arg Asp Gln Gly Gly Asn Gln Arg Gly Gly Arg
                115                 120

<210> SEQ ID NO 89
<211> LENGTH: 377
<212> TYPE: DNA
<213> ORGANISM: Homo sapiens

<400> SEQUENCE: 89
gaaattgtgt tgacgcagtc tccaggcacc ctgtctttgt ctccagggga aagagccacc        60
ctctcctgca gggccagtca gagtgttagc agcagctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagttta ttactgtcag cagcgagacg aataacggta aggcggttta       300
ccaggtttaa acgcgtattg ggaaggcgcg tctcattcgg ccaagggacc aaggtggaaa       360
tcaaacgggc ggccgca                                                      377

<210> SEQ ID NO 90
<211> LENGTH: 124
<212> TYPE: PRT
<213> ORGANISM: Homo sapiens

<400> SEQUENCE: 90

Gly Asn Cys Val Asp Ala Val Ser Arg His Pro Val Phe Val Ser Arg
1               5                   10                  15
Gly Lys Ser His Pro Leu Leu Gln Gly Gln Ser Glu Cys Gln Gln Leu
                20                  25                  30
Leu Ser Leu Val Pro Ala Glu Thr Trp Pro Gly Ser Gln Ala Pro His
            35                  40                  45

```
Leu Trp Cys Ile Gln Gln Gly His Trp His Pro Arg Gln Val Gln Trp
            50                  55                  60

Gln Trp Val Trp Asp Arg Leu His Ser His His Gln Gln Thr Gly Ala
65                  70                  75                  80

Arg Phe Cys Ser Leu Leu Leu Ser Ala Ala Arg Arg Ile Thr Val Arg
                    85                  90                  95

Arg Phe Thr Arg Phe Lys Arg Val Leu Gly Arg Val Ser Phe Gly
                100                 105                 110

Gln Gly Thr Lys Val Glu Ile Lys Arg Ala Ala Ala
            115                 120
```

<210> SEQ ID NO 91
<211> LENGTH: 123
<212> TYPE: PRT
<213> ORGANISM: Homo sapiens

<400> SEQUENCE: 91

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Arg Asp Glu Arg Gly
                85                  90                  95

Gly Leu Pro Asp Leu Asn Ala Tyr Trp Glu Gly Ala Ser His Ser Ala
            100                 105                 110

Lys Gly Pro Arg Trp Lys Ser Asn Gly Arg Pro
        115                 120
```

<210> SEQ ID NO 92
<211> LENGTH: 123
<212> TYPE: PRT
<213> ORGANISM: Homo sapiens

<400> SEQUENCE: 92

```
Arg Lys Leu Cys Arg Ser Leu Gln Ala Pro Cys Leu Cys Leu Gln Gly
1               5                   10                  15

Lys Glu Pro Pro Ser Pro Ala Gly Pro Val Arg Val Leu Ala Ala Ala
            20                  25                  30

Thr Pro Gly Thr Ser Arg Asn Leu Ala Arg Leu Pro Gly Ser Ser Ser
        35                  40                  45

Met Val His Pro Ala Gly Pro Leu Ala Ser Gln Thr Gly Ser Val Ala
    50                  55                  60

Val Gly Leu Gly Gln Thr Ser Leu Ser Pro Ser Ala Asp Trp Ser Leu
65                  70                  75                  80

Lys Ile Leu Gln Phe Ile Thr Val Ser Ser Glu Thr Asn Asn Gly Lys
                85                  90                  95

Ala Val Tyr Gln Val Thr Arg Ile Gly Lys Ala Arg Leu Ile Arg Pro
            100                 105                 110

Arg Asp Gln Gly Gly Asn Gln Thr Gly Gly Arg
        115                 120
```

<210> SEQ ID NO 93
<211> LENGTH: 380
<212> TYPE: DNA
<213> ORGANISM: Homo sapiens

<400> SEQUENCE: 93

```
cagtctgtgt tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata gcgaccctc agggattcct      180
gaccgattct ctggctccaa gtctggcacg tcagccaccc tgggcatcac cggactccag     240
actggggacg aggccgatta ttactgcgga acaggagacg aataacggta aggcggttta     300
ccaggtttaa acgcgtattg ggaaggcgcg tctctgtgtt cggcggaggg accaagctga     360
ccgtcctagg ggcggccgca                                                 380
```

<210> SEQ ID NO 94
<211> LENGTH: 122
<212> TYPE: PRT
<213> ORGANISM: Homo sapiens

<400> SEQUENCE: 94

| Ala | Val | Cys | Val | Asp | Ala | Ala | Ala | Leu | Ser | Val | Cys | Gly | Pro | Arg | Thr |
|---|---|---|---|---|---|---|---|---|---|---|---|---|---|---|---|
| 1 | | | | 5 | | | | | 10 | | | | | 15 | |

| Glu | Gly | His | His | Leu | Leu | Leu | Trp | Lys | Gln | Leu | Gln | His | Trp | Glu | Leu |
|---|---|---|---|---|---|---|---|---|---|---|---|---|---|---|---|
| | | | 20 | | | | | 25 | | | | | 30 | | |

| Cys | Ile | Leu | Val | Pro | Ala | Ala | Pro | Arg | Asn | Ser | Pro | Gln | Thr | Pro | His |
|---|---|---|---|---|---|---|---|---|---|---|---|---|---|---|---|
| | | | 35 | | | | | 40 | | | | | 45 | | |

| Leu | Gln | Ala | Thr | Leu | Arg | Asp | Ser | Pro | Ile | Leu | Trp | Leu | Gln | Val | Trp |
|---|---|---|---|---|---|---|---|---|---|---|---|---|---|---|---|
| | 50 | | | | | 55 | | | | | 60 | | | | |

| His | Val | Ser | His | Pro | Gly | His | His | Arg | Thr | Pro | Asp | Trp | Gly | Arg | Gly |
|---|---|---|---|---|---|---|---|---|---|---|---|---|---|---|---|
| 65 | | | | | 70 | | | | | 75 | | | | | 80 |

| Arg | Leu | Leu | Leu | Arg | Asn | Arg | Arg | Ile | Thr | Val | Arg | Phe | Thr |
|---|---|---|---|---|---|---|---|---|---|---|---|---|---|
| | | | | 85 | | | | | 90 | | | | 95 |

| Arg | Phe | Lys | Arg | Val | Leu | Gly | Arg | Val | Ser | Val | Phe | Gly | Gly | Gly |
|---|---|---|---|---|---|---|---|---|---|---|---|---|---|---|
| | | | 100 | | | | | 105 | | | | | 110 | |

| Thr | Lys | Leu | Thr | Val | Leu | Gly | Ala | Ala | Ala |
|---|---|---|---|---|---|---|---|---|---|
| | | 115 | | | | | 120 | | |

<210> SEQ ID NO 95
<211> LENGTH: 122
<212> TYPE: PRT
<213> ORGANISM: Homo sapiens

<400> SEQUENCE: 95

| Gln | Ser | Val | Leu | Thr | Gln | Pro | Pro | Ser | Val | Ser | Ala | Ala | Pro | Gly | Gln |
|---|---|---|---|---|---|---|---|---|---|---|---|---|---|---|---|
| 1 | | | | 5 | | | | | 10 | | | | | 15 | |

| Lys | Val | Thr | Ile | Ser | Cys | Ser | Gly | Ser | Ser | Asn | Ile | Gly | Asn | Asn |
|---|---|---|---|---|---|---|---|---|---|---|---|---|---|---|
| | | | 20 | | | | | 25 | | | | | 30 | |

| Tyr | Val | Ser | Trp | Tyr | Gln | Gln | Leu | Pro | Gly | Thr | Ala | Pro | Lys | Leu | Leu |
|---|---|---|---|---|---|---|---|---|---|---|---|---|---|---|---|
| | | | 35 | | | | | 40 | | | | | 45 | | |

| Ile | Tyr | Asp | Asn | Asn | Lys | Arg | Pro | Ser | Gly | Ile | Pro | Asp | Arg | Phe | Ser |
|---|---|---|---|---|---|---|---|---|---|---|---|---|---|---|---|
| | | 50 | | | | | 55 | | | | | 60 | | | |

| Gly | Ser | Lys | Ser | Gly | Thr | Ser | Ala | Thr | Leu | Gly | Ile | Thr | Gly | Leu | Gln |
|---|---|---|---|---|---|---|---|---|---|---|---|---|---|---|---|
| 65 | | | | | 70 | | | | | 75 | | | | | 80 |

| Thr | Gly | Asp | Glu | Ala | Asp | Tyr | Tyr | Cys | Gly | Thr | Gly | Asp | Glu | Arg | Gly |
|---|---|---|---|---|---|---|---|---|---|---|---|---|---|---|---|
| | | | | 85 | | | | | 90 | | | | | 95 | |

```
Gly Leu Pro Gly Leu Asn Ala Tyr Trp Glu Gly Ala Ser Leu Cys Ser
                100                 105                 110

Ala Glu Gly Pro Ser Pro Ser Gly Arg Pro
            115                 120

<210> SEQ ID NO 96
<211> LENGTH: 125
<212> TYPE: PRT
<213> ORGANISM: Homo sapiens

<400> SEQUENCE: 96

Arg Ser Leu Cys Arg Ser Arg Pro Gln Cys Leu Arg Pro Gln Asp Arg
1               5                   10                  15

Arg Ser Pro Ser Pro Ala Leu Glu Ala Ala Pro Thr Leu Gly Ile Ile
            20                  25                  30

Met Tyr Pro Gly Thr Ser Ser Gln Glu Gln Pro Pro Asn Ser Ser
            35                  40                  45

Phe Met Thr Ile Ile Ser Asp Pro Gln Gly Phe Leu Thr Asp Ser Leu
50                  55                  60

Ala Pro Ser Leu Ala Arg Gln Pro Pro Trp Ala Ser Pro Asp Ser Arg
65                  70                  75                  80

Leu Gly Thr Arg Pro Ile Ile Thr Ala Glu Gln Glu Thr Asn Asn Gly
                85                  90                  95

Lys Ala Val Tyr Gln Val Thr Arg Ile Gly Lys Ala Arg Leu Cys Val
                100                 105                 110

Arg Arg Arg Asp Gln Ala Asp Arg Pro Arg Gly Gly Arg
            115                 120                 125

<210> SEQ ID NO 97
<211> LENGTH: 380
<212> TYPE: DNA
<213> ORGANISM: Homo sapiens

<400> SEQUENCE: 97
cagtctgtgc tgactcagcc accctcagcg tctgggaccc ccgggcagag ggtcaccatc      60
tcttgttctg gaagcagctc caacatcgga agtaatactg taaactggta ccagcagctc    120
ccaggaacgg cccccaaact cctcatctat agtaataatc agcggccctc agggGtccct    180
gaccgattct ctggctccaa gtctggcacc tcagcctccc tggccatcag tgggctccag    240
tctgaggatg aggctgatta ttactgtgca gcaggagacg aataacggta aggcggttta    300
ccaggtttaa acgcgtattg ggaaggcgcg tctctgtgtt cggcggaggg accaagctga    360
ccgtcctagg ggcggccgca                                                 380

<210> SEQ ID NO 98
<211> LENGTH: 119
<212> TYPE: PRT
<213> ORGANISM: Homo sapiens

<400> SEQUENCE: 98

Ala Val Cys Ala Asp Ser Ala Thr Leu Ser Val Trp Asp Pro Arg Ala
1               5                   10                  15

Glu Gly His His Leu Leu Phe Trp Lys Gln Leu Gln His Arg Lys Tyr
            20                  25                  30

Cys Lys Leu Val Pro Ala Ala Pro Arg Asn Gly Pro Gln Thr Pro His
            35                  40                  45

Leu Ser Ala Ala Leu Arg Gly Pro Pro Ile Leu Trp Leu Gln Val Trp
```

```
                50                  55                  60
His Leu Ser Leu Pro Gly His Gln Trp Ala Pro Val Gly Gly Leu Leu
 65                  70                  75                  80

Leu Cys Ser Arg Arg Arg Ile Thr Val Arg Arg Phe Thr Arg Phe Lys
                 85                  90                  95

Arg Val Leu Gly Arg Arg Val Ser Val Phe Gly Gly Thr Lys Leu
                100                 105                 110

Thr Val Leu Gly Ala Ala Ala
            115
```

<210> SEQ ID NO 99
<211> LENGTH: 122
<212> TYPE: PRT
<213> ORGANISM: Homo sapiens

<400> SEQUENCE: 99

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
                 20                  25                  30

Thr Val Asn Trp Tyr Gln Gln Leu Pro Gly Thr Ala Pro Lys Leu Leu
             35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Gly Asp Glu Arg Gly
                 85                  90                  95

Gly Leu Pro Gly Leu Asn Ala Tyr Trp Glu Gly Ala Ser Leu Cys Ser
                100                 105                 110

Ala Glu Gly Pro Ser Pro Ser Gly Arg Pro
            115                 120
```

<210> SEQ ID NO 100
<211> LENGTH: 124
<212> TYPE: PRT
<213> ORGANISM: Homo sapiens

<400> SEQUENCE: 100

```
Arg Ser Leu Cys Leu Ser His Pro Gln Arg Leu Gly Pro Pro Gly Arg
 1               5                  10                  15

Gly Ser Pro Ser Leu Val Leu Glu Ala Ala Pro Thr Ser Glu Val Ile
                 20                  25                  30

Leu Thr Gly Thr Ser Ser Gln Glu Arg Pro Pro Asn Ser Ser Ser
             35                  40                  45

Ile Val Ile Ile Ser Gly Pro Gln Gly Ser Leu Thr Asp Ser Leu Ala
 50                  55                  60

Pro Ser Leu Ala Pro Gln Pro Trp Pro Ser Val Gly Ser Ser Leu
 65                  70                  75                  80

Arg Met Arg Leu Ile Ile Thr Val Gln Gln Glu Thr Asn Asn Gly Lys
                 85                  90                  95

Ala Val Tyr Gln Val Thr Arg Ile Gly Lys Ala Arg Leu Cys Val Arg
                100                 105                 110

Arg Arg Asp Gln Ala Asp Arg Pro Arg Gly Gly Arg
            115                 120
```

-continued

```
<210> SEQ ID NO 101
<211> LENGTH: 19
<212> TYPE: PRT
<213> ORGANISM: Homo sapiens

<400> SEQUENCE: 101

Cys Ala Lys Ala Phe Arg Pro Asn Trp Gly Ser Arg Val Leu Tyr Phe
1               5                   10                  15

Asp Tyr Trp

<210> SEQ ID NO 102
<211> LENGTH: 12
<212> TYPE: PRT
<213> ORGANISM: Homo sapiens

<400> SEQUENCE: 102

Cys Ala Lys Leu Asn Trp Gly Trp Phe Asp Pro Trp
1               5                   10

<210> SEQ ID NO 103
<211> LENGTH: 12
<212> TYPE: PRT
<213> ORGANISM: Homo sapiens

<400> SEQUENCE: 103

Cys Ala Lys Gly Trp Glu Gly Glu Tyr Asp Tyr Trp
1               5                   10

<210> SEQ ID NO 104
<211> LENGTH: 17
<212> TYPE: PRT
<213> ORGANISM: Homo sapiens

<400> SEQUENCE: 104

Cys Ala Lys Asp Leu Trp Leu Asp Ser Ser Ser Asn Trp Phe Asp Pro
1               5                   10                  15

Trp

<210> SEQ ID NO 105
<211> LENGTH: 11
<212> TYPE: PRT
<213> ORGANISM: Homo sapiens

<400> SEQUENCE: 105

Cys Ala Lys Asp Leu Pro Gly Asp Pro His Trp
1               5                   10

<210> SEQ ID NO 106
<211> LENGTH: 13
<212> TYPE: PRT
<213> ORGANISM: Homo sapiens

<400> SEQUENCE: 106

Cys Ala Lys Ala Pro Pro Thr Gly Tyr Phe Asp Tyr Trp
1               5                   10

<210> SEQ ID NO 107
<211> LENGTH: 14
<212> TYPE: PRT
<213> ORGANISM: Homo sapiens

<400> SEQUENCE: 107

Cys Ala Lys Val Gly Leu Thr Gly Val His Phe Asp Tyr Trp
1               5                   10
```

<210> SEQ ID NO 108
<211> LENGTH: 16
<212> TYPE: PRT
<213> ORGANISM: Homo sapiens

<400> SEQUENCE: 108

Cys Ala Lys Asp Ser Tyr Gly Ser Gly Ser Tyr Tyr Asn Asp Tyr Trp
1               5                   10                  15

<210> SEQ ID NO 109
<211> LENGTH: 18
<212> TYPE: PRT
<213> ORGANISM: Homo sapiens

<400> SEQUENCE: 109

Cys Ala Lys Val Ala Gly Thr Trp Gly Arg Val Ala Tyr Tyr Phe Asp
1               5                   10                  15

Tyr Trp

<210> SEQ ID NO 110
<211> LENGTH: 15
<212> TYPE: PRT
<213> ORGANISM: Homo sapiens

<400> SEQUENCE: 110

Cys Ala Lys Val Thr Gly Val Phe Val Gly Asn Phe Asp Tyr Trp
1               5                   10                  15

<210> SEQ ID NO 111
<211> LENGTH: 15
<212> TYPE: PRT
<213> ORGANISM: Homo sapiens

<400> SEQUENCE: 111

Cys Ala Lys Asp Ala Arg Asn Ser Gly Ser Tyr Phe Asp Tyr Trp
1               5                   10                  15

<210> SEQ ID NO 112
<211> LENGTH: 14
<212> TYPE: PRT
<213> ORGANISM: Homo sapiens

<400> SEQUENCE: 112

Cys Ala Lys Gly Val Arg Thr Gly Val Val Phe Asp Tyr Trp
1               5                   10

<210> SEQ ID NO 113
<211> LENGTH: 19
<212> TYPE: PRT
<213> ORGANISM: Homo sapiens

<400> SEQUENCE: 113

Cys Ala Lys Gly Val Val Asn Trp Gly Thr Arg Lys Gly Trp Phe
1               5                   10                  15

Asp Pro Trp

<210> SEQ ID NO 114
<211> LENGTH: 11
<212> TYPE: PRT
<213> ORGANISM: Homo sapiens

<400> SEQUENCE: 114

-continued

Cys Ala Lys Trp Gly Gly Trp Phe Asp Pro Trp
1               5                   10

<210> SEQ ID NO 115
<211> LENGTH: 13
<212> TYPE: PRT
<213> ORGANISM: Homo sapiens

<400> SEQUENCE: 115

Cys Ala Lys Arg Arg Asp Asn Trp Gly Ser Val Asp Trp
1               5                   10

<210> SEQ ID NO 116
<211> LENGTH: 15
<212> TYPE: PRT
<213> ORGANISM: Homo sapiens

<400> SEQUENCE: 116

Cys Ala Lys Gly Ser Gly Phe Ser Ser Gly Trp Phe Asp Ser Trp
1               5                   10                  15

<210> SEQ ID NO 117
<211> LENGTH: 44
<212> TYPE: DNA
<213> ORGANISM: Homo sapiens
<220> FEATURE:
<221> NAME/KEY: misc_feature
<222> LOCATION: (13)..(14)
<223> OTHER INFORMATION: n is a, t, c or g
<220> FEATURE:
<221> NAME/KEY: misc_feature
<222> LOCATION: (16)..(17)
<223> OTHER INFORMATION: n is a, t, c or g
<220> FEATURE:
<221> NAME/KEY: misc_feature
<222> LOCATION: (19)..(20)
<223> OTHER INFORMATION: n is a, t, c or g
<220> FEATURE:
<221> NAME/KEY: misc_feature
<222> LOCATION: (22)..(23)
<223> OTHER INFORMATION: n is a, t, c or g

<400> SEQUENCE: 117
acgtctccga gannsnnsnn snnsatggat tattggggga gacg          44

<210> SEQ ID NO 118
<211> LENGTH: 14
<212> TYPE: PRT
<213> ORGANISM: Homo sapiens
<220> FEATURE:
<221> NAME/KEY: MISC_FEATURE
<222> LOCATION: (5)..(8)
<223> OTHER INFORMATION: Xaa is Cys, Trp, Arg, Ser or Gly

<400> SEQUENCE: 118

Thr Ser Pro Arg Xaa Xaa Xaa Xaa Met Asp Tyr Trp Gly Arg
1               5                   10

<210> SEQ ID NO 119
<211> LENGTH: 14
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Asp or Glu
<220> FEATURE:
<221> NAME/KEY: MISC_FEATURE
<222> LOCATION: (5)..(8)
<223> OTHER INFORMATION: Xaa is Ser, Pro, Thr, Ala, Cys, Trp, Arg or Gly

<400> SEQUENCE: 119

Arg Leu Arg Xaa Xaa Xaa Xaa Xaa Trp Ile Ile Gly Gly Asp
1               5                   10

<210> SEQ ID NO 120
<211> LENGTH: 25
<212> TYPE: DNA
<213> ORGANISM: Artificial Sequence
<220> FEATURE:
<223> OTHER INFORMATION: chemically synthesized

<400> SEQUENCE: 120
tgtttctaat cgcaggtgcc agatg                                         25

<210> SEQ ID NO 121
<211> LENGTH: 25
<212> TYPE: DNA
<213> ORGANISM: Artificial Sequence
<220> FEATURE:
<223> OTHER INFORMATION: chemically synthesized

<400> SEQUENCE: 121
atttatgtta tgacttgtta cactg                                         25

<210> SEQ ID NO 122
<211> LENGTH: 25
<212> TYPE: DNA
<213> ORGANISM: Artificial Sequence
<220> FEATURE:
<223> OTHER INFORMATION: chemically synthesized

<400> SEQUENCE: 122
tatttgtttt tatgtttcca atctc                                         25

<210> SEQ ID NO 123
<211> LENGTH: 25
<212> TYPE: DNA
<213> ORGANISM: Artificial Sequence
<220> FEATURE:
<223> OTHER INFORMATION: chemically synthesized

<400> SEQUENCE: 123
ccttggaggt ttatgttatg acttg                                         25

<210> SEQ ID NO 124
<211> LENGTH: 25
<212> TYPE: DNA
<213> ORGANISM: Artificial Sequence
<220> FEATURE:
<223> OTHER INFORMATION: chemically synthesized

<400> SEQUENCE: 124
ttatttccaa tttcagatac caccg                                         25

<210> SEQ ID NO 125
<211> LENGTH: 25
<212> TYPE: DNA
<213> ORGANISM: Artificial Sequence
<220> FEATURE:
<223> OTHER INFORMATION: chemically synthesized

<400> SEQUENCE: 125
ttgttggggt ttttgtttca tgtgg                                         25

```
<210> SEQ ID NO 126
<211> LENGTH: 25
<212> TYPE: DNA
<213> ORGANISM: Artificial Sequence
<220> FEATURE:
<223> OTHER INFORMATION: chemically synthesized

<400> SEQUENCE: 126
tatttccaat tcagatacc actgg                                          25

<210> SEQ ID NO 127
<211> LENGTH: 25
<212> TYPE: DNA
<213> ORGANISM: Artificial Sequence
<220> FEATURE:
<223> OTHER INFORMATION: chemically synthesized

<400> SEQUENCE: 127
atgttgaatc actgtgggag gccag                                         25

<210> SEQ ID NO 128
<211> LENGTH: 25
<212> TYPE: DNA
<213> ORGANISM: Artificial Sequence
<220> FEATURE:
<223> OTHER INFORMATION: chemically synthesized

<400> SEQUENCE: 128
ttatttccaa tctcagatac caccg                                         25

<210> SEQ ID NO 129
<211> LENGTH: 25
<212> TYPE: DNA
<213> ORGANISM: Artificial Sequence
<220> FEATURE:
<223> OTHER INFORMATION: chemically synthesized

<400> SEQUENCE: 129
ttttgtttca agctgaatca ctgtg                                         25

<210> SEQ ID NO 130
<211> LENGTH: 25
<212> TYPE: DNA
<213> ORGANISM: Artificial Sequence
<220> FEATURE:
<223> OTHER INFORMATION: chemically synthesized

<400> SEQUENCE: 130
atgtctgtgt ctctctcact tccag                                         25

<210> SEQ ID NO 131
<211> LENGTH: 25
<212> TYPE: DNA
<213> ORGANISM: Artificial Sequence
<220> FEATURE:
<223> OTHER INFORMATION: chemically synthesized

<400> SEQUENCE: 131
ttccccattg gcctggagca ctgtg                                         25

<210> SEQ ID NO 132
<211> LENGTH: 25
<212> TYPE: DNA
<213> ORGANISM: Artificial Sequence
<220> FEATURE:
<223> OTHER INFORMATION: chemically synthesized
```

<400> SEQUENCE: 132
gtgtctgtgt ctctcctgct tccag                                              25

<210> SEQ ID NO 133
<211> LENGTH: 25
<212> TYPE: DNA
<213> ORGANISM: Artificial Sequence
<220> FEATURE:
<223> OTHER INFORMATION: chemically synthesized

<400> SEQUENCE: 133
cttgtctcag ttccccattg ggctg                                              25

<210> SEQ ID NO 134
<211> LENGTH: 25
<212> TYPE: DNA
<213> ORGANISM: Artificial Sequence
<220> FEATURE:
<223> OTHER INFORMATION: chemically synthesized

<400> SEQUENCE: 134
atctcatcca cttctgtgtt ctctc                                              25

<210> SEQ ID NO 135
<211> LENGTH: 25
<212> TYPE: DNA
<213> ORGANISM: Artificial Sequence
<220> FEATURE:
<223> OTHER INFORMATION: chemically synthesized

<400> SEQUENCE: 135
ttgggtttct gacaccctca ggatg                                              25

<210> SEQ ID NO 136
<211> LENGTH: 25
<212> TYPE: DNA
<213> ORGANISM: Artificial Sequence
<220> FEATURE:
<223> OTHER INFORMATION: chemically synthesized

<400> SEQUENCE: 136
caggccagtc atgtgagact tcacc                                              25

<210> SEQ ID NO 137
<211> LENGTH: 25
<212> TYPE: DNA
<213> ORGANISM: Artificial Sequence
<220> FEATURE:
<223> OTHER INFORMATION: chemically synthesized

<400> SEQUENCE: 137
ctgcctcctc cctggggttt ctgaa                                              25

<210> SEQ ID NO 138
<211> LENGTH: 25
<212> TYPE: DNA
<213> ORGANISM: Artificial Sequence
<220> FEATURE:
<223> OTHER INFORMATION: chemically synthesized

<400> SEQUENCE: 138
cccctgtgtc ctctccacag gtgtc                                              25

<210> SEQ ID NO 139
<211> LENGTH: 25

```
<212> TYPE: DNA
<213> ORGANISM: Artificial Sequence
<220> FEATURE:
<223> OTHER INFORMATION: chemically synthesized

<400> SEQUENCE: 139
ccggcacagc tgccttctcc ctcag                                      25

<210> SEQ ID NO 140
<211> LENGTH: 18
<212> TYPE: DNA
<213> ORGANISM: Artificial Sequence
<220> FEATURE:
<223> OTHER INFORMATION: chemically synthesized

<400> SEQUENCE: 140
gaggtgcagc tgttggag                                              18

<210> SEQ ID NO 141
<211> LENGTH: 26
<212> TYPE: DNA
<213> ORGANISM: Artificial Sequence
<220> FEATURE:
<223> OTHER INFORMATION: chemically synthesized

<400> SEQUENCE: 141
tctgaccagg gtttctttt gtttgc                                      26

<210> SEQ ID NO 142
<211> LENGTH: 25
<212> TYPE: DNA
<213> ORGANISM: Artificial Sequence
<220> FEATURE:
<223> OTHER INFORMATION: chemically synthesized

<400> SEQUENCE: 142
ttgtgtctgg gctcacaatg acttc                                      25

<210> SEQ ID NO 143
<211> LENGTH: 24
<212> TYPE: DNA
<213> ORGANISM: Artificial Sequence
<220> FEATURE:
<223> OTHER INFORMATION: chemically synthesized

<400> SEQUENCE: 143
tggcattttc tgataacggt gtcc                                       24

<210> SEQ ID NO 144
<211> LENGTH: 25
<212> TYPE: DNA
<213> ORGANISM: Artificial Sequence
<220> FEATURE:
<223> OTHER INFORMATION: chemically synthesized

<400> SEQUENCE: 144
ctgcagggag gtttgtgtct gggcg                                      25

<210> SEQ ID NO 145
<211> LENGTH: 25
<212> TYPE: DNA
<213> ORGANISM: Artificial Sequence
<220> FEATURE:
<223> OTHER INFORMATION: chemically synthesized

<400> SEQUENCE: 145
```
atatgtgtgg cagtttctga ccttg                                                25

<210> SEQ ID NO 146
<211> LENGTH: 25
<212> TYPE: DNA
<213> ORGANISM: Artificial Sequence
<220> FEATURE:
<223> OTHER INFORMATION: chemically synthesized

<400> SEQUENCE: 146
ggtttgtgtc tggtgtcaca ctgac                                                25

<210> SEQ ID NO 147
<211> LENGTH: 25
<212> TYPE: DNA
<213> ORGANISM: Artificial Sequence
<220> FEATURE:
<223> OTHER INFORMATION: chemically synthesized

<400> SEQUENCE: 147
gagtctgtgc cggaagtgca gctgg                                                25

<210> SEQ ID NO 148
<211> LENGTH: 21
<212> TYPE: DNA
<213> ORGANISM: Artificial Sequence
<220> FEATURE:
<223> OTHER INFORMATION: chemically synthesized

<400> SEQUENCE: 148
tatcaggtgc agctggtgca g                                                    21

<210> SEQ ID NO 149
<211> LENGTH: 21
<212> TYPE: DNA
<213> ORGANISM: Artificial Sequence
<220> FEATURE:
<223> OTHER INFORMATION: chemically synthesized

<400> SEQUENCE: 149
tatcaggtgc agctggtgga g                                                    21

<210> SEQ ID NO 150
<211> LENGTH: 21
<212> TYPE: DNA
<213> ORGANISM: Artificial Sequence
<220> FEATURE:
<223> OTHER INFORMATION: chemically synthesized

<400> SEQUENCE: 150
tatgaggtgc agctggtgca g                                                    21

<210> SEQ ID NO 151
<211> LENGTH: 23
<212> TYPE: DNA
<213> ORGANISM: Artificial Sequence
<220> FEATURE:
<223> OTHER INFORMATION: chemically synthesized

<400> SEQUENCE: 151
atatctctcg cacagtaata cac                                                  23

<210> SEQ ID NO 152
<211> LENGTH: 23
<212> TYPE: DNA
<213> ORGANISM: Artificial Sequence -continued

```
<220> FEATURE:
<223> OTHER INFORMATION: chemically synthesized

<400> SEQUENCE: 152
atatctctcg cacagtaata tac                                             23

<210> SEQ ID NO 153
<211> LENGTH: 23
<212> TYPE: DNA
<213> ORGANISM: Artificial Sequence
<220> FEATURE:
<223> OTHER INFORMATION: chemically synthesized

<400> SEQUENCE: 153
atatgtctcg cacagtaata cat                                             23

<210> SEQ ID NO 154
<211> LENGTH: 32
<212> TYPE: DNA
<213> ORGANISM: Artificial Sequence
<220> FEATURE:
<223> OTHER INFORMATION: chemically synthesized

<400> SEQUENCE: 154
tatgacatcc agatgaccca gtctccatcc tc                                   32

<210> SEQ ID NO 155
<211> LENGTH: 20
<212> TYPE: DNA
<213> ORGANISM: Artificial Sequence
<220> FEATURE:
<223> OTHER INFORMATION: chemically synthesized

<400> SEQUENCE: 155
ataggagggg tactgtaact                                                 20

<210> SEQ ID NO 156
<211> LENGTH: 20
<212> TYPE: DNA
<213> ORGANISM: Artificial Sequence
<220> FEATURE:
<223> OTHER INFORMATION: chemically synthesized

<400> SEQUENCE: 156
ataggaggga gattatcata                                                 20

<210> SEQ ID NO 157
<211> LENGTH: 24
<212> TYPE: DNA
<213> ORGANISM: Artificial Sequence
<220> FEATURE:
<223> OTHER INFORMATION: chemically synthesized

<400> SEQUENCE: 157
tatgaaattg tgttgacgca gtct                                            24

<210> SEQ ID NO 158
<211> LENGTH: 23
<212> TYPE: DNA
<213> ORGANISM: Artificial Sequence
<220> FEATURE:
<223> OTHER INFORMATION: chemically synthesized

<400> SEQUENCE: 158
ataggaggtg agctaccata ctg                                             23
```

<210> SEQ ID NO 159
<211> LENGTH: 24
<212> TYPE: DNA
<213> ORGANISM: Artificial Sequence
<220> FEATURE:
<223> OTHER INFORMATION: chemically synthesized

<400> SEQUENCE: 159
tatgaaatag tgatgacgca gtct                                         24

<210> SEQ ID NO 160
<211> LENGTH: 23
<212> TYPE: DNA
<213> ORGANISM: Artificial Sequence
<220> FEATURE:
<223> OTHER INFORMATION: chemically synthesized

<400> SEQUENCE: 160
ataggaggcc agttattata ctg                                          23

<210> SEQ ID NO 161
<211> LENGTH: 23
<212> TYPE: DNA
<213> ORGANISM: Artificial Sequence
<220> FEATURE:
<223> OTHER INFORMATION: chemically synthesized

<400> SEQUENCE: 161
cagcgtagca actggcctcc tat                                          23

<210> SEQ ID NO 162
<211> LENGTH: 20
<212> TYPE: DNA
<213> ORGANISM: Artificial Sequence
<220> FEATURE:
<223> OTHER INFORMATION: chemically synthesized

<400> SEQUENCE: 162
tacagtctgt gctgactcag                                              20

<210> SEQ ID NO 163
<211> LENGTH: 23
<212> TYPE: DNA
<213> ORGANISM: Artificial Sequence
<220> FEATURE:
<223> OTHER INFORMATION: chemically synthesized

<400> SEQUENCE: 163
ataggaccat tcaggctgtc atc                                          23

<210> SEQ ID NO 164
<211> LENGTH: 21
<212> TYPE: DNA
<213> ORGANISM: Artificial Sequence
<220> FEATURE:
<223> OTHER INFORMATION: chemically synthesized

<400> SEQUENCE: 164
tatcagtctg tgttgacgca g                                            21

<210> SEQ ID NO 165
<211> LENGTH: 22
<212> TYPE: DNA
<213> ORGANISM: Artificial Sequence
<220> FEATURE:
<223> OTHER INFORMATION: chemically synthesized

```
<400> SEQUENCE: 165
ataggagcac tcaggctgct at                                              22

<210> SEQ ID NO 166
<211> LENGTH: 33
<212> TYPE: DNA
<213> ORGANISM: Artificial Sequence
<220> FEATURE:
<223> OTHER INFORMATION: chemically synthesized

<400> SEQUENCE: 166
cagccggcca tggcccaggt gcagctggtg cag                                  33

<210> SEQ ID NO 167
<211> LENGTH: 33
<212> TYPE: DNA
<213> ORGANISM: Artificial Sequence
<220> FEATURE:
<223> OTHER INFORMATION: chemically synthesized

<400> SEQUENCE: 167
cagccggcca tggcccaggt gcagctggtg gag                                  33

<210> SEQ ID NO 168
<211> LENGTH: 33
<212> TYPE: DNA
<213> ORGANISM: Artificial Sequence
<220> FEATURE:
<223> OTHER INFORMATION: chemically synthesized

<400> SEQUENCE: 168
cagccggcca tggccgaggt gcagctgttg gag                                  33

<210> SEQ ID NO 169
<211> LENGTH: 43
<212> TYPE: DNA
<213> ORGANISM: Artificial Sequence
<220> FEATURE:
<223> OTHER INFORMATION: chemically synthesized

<400> SEQUENCE: 169
cagccggcca tggccgaggt gcagctggtg gagtctgggg gag                       43

<210> SEQ ID NO 170
<211> LENGTH: 33
<212> TYPE: DNA
<213> ORGANISM: Artificial Sequence
<220> FEATURE:
<223> OTHER INFORMATION: chemically synthesized

<400> SEQUENCE: 170
cagccggcca tggccgaggt gcagctggtg cag                                  33

<210> SEQ ID NO 171
<211> LENGTH: 37
<212> TYPE: DNA
<213> ORGANISM: Artificial Sequence
<220> FEATURE:
<223> OTHER INFORMATION: chemically synthesized

<400> SEQUENCE: 171
cttaccgtta ttcgtctcat ctcgcacagt aatacac                              37

<210> SEQ ID NO 172
```

```
<211> LENGTH: 37
<212> TYPE: DNA
<213> ORGANISM: Artificial Sequence
<220> FEATURE:
<223> OTHER INFORMATION: chemically synthesized

<400> SEQUENCE: 172
cttaccgtta ttcgtctcat ttcgcacagt aatatac                              37

<210> SEQ ID NO 173
<211> LENGTH: 42
<212> TYPE: DNA
<213> ORGANISM: Artificial Sequence
<220> FEATURE:
<223> OTHER INFORMATION: chemically synthesized

<400> SEQUENCE: 173
ctcgcacagt aatacacagc cgtgtcctcg gctctcaggc tg                        42

<210> SEQ ID NO 174
<211> LENGTH: 37
<212> TYPE: DNA
<213> ORGANISM: Artificial Sequence
<220> FEATURE:
<223> OTHER INFORMATION: chemically synthesized

<400> SEQUENCE: 174
cttaccgtta ttcgtctcat ctcgcacagt aatacat                              37

<210> SEQ ID NO 175
<211> LENGTH: 47
<212> TYPE: DNA
<213> ORGANISM: Artificial Sequence
<220> FEATURE:
<223> OTHER INFORMATION: chemically synthesized

<400> SEQUENCE: 175
caatacgcgt ttaaacctgg taaaccgcct taccgttatt cgtctca                   47

<210> SEQ ID NO 176
<211> LENGTH: 48
<212> TYPE: DNA
<213> ORGANISM: Artificial Sequence
<220> FEATURE:
<223> OTHER INFORMATION: chemically synthesized

<400> SEQUENCE: 176
gttccctggc cccaagagac gcgccttccc aatacgcgtt taaacctg                  48

<210> SEQ ID NO 177
<211> LENGTH: 45
<212> TYPE: DNA
<213> ORGANISM: Artificial Sequence
<220> FEATURE:
<223> OTHER INFORMATION: chemically synthesized

<400> SEQUENCE: 177
cctccaccgc tcgagactgt gaccagggtt ccctggcccc aagag                     45

<210> SEQ ID NO 178
<211> LENGTH: 30
<212> TYPE: DNA
<213> ORGANISM: Artificial Sequence
<220> FEATURE:
<223> OTHER INFORMATION: chemically synthesized

<400> SEQUENCE: 178
```
cgggtcgacg gacatccaga tgacccagtc                                30

<210> SEQ ID NO 179
<211> LENGTH: 36
<212> TYPE: DNA
<213> ORGANISM: Artificial Sequence
<220> FEATURE:
<223> OTHER INFORMATION: chemically synthesized

<400> SEQUENCE: 179
cgggtcgacg gaaattgtgt tgacacagtc tccagc                         36

<210> SEQ ID NO 180
<211> LENGTH: 36
<212> TYPE: DNA
<213> ORGANISM: Artificial Sequence
<220> FEATURE:
<223> OTHER INFORMATION: chemically synthesized

<400> SEQUENCE: 180
cgggtcgacg gaaatagtga tgacgcagtc tccagc                         36

<210> SEQ ID NO 181
<211> LENGTH: 36
<212> TYPE: DNA
<213> ORGANISM: Artificial Sequence
<220> FEATURE:
<223> OTHER INFORMATION: chemically synthesized

<400> SEQUENCE: 181
cgggtcgacg gaaattgtgt tgacgcagtc tccagg                         36

<210> SEQ ID NO 182
<211> LENGTH: 45
<212> TYPE: DNA
<213> ORGANISM: Artificial Sequence
<220> FEATURE:
<223> OTHER INFORMATION: chemically synthesized

<400> SEQUENCE: 182
ccttaccgtt attcgtctcg ctgctgacag taatatgttg caata               45

<210> SEQ ID NO 183
<211> LENGTH: 45
<212> TYPE: DNA
<213> ORGANISM: Artificial Sequence
<220> FEATURE:
<223> OTHER INFORMATION: chemically synthesized

<400> SEQUENCE: 183
ccttaccgtt attcgtctcg ctgctgacag tagtaagttg caaaa               45

<210> SEQ ID NO 184
<211> LENGTH: 47
<212> TYPE: DNA
<213> ORGANISM: Artificial Sequence
<220> FEATURE:
<223> OTHER INFORMATION: chemically synthesized

<400> SEQUENCE: 184
ccttaccgtt attcgtctcg ctgctgacag taataaactg caaaatc             47

<210> SEQ ID NO 185
<211> LENGTH: 47
<212> TYPE: DNA

<210> SEQ ID NO 185
<211> LENGTH: 47
<212> TYPE: DNA
<213> ORGANISM: Artificial Sequence
<220> FEATURE:
<223> OTHER INFORMATION: chemically synthesized

<400> SEQUENCE: 185
ccaatacgcg tttaaacctg gtaaaccgcc ttaccgttat tcgtctc             47

<210> SEQ ID NO 186
<211> LENGTH: 46
<212> TYPE: DNA
<213> ORGANISM: Artificial Sequence
<220> FEATURE:
<223> OTHER INFORMATION: chemically synthesized

<400> SEQUENCE: 186
ggtcccttgg ccgaatgaga cgcgccttcc caatacgcgt ttaaac              46

<210> SEQ ID NO 187
<211> LENGTH: 45
<212> TYPE: DNA
<213> ORGANISM: Artificial Sequence
<220> FEATURE:
<223> OTHER INFORMATION: chemically synthesized

<400> SEQUENCE: 187
gtgcggccgc ccgtttgatt tccaccttgg tcccttggcc gaatg               45

<210> SEQ ID NO 188
<211> LENGTH: 45
<212> TYPE: DNA
<213> ORGANISM: Artificial Sequence
<220> FEATURE:
<223> OTHER INFORMATION: chemically synthesized

<400> SEQUENCE: 188
gtgcggccgc ccctttgatt tccaccttgg tcccttggcc gaatg               45

<210> SEQ ID NO 189
<211> LENGTH: 32
<212> TYPE: DNA
<213> ORGANISM: Artificial Sequence
<220> FEATURE:
<223> OTHER INFORMATION: chemically synthesized

<400> SEQUENCE: 189
cgggtcgacg cagtctgtgc tgactcagcc ac                             32

<210> SEQ ID NO 190
<211> LENGTH: 32
<212> TYPE: DNA
<213> ORGANISM: Artificial Sequence
<220> FEATURE:
<223> OTHER INFORMATION: chemically synthesized

<400> SEQUENCE: 190
cgggtcgacg cagtctgtgt tgacgcagcc gc                             32

<210> SEQ ID NO 191
<211> LENGTH: 38
<212> TYPE: DNA
<213> ORGANISM: Artificial Sequence
<220> FEATURE:
<223> OTHER INFORMATION: chemically synthesized

<400> SEQUENCE: 191
ccttaccgtt attcgtctcc tgctgcacag taataatc                       38

<210> SEQ ID NO 192
<211> LENGTH: 38
<212> TYPE: DNA
<213> ORGANISM: Artificial Sequence
<220> FEATURE:
<223> OTHER INFORMATION: chemically synthesized

<400> SEQUENCE: 192
ccttaccgtt attcgtctcc tgttccgcag taataatc                    38

<210> SEQ ID NO 193
<211> LENGTH: 46
<212> TYPE: DNA
<213> ORGANISM: Artificial Sequence
<220> FEATURE:
<223> OTHER INFORMATION: chemically synthesized

<400> SEQUENCE: 193
ccctccgccg aacacagaga cgcgccttcc caatacgcgt ttaaac           46

<210> SEQ ID NO 194
<211> LENGTH: 49
<212> TYPE: DNA
<213> ORGANISM: Artificial Sequence
<220> FEATURE:
<223> OTHER INFORMATION: chemically synthesized

<400> SEQUENCE: 194
gtgcggccgc ccctaggacg gtcagcttgg tccctccgcc gaacacaga        49

<210> SEQ ID NO 195
<211> LENGTH: 43
<212> TYPE: DNA
<213> ORGANISM: Artificial Sequence
<220> FEATURE:
<223> OTHER INFORMATION: chemically synthesized

<400> SEQUENCE: 195
ccgcacagcc ggccatggcc caggtgcagc tggtgcagtc tgg              43

<210> SEQ ID NO 196
<211> LENGTH: 43
<212> TYPE: DNA
<213> ORGANISM: Artificial Sequence
<220> FEATURE:
<223> OTHER INFORMATION: chemically synthesized

<400> SEQUENCE: 196
ccgcacagcc ggccatggcc gaggtgcagc tggtggagtc tgg              43

<210> SEQ ID NO 197
<211> LENGTH: 43
<212> TYPE: DNA
<213> ORGANISM: Artificial Sequence
<220> FEATURE:
<223> OTHER INFORMATION: chemically synthesized

<400> SEQUENCE: 197
ccgcacagcc ggccatggcc cagrtcacct tgctcgagtc tgg              43

<210> SEQ ID NO 198
<211> LENGTH: 43
<212> TYPE: DNA
<213> ORGANISM: Artificial Sequence
<220> FEATURE:

```
<223> OTHER INFORMATION: chemically synthesized

<400> SEQUENCE: 198
ccgcacagcc ggccatggcc caggtgcagc tgcaggagtc ggg                43

<210> SEQ ID NO 199
<211> LENGTH: 43
<212> TYPE: DNA
<213> ORGANISM: Artificial Sequence
<220> FEATURE:
<223> OTHER INFORMATION: chemically synthesized

<400> SEQUENCE: 199
ccgcacagcc ggccatggcc cagctgcagc tgcaggagtc cgg                43

<210> SEQ ID NO 200
<211> LENGTH: 43
<212> TYPE: DNA
<213> ORGANISM: Artificial Sequence
<220> FEATURE:
<223> OTHER INFORMATION: chemically synthesized

<400> SEQUENCE: 200
ccgcacagcc ggccatggcc caggtgcagc tacagcagtg ggg                43

<210> SEQ ID NO 201
<211> LENGTH: 32
<212> TYPE: DNA
<213> ORGANISM: Artificial Sequence
<220> FEATURE:
<223> OTHER INFORMATION: chemically synthesized

<400> SEQUENCE: 201
tggagtgggt ctcagctatt agtggtagtg gt                            32

<210> SEQ ID NO 202
<211> LENGTH: 45
<212> TYPE: DNA
<213> ORGANISM: Artificial Sequence
<220> FEATURE:
<223> OTHER INFORMATION: chemically synthesized

<400> SEQUENCE: 202
cgatgggccc ttggtggagg ctgaggagac rgtgaccagg gtgcc              45

<210> SEQ ID NO 203
<211> LENGTH: 45
<212> TYPE: DNA
<213> ORGANISM: Artificial Sequence
<220> FEATURE:
<223> OTHER INFORMATION: chemically synthesized

<400> SEQUENCE: 203
cgatgggccc ttggtggagg ctgaagagac ggtgaccrtk gtccc              45

<210> SEQ ID NO 204
<211> LENGTH: 45
<212> TYPE: DNA
<213> ORGANISM: Artificial Sequence
<220> FEATURE:
<223> OTHER INFORMATION: chemically synthesized

<400> SEQUENCE: 204
cgatgggccc ttggtggagg ctgaggagac ggtgaccagg gttcc              45
```

```
<210> SEQ ID NO 205
<211> LENGTH: 35
<212> TYPE: DNA
<213> ORGANISM: Artificial Sequence
<220> FEATURE:
<223> OTHER INFORMATION: chemically synthesized

<400> SEQUENCE: 205
gagccgagga cacggccgga tgttactgtg cgaga                              35

<210> SEQ ID NO 206
<211> LENGTH: 35
<212> TYPE: DNA
<213> ORGANISM: Artificial Sequence
<220> FEATURE:
<223> OTHER INFORMATION: chemically synthesized

<400> SEQUENCE: 206
gagccgagga cacggccgga tgttactgtg cgaaa                              35

<210> SEQ ID NO 207
<211> LENGTH: 32
<212> TYPE: DNA
<213> ORGANISM: Artificial Sequence
<220> FEATURE:
<223> OTHER INFORMATION: chemically synthesized

<400> SEQUENCE: 207
gaggagacgg tgacggatgt gccctggccc ca                                 32

<210> SEQ ID NO 208
<211> LENGTH: 32
<212> TYPE: DNA
<213> ORGANISM: Artificial Sequence
<220> FEATURE:
<223> OTHER INFORMATION: chemically synthesized

<400> SEQUENCE: 208
gaggagacgg tgacggatgt gccacggccc ca                                 32

<210> SEQ ID NO 209
<211> LENGTH: 32
<212> TYPE: DNA
<213> ORGANISM: Artificial Sequence
<220> FEATURE:
<223> OTHER INFORMATION: chemically synthesized

<400> SEQUENCE: 209
gaggagacgg tgacggatgt yccttggccc ca                                 32

<210> SEQ ID NO 210
<211> LENGTH: 26
<212> TYPE: DNA
<213> ORGANISM: Artificial Sequence
<220> FEATURE:
<223> OTHER INFORMATION: chemically synthesized

<400> SEQUENCE: 210
atgatgctgc tggcacgtct ccgaga                                        26

<210> SEQ ID NO 211
<211> LENGTH: 35
<212> TYPE: DNA
<213> ORGANISM: Artificial Sequence
<220> FEATURE:
<223> OTHER INFORMATION: chemically synthesized
```

```
<400> SEQUENCE: 211
ccacgtcatc cgatccgtct cccccaataa tccat                           35

<210> SEQ ID NO 212
<211> LENGTH: 35
<212> TYPE: DNA
<213> ORGANISM: Artificial Sequence
<220> FEATURE:
<223> OTHER INFORMATION: chemically synthesized

<400> SEQUENCE: 212
ccacgtcatc cgatccgtct cccccaataa tcaaa                           35

<210> SEQ ID NO 213
<211> LENGTH: 50
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 213
gctggcacgt ctccgagann snnsnnsnns tttgattatt gggggagacg           50

<210> SEQ ID NO 214
<211> LENGTH: 50
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 214
gctggcacgt ctccgagann snnsnnsnns atggattatt gggggagacg           50

<210> SEQ ID NO 215
<211> LENGTH: 53
<212> TYPE: DNA
<213> ORGANISM: Artificial Sequence
<220> FEATURE:
<223> OTHER INFORMATION: chemically synthesized
```

```
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 215
gctggcacgt ctccgagann snnsnnsnns nnstttgatt attgggggag acg      53

<210> SEQ ID NO 216
<211> LENGTH: 53
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 216
gctggcacgt ctccgagann snnsnnsnns nnsatggatt attgggggag acg      53

<210> SEQ ID NO 217
<211> LENGTH: 56
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
```

```
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 217
gctggcacgt ctccgagann snnsnnsnns nnsnnstttg attattgggg gagacg        56

<210> SEQ ID NO 218
<211> LENGTH: 56
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 218
gctggcacgt ctccgagann snnsnnsnns nnsnnsatgg attattgggg gagacg        56

<210> SEQ ID NO 219
<211> LENGTH: 56
<212> TYPE: DNA
<213> ORGANISM: Artificial Sequence
<220> FEATURE:
<223> OTHER INFORMATION: chemically synthesized

<400> SEQUENCE: 219
gctggcacgt ctccgagadv kdvkdvkdvk dvkdvktttg attattgggg gagacg        56

<210> SEQ ID NO 220
<211> LENGTH: 56
<212> TYPE: DNA
<213> ORGANISM: Artificial Sequence
<220> FEATURE:
<223> OTHER INFORMATION: chemically synthesized

<400> SEQUENCE: 220
gctggcacgt ctccgagadv kdvkdvkdvk dvkdvkatgg attattgggg gagacg        56

<210> SEQ ID NO 221
<211> LENGTH: 59
<212> TYPE: DNA
<213> ORGANISM: Artificial Sequence
```

```
<220> FEATURE:
<223> OTHER INFORMATION: chemically synthesized

<400> SEQUENCE: 221
gctggcacgt ctccgagadv kdvkdvkdvk dvkdvkdvkt ttgattattg ggggagacg      59

<210> SEQ ID NO 222
<211> LENGTH: 59
<212> TYPE: DNA
<213> ORGANISM: Artificial Sequence
<220> FEATURE:
<223> OTHER INFORMATION: chemically synthesized

<400> SEQUENCE: 222
gctggcacgt ctccgagadv kdvkdvkdvk dvkdvkdvka tggattattg ggggagacg      59

<210> SEQ ID NO 223
<211> LENGTH: 59
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 223
gctggcacgt ctccgaganv tnvtnvtnvt nvtnvtnvtt ttgattattg ggggagacg      59

<210> SEQ ID NO 224
<211> LENGTH: 59
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
```

<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 224
gctggcacgt ctccgaganv tnvtnvtnvt nvtnvtnvta tggattattg ggggagacg        59

<210> SEQ ID NO 225
<211> LENGTH: 62
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 225
gctggcacgt ctccgaganv tnvtnvtnvt nvtnvtnvtn vttttgatta ttgggggaga        60
cg        62

<210> SEQ ID NO 226
<211> LENGTH: 62
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 226
gctggcacgt ctccgaganv tnvtnvtnvt nvtnvtnvtn vtatggatta ttgggggaga     60
cg                                                                  62

<210> SEQ ID NO 227
<211> LENGTH: 65
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

<400> SEQUENCE: 227

```
gctggcacgt ctccgaganv tnvtnvtnvt nvtnvtnvtn vtnvttttga ttattggggg    60
agacg                                                                65
```

<210> SEQ ID NO 228
<211> LENGTH: 65
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

<400> SEQUENCE: 228

```
gctggcacgt ctccgaganv tnvtnvtnvt nvtnvtnvtn vtnvtatgga ttattggggg    60
agacg                                                                65
```

<210> SEQ ID NO 229
<211> LENGTH: 65
<212> TYPE: DNA
<213> ORGANISM: Artificial Sequence
<220> FEATURE:
<223> OTHER INFORMATION: chemically synthesized

<400> SEQUENCE: 229

```
gctggcacgt ctccgagadv tdvtdvtdvt dvtdvtdvtd vtdvttttga ttattggggg    60
agacg                                                                65
```

<210> SEQ ID NO 230
<211> LENGTH: 65
<212> TYPE: DNA
<213> ORGANISM: Artificial Sequence
<220> FEATURE:
<223> OTHER INFORMATION: chemically synthesized

<400> SEQUENCE: 230

```
gctggcacgt ctccgagadv tdvtdvtdvt dvtdvtdvtd vtdvtatgga ttattggggg    60
``` agacg 65

<210> SEQ ID NO 231
<211> LENGTH: 68
<212> TYPE: DNA
<213> ORGANISM: Artificial Sequence
<220> FEATURE:
<223> OTHER INFORMATION: chemically synthesized

<400> SEQUENCE: 231
gctggcacgt ctccgagadv tdvtdvtdvt dvtdvtdvtd vtdvtdvttt tgattattgg    60
gggagacg                                                            68

<210> SEQ ID NO 232
<211> LENGTH: 68
<212> TYPE: DNA
<213> ORGANISM: Artificial Sequence
<220> FEATURE:
<223> OTHER INFORMATION: chemically synthesized

<400> SEQUENCE: 232
gctggcacgt ctccgagadv tdvtdvtdvt dvtdvtdvtd vtdvtdvtat ggattattgg    60
gggagacg                                                            68

<210> SEQ ID NO 233
<211> LENGTH: 26
<212> TYPE: DNA
<213> ORGANISM: Artificial Sequence
<220> FEATURE:
<223> OTHER INFORMATION: chemically synthesized

<400> SEQUENCE: 233
ccggtgtagc gaaggcgtct cagcag                                        26

<210> SEQ ID NO 234
<211> LENGTH: 32
<212> TYPE: DNA
<213> ORGANISM: Artificial Sequence
<220> FEATURE:
<223> OTHER INFORMATION: chemically synthesized

<400> SEQUENCE: 234
tagggtcgcc ttgatcgtct cccgaaggtc gg                                 32

<210> SEQ ID NO 235
<211> LENGTH: 45
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t

<400> SEQUENCE: 235
gaaggcgtct cagcagnnsn nsnnsnnscc gaccttcggg agacg        45

<210> SEQ ID NO 236
<211> LENGTH: 48
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 236
gaaggcgtct cagcagnnsn nsnnsnnscc gnnsaccttc gggagacg        48

<210> SEQ ID NO 237
<211> LENGTH: 51
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 237
gaaggcgtct cagcagnnsn nsnnsnnsnn sccgnnsacc ttcgggagac g        51

<210> SEQ ID NO 238
<211> LENGTH: 32
<212> TYPE: DNA
<213> ORGANISM: Artificial Sequence
<220> FEATURE:
<223> OTHER INFORMATION: chemically synthesized

<400> SEQUENCE: 238
cggtcagtcg caatacgtct ccagcatggg at                                    32

<210> SEQ ID NO 239
<211> LENGTH: 32
<212> TYPE: DNA
<213> ORGANISM: Artificial Sequence
<220> FEATURE:
<223> OTHER INFORMATION: chemically synthesized

<400> SEQUENCE: 239
cggtcagtcg caatacgtct ccagcatatg at                                    32

<210> SEQ ID NO 240
<211> LENGTH: 32
<212> TYPE: DNA
<213> ORGANISM: Artificial Sequence
<220> FEATURE:
<223> OTHER INFORMATION: chemically synthesized

<400> SEQUENCE: 240
caggaccagt ctcgtgagga tcgtctcaac ac                                    32

<210> SEQ ID NO 241
<211> LENGTH: 46
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t

<400> SEQUENCE: 241
cgtctccagc atgggatnns nnsnnsnnsg tgttgagacg atcctc                     46

<210> SEQ ID NO 242
<211> LENGTH: 46
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)

<223> OTHER INFORMATION: n is a, c, g, or t

<400> SEQUENCE: 242
cgtctccagc atatgatnns nnsnnsnnsg tgttgagacg atcctc                    46

<210> SEQ ID NO 243
<211> LENGTH: 49
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 243
cgtctccagc atgggatnns nnsnnsnnsn nsgtgttgag acgatcctc                 49

<210> SEQ ID NO 244
<211> LENGTH: 49
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 244
cgtctccagc atatgatnns nnsnnsnnsn nsgtgttgag acgatcctc                 49

<210> SEQ ID NO 245
<211> LENGTH: 52
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature

```
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t

<400> SEQUENCE: 245
cgtctccagc atgggatnns nnsnnsnnsn nsnnsgtgtt gagacgatcc tc          52

<210> SEQ ID NO 246
<211> LENGTH: 52
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t

<400> SEQUENCE: 246
cgtctccagc atatgatnns nnsnnsnnsn nsnnsgtgtt gagacgatcc tc          52

<210> SEQ ID NO 247
<211> LENGTH: 32
<212> TYPE: DNA
<213> ORGANISM: Artificial Sequence
<220> FEATURE:
<223> OTHER INFORMATION: chemically synthesized

<400> SEQUENCE: 247
cggtcagtcg caatacgtct cgaacatggg at                               32

<210> SEQ ID NO 248
<211> LENGTH: 32
<212> TYPE: DNA
```

```
<213> ORGANISM: Artificial Sequence
<220> FEATURE:
<223> OTHER INFORMATION: chemically synthesized

<400> SEQUENCE: 248
cggtcagtcg caatacgtct cgaacatggg at                                    32

<210> SEQ ID NO 249
<211> LENGTH: 46
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t

<400> SEQUENCE: 249
cgtctcgaac atgggatnns nnsnnsnnsg tgttgagacg atcctc                     46

<210> SEQ ID NO 250
<211> LENGTH: 46
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t

<400> SEQUENCE: 250
cgtctcgaac atatgatnns nnsnnsnnsg tgttgagacg atcctc                     46

<210> SEQ ID NO 251
<211> LENGTH: 49
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
```

```
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 251
cgtctcgaac atgggatnns nnsnnsnnsn nsgtgttgag acgatcctc        49

<210> SEQ ID NO 252
<211> LENGTH: 49
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 252
cgtctcgaac atatgatnns nnsnnsnnsn nsgtgttgag acgatcctc        49

<210> SEQ ID NO 253
<211> LENGTH: 52
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
```

<223> OTHER INFORMATION: n is a, c, g, or t

<400> SEQUENCE: 253
cgtctcgaac atgggatnns nnsnnsnnsn nsnnsgtgtt gagacgatcc tc    52

<210> SEQ ID NO 254
<211> LENGTH: 52
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t

<400> SEQUENCE: 254
cgtctcgaac atgggatnns nnsnnsnnsn nsnnsgtgtt gagacgatcc tc    52

<210> SEQ ID NO 255
<211> LENGTH: 21
<212> TYPE: DNA
<213> ORGANISM: Artificial Sequence
<220> FEATURE:
<223> OTHER INFORMATION: chemically synthesized

<400> SEQUENCE: 255
ctcttctgag atgagttttt g    21

<210> SEQ ID NO 256
<211> LENGTH: 43
<212> TYPE: DNA
<213> ORGANISM: Artificial Sequence
<220> FEATURE:
<223> OTHER INFORMATION: chemically synthesized

<400> SEQUENCE: 256
atgcggccca gccggccatg gccsaggtyc agctbcagca gtc    43

<210> SEQ ID NO 257
<211> LENGTH: 43
<212> TYPE: DNA
<213> ORGANISM: Artificial Sequence
<220> FEATURE:
<223> OTHER INFORMATION: chemically synthesized

<400> SEQUENCE: 257
atgcggccca gccggccatg gcccaggttc acctgcagca rtc    43

<210> SEQ ID NO 258
<211> LENGTH: 43
<212> TYPE: DNA
<213> ORGANISM: Artificial Sequence
<220> FEATURE:
<223> OTHER INFORMATION: chemically synthesized

<400> SEQUENCE: 258
atgcggccca gccggccatg gcccaggtrc agctgaagga gtc        43

<210> SEQ ID NO 259
<211> LENGTH: 43
<212> TYPE: DNA
<213> ORGANISM: Artificial Sequence
<220> FEATURE:
<223> OTHER INFORMATION: chemically synthesized

<400> SEQUENCE: 259
atgcggccca gccggccatg gcccaggtcc aactvcagca rcc        43

<210> SEQ ID NO 260
<211> LENGTH: 43
<212> TYPE: DNA
<213> ORGANISM: Artificial Sequence
<220> FEATURE:
<223> OTHER INFORMATION: chemically synthesized

<400> SEQUENCE: 260
atgcggccca gccggccatg gcccagatcc agttggtvca gtc        43

<210> SEQ ID NO 261
<211> LENGTH: 43
<212> TYPE: DNA
<213> ORGANISM: Artificial Sequence
<220> FEATURE:
<223> OTHER INFORMATION: chemically synthesized

<400> SEQUENCE: 261
atgcggccca gccggccatg gcccaggtgc agctgaagsa stc        43

<210> SEQ ID NO 262
<211> LENGTH: 43
<212> TYPE: DNA
<213> ORGANISM: Artificial Sequence
<220> FEATURE:
<223> OTHER INFORMATION: chemically synthesized

<400> SEQUENCE: 262
atgcggccca gccggccatg gccgaggtgc agskggtgga gtc        43

<210> SEQ ID NO 263
<211> LENGTH: 43
<212> TYPE: DNA
<213> ORGANISM: Artificial Sequence
<220> FEATURE:
<223> OTHER INFORMATION: chemically synthesized

<400> SEQUENCE: 263
atgcggccca gccggccatg gccgaagtga arsttgagga gtc        43

<210> SEQ ID NO 264
<211> LENGTH: 43
<212> TYPE: DNA
<213> ORGANISM: Artificial Sequence
<220> FEATURE:
<223> OTHER INFORMATION: chemically synthesized

<400> SEQUENCE: 264
atgcggccca gccggccatg gccgakgtsv agcttcagga gtc        43

<210> SEQ ID NO 265
<211> LENGTH: 43
<212> TYPE: DNA
<213> ORGANISM: Artificial Sequence
<220> FEATURE:
<223> OTHER INFORMATION: chemically synthesized

<400> SEQUENCE: 265
atgcggccca gccggccatg gccgaggtga asstggtgga atc        43

<210> SEQ ID NO 266
<211> LENGTH: 43
<212> TYPE: DNA
<213> ORGANISM: Artificial Sequence
<220> FEATURE:
<223> OTHER INFORMATION: chemically synthesized

<400> SEQUENCE: 266
atgcggccca gccggccatg gccgaggtga agctgrtgga rtc        43

<210> SEQ ID NO 267
<211> LENGTH: 43
<212> TYPE: DNA
<213> ORGANISM: Artificial Sequence
<220> FEATURE:
<223> OTHER INFORMATION: chemically synthesized

<400> SEQUENCE: 267
atgcggccca gccggccatg gccgargtga agctgrtgga gtc        43

<210> SEQ ID NO 268
<211> LENGTH: 43
<212> TYPE: DNA
<213> ORGANISM: Artificial Sequence
<220> FEATURE:
<223> OTHER INFORMATION: chemically synthesized

<400> SEQUENCE: 268
atgcggccca gccggccatg gccgaagtgc agctgttgga gac        43

<210> SEQ ID NO 269
<211> LENGTH: 43
<212> TYPE: DNA
<213> ORGANISM: Artificial Sequence
<220> FEATURE:
<223> OTHER INFORMATION: chemically synthesized

<400> SEQUENCE: 269
atgcggccca gccggccatg gccgargtga agcttctcsa gtc        43

<210> SEQ ID NO 270
<211> LENGTH: 42
<212> TYPE: DNA
<213> ORGANISM: Artificial Sequence
<220> FEATURE:
<223> OTHER INFORMATION: chemically synthesized

<400> SEQUENCE: 270
atgcggccca gccggccatg gcccargtta ctctgaaaga gt        42

<210> SEQ ID NO 271
<211> LENGTH: 41

<210> SEQ ID NO 271
<211> LENGTH: 41
<212> TYPE: DNA
<213> ORGANISM: Artificial Sequence
<220> FEATURE:
<223> OTHER INFORMATION: chemically synthesized

<400> SEQUENCE: 271
cctgaaccgc cgcctccgct cgagacggtg accgtggtcc c         41

<210> SEQ ID NO 272
<211> LENGTH: 41
<212> TYPE: DNA
<213> ORGANISM: Artificial Sequence
<220> FEATURE:
<223> OTHER INFORMATION: chemically synthesized

<400> SEQUENCE: 272
cctgaaccgc cgcctccgct cgagactgtg agagtggtgc c         41

<210> SEQ ID NO 273
<211> LENGTH: 41
<212> TYPE: DNA
<213> ORGANISM: Artificial Sequence
<220> FEATURE:
<223> OTHER INFORMATION: chemically synthesized

<400> SEQUENCE: 273
cctgaaccgc cgcctccgct cgagacagtg accagagtcc c         41

<210> SEQ ID NO 274
<211> LENGTH: 41
<212> TYPE: DNA
<213> ORGANISM: Artificial Sequence
<220> FEATURE:
<223> OTHER INFORMATION: chemically synthesized

<400> SEQUENCE: 274
cctgaaccgc cgcctccgct cgagacggtg actgaggttc c         41

<210> SEQ ID NO 275
<211> LENGTH: 35
<212> TYPE: DNA
<213> ORGANISM: Artificial Sequence
<220> FEATURE:
<223> OTHER INFORMATION: chemically synthesized

<400> SEQUENCE: 275
gagccgagga cacggccgga tgttactgtg cgaga                35

<210> SEQ ID NO 276
<211> LENGTH: 31
<212> TYPE: DNA
<213> ORGANISM: Artificial Sequence
<220> FEATURE:
<223> OTHER INFORMATION: chemically synthesized

<400> SEQUENCE: 276
ggggcgcagg gacatccgtc accgtctcct c                    31

<210> SEQ ID NO 277
<211> LENGTH: 32
<212> TYPE: DNA
<213> ORGANISM: Artificial Sequence
<220> FEATURE:
<223> OTHER INFORMATION: chemically synthesized

<400> SEQUENCE: 277

```
gaggagactg tgagggatgt gccttggccc ca                               32
```

<210> SEQ ID NO 278
<211> LENGTH: 32
<212> TYPE: DNA
<213> ORGANISM: Artificial Sequence
<220> FEATURE:
<223> OTHER INFORMATION: chemically synthesized

<400> SEQUENCE: 278

```
gaggagacgg tgacggatgt gccctggccc ca                               32
```

<210> SEQ ID NO 279
<211> LENGTH: 32
<212> TYPE: DNA
<213> ORGANISM: Artificial Sequence
<220> FEATURE:
<223> OTHER INFORMATION: chemically synthesized

<400> SEQUENCE: 279

```
gaggagacgg tgacggatgt tccttgaccc ca                               32
```

<210> SEQ ID NO 280
<211> LENGTH: 14
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Ile or Met
<220> FEATURE:
<221> NAME/KEY: MISC_FEATURE
<222> LOCATION: (5)..(8)
<223> OTHER INFORMATION: Xaa is Leu, Pro, His, Gln, Arg, Val, Ala, Asp,
      Glu or Gly

<400> SEQUENCE: 280

```
Val Ser Glu Xaa Xaa Xaa Xaa Xaa Gly Leu Leu Gly Glu Thr
1               5                   10
```

<210> SEQ ID NO 281
<211> LENGTH: 13
<212> TYPE: DNA
<213> ORGANISM: Artificial Sequence
<220> FEATURE:
<223> OTHER INFORMATION: chemically synthesized

<400> SEQUENCE: 281

```
ttactgtgcg aga                                                    13
```

<210> SEQ ID NO 282
<211> LENGTH: 13
<212> TYPE: DNA
<213> ORGANISM: Artificial Sequence
<220> FEATURE:
<223> OTHER INFORMATION: chemically synthesized

<400> SEQUENCE: 282

```
ttactgtgca aga                                                    13
```

<210> SEQ ID NO 283
<211> LENGTH: 13
<212> TYPE: DNA
<213> ORGANISM: Artificial Sequence
<220> FEATURE:
<223> OTHER INFORMATION: chemically synthesized

<400> SEQUENCE: 283

-continued tttctgtgca aga                            13

<210> SEQ ID NO 284
<211> LENGTH: 13
<212> TYPE: DNA
<213> ORGANISM: Artificial Sequence
<220> FEATURE:
<223> OTHER INFORMATION: chemically synthesized

<400> SEQUENCE: 284
ctactgtgcc aga                            13

<210> SEQ ID NO 285
<211> LENGTH: 13
<212> TYPE: DNA
<213> ORGANISM: Artificial Sequence
<220> FEATURE:
<223> OTHER INFORMATION: chemically synthesized

<400> SEQUENCE: 285
tggggccagg gaa                            13

<210> SEQ ID NO 286
<211> LENGTH: 13
<212> TYPE: DNA
<213> ORGANISM: Artificial Sequence
<220> FEATURE:
<223> OTHER INFORMATION: chemically synthesized

<400> SEQUENCE: 286
tggggcgcag gga                            13

<210> SEQ ID NO 287
<211> LENGTH: 13
<212> TYPE: DNA
<213> ORGANISM: Artificial Sequence
<220> FEATURE:
<223> OTHER INFORMATION: chemically synthesized

<400> SEQUENCE: 287
tggggccaag gca                            13

<210> SEQ ID NO 288
<211> LENGTH: 13
<212> TYPE: DNA
<213> ORGANISM: Artificial Sequence
<220> FEATURE:
<223> OTHER INFORMATION: chemically synthesized

<400> SEQUENCE: 288
tggggccagg gca                            13

<210> SEQ ID NO 289
<211> LENGTH: 13
<212> TYPE: DNA
<213> ORGANISM: Artificial Sequence
<220> FEATURE:
<223> OTHER INFORMATION: chemically synthesized

<400> SEQUENCE: 289
tggggtcagg gca                            13